US010928402B2

(12) United States Patent
Ezrin et al.

(10) Patent No.: US 10,928,402 B2
(45) Date of Patent: Feb. 23, 2021

(54) TREATMENT OF SPONTANEOUS PRETERM BIRTH

(71) Applicant: NX Prenatal Inc., Louisville, KY (US)

(72) Inventors: Alan M. Ezrin, Miami, FL (US); Brian D. Brohman, Prospect, KY (US)

(73) Assignee: NX PRENATAL INC., Louisville, KY (US)

(*) Notice: Subject to any disclaimer, the term of this patent is extended or adjusted under 35 U.S.C. 154(b) by 0 days.

(21) Appl. No.: 14/655,705

(22) PCT Filed: Dec. 26, 2013

(86) PCT No.: PCT/US2013/077868
§ 371 (c)(1),
(2) Date: Jun. 25, 2015

(87) PCT Pub. No.: WO2014/105985
PCT Pub. Date: Jul. 3, 2014

(65) Prior Publication Data
US 2015/0355188 A1 Dec. 10, 2015

Related U.S. Application Data

(63) Continuation-in-part of application No. 13/797,933, filed on Mar. 12, 2013, now abandoned.

(60) Provisional application No. 61/747,150, filed on Dec. 28, 2012.

(51) Int. Cl.
*G01N 33/68* (2006.01)
*A61K 31/57* (2006.01)

(52) U.S. Cl.
CPC .......... *G01N 33/689* (2013.01); *A61K 31/57* (2013.01); *G01N 2800/368* (2013.01); *G01N 2800/60* (2013.01)

(58) Field of Classification Search
CPC .......... G01N 33/689; G01N 2800/368; G01N 33/6848; G01N 2800/50; G01N 2333/471
See application file for complete search history.

(56) References Cited

U.S. PATENT DOCUMENTS

| | | | |
|---|---|---|---|
| 9,068,990 B2 | 6/2015 | Taylor et al. | |
| 9,417,249 B2 * | 8/2016 | Taylor | G01N 33/6893 |
| 10,247,736 B2 | 4/2019 | Graves et al. | |
| 2010/0137263 A1 * | 6/2010 | Smith | G01N 33/689 514/169 |
| 2010/0190652 A1 | 7/2010 | Nagalla et al. | |
| 2010/0297679 A1 | 11/2010 | Graves et al. | |
| 2011/0236953 A1 | 9/2011 | Walsh et al. | |
| 2012/0021442 A1 * | 1/2012 | Buhimschi | G01N 33/569 435/7.92 |
| 2013/0058931 A1 | 3/2013 | Taylor et al. | |
| 2014/0186332 A1 | 7/2014 | Ezrin et al. | |
| 2014/0287950 A1 | 9/2014 | Hickok et al. | |
| 2015/0355188 A1 | 12/2015 | Ezrin et al. | |
| 2016/0375025 A1 | 12/2016 | Boshoff et al. | |
| 2017/0022565 A1 | 1/2017 | Boniface et al. | |
| 2019/0041391 A1 | 2/2019 | Brohman | |

FOREIGN PATENT DOCUMENTS

| | | |
|---|---|---|
| WO | WO-2008/056114 A1 | 5/2008 |
| WO | WO-2008/063928 A2 | 5/2008 |
| WO | WO-2008/063928 A3 | 5/2008 |
| WO | WO-2008/098734 A1 | 8/2008 |
| WO | WO-2009/031721 A1 | 3/2009 |
| WO | WO-2011/112993 A2 | 9/2011 |
| WO | WO-2011/112993 A3 | 9/2011 |
| WO | WO-2012/174282 A2 | 12/2012 |
| WO | WO-2012/174282 A3 | 12/2012 |
| WO | WO-2013/040211 A1 | 3/2013 |
| WO | WO-2013/184830 A1 | 12/2013 |
| WO | WO-2014/105985 A1 | 7/2014 |
| WO | WO-2014/110098 A1 | 7/2014 |
| WO | WO-2014/144129 A2 | 9/2014 |
| WO | WO-2014/144129 A3 | 9/2014 |
| WO | WO-2014/160237 A2 | 10/2014 |
| WO | WO-2014/160237 A3 | 10/2014 |
| WO | WO-2017/096405 A1 | 6/2017 |
| WO | WO-2019/152745 A1 | 8/2019 |

OTHER PUBLICATIONS

Berghella et al. Cerclage for Short Cervix on Ultrasonography in Women With Singleton Gestations and Previous Preterm Birth. Obstetrics and Gynecology, 2011; 117(3):663-671.*
Gupta et al. 17-alpha hydroxyprogesterone caproate for the prevention of preterm birth. Women's Health London, Jan. 2012; 8(1):21-30.*
Pereira et al. Identification of Novel Protein Biomarkers of Preterm Birth in Human Cervical-Vaginal Fluid. Journal of Proteome Research, 2007; 6:1269-1276.*
Esplin et al. Proteomic identification of serum peptides predicting subsequent spontaneous preterm birth. American Journal of Obstetrics and Gynecology, 2011; 204:391. E1-8.*
Stella et al. Preterm labor biomarker discovery in serum using 3 proteomic profiling methodologies. American Journal of Obstetrics and Gynecology, 2009; 201:387.e1-13.*
Goldenberg et al. Biochemical Markers for the predication of preterm birth. American Journal of Obstetrics and Gynecology, 2005; 192: S36-46).*

(Continued)

*Primary Examiner* — Vanessa L. Ford
*Assistant Examiner* — Sandra E Dillahunt
(74) *Attorney, Agent, or Firm* — Cooley LLP

(57) ABSTRACT

The present disclosure relates to biomarkers of preterm birth, biomarkers of term birth, and methods of use thereof. In particular, the present disclosure provides methods of determining whether a pregnant woman is at an increased risk for premature delivery. The present disclosure further provides methods for decreasing a pregnant woman's risk for premature delivery.

29 Claims, 2 Drawing Sheets
Specification includes a Sequence Listing.

(56) References Cited

OTHER PUBLICATIONS

Hassan et al. Vaginal progesterone reduces the rate of preterm birth in women with a sonographic short cervix: a multicenter, randomized, double-blind, placebo-controlled trial. Ultrasound Obstet Gynecol, 2011; 38(1): 18-31) (Year: 2011).*
Pereira et al. Insights into the multifactorial nature of preterm birth: proteomic profiling of the maternal serum glycoproteome and maternal serum peptidome among women in preterm labor. American Journal of Obstetrics and Gynecology. 2010; 202: 555-558 (Year: 2010).*
Behrman et al. (Institute of Medicine (US) Committee on Understanding Premature Birth and Assuring Healthy Outcomes; Preterm Birth: Causes, Consequences, and Prevention. Washington (DC): National Academies Press (US); 2007. 9, Diagnosis and Treatment of Conditions Leading to Spontaneous (Year: 2007).*
Behrman et al. (Institute of Medicine (US) Committee on Understanding Premature Birth and Assuring Healthy Outcomes; Preterm Birth: Causes, Consequences, and Prevention. Washington (DC): National Academies Press (US); 2007. (Year: 2007)*
Pereira et al. American Journal of Obstetrics and Gynecology. 2010; 202:555-558 (Year: 2010).*
Ables, A.Z. et al. (2005). "Preterm Labor: Diagnostic and Therapeutic Options are Not All Alike," *The Journal of Family Practice* 54(3):245-252.
Atay, S. et al. (2011). "Trophoblast-Derived Exosomes Mediate Monocyte Recruitment and Differentiation," *American Journal of Reproductive Immunology* 65:65-77.
Beer, L.A. et al. (2011). "Systematic Discovery of Ectopic Pregnancy Serum Biomarkers Using 3-D Protein Profiling Coupled with Label-free Quantitation," *Journal of Proteome Research* 10(3)1126-1138.
Behrman, R.E. et al. (2007). "Diagnosis and treatment of conditions leading to spontaneous preterm birth," National Institute of Health, 27 total pages.
Buhimschi, I.A. et al. (2005). "Proteomic Biomarker Analysis of Amniotic Fluid for Identification of Intra-Amniotic Inflammation," *BJOG: An International Journal of Obstetrics and Gynaecology* 112:173-181.
Buhimschi, C.S. et al. (2007). "Proteomic Biomarkers of Adverse Pregnancy Outcome in Preterm Birth: A Theranostics Opportunity," *B,bertliev. Obstet. Gynecol.* 2(6):743-753.
Conde-Agudelo, A. et al. (2011). "Novel Biomarkers for the Prediction of the Spontaneous Preterm Birth Phenotype: A Systematic Review and Meta-Analysis," *BJOG: An International Journal of Obstetrics and Gynaecology*, pp. 1042-1054.
Da Fonseca, E.B. et al. (2003). "Prophylactic administration of progesterone by vaginal suppository to reduce the incidence of spontaneous preterm birth in women at increased risk: A randomized placebo-controlled double-blind study," *Am. J. Obstetrics Gynecology* 188(2):419-424.
Extended European Search Report dated Aug. 29, 2016, for European Patent Application No. 13 867 314.0, filed on Dec. 26, 2013, 18 pages.
Esplin, M.S. et al. (2011). "Proteomic Identification of Serum Peptides Predicting Subsequent Spontaneous Preterm Birth," *American Journal of Obstetrics & Gynecology* 204:391.e1-391.e8.
Final Office Action dated Mar. 3, 2016, for U.S. Appl. No. 13/797,933, filed Mar. 12, 2013, 11 pages.
Gercel-Taylor, C. et al. (2012). "Nanoparticle Analysis of Circulating Cell-Derived Vesicles in Ovarian Cancer Patients," *Analytical Biochemistry* 428:44-53.
Goldenberg, R.L. et al. (2005). "Biochemical Markers for the Prediction of Preterm Birth," *American Journal of Obstetrics & Gynecology* 192:S36-S46.
Goldenbergr.L. et al. (2008). "Preterm Birth 1: Epidemiology and Causes of Preterm Birth," *The Lancet* 371:75-84.
Hassan, S.S. et al. (2011). "Vaginal progesterone reduces the rate of preterm birth in women with a sonographic short cervix: a multi-center, randomized, double-blind, placebo-controlled trial," *Ultrasound in Obstetrics and Gynecology* 38(1):18-31.
Honest et al., "Screening to Prevent Spontaneous Preterm Birth: Systematic Reviews of Accuracy and Effectiveness Literature with Economic Modelling", Health Technology Assessment, vol. 13, No. 43, Chapter. 1, Sep. 2009, pp. 17 pages.
International Search Report dated Mar. 21, 2014, for PCT Application No. PCT/US2013/077868, filed on Dec. 26, 2013, 3 pages.
Koenig, T. et al. (2008). "Robust Prediction of the MASCOT Score for an Improved Quality Assessment in Mass Spectrometric Proteomics," *Journal of Proteome Research* 7(9):3708-3717.
Liu, C. et al. (2011). "Proteomic analysis of human serum for Finding pathogenic factors and potential biomarkers in preeclampsia," *Placenta* 32:168-174.
Mathivanan, S. et al. (2011). "ExoCarta 2012: Database of Exosomal Proteins, RNA and Lipids," *Nucleic Acids Research* 40:D1241-D1244.
Mincheva-Nilsson, L. (2010). "Placental Exosome-Mediated Immune Protection of the Fetus: Feeling Groovy in a Cloud of Exosomes," *Expert Review of Obstetrics & Gynecology* 5(5):619-634.
National Research Council (2007). "Diagnosis and Treatment of Conditions Leading to Spontaneous Preterm Birth," The National Academies Press, pp. 259-307.
Non-Final Office Action dated Mar. 13, 2015, for U.S. Appl. No. 13/797,933, filed Mar. 12, 2013, 14 pages.
Olver, C. et al. (2007). "Proteomic Analysis of Secreted Exosomes," Subcellular Biochemistry 43:99-131.
Pant, S. et al. (2012). "The Multifaceted Exosome: Biogenesis, Role in Normal and Aberrant Cellular Function, and Frontiers for Pharmacological and Biomarker Opportunities," *Biochemical Pharmacology* 83:1484-1494.
Pappin, D.J.C. et al. (1993). "Rapid Identification of Proteins by Peptide-Mass Fingerprinting," *Current Biology* 3(6):327-332.
Partial European Search Report dated May 3, 2016, for European Patent Application No. 13 867 314.0, filed on Dec. 26, 2013, 11 pages.
Pereira et al. (2010). "Insights into the multifactorial nature of preterm birth: proteomic profiling of the maternal serum glycoproteome and maternal serum peptidome among women in preterm labor," *American Journal of Obstetrics and Gynecology* 202:555-558.
Perkins, D.N. et al. (1999). "Probability-Based Protein Identification by Searching Sequence Databases Using Mass Spectrometry Data," *Electrophoresis* 20:3551-3567.
Practice Bulletin No. 130 (2012). "Prediction and Prevention of Preterm Birth," *Obstetrics & Gynecology* 120(4):964-973.
Redman, C.W.G. et al. (2012). "Review: Does Size Matter? Placental Debris and the Pathophysiology of Pre-Eclampsia," *Trophoblast Research* 33(Supplement A) 26:S48-S54.
Sabapatha, A. et al. (2006). "Specific Isolation of Placenta-Derived Exosomes from the Circulation of Pregnant Women and Their Immunoregulatory Consequences," *American Journal of Reproductive Immunology* 56:345-355.
Saunders, R.D. et al. (2012). "Alterations in Antibody Subclass Immune Reactivity to Trophoblast-derived Fetal Fibronectin and a2-Macroglobulin in Women with Recurrent Pregnancy Loss," *American Journal of Reproductive Immunology* 68:438-449.
Shah, S.J. et al. (2009). "Identification and Quantification of Preterm Birth Biomarkers in Human Cervicovaginal Fluid by Liquid Chromatography/Tandem Mass Spectrometry," *Journal of Proteome Research* 8(5):2407-2417.
Simpson, R.J. et al. (2008). "Proteomic Profiling of Exosomes: Current Perspectives," *Proteomics* 8:4083-4099.
Singh, P.P. et al. (2012). "Exosomes Isolated from Mycobacteria-Infected Mice or Cultured Macrophages can Recruit and Activate Immune Cells in Vitro and in Vivo," *Journal of Immunology* 189(2):777-785.
Stella, C.L. et al. (2009). "Preterm Labor Biomarker Discovery in Serum Using 3 Proteomic Profiling Methodologies," *American Journal of Obstetrics & Gynecology* 387: .e1-387.e13.
Stenczer, B. et al. (2012). "Circulating levels of thrombospondin-1 are decreased in HELLP syndrome," *Thrombosis Research* 129:470-473.

(56) References Cited

OTHER PUBLICATIONS

Tang, H-Y. et al. (2011). "Rapid Verification of Candidate Serological Biomarkers Using Gel-based, Label-free Multiple Reaction Monitoring," *Journal Proteome Research* 10:4005-4017.

Taylor, D.D. et al. (2006). "Pregnancy-Associated Exosomes and their Modulation of T cell Signaling," *The Journal of Immunology* 176:1534-1542.

Thery, C. (2011). "Exosomes: Secreted Vesicles and Intercellular Communications," *F1000 Biology Reports* 3(15):1-8.

Tita, A.T.N. et al. (2009). "Progesterone for Preterm Birth Prevention: An Evolving Intervention," *American Journal of Obstetrics & Synecology* 200(3):219-224.

Wen, Q. et al. (2013). "Peptidomic Identification of Serum Peptides Diagnosing Preeclampsia," *PLoS One* 8(6):e65571.

Weismiller, D.G. (1999). "Preterm labor," *Am. Fam. Physician* 59(3):593-602.

Written Opinion of the International Searching Authority dated Mar. 21, 2014, for PCT Application No. PCT/US2013/077868, filed on Dec. 26, 2013, 8 pages.

International Preliminary Report on Patentability dated Jun. 30, 2015, for PCT Application No. PCT/US2013/077868, filed on Dec. 26, 2013, 9 pages.

De Menezes-Neto, A. et al. (2015). "Size-exclusion chromatography as a stand-alone methodology identifies novel markers in mass spectrometry analyses of plasma-derived vesicles from healthy individuals," *J. Extracellular Vesicles* 4:27378, 14 total pages.

Ezrin, A.M. et al. (2015). "Circulating serum-derived microparticles provide novel proteomic biomarkers of spontaneous preterm birth," *Am. J. Perinatol.* 32:605-614.

Intermountain Healthcare (2014). Cervical Cerclage, 2 total pages.

Intermountain Healthcare (2014). Prevention and Management of Preterm Birth, 28 total pages.

Intermountain Healthcare (2014). 17P for preventing preterm birth, 2 total pages.

International Search Report dated Feb. 21, 2017, for PCT Application No. PCT/US2016/065024, filed on Dec. 5, 2016, 3 pages.

Non-Final Office Action dated Jun. 7, 2017, for U.S. Appl. No. 13/797,933, filed Mar. 12, 2013, 19 pages.

Society for Maternal-Fetal Medicine and the SMFM Foundation. "High-risk pregnancy care, research, and education for over 35 years," 34 total pages.

Taylor, DD. Et al. (2011). "Exosome isolation for proteomic analyses and RNA profiling," *Methods Mol. Biol.* 728:235-246.

Written Opinion of the International Searching Authority dated Feb. 21, 2017, for PCT Application No. PCT/US2016/065024, filed on Dec. 5, 2016, 10 pages.

Cantonwine, D. E. et al. "Evaluation of proteomic biomarkers associated with circulating microparticles as an effective means to stratify the risk of spontaneous preterm birth", Am J Obstet Gynecol. ;214(5):631. May 2016. Epub Feb. 11, 2016.

Extended European Search Report dated Aug. 22, 2019, for European Patent Application No. 16871740.3, filed on Dec. 26, 2013, 5 pages.

Final Office Action dated Nov. 16, 2018, for U.S. Appl. No. 13/797,933, filed Mar. 12, 2013, 22 pages.

International Preliminary Report on Patentability dated Jun. 5, 2018, for PCT Application No. PCT/US2016/065024, filed on Dec. 5, 2016, 11 pages.

International Search Report and Written Opinion dated Apr. 24, 2019 for International Patent Application No. PCT/US2019/016192, filed Jan. 31, 2019, 11 pages.

Mcelrath, T., et al., "Extracellular vesicle proteomic markers obtained at 12 weeks predict spontaneous preterm birth less than 35 weeks gestation: a validation with specific characterization of marker behavior by fetal gender and parity", American Journal of Obstetrics and Gynecology; 128(1);14:S12. Jan. 2018.

Non-Final Office Action dated May 18, 2020, for U.S. Appl. No. 15/997,540, filed Jun. 4, 2018, 20 pages.

UWPR (Oct. 4, 2011). "Protein Reduction, Alkylation, Digestion"; University of Washington Proteomics Resource: 1-8.

Torzewski, M. et al. (2014). "Animal Models of C-Reactive Protein", Mediators of Inflammation; Hindawi Publishing Corporation 2014: 8 pgs.

Van Der Vekens, et al. (2013). "Human and equine cardiovascular biomarkers: beware to compare", Cardiovascular Endocrinology: 2(4):67-76.

International Preliminary Report on Patentability dated Aug. 4, 2020, for PCT Application No. PCT/US2019/016192, filed Jan. 31, 2019, 8 pages.

Notice of Allowance dated Oct. 15, 2020, for U.S. Appl. No. 15/997,540, filed Jun. 4, 2018, 7 pages.

\* cited by examiner

SEQUENCE LISTING

```
<160> NUMBER OF SEQ ID NOS: 100

<210> SEQ ID NO 1
<211> LENGTH: 1474
<212> TYPE: PRT
<213> ORGANISM: Homo sapiens

<400> SEQUENCE: 1

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45
```

-continued

```
Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
```

```
                465                 470                 475                 480
        Ile Leu Asn Gly Gly Thr Leu Leu Gly Leu Lys Lys Leu Ser Phe Tyr
                        485                 490                 495

Tyr Leu Ile Met Ala Lys Gly Gly Ile Val Arg Thr Gly Thr His Gly
                        500                 505                 510

Leu Leu Val Lys Gln Glu Asp Met Lys Gly His Phe Ser Ile Ser Ile
                        515                 520                 525

Pro Val Lys Ser Asp Ile Ala Pro Val Ala Arg Leu Leu Ile Tyr Ala
                        530                 535                 540

Val Leu Pro Thr Gly Asp Val Ile Gly Asp Ser Ala Lys Tyr Asp Val
        545                 550                 555                 560

Glu Asn Cys Leu Ala Asn Lys Val Asp Leu Ser Phe Ser Pro Ser Gln
                        565                 570                 575

Ser Leu Pro Ala Ser His Ala His Leu Arg Val Thr Ala Ala Pro Gln
                        580                 585                 590

Ser Val Cys Ala Leu Arg Ala Val Asp Gln Ser Val Leu Leu Met Lys
                        595                 600                 605

Pro Asp Ala Glu Leu Ser Ala Ser Ser Val Tyr Asn Leu Leu Pro Glu
                        610                 615                 620

Lys Asp Leu Thr Gly Phe Pro Gly Pro Leu Asn Asp Gln Asp Asn Glu
        625                 630                 635                 640

Asp Cys Ile Asn Arg His Asn Val Tyr Ile Asn Gly Ile Thr Tyr Thr
                        645                 650                 655

Pro Val Ser Ser Thr Asn Glu Lys Asp Met Tyr Ser Phe Leu Glu Asp
                        660                 665                 670

Met Gly Leu Lys Ala Phe Thr Asn Ser Lys Ile Arg Lys Pro Lys Met
                        675                 680                 685

Cys Pro Gln Leu Gln Gln Tyr Glu Met His Gly Pro Glu Gly Leu Arg
                        690                 695                 700

Val Gly Phe Tyr Glu Ser Asp Val Met Gly Arg Gly His Ala Arg Leu
        705                 710                 715                 720

Val His Val Glu Glu Pro His Thr Glu Thr Val Arg Lys Tyr Phe Pro
                        725                 730                 735

Glu Thr Trp Ile Trp Asp Leu Val Val Val Asn Ser Ala Gly Val Ala
                        740                 745                 750

Glu Val Gly Val Thr Val Pro Asp Thr Ile Thr Glu Trp Lys Ala Gly
                        755                 760                 765

Ala Phe Cys Leu Ser Glu Asp Ala Gly Leu Gly Ile Ser Ser Thr Ala
        770                 775                 780

Ser Leu Arg Ala Phe Gln Pro Phe Phe Val Glu Leu Thr Met Pro Tyr
        785                 790                 795                 800

Ser Val Ile Arg Gly Glu Ala Phe Thr Leu Lys Ala Thr Val Leu Asn
                        805                 810                 815

Tyr Leu Pro Lys Cys Ile Arg Val Ser Val Gln Leu Glu Ala Ser Pro
                        820                 825                 830

Ala Phe Leu Ala Val Pro Val Glu Lys Glu Gln Ala Pro His Cys Ile
                        835                 840                 845

Cys Ala Asn Gly Arg Gln Thr Val Ser Trp Ala Val Thr Pro Lys Ser
                        850                 855                 860

Leu Gly Asn Val Asn Phe Thr Val Ser Ala Glu Ala Leu Glu Ser Gln
        865                 870                 875                 880

Glu Leu Cys Gly Thr Glu Val Pro Ser Val Pro Glu His Gly Arg Lys
                        885                 890                 895
```

```
Asp Thr Val Ile Lys Pro Leu Leu Val Glu Pro Gly Leu Glu Lys
            900                 905                 910
Glu Thr Thr Phe Asn Ser Leu Leu Cys Pro Ser Gly Glu Val Ser
            915                 920                 925
Glu Glu Leu Ser Leu Lys Leu Pro Pro Asn Val Glu Glu Ser Ala
            930                 935                 940
Arg Ala Ser Val Ser Val Leu Gly Asp Ile Leu Gly Ser Ala Met Gln
945                 950                 955                 960
Asn Thr Gln Asn Leu Leu Gln Met Pro Tyr Gly Cys Gly Glu Gln Asn
            965                 970                 975
Met Val Leu Phe Ala Pro Asn Ile Tyr Val Leu Asp Tyr Leu Asn Glu
            980                 985                 990
Thr Gln Gln Leu Thr Pro Glu Ile Lys Ser Lys Ala Ile Gly Tyr Leu
            995                 1000                1005
Asn Thr Gly Tyr Gln Arg Gln Leu Asn Tyr Lys His Tyr Asp Gly Ser
            1010                1015                1020
Tyr Ser Thr Phe Gly Glu Arg Tyr Gly Arg Asn Gln Gly Asn Thr Trp
1025                1030                1035                1040
Leu Thr Ala Phe Val Leu Lys Thr Phe Ala Gln Ala Arg Ala Tyr Ile
            1045                1050                1055
Phe Ile Asp Glu Ala His Ile Thr Gln Ala Leu Ile Trp Leu Ser Gln
            1060                1065                1070
Arg Gln Lys Asp Asn Gly Cys Phe Arg Ser Ser Gly Ser Leu Leu Asn
            1075                1080                1085
Asn Ala Ile Lys Gly Gly Val Glu Asp Glu Val Thr Leu Ser Ala Tyr
            1090                1095                1100
Ile Thr Ile Ala Leu Leu Glu Ile Pro Leu Thr Val Thr His Pro Val
1105                1110                1115                1120
Val Arg Asn Ala Leu Phe Cys Leu Glu Ser Ala Trp Lys Thr Ala Gln
            1125                1130                1135
Glu Gly Asp His Gly Ser His Val Tyr Thr Lys Ala Leu Leu Ala Tyr
            1140                1145                1150
Ala Phe Ala Leu Ala Gly Asn Gln Asp Lys Arg Lys Glu Val Leu Lys
            1155                1160                1165
Ser Leu Asn Glu Glu Ala Val Lys Lys Asp Asn Ser Val His Trp Glu
            1170                1175                1180
Arg Pro Gln Lys Pro Lys Ala Pro Val Gly His Phe Tyr Glu Pro Gln
1185                1190                1195                1200
Ala Pro Ser Ala Glu Val Glu Met Thr Ser Tyr Val Leu Leu Ala Tyr
            1205                1210                1215
Leu Thr Ala Gln Pro Ala Pro Thr Ser Glu Asp Leu Thr Ser Ala Thr
            1220                1225                1230
Asn Ile Val Lys Trp Ile Thr Lys Gln Gln Asn Ala Gln Gly Gly Phe
            1235                1240                1245
Ser Ser Thr Gln Asp Thr Val Val Ala Leu His Ala Leu Ser Lys Tyr
            1250                1255                1260
Gly Ala Ala Thr Phe Thr Arg Thr Gly Lys Ala Ala Gln Val Thr Ile
1265                1270                1275                1280
Gln Ser Ser Gly Thr Phe Ser Ser Lys Phe Gln Val Asp Asn Asn Asn
            1285                1290                1295
Arg Leu Leu Leu Gln Gln Val Ser Leu Pro Glu Leu Pro Gly Glu Tyr
            1300                1305                1310
```

```
Ser Met Lys Val Thr Gly Glu Gly Cys Val Tyr Leu Gln Thr Ser Leu
    1315                1320                1325

Lys Tyr Asn Ile Leu Pro Glu Lys Glu Phe Pro Phe Ala Leu Gly
    1330                1335                1340

Val Gln Thr Leu Pro Gln Thr Cys Asp Glu Pro Lys Ala His Thr Ser
1345                1350                1355                1360

Phe Gln Ile Ser Leu Ser Val Ser Tyr Thr Gly Ser Arg Ser Ala Ser
                1365                1370                1375

Asn Met Ala Ile Val Asp Val Lys Met Val Ser Gly Phe Ile Pro Leu
            1380                1385                1390

Lys Pro Thr Val Lys Met Leu Glu Arg Ser Asn His Val Ser Arg Thr
            1395                1400                1405

Glu Val Ser Ser Asn His Val Leu Ile Tyr Leu Asp Lys Val Ser Asn
            1410                1415                1420

Gln Thr Leu Ser Leu Phe Phe Thr Val Leu Gln Asp Val Pro Val Arg
1425                1430                1435                1440

Asp Leu Lys Pro Ala Ile Val Lys Val Tyr Asp Tyr Tyr Glu Thr Asp
                1445                1450                1455

Glu Phe Ala Ile Ala Glu Tyr Asn Ala Pro Cys Ser Lys Asp Leu Gly
            1460                1465                1470

Asn Ala
```

<210> SEQ ID NO 2
<211> LENGTH: 4563
<212> TYPE: PRT
<213> ORGANISM: Homo sapiens

<400> SEQUENCE: 2

```
Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
                35                  40                  45

Leu Arg Lys Tyr Thr Tyr Asn Tyr Glu Ala Glu Ser Ser Ser Gly Val
    50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Thr Leu Lys Glu Val Tyr Gly Phe Asn Pro Glu Gly Lys Ala Leu
                100                 105                 110

Leu Lys Lys Thr Lys Asn Ser Glu Glu Phe Ala Ala Ala Met Ser Arg
            115                 120                 125

Tyr Glu Leu Lys Leu Ala Ile Pro Glu Gly Lys Gln Val Phe Leu Tyr
    130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
    195                 200                 205
```

-continued

Leu Gly Gln Cys Asp Arg Phe Lys Pro Ile Arg Thr Gly Ile Ser Pro
210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
            245                 250                 255

Ala Glu Ala Ile Cys Lys Glu Gln His Leu Phe Leu Pro Phe Ser Tyr
            260                 265                 270

Lys Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
290                 295                 300

Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
            325                 330                 335

Ile Ser Glu Gln Asn Ile Gln Arg Ala Asn Leu Phe Asn Lys Leu Val
            340                 345                 350

Thr Glu Leu Arg Gly Leu Ser Asp Glu Ala Val Thr Ser Leu Leu Pro
        355                 360                 365

Gln Leu Ile Glu Val Ser Ser Pro Ile Thr Leu Gln Ala Leu Val Gln
370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
            405                 410                 415

Leu Ile Pro Glu Pro Ser Ala Gln Gln Leu Arg Glu Ile Phe Asn Met
            420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
            485                 490                 495

Gln Thr Met Glu Gln Leu Thr Pro Glu Leu Lys Ser Ser Ile Leu Lys
            500                 505                 510

Cys Val Gln Ser Thr Lys Pro Ser Leu Met Ile Gln Lys Ala Ala Ile
        515                 520                 525

Gln Ala Leu Arg Lys Met Glu Pro Lys Asp Lys Asp Gln Glu Val Leu
530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
            565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Leu Asp Ile
        595                 600                 605

Gln Asp Leu Lys Lys Leu Val Lys Glu Ala Leu Lys Glu Ser Gln Leu
610                 615                 620

Pro Thr Val Met Asp Phe Arg Lys Phe Ser Arg Asn Tyr Gln Leu Tyr

```
                625                 630                 635                 640
Lys Ser Val Ser Leu Pro Ser Leu Asp Pro Ala Ser Ala Lys Ile Glu
                    645                 650                 655
Gly Asn Leu Ile Phe Asp Pro Asn Asn Tyr Leu Pro Lys Glu Ser Met
                    660                 665                 670
Leu Lys Thr Thr Leu Thr Ala Phe Gly Phe Ala Ser Ala Asp Leu Ile
                    675                 680                 685
Glu Ile Gly Leu Glu Gly Lys Gly Phe Glu Pro Thr Leu Glu Ala Leu
            690                 695                 700
Phe Gly Lys Gln Gly Phe Phe Pro Asp Ser Val Asn Lys Ala Leu Tyr
705                 710                 715                 720
Trp Val Asn Gly Gln Val Pro Asp Gly Val Ser Lys Val Leu Val Asp
                725                 730                 735
His Phe Gly Tyr Thr Lys Asp Asp Lys His Glu Gln Asp Met Val Asn
                740                 745                 750
Gly Ile Met Leu Ser Val Glu Lys Leu Ile Lys Asp Leu Lys Ser Lys
                755                 760                 765
Glu Val Pro Glu Ala Arg Ala Tyr Leu Arg Ile Leu Gly Glu Glu Leu
            770                 775                 780
Gly Phe Ala Ser Leu His Asp Leu Gln Leu Leu Gly Lys Leu Leu Leu
785                 790                 795                 800
Met Gly Ala Arg Thr Leu Gln Gly Ile Pro Gln Met Ile Gly Glu Val
                805                 810                 815
Ile Arg Lys Gly Ser Lys Asn Asp Phe Phe Leu His Tyr Ile Phe Met
                820                 825                 830
Glu Asn Ala Phe Glu Leu Pro Thr Gly Ala Gly Leu Gln Leu Gln Ile
            835                 840                 845
Ser Ser Ser Gly Val Ile Ala Pro Gly Ala Lys Ala Gly Val Lys Leu
        850                 855                 860
Glu Val Ala Asn Met Gln Ala Glu Leu Val Ala Lys Pro Ser Val Ser
865                 870                 875                 880
Val Glu Phe Val Thr Asn Met Gly Ile Ile Pro Asp Phe Ala Arg
                885                 890                 895
Ser Gly Val Gln Met Asn Thr Asn Phe Phe His Glu Ser Gly Leu Glu
                900                 905                 910
Ala His Val Ala Leu Lys Ala Gly Lys Leu Lys Phe Ile Ile Pro Ser
            915                 920                 925
Pro Lys Arg Pro Val Lys Leu Leu Ser Gly Gly Asn Thr Leu His Leu
        930                 935                 940
Val Ser Thr Thr Lys Thr Glu Val Ile Pro Pro Leu Ile Glu Asn Arg
945                 950                 955                 960
Gln Ser Trp Ser Val Cys Lys Gln Val Phe Pro Gly Leu Asn Tyr Cys
                965                 970                 975
Thr Ser Gly Ala Tyr Ser Asn Ala Ser Ser Thr Asp Ser Ala Ser Tyr
            980                 985                 990
Tyr Pro Leu Thr Gly Asp Thr Arg Leu Glu Leu Glu Leu Arg Pro Thr
        995                 1000                1005
Gly Glu Ile Glu Gln Tyr Ser Val Ser Ala Thr Tyr Glu Leu Gln Arg
        1010                1015                1020
Glu Asp Arg Ala Leu Val Asp Thr Leu Lys Phe Val Thr Gln Ala Glu
1025                1030                1035                1040
Gly Ala Lys Gln Thr Glu Ala Thr Met Thr Phe Lys Tyr Asn Arg Gln
                1045                1050                1055
```

Ser Met Thr Leu Ser Ser Glu Val Gln Ile Pro Asp Phe Asp Val Asp
            1060                1065                1070

Leu Gly Thr Ile Leu Arg Val Asn Asp Glu Ser Thr Glu Gly Lys Thr
        1075                1080                1085

Ser Tyr Arg Leu Thr Leu Asp Ile Gln Asn Lys Lys Ile Thr Glu Val
1090                1095                1100

Ala Leu Met Gly His Leu Ser Cys Asp Thr Lys Glu Glu Arg Lys Ile
1105                1110                1115                1120

Lys Gly Val Ile Ser Ile Pro Arg Leu Gln Ala Glu Ala Arg Ser Glu
            1125                1130                1135

Ile Leu Ala His Trp Ser Pro Ala Lys Leu Leu Leu Gln Met Asp Ser
        1140                1145                1150

Ser Ala Thr Ala Tyr Gly Ser Thr Val Ser Lys Arg Val Ala Trp His
    1155                1160                1165

Tyr Asp Glu Glu Lys Ile Glu Phe Glu Trp Asn Thr Gly Thr Asn Val
1170                1175                1180

Asp Thr Lys Lys Met Thr Ser Asn Phe Pro Val Asp Leu Ser Asp Tyr
1185                1190                1195                1200

Pro Lys Ser Leu His Met Tyr Ala Asn Arg Leu Leu Asp His Arg Val
            1205                1210                1215

Pro Gln Thr Asp Met Thr Phe Arg His Val Gly Ser Lys Leu Ile Val
        1220                1225                1230

Ala Met Ser Ser Trp Leu Gln Lys Ala Ser Gly Ser Leu Pro Tyr Thr
    1235                1240                1245

Gln Thr Leu Gln Asp His Leu Asn Ser Leu Lys Glu Phe Asn Leu Gln
1250                1255                1260

Asn Met Gly Leu Pro Asp Phe His Ile Pro Glu Asn Leu Phe Leu Lys
1265                1270                1275                1280

Ser Asp Gly Arg Val Lys Tyr Thr Leu Asn Lys Asn Ser Leu Lys Ile
            1285                1290                1295

Glu Ile Pro Leu Pro Phe Gly Gly Lys Ser Ser Arg Asp Leu Lys Met
        1300                1305                1310

Leu Glu Thr Val Arg Thr Pro Ala Leu His Phe Lys Ser Val Gly Phe
    1315                1320                1325

His Leu Pro Ser Arg Glu Phe Gln Val Pro Thr Phe Thr Ile Pro Lys
1330                1335                1340

Leu Tyr Gln Leu Gln Val Pro Leu Leu Gly Val Leu Asp Leu Ser Thr
1345                1350                1355                1360

Asn Val Tyr Ser Asn Leu Tyr Asn Trp Ser Ala Ser Tyr Ser Gly Gly
            1365                1370                1375

Asn Thr Ser Thr Asp His Phe Ser Leu Arg Ala Arg Tyr His Met Lys
        1380                1385                1390

Ala Asp Ser Val Val Asp Leu Leu Ser Tyr Asn Val Gln Gly Ser Gly
    1395                1400                1405

Glu Thr Thr Tyr Asp His Lys Asn Thr Phe Thr Leu Ser Tyr Asp Gly
        1410                1415                1420

Ser Leu Arg His Lys Phe Leu Asp Ser Asn Ile Lys Phe Ser His Val
1425                1430                1435                1440

Glu Lys Leu Gly Asn Asn Pro Val Ser Lys Gly Leu Leu Ile Phe Asp
            1445                1450                1455

Ala Ser Ser Ser Trp Gly Pro Gln Met Ser Ala Ser Val His Leu Asp
        1460                1465                1470

-continued

Ser Lys Lys Lys Gln His Leu Phe Val Lys Glu Val Lys Ile Asp Gly
        1475                1480                1485

Gln Phe Arg Val Ser Ser Phe Tyr Ala Lys Gly Thr Tyr Gly Leu Ser
    1490                1495                1500

Cys Gln Arg Asp Pro Asn Thr Gly Arg Leu Asn Gly Glu Ser Asn Leu
1505                1510                1515                1520

Arg Phe Asn Ser Ser Tyr Leu Gln Gly Thr Asn Gln Ile Thr Gly Arg
        1525                1530                1535

Tyr Glu Asp Gly Thr Leu Ser Leu Thr Ser Thr Ser Asp Leu Gln Ser
            1540                1545                1550

Gly Ile Ile Lys Asn Thr Ala Ser Leu Lys Tyr Glu Asn Tyr Glu Leu
        1555                1560                1565

Thr Leu Lys Ser Asp Thr Asn Gly Lys Tyr Lys Asn Phe Ala Thr Ser
    1570                1575                1580

Asn Lys Met Asp Met Thr Phe Ser Lys Gln Asn Ala Leu Leu Arg Ser
1585                1590                1595                1600

Glu Tyr Gln Ala Asp Tyr Glu Ser Leu Arg Phe Phe Ser Leu Leu Ser
        1605                1610                1615

Gly Ser Leu Asn Ser His Gly Leu Glu Leu Asn Ala Asp Ile Leu Gly
            1620                1625                1630

Thr Asp Lys Ile Asn Ser Gly Ala His Lys Ala Thr Leu Arg Ile Gly
        1635                1640                1645

Gln Asp Gly Ile Ser Thr Ser Ala Thr Thr Asn Leu Lys Cys Ser Leu
    1650                1655                1660

Leu Val Leu Glu Asn Glu Leu Asn Ala Glu Leu Gly Leu Ser Gly Ala
1665                1670                1675                1680

Ser Met Lys Leu Thr Thr Asn Gly Arg Phe Arg Glu His Asn Ala Lys
        1685                1690                1695

Phe Ser Leu Asp Gly Lys Ala Ala Leu Thr Glu Leu Ser Leu Gly Ser
            1700                1705                1710

Ala Tyr Gln Ala Met Ile Leu Gly Val Asp Ser Lys Asn Ile Phe Asn
        1715                1720                1725

Phe Lys Val Ser Gln Glu Gly Leu Lys Leu Ser Asn Asp Met Met Gly
    1730                1735                1740

Ser Tyr Ala Glu Met Lys Phe Asp His Thr Asn Ser Leu Asn Ile Ala
1745                1750                1755                1760

Gly Leu Ser Leu Asp Phe Ser Ser Lys Leu Asp Asn Ile Tyr Ser Ser
        1765                1770                1775

Asp Lys Phe Tyr Lys Gln Thr Val Asn Leu Gln Leu Gln Pro Tyr Ser
        1780                1785                1790

Leu Val Thr Thr Leu Asn Ser Asp Leu Lys Tyr Asn Ala Leu Asp Leu
    1795                1800                1805

Thr Asn Asn Gly Lys Leu Arg Leu Glu Pro Leu Lys Leu His Val Ala
    1810                1815                1820

Gly Asn Leu Lys Gly Ala Tyr Gln Asn Asn Glu Ile Lys His Ile Tyr
1825                1830                1835                1840

Ala Ile Ser Ser Ala Ala Leu Ser Ala Ser Tyr Lys Ala Asp Thr Val
        1845                1850                1855

Ala Lys Val Gln Gly Val Glu Phe Ser His Arg Leu Asn Thr Asp Ile
            1860                1865                1870

Ala Gly Leu Ala Ser Ala Ile Asp Met Ser Thr Asn Tyr Asn Ser Asp
        1875                1880                1885

Ser Leu His Phe Ser Asn Val Phe Arg Ser Val Met Ala Pro Phe Thr

```
                    1890                1895                1900
Met Thr Ile Asp Ala His Thr Asn Gly Asn Gly Lys Leu Ala Leu Trp
1905                1910                1915                1920

Gly Glu His Thr Gly Gln Leu Tyr Ser Lys Phe Leu Lys Ala Glu
                1925                1930                1935

Pro Leu Ala Phe Thr Phe Ser His Asp Tyr Lys Gly Ser Thr Ser His
            1940                1945                1950

His Leu Val Ser Arg Lys Ser Ile Ser Ala Ala Leu Glu His Lys Val
        1955                1960                1965

Ser Ala Leu Leu Thr Pro Ala Glu Gln Thr Gly Thr Trp Lys Leu Lys
    1970                1975                1980

Thr Gln Phe Asn Asn Asn Glu Tyr Ser Gln Asp Leu Asp Ala Tyr Asn
1985                1990                1995                2000

Thr Lys Asp Lys Ile Gly Val Glu Leu Thr Gly Arg Thr Leu Ala Asp
                2005                2010                2015

Leu Thr Leu Leu Asp Ser Pro Ile Lys Val Pro Leu Leu Ser Glu
            2020                2025                2030

Pro Ile Asn Ile Ile Asp Ala Leu Glu Met Arg Asp Ala Val Glu Lys
        2035                2040                2045

Pro Gln Glu Phe Thr Ile Val Ala Phe Val Lys Tyr Asp Lys Asn Gln
    2050                2055                2060

Asp Val His Ser Ile Asn Leu Pro Phe Glu Thr Leu Gln Glu Tyr
2065                2070                2075                2080

Phe Glu Arg Asn Arg Gln Thr Ile Ile Val Val Leu Glu Asn Val Gln
                2085                2090                2095

Arg Asn Leu Lys His Ile Asn Ile Asp Gln Phe Val Arg Lys Tyr Arg
            2100                2105                2110

Ala Ala Leu Gly Lys Leu Pro Gln Gln Ala Asn Asp Tyr Leu Asn Ser
        2115                2120                2125

Phe Asn Trp Glu Arg Gln Val Ser His Ala Lys Glu Lys Leu Thr Ala
    2130                2135                2140

Leu Thr Lys Lys Tyr Arg Ile Thr Glu Asn Asp Ile Gln Ile Ala Leu
2145                2150                2155                2160

Asp Asp Ala Lys Ile Asn Phe Asn Glu Lys Leu Ser Gln Leu Gln Thr
                2165                2170                2175

Tyr Met Ile Gln Phe Asp Gln Tyr Ile Lys Asp Ser Tyr Asp Leu His
            2180                2185                2190

Asp Leu Lys Ile Ala Ile Ala Asn Ile Asp Glu Ile Ile Glu Lys
        2195                2200                2205

Leu Lys Ser Leu Asp Glu His Tyr His Ile Arg Val Asn Leu Val Lys
    2210                2215                2220

Thr Ile His Asp Leu His Leu Phe Ile Glu Asn Ile Asp Phe Asn Lys
2225                2230                2235                2240

Ser Gly Ser Ser Thr Ala Ser Trp Ile Gln Asn Val Asp Thr Lys Tyr
                2245                2250                2255

Gln Ile Arg Ile Gln Ile Gln Glu Lys Leu Gln Gln Leu Lys Arg His
            2260                2265                2270

Ile Gln Asn Ile Asp Ile Gln His Leu Ala Gly Lys Leu Lys Gln His
        2275                2280                2285

Ile Glu Ala Ile Asp Val Arg Val Leu Leu Asp Gln Leu Gly Thr Thr
    2290                2295                2300

Ile Ser Phe Glu Arg Ile Asn Asp Ile Leu Glu His Val Lys His Phe
2305                2310                2315                2320
```

```
Val Ile Asn Leu Ile Gly Asp Phe Glu Val Ala Glu Lys Ile Asn Ala
            2325                2330                2335

Phe Arg Ala Lys Val His Glu Leu Ile Glu Arg Tyr Glu Val Asp Gln
            2340                2345                2350

Gln Ile Gln Val Leu Met Asp Lys Leu Val Glu Leu Ala His Gln Tyr
            2355                2360                2365

Lys Leu Lys Glu Thr Ile Gln Lys Leu Ser Asn Val Leu Gln Gln Val
            2370                2375                2380

Lys Ile Lys Asp Tyr Phe Glu Lys Leu Val Gly Phe Ile Asp Asp Ala
2385                2390                2395                2400

Val Lys Lys Leu Asn Glu Leu Ser Phe Lys Thr Phe Ile Glu Asp Val
            2405                2410                2415

Asn Lys Phe Leu Asp Met Leu Ile Lys Lys Leu Lys Ser Phe Asp Tyr
            2420                2425                2430

His Gln Phe Val Asp Glu Thr Asn Asp Lys Ile Arg Glu Val Thr Gln
            2435                2440                2445

Arg Leu Asn Gly Glu Ile Gln Ala Leu Glu Leu Pro Gln Lys Ala Glu
            2450                2455                2460

Ala Leu Lys Leu Phe Leu Glu Glu Thr Lys Ala Thr Val Ala Val Tyr
2465                2470                2475                2480

Leu Glu Ser Leu Gln Asp Thr Lys Ile Thr Leu Ile Ile Asn Trp Leu
            2485                2490                2495

Gln Glu Ala Leu Ser Ser Ala Ser Leu Ala His Met Lys Ala Lys Phe
            2500                2505                2510

Arg Glu Thr Leu Glu Asp Thr Arg Asp Arg Met Tyr Gln Met Asp Ile
            2515                2520                2525

Gln Gln Glu Leu Gln Arg Tyr Leu Ser Leu Val Gly Gln Val Tyr Ser
            2530                2535                2540

Thr Leu Val Thr Tyr Ile Ser Asp Trp Trp Thr Leu Ala Ala Lys Asn
2545                2550                2555                2560

Leu Thr Asp Phe Ala Glu Gln Tyr Ser Ile Gln Asp Trp Ala Lys Arg
            2565                2570                2575

Met Lys Ala Leu Val Glu Gln Gly Phe Thr Val Pro Glu Ile Lys Thr
            2580                2585                2590

Ile Leu Gly Thr Met Pro Ala Phe Glu Val Ser Leu Gln Ala Leu Gln
            2595                2600                2605

Lys Ala Thr Phe Gln Thr Pro Asp Phe Ile Val Pro Leu Thr Asp Leu
            2610                2615                2620

Arg Ile Pro Ser Val Gln Ile Asn Phe Lys Asp Leu Lys Asn Ile Lys
2625                2630                2635                2640

Ile Pro Ser Arg Phe Ser Thr Pro Glu Phe Thr Ile Leu Asn Thr Phe
            2645                2650                2655

His Ile Pro Ser Phe Thr Ile Asp Phe Val Glu Met Lys Val Lys Ile
            2660                2665                2670

Ile Arg Thr Ile Asp Gln Met Leu Asn Ser Glu Leu Gln Trp Pro Val
            2675                2680                2685

Pro Asp Ile Tyr Leu Arg Asp Leu Lys Val Glu Asp Ile Pro Leu Ala
            2690                2695                2700

Arg Ile Thr Leu Pro Asp Phe Arg Leu Pro Glu Ile Ala Ile Pro Glu
2705                2710                2715                2720

Phe Ile Ile Pro Thr Leu Asn Leu Asn Asp Phe Gln Val Pro Asp Leu
            2725                2730                2735
```

-continued

His Ile Pro Glu Phe Gln Leu Pro His Ile Ser His Thr Ile Glu Val
                2740                2745                2750

Pro Thr Phe Gly Lys Leu Tyr Ser Ile Leu Lys Ile Gln Ser Pro Leu
                2755                2760                2765

Phe Thr Leu Asp Ala Asn Ala Asp Ile Gly Asn Gly Thr Thr Ser Ala
                2770                2775            2780

Asn Glu Ala Gly Ile Ala Ala Ser Ile Thr Ala Lys Gly Glu Ser Lys
2785            2790                2795                2800

Leu Glu Val Leu Asn Phe Asp Phe Gln Ala Asn Ala Gln Leu Ser Asn
                2805                2810                2815

Pro Lys Ile Asn Pro Leu Ala Leu Lys Glu Ser Val Lys Phe Ser Ser
                2820                2825                2830

Lys Tyr Leu Arg Thr Glu His Gly Ser Glu Met Leu Phe Phe Gly Asn
                2835                2840                2845

Ala Ile Glu Gly Lys Ser Asn Thr Val Ala Ser Leu His Thr Glu Lys
                2850                2855                2860

Asn Thr Leu Glu Leu Ser Asn Gly Val Ile Val Lys Ile Asn Asn Gln
2865                2870                2875                2880

Leu Thr Leu Asp Ser Asn Thr Lys Tyr Phe His Lys Leu Asn Ile Pro
                2885                2890                2895

Lys Leu Asp Phe Ser Ser Gln Ala Asp Leu Arg Asn Glu Ile Lys Thr
                2900                2905                2910

Leu Leu Lys Ala Gly His Ile Ala Trp Thr Ser Ser Gly Lys Gly Ser
                2915                2920                2925

Trp Lys Trp Ala Cys Pro Arg Phe Ser Asp Glu Gly Thr His Glu Ser
                2930                2935                2940

Gln Ile Ser Phe Thr Ile Glu Gly Pro Leu Thr Ser Phe Gly Leu Ser
2945                2950                2955                2960

Asn Lys Ile Asn Ser Lys His Leu Arg Val Asn Gln Asn Leu Val Tyr
                2965                2970                2975

Glu Ser Gly Ser Leu Asn Phe Ser Lys Leu Glu Ile Gln Ser Gln Val
                2980                2985                2990

Asp Ser Gln His Val Gly His Ser Val Leu Thr Ala Lys Gly Met Ala
                2995                3000                3005

Leu Phe Gly Glu Gly Lys Ala Glu Phe Thr Gly Arg His Asp Ala His
                3010                3015                3020

Leu Asn Gly Lys Val Ile Gly Thr Leu Lys Asn Ser Leu Phe Phe Ser
3025                3030                3035                3040

Ala Gln Pro Phe Glu Ile Thr Ala Ser Thr Asn Asn Glu Gly Asn Leu
                3045                3050                3055

Lys Val Arg Phe Pro Leu Arg Leu Thr Gly Lys Ile Asp Phe Leu Asn
                3060                3065                3070

Asn Tyr Ala Leu Phe Leu Ser Pro Ser Ala Gln Gln Ala Ser Trp Gln
                3075                3080                3085

Val Ser Ala Arg Phe Asn Gln Tyr Lys Tyr Asn Gln Asn Phe Ser Ala
                3090                3095                3100

Gly Asn Asn Glu Asn Ile Met Glu Ala His Val Gly Ile Asn Gly Glu
3105                3110                3115                3120

Ala Asn Leu Asp Phe Leu Asn Ile Pro Leu Thr Ile Pro Glu Met Arg
                3125                3130                3135

Leu Pro Tyr Thr Ile Ile Thr Thr Pro Pro Leu Lys Asp Phe Ser Leu
                3140                3145                3150

Trp Glu Lys Thr Gly Leu Lys Glu Phe Leu Lys Thr Thr Lys Gln Ser

-continued

```
              3155                3160                3165
Phe Asp Leu Ser Val Lys Ala Gln Tyr Lys Lys Asn Lys His Arg His
    3170                3175                3180
Ser Ile Thr Asn Pro Leu Ala Val Leu Cys Glu Phe Ile Ser Gln Ser
3185                3190                3195                3200
Ile Lys Ser Phe Asp Arg His Phe Glu Lys Asn Arg Asn Asn Ala Leu
            3205                3210                3215
Asp Phe Val Thr Lys Ser Tyr Asn Glu Thr Lys Ile Lys Phe Asp Lys
        3220                3225                3230
Tyr Lys Ala Glu Lys Ser His Asp Glu Leu Pro Arg Thr Phe Gln Ile
    3235                3240                3245
Pro Gly Tyr Thr Val Pro Val Asn Val Glu Val Ser Pro Phe Thr
        3250                3255                3260
Ile Glu Met Ser Ala Phe Gly Tyr Val Phe Pro Lys Ala Val Ser Met
3265                3270                3275                3280
Pro Ser Phe Ser Ile Leu Gly Ser Asp Val Arg Val Pro Ser Tyr Thr
            3285                3290                3295
Leu Ile Leu Pro Ser Leu Glu Leu Pro Val Leu His Val Pro Arg Asn
        3300                3305                3310
Leu Lys Leu Ser Leu Pro Asp Phe Lys Glu Leu Cys Thr Ile Ser His
    3315                3320                3325
Ile Phe Ile Pro Ala Met Gly Asn Ile Thr Tyr Asp Phe Ser Phe Lys
    3330                3335                3340
Ser Ser Val Ile Thr Leu Asn Thr Asn Ala Glu Leu Phe Asn Gln Ser
3345                3350                3355                3360
Asp Ile Val Ala His Leu Leu Ser Ser Ser Ser Val Ile Asp Ala
            3365                3370                3375
Leu Gln Tyr Lys Leu Glu Gly Thr Thr Arg Leu Thr Arg Lys Arg Gly
        3380                3385                3390
Leu Lys Leu Ala Thr Ala Leu Ser Leu Ser Asn Lys Phe Val Glu Gly
    3395                3400                3405
Ser His Asn Ser Thr Val Ser Leu Thr Thr Lys Asn Met Glu Val Ser
    3410                3415                3420
Val Ala Thr Thr Thr Lys Ala Gln Ile Pro Ile Leu Arg Met Asn Phe
3425                3430                3435                3440
Lys Gln Glu Leu Asn Gly Asn Thr Lys Ser Lys Pro Thr Val Ser Ser
            3445                3450                3455
Ser Met Glu Phe Lys Tyr Asp Phe Asn Ser Ser Met Leu Tyr Ser Thr
        3460                3465                3470
Ala Lys Gly Ala Val Asp His Lys Leu Ser Leu Glu Ser Leu Thr Ser
    3475                3480                3485
Tyr Phe Ser Ile Glu Ser Ser Thr Lys Gly Asp Val Lys Gly Ser Val
    3490                3495                3500
Leu Ser Arg Glu Tyr Ser Gly Thr Ile Ala Ser Glu Ala Asn Thr Tyr
3505                3510                3515                3520
Leu Asn Ser Lys Ser Thr Arg Ser Ser Val Lys Leu Gln Gly Thr Ser
            3525                3530                3535
Lys Ile Asp Asp Ile Trp Asn Leu Glu Val Lys Glu Asn Phe Ala Gly
        3540                3545                3550
Glu Ala Thr Leu Gln Arg Ile Tyr Ser Leu Trp Glu His Ser Thr Lys
    3555                3560                3565
Asn His Leu Gln Leu Glu Gly Leu Phe Phe Thr Asn Gly Glu His Thr
    3570                3575                3580
```

```
Ser Lys Ala Thr Leu Glu Leu Ser Pro Trp Gln Met Ser Ala Leu Val
3585                3590                3595                3600

Gln Val His Ala Ser Gln Pro Ser Ser Phe His Asp Phe Pro Asp Leu
            3605                3610                3615

Gly Gln Glu Val Ala Leu Asn Ala Asn Thr Lys Asn Gln Lys Ile Arg
        3620                3625                3630

Trp Lys Asn Glu Val Arg Ile His Ser Gly Ser Phe Gln Ser Gln Val
    3635                3640                3645

Glu Leu Ser Asn Asp Gln Glu Lys Ala His Leu Asp Ile Ala Gly Ser
3650                3655                3660

Leu Glu Gly His Leu Arg Phe Leu Lys Asn Ile Ile Leu Pro Val Tyr
3665                3670                3675                3680

Asp Lys Ser Leu Trp Asp Phe Leu Lys Leu Asp Val Thr Thr Ser Ile
            3685                3690                3695

Gly Arg Arg Gln His Leu Arg Val Ser Thr Ala Phe Val Tyr Thr Lys
        3700                3705                3710

Asn Pro Asn Gly Tyr Ser Phe Ser Ile Pro Val Lys Val Leu Ala Asp
    3715                3720                3725

Lys Phe Ile Ile Pro Gly Leu Lys Leu Asn Asp Leu Asn Ser Val Leu
3730                3735                3740

Val Met Pro Thr Phe His Val Pro Phe Thr Asp Leu Gln Val Pro Ser
3745                3750                3755                3760

Cys Lys Leu Asp Phe Arg Glu Ile Gln Ile Tyr Lys Lys Leu Arg Thr
            3765                3770                3775

Ser Ser Phe Ala Leu Asn Leu Pro Thr Leu Pro Glu Val Lys Phe Pro
        3780                3785                3790

Glu Val Asp Val Leu Thr Lys Tyr Ser Gln Pro Glu Asp Ser Leu Ile
    3795                3800                3805

Pro Phe Phe Glu Ile Thr Val Pro Glu Ser Gln Leu Thr Val Ser Gln
3810                3815                3820

Phe Thr Leu Pro Lys Ser Val Ser Asp Gly Ile Ala Ala Leu Asp Leu
3825                3830                3835                3840

Asn Ala Val Ala Asn Lys Ile Ala Asp Phe Glu Leu Pro Thr Ile Ile
            3845                3850                3855

Val Pro Glu Gln Thr Ile Glu Ile Pro Ser Ile Lys Phe Ser Val Pro
        3860                3865                3870

Ala Gly Ile Val Ile Pro Ser Phe Gln Ala Leu Thr Ala Arg Phe Glu
    3875                3880                3885

Val Asp Ser Pro Val Tyr Asn Ala Thr Trp Ser Ala Ser Leu Lys Asn
3890                3895                3900

Lys Ala Asp Tyr Val Glu Thr Val Leu Asp Ser Thr Cys Ser Ser Thr
3905                3910                3915                3920

Val Gln Phe Leu Glu Tyr Glu Leu Asn Val Leu Gly Thr His Lys Ile
            3925                3930                3935

Glu Asp Gly Thr Leu Ala Ser Lys Thr Lys Gly Thr Phe Ala His Arg
        3940                3945                3950

Asp Phe Ser Ala Glu Tyr Glu Glu Asp Gly Lys Tyr Glu Gly Leu Gln
    3955                3960                3965

Glu Trp Glu Gly Lys Ala His Leu Asn Ile Lys Ser Pro Ala Phe Thr
3970                3975                3980

Asp Leu His Leu Arg Tyr Gln Lys Asp Lys Lys Gly Ile Ser Thr Ser
3985                3990                3995                4000
```

-continued

Ala Ala Ser Pro Ala Val Gly Thr Val Gly Met Asp Met Asp Glu Asp
                    4005                4010                4015

Asp Asp Phe Ser Lys Trp Asn Phe Tyr Tyr Ser Pro Gln Ser Ser Pro
            4020                4025                4030

Asp Lys Lys Leu Thr Ile Phe Lys Thr Glu Leu Arg Val Arg Glu Ser
            4035                4040                4045

Asp Glu Glu Thr Gln Ile Lys Val Asn Trp Glu Glu Ala Ala Ser
            4050                4055                4060

Gly Leu Leu Thr Ser Leu Lys Asp Asn Val Pro Lys Ala Thr Gly Val
4065                4070                4075                4080

Leu Tyr Asp Tyr Val Asn Lys Tyr His Trp Glu His Thr Gly Leu Thr
                4085                4090                4095

Leu Arg Glu Val Ser Ser Lys Leu Arg Arg Asn Leu Gln Asn Asn Ala
                4100                4105                4110

Glu Trp Val Tyr Gln Gly Ala Ile Arg Gln Ile Asp Asp Ile Asp Val
                4115                4120                4125

Arg Phe Gln Lys Ala Ala Ser Gly Thr Thr Gly Thr Tyr Gln Glu Trp
            4130                4135                4140

Lys Asp Lys Ala Gln Asn Leu Tyr Gln Glu Leu Leu Thr Gln Glu Gly
4145                4150                4155                4160

Gln Ala Ser Phe Gln Gly Leu Lys Asp Asn Val Phe Asp Gly Leu Val
                4165                4170                4175

Arg Val Thr Gln Glu Phe His Met Lys Val Lys His Leu Ile Asp Ser
                4180                4185                4190

Leu Ile Asp Phe Leu Asn Phe Pro Arg Phe Gln Phe Pro Gly Lys Pro
            4195                4200                4205

Gly Ile Tyr Thr Arg Glu Glu Leu Cys Thr Met Phe Ile Arg Glu Val
4210                4215                4220

Gly Thr Val Leu Ser Gln Val Tyr Ser Lys Val His Asn Gly Ser Glu
4225                4230                4235                4240

Ile Leu Phe Ser Tyr Phe Gln Asp Leu Val Ile Thr Leu Pro Phe Glu
                4245                4250                4255

Leu Arg Lys His Lys Leu Ile Asp Val Ile Ser Met Tyr Arg Glu Leu
                4260                4265                4270

Leu Lys Asp Leu Ser Lys Glu Ala Gln Glu Val Phe Lys Ala Ile Gln
            4275                4280                4285

Ser Leu Lys Thr Thr Glu Val Leu Arg Asn Leu Gln Asp Leu Leu Gln
            4290                4295                4300

Phe Ile Phe Gln Leu Ile Glu Asp Asn Ile Lys Gln Leu Lys Glu Met
4305                4310                4315                4320

Lys Phe Thr Tyr Leu Ile Asn Tyr Ile Gln Asp Glu Ile Asn Thr Ile
            4325                4330                4335

Phe Ser Asp Tyr Ile Pro Tyr Val Phe Lys Leu Leu Lys Glu Asn Leu
            4340                4345                4350

Cys Leu Asn Leu His Lys Phe Asn Glu Phe Ile Gln Asn Glu Leu Gln
            4355                4360                4365

Glu Ala Ser Gln Glu Leu Gln Gln Ile His Gln Tyr Ile Met Ala Leu
            4370                4375                4380

Arg Glu Glu Tyr Phe Asp Pro Ser Ile Val Gly Trp Thr Val Lys Tyr
4385                4390                4395                4400

Tyr Glu Leu Glu Glu Lys Ile Val Ser Leu Ile Lys Asn Leu Leu Val
                4405                4410                4415

Ala Leu Lys Asp Phe His Ser Glu Tyr Ile Val Ser Ala Ser Asn Phe

```
                    4420            4425            4430
Thr Ser Gln Leu Ser Ser Gln Val Glu Gln Phe Leu His Arg Asn Ile
            4435            4440            4445

Gln Glu Tyr Leu Ser Ile Leu Thr Asp Pro Asp Gly Lys Gly Lys Glu
            4450            4455            4460

Lys Ile Ala Glu Leu Ser Ala Thr Ala Gln Glu Ile Ile Lys Ser Gln
4465            4470            4475            4480

Ala Ile Ala Thr Lys Lys Ile Ile Ser Asp Tyr His Gln Gln Phe Arg
            4485            4490            4495

Tyr Lys Leu Gln Asp Phe Ser Asp Gln Leu Ser Asp Tyr Tyr Glu Lys
            4500            4505            4510

Phe Ile Ala Glu Ser Lys Arg Leu Ile Asp Leu Ser Ile Gln Asn Tyr
            4515            4520            4525

His Thr Phe Leu Ile Tyr Ile Thr Glu Leu Leu Lys Lys Leu Gln Ser
            4530            4535            4540

Thr Thr Val Met Asn Pro Tyr Met Lys Leu Ala Pro Gly Glu Leu Thr
4545            4550            4555            4560

Ile Ile Leu

<210> SEQ ID NO 3
<211> LENGTH: 345
<212> TYPE: PRT
<213> ORGANISM: Homo sapiens

<400> SEQUENCE: 3

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
    50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
    130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
    210                 215                 220

Tyr Tyr Lys Asp Lys Ala Thr Phe Gly Cys His Asp Gly Tyr Ser Leu
```

```
                225                 230                 235                 240
Asp Gly Pro Glu Glu Ile Glu Cys Thr Lys Leu Gly Asn Trp Ser Ala
                    245                 250                 255

Met Pro Ser Cys Lys Ala Ser Cys Lys Val Pro Val Lys Lys Ala Thr
                260                 265                 270

Val Val Tyr Gln Gly Glu Arg Val Lys Ile Gln Lys Phe Lys Asn
                275                 280                 285

Gly Met Leu His Gly Asp Lys Val Ser Phe Phe Cys Lys Asn Lys Glu
                290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                    325                 330                 335

Thr Asp Ala Ser Asp Val Lys Pro Cys
                340                 345

<210> SEQ ID NO 4
<211> LENGTH: 705
<212> TYPE: PRT
<213> ORGANISM: Homo sapiens

<400> SEQUENCE: 4

Met Trp Leu Leu Tyr Leu Leu Val Pro Ala Leu Phe Cys Arg Ala Gly
1               5                   10                  15

Gly Ser Ile Pro Ile Pro Gln Lys Leu Phe Gly Glu Val Thr Ser Pro
                20                  25                  30

Leu Phe Pro Lys Pro Tyr Pro Asn Asn Phe Glu Thr Thr Thr Val Ile
            35                  40                  45

Thr Val Pro Thr Gly Tyr Arg Val Lys Leu Val Phe Gln Gln Phe Asp
        50                  55                  60

Leu Glu Pro Ser Glu Gly Cys Phe Tyr Asp Tyr Val Lys Ile Ser Ala
65                  70                  75                  80

Asp Lys Lys Ser Leu Gly Arg Phe Cys Gly Gln Leu Gly Ser Pro Leu
                85                  90                  95

Gly Asn Pro Pro Gly Lys Lys Glu Phe Met Ser Gln Gly Asn Lys Met
            100                 105                 110

Leu Leu Thr Phe His Thr Asp Phe Ser Asn Glu Glu Asn Gly Thr Ile
        115                 120                 125

Met Phe Tyr Lys Gly Phe Leu Ala Tyr Tyr Gln Ala Val Asp Leu Asp
130                 135                 140

Glu Cys Ala Ser Arg Ser Lys Ser Gly Glu Glu Asp Pro Gln Pro Gln
145                 150                 155                 160

Cys Gln His Leu Cys His Asn Tyr Val Gly Gly Tyr Phe Cys Ser Cys
                165                 170                 175

Arg Pro Gly Tyr Glu Leu Gln Glu Asp Thr His Ser Cys Gln Ala Glu
            180                 185                 190

Cys Ser Ser Glu Leu Tyr Thr Glu Ala Ser Gly Tyr Ile Ser Ser Leu
        195                 200                 205

Glu Tyr Pro Arg Ser Tyr Pro Pro Asp Leu Arg Cys Asn Tyr Ser Ile
    210                 215                 220

Arg Val Glu Arg Gly Leu Thr Leu His Leu Lys Phe Leu Glu Pro Phe
225                 230                 235                 240

Asp Ile Asp Asp His Gln Gln Val His Cys Pro Tyr Asp Gln Leu Gln
                245                 250                 255
```

```
Ile Tyr Ala Asn Gly Lys Asn Ile Gly Glu Phe Cys Gly Lys Gln Arg
            260                 265                 270

Pro Pro Asp Leu Asp Thr Ser Ser Asn Ala Val Asp Leu Leu Phe Phe
            275                 280                 285

Thr Asp Glu Ser Gly Asp Ser Arg Gly Trp Lys Leu Arg Tyr Thr Thr
            290                 295                 300

Glu Ile Ile Lys Cys Pro Gln Pro Lys Thr Leu Asp Glu Phe Thr Ile
305                 310                 315                 320

Ile Gln Asn Leu Gln Pro Gln Tyr Gln Phe Arg Asp Tyr Phe Ile Ala
                325                 330                 335

Thr Cys Lys Gln Gly Tyr Gln Leu Ile Glu Gly Asn Gln Val Leu His
            340                 345                 350

Ser Phe Thr Ala Val Cys Gln Asp Asp Gly Thr Trp His Arg Ala Met
            355                 360                 365

Pro Arg Cys Lys Ile Lys Asp Cys Gly Gln Pro Arg Asn Leu Pro Asn
            370                 375                 380

Gly Asp Phe Arg Tyr Thr Thr Thr Met Gly Val Asn Thr Tyr Lys Ala
385                 390                 395                 400

Arg Ile Gln Tyr Tyr Cys His Glu Pro Tyr Tyr Lys Met Gln Thr Arg
                405                 410                 415

Ala Gly Ser Arg Glu Ser Glu Gln Gly Val Tyr Thr Cys Thr Ala Gln
            420                 425                 430

Gly Ile Trp Lys Asn Glu Gln Lys Gly Glu Lys Ile Pro Arg Cys Leu
            435                 440                 445

Pro Val Cys Gly Lys Pro Val Asn Pro Val Glu Gln Arg Gln Arg Ile
450                 455                 460

Ile Gly Gly Gln Lys Ala Lys Met Gly Asn Phe Pro Trp Gln Val Phe
465                 470                 475                 480

Thr Asn Ile His Gly Arg Gly Gly Ala Leu Leu Gly Asp Arg Trp
                485                 490                 495

Ile Leu Thr Ala Ala His Thr Leu Tyr Pro Lys Glu His Glu Ala Gln
            500                 505                 510

Ser Asn Ala Ser Leu Asp Val Phe Leu Gly His Thr Asn Val Glu Glu
            515                 520                 525

Leu Met Lys Leu Gly Asn His Pro Ile Arg Arg Val Ser Val His Pro
530                 535                 540

Asp Tyr Arg Gln Asp Glu Ser Tyr Asn Phe Glu Gly Asp Ile Ala Leu
545                 550                 555                 560

Leu Glu Leu Glu Asn Ser Val Thr Leu Gly Pro Asn Leu Leu Pro Ile
                565                 570                 575

Cys Leu Pro Asp Asn Asp Thr Phe Tyr Asp Leu Gly Leu Met Gly Tyr
            580                 585                 590

Val Ser Gly Phe Gly Val Met Glu Glu Lys Ile Ala His Asp Leu Arg
            595                 600                 605

Phe Val Arg Leu Pro Val Ala Asn Pro Gln Ala Cys Glu Asn Trp Leu
610                 615                 620

Arg Gly Lys Asn Arg Met Asp Val Phe Ser Gln Asn Met Phe Cys Ala
625                 630                 635                 640

Gly His Pro Ser Leu Lys Gln Asp Ala Cys Gln Gly Asp Ser Gly Gly
                645                 650                 655

Val Phe Ala Val Arg Asp Pro Asn Thr Asp Arg Trp Val Ala Thr Gly
            660                 665                 670

Ile Val Ser Trp Gly Ile Gly Cys Ser Arg Gly Tyr Gly Phe Tyr Thr
```

```
                675                 680                 685
Lys Val Leu Asn Tyr Val Asp Trp Ile Lys Lys Glu Met Glu Glu Glu
    690                 695                 700
Asp
705

<210> SEQ ID NO 5
<211> LENGTH: 688
<212> TYPE: PRT
<213> ORGANISM: Homo sapiens

<400> SEQUENCE: 5

Met Trp Cys Ile Val Leu Phe Ser Leu Leu Ala Trp Val Tyr Ala Glu
1               5                   10                  15

Pro Thr Met Tyr Gly Glu Ile Leu Ser Pro Asn Tyr Pro Gln Ala Tyr
            20                  25                  30

Pro Ser Glu Val Glu Lys Ser Trp Asp Ile Glu Val Pro Glu Gly Tyr
        35                  40                  45

Gly Ile His Leu Tyr Phe Thr His Leu Asp Ile Glu Leu Ser Glu Asn
    50                  55                  60

Cys Ala Tyr Asp Ser Val Gln Ile Ile Ser Gly Asp Thr Glu Glu Gly
65                  70                  75                  80

Arg Leu Cys Gly Gln Arg Ser Ser Asn Pro His Ser Pro Ile Val
                85                  90                  95

Glu Glu Phe Gln Val Pro Tyr Asn Lys Leu Gln Val Ile Phe Lys Ser
            100                 105                 110

Asp Phe Ser Asn Glu Glu Arg Phe Thr Gly Phe Ala Ala Tyr Tyr Val
        115                 120                 125

Ala Thr Asp Ile Asn Glu Cys Thr Asp Phe Val Asp Val Pro Cys Ser
    130                 135                 140

His Phe Cys Asn Asn Phe Ile Gly Gly Tyr Phe Cys Ser Cys Pro Pro
145                 150                 155                 160

Glu Tyr Phe Leu His Asp Asp Met Lys Asn Cys Gly Val Asn Cys Ser
                165                 170                 175

Gly Asp Val Phe Thr Ala Leu Ile Gly Glu Ile Ala Ser Pro Asn Tyr
            180                 185                 190

Pro Lys Pro Tyr Pro Glu Asn Ser Arg Cys Glu Tyr Gln Ile Arg Leu
        195                 200                 205

Glu Lys Gly Phe Gln Val Val Val Thr Leu Arg Arg Glu Asp Phe Asp
    210                 215                 220

Val Glu Ala Ala Asp Ser Ala Gly Asn Cys Leu Asp Ser Leu Val Phe
225                 230                 235                 240

Val Ala Gly Asp Arg Gln Phe Gly Pro Tyr Cys Gly His Gly Phe Pro
                245                 250                 255

Gly Pro Leu Asn Ile Glu Thr Lys Ser Asn Ala Leu Asp Ile Ile Phe
            260                 265                 270

Gln Thr Asp Leu Thr Gly Gln Lys Lys Gly Trp Lys Leu Arg Tyr His
        275                 280                 285

Gly Asp Pro Met Pro Cys Pro Lys Glu Asp Thr Pro Asn Ser Val Trp
    290                 295                 300

Glu Pro Ala Lys Ala Lys Tyr Val Phe Arg Asp Val Val Gln Ile Thr
305                 310                 315                 320

Cys Leu Asp Gly Phe Glu Val Val Glu Gly Arg Val Gly Ala Thr Ser
                325                 330                 335
```

```
Phe Tyr Ser Thr Cys Gln Ser Asn Gly Lys Trp Ser Asn Ser Lys Leu
            340                 345                 350

Lys Cys Gln Pro Val Asp Cys Gly Ile Pro Glu Ser Ile Glu Asn Gly
        355                 360                 365

Lys Val Glu Asp Pro Glu Ser Thr Leu Phe Gly Ser Val Ile Arg Tyr
    370                 375                 380

Thr Cys Glu Glu Pro Tyr Tyr Met Glu Asn Gly Gly Gly Gly Glu
385                 390                 395                 400

Tyr His Cys Ala Gly Asn Gly Ser Trp Val Asn Glu Val Leu Gly Pro
                405                 410                 415

Glu Leu Pro Lys Cys Val Pro Val Cys Gly Val Pro Arg Glu Pro Phe
            420                 425                 430

Glu Glu Lys Gln Arg Ile Ile Gly Gly Ser Asp Ala Asp Ile Lys Asn
        435                 440                 445

Phe Pro Trp Gln Val Phe Phe Asp Asn Pro Trp Ala Gly Gly Ala Leu
    450                 455                 460

Ile Asn Glu Tyr Trp Val Leu Thr Ala Ala His Val Val Glu Gly Asn
465                 470                 475                 480

Arg Glu Pro Thr Met Tyr Val Gly Ser Thr Ser Val Gln Thr Ser Arg
                485                 490                 495

Leu Ala Lys Ser Lys Met Leu Thr Pro Glu His Val Phe Ile His Pro
            500                 505                 510

Gly Trp Lys Leu Leu Glu Val Pro Glu Gly Arg Thr Asn Phe Asp Asn
        515                 520                 525

Asp Ile Ala Leu Val Arg Leu Lys Asp Pro Val Lys Met Gly Pro Thr
    530                 535                 540

Val Ser Pro Ile Cys Leu Pro Gly Thr Ser Ser Asp Tyr Asn Leu Met
545                 550                 555                 560

Asp Gly Asp Leu Gly Leu Ile Ser Gly Trp Gly Arg Thr Glu Lys Arg
                565                 570                 575

Asp Arg Ala Val Arg Leu Lys Ala Ala Arg Leu Pro Val Ala Pro Leu
            580                 585                 590

Arg Lys Cys Lys Glu Val Lys Val Glu Lys Pro Thr Ala Asp Ala Glu
        595                 600                 605

Ala Tyr Val Phe Thr Pro Asn Met Ile Cys Ala Gly Gly Glu Lys Gly
    610                 615                 620

Met Asp Ser Cys Lys Gly Asp Ser Gly Gly Ala Phe Ala Val Gln Asp
625                 630                 635                 640

Pro Asn Asp Lys Thr Lys Phe Tyr Ala Ala Gly Leu Val Ser Trp Gly
                645                 650                 655

Pro Gln Cys Gly Thr Tyr Gly Leu Tyr Thr Arg Val Lys Asn Tyr Val
            660                 665                 670

Asp Trp Ile Met Lys Thr Met Gln Glu Asn Ser Thr Pro Arg Glu Asp
        675                 680                 685

<210> SEQ ID NO 6
<211> LENGTH: 1663
<212> TYPE: PRT
<213> ORGANISM: Homo sapiens

<400> SEQUENCE: 6

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30
```

```
Ile Leu Arg Leu Glu Ser Glu Thr Met Val Leu Glu Ala His Asp
         35                  40                  45

Ala Gln Gly Asp Val Pro Val Thr Val Thr Val His Asp Phe Pro Gly
 50                  55                  60

Lys Lys Leu Val Leu Ser Ser Glu Lys Thr Val Leu Thr Pro Ala Thr
 65                  70                  75                  80

Asn His Met Gly Asn Val Thr Phe Thr Ile Pro Ala Asn Arg Glu Phe
                 85                  90                  95

Lys Ser Glu Lys Gly Arg Asn Lys Phe Val Thr Val Gln Ala Thr Phe
                100                 105                 110

Gly Thr Gln Val Val Glu Lys Val Val Leu Val Ser Leu Gln Ser Gly
            115                 120                 125

Tyr Leu Phe Ile Gln Thr Asp Lys Thr Ile Tyr Thr Pro Gly Ser Thr
130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
                180                 185                 190

Trp Asp Ile Pro Glu Leu Val Asn Met Gly Gln Trp Lys Ile Arg Ala
                195                 200                 205

Tyr Tyr Glu Asn Ser Pro Gln Gln Val Phe Ser Thr Glu Phe Glu Val
210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
                260                 265                 270

Phe Gly Ile Gln Asp Gly Glu Gln Arg Ile Ser Leu Pro Glu Ser Leu
            275                 280                 285

Lys Arg Ile Pro Ile Glu Asp Gly Ser Gly Glu Val Val Leu Ser Arg
290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
                340                 345                 350

Tyr Gln Ile His Phe Thr Lys Thr Pro Lys Tyr Phe Lys Pro Gly Met
                355                 360                 365

Pro Phe Asp Leu Met Val Phe Val Thr Asn Pro Asp Gly Ser Pro Ala
370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
                420                 425                 430

Glu Ala Glu Gln Ala Thr Arg Thr Met Gln Ala Leu Pro Tyr Ser Thr
                435                 440                 445
```

-continued

Val Gly Asn Ser Asn Asn Tyr Leu His Leu Ser Val Leu Arg Thr Glu
450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
                515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
                580                 585                 590

Val Val Leu Val Ala Val Asp Lys Gly Val Phe Val Leu Asn Lys Lys
                595                 600                 605

Asn Lys Leu Thr Gln Ser Lys Ile Trp Asp Val Val Glu Lys Ala Asp
                610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
                660                 665                 670

Val Gln Leu Thr Glu Lys Arg Met Asp Lys Val Gly Lys Tyr Pro Lys
                675                 680                 685

Glu Leu Arg Lys Cys Cys Glu Asp Gly Met Arg Glu Asn Pro Met Arg
690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
                740                 745                 750

Glu Asp Ile Ile Ala Glu Glu Asn Ile Val Ser Arg Ser Glu Phe Pro
                755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Val Arg Asn Glu Gln Val Glu Ile Arg
                835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg

-continued

```
                865                 870                 875                 880
Arg His Gln Gln Thr Val Thr Ile Pro Pro Lys Ser Ser Leu Ser Val
                    885                 890                 895
Pro Tyr Val Ile Val Pro Leu Lys Thr Gly Leu Gln Glu Val Glu Val
                    900                 905                 910
Lys Ala Ala Val Tyr His His Phe Ile Ser Asp Gly Val Arg Lys Ser
                    915                 920                 925
Leu Lys Val Val Pro Glu Gly Ile Arg Met Asn Lys Thr Val Ala Val
                    930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                    965                 970                 975
Glu Thr Arg Ile Leu Leu Gln Gly Thr Pro Val Ala Gln Met Thr Glu
                    980                 985                 990
Asp Ala Val Asp Ala Glu Arg Leu Lys His Leu Ile Val Thr Pro Ser
                    995                 1000                1005
Gly Cys Gly Glu Gln Asn Met Ile Gly Met Thr Pro Thr Val Ile Ala
                    1010                1015                1020
Val His Tyr Leu Asp Glu Thr Glu Gln Trp Glu Lys Phe Gly Leu Glu
1025                1030                1035                1040
Lys Arg Gln Gly Ala Leu Glu Leu Ile Lys Lys Gly Tyr Thr Gln Gln
                    1045                1050                1055
Leu Ala Phe Arg Gln Pro Ser Ser Ala Phe Ala Ala Phe Val Lys Arg
                    1060                1065                1070
Ala Pro Ser Thr Trp Leu Thr Ala Tyr Val Val Lys Val Phe Ser Leu
                    1075                1080                1085
Ala Val Asn Leu Ile Ala Ile Asp Ser Gln Val Leu Cys Gly Ala Val
                    1090                1095                1100
Lys Trp Leu Ile Leu Glu Lys Gln Lys Pro Asp Gly Val Phe Gln Glu
1105                1110                1115                1120
Asp Ala Pro Val Ile His Gln Glu Met Ile Gly Gly Leu Arg Asn Asn
                    1125                1130                1135
Asn Glu Lys Asp Met Ala Leu Thr Ala Phe Val Leu Ile Ser Leu Gln
                    1140                1145                1150
Glu Ala Lys Asp Ile Cys Glu Glu Gln Val Asn Ser Leu Pro Gly Ser
                    1155                1160                1165
Ile Thr Lys Ala Gly Asp Phe Leu Glu Ala Asn Tyr Met Asn Leu Gln
                    1170                1175                1180
Arg Ser Tyr Thr Val Ala Ile Ala Gly Tyr Ala Leu Ala Gln Met Gly
1185                1190                1195                1200
Arg Leu Lys Gly Pro Leu Leu Asn Lys Phe Leu Thr Thr Ala Lys Asp
                    1205                1210                1215
Lys Asn Arg Trp Glu Asp Pro Gly Lys Gln Leu Tyr Asn Val Glu Ala
                    1220                1225                1230
Thr Ser Tyr Ala Leu Leu Ala Leu Leu Gln Leu Lys Asp Phe Asp Phe
                    1235                1240                1245
Val Pro Pro Val Val Arg Trp Leu Asn Glu Gln Arg Tyr Tyr Gly Gly
                    1250                1255                1260
Gly Tyr Gly Ser Thr Gln Ala Thr Phe Met Val Phe Gln Ala Leu Ala
1265                1270                1275                1280
Gln Tyr Gln Lys Asp Ala Pro Asp His Gln Glu Leu Asn Leu Asp Val
                    1285                1290                1295
```

Ser Leu Gln Leu Pro Ser Arg Ser Ser Lys Ile Thr His Arg Ile His
            1300                1305                1310

Trp Glu Ser Ala Ser Leu Leu Arg Ser Glu Glu Thr Lys Glu Asn Glu
        1315                1320                1325

Gly Phe Thr Val Thr Ala Glu Gly Lys Gly Gln Gly Thr Leu Ser Val
    1330                1335                1340

Val Thr Met Tyr His Ala Lys Ala Lys Asp Gln Leu Thr Cys Asn Lys
1345                1350                1355                1360

Phe Asp Leu Lys Val Thr Ile Lys Pro Ala Pro Glu Thr Glu Lys Arg
            1365                1370                1375

Pro Gln Asp Ala Lys Asn Thr Met Ile Leu Glu Ile Cys Thr Arg Tyr
        1380                1385                1390

Arg Gly Asp Gln Asp Ala Thr Met Ser Ile Leu Asp Ile Ser Met Met
    1395                1400                1405

Thr Gly Phe Ala Pro Asp Thr Asp Asp Leu Lys Gln Leu Ala Asn Gly
    1410                1415                1420

Val Asp Arg Tyr Ile Ser Lys Tyr Glu Leu Asp Lys Ala Phe Ser Asp
1425                1430                1435                1440

Arg Asn Thr Leu Ile Ile Tyr Leu Asp Lys Val Ser His Ser Glu Asp
            1445                1450                1455

Asp Cys Leu Ala Phe Lys Val His Gln Tyr Phe Asn Val Glu Leu Ile
        1460                1465                1470

Gln Pro Gly Ala Val Lys Val Tyr Ala Tyr Tyr Asn Leu Glu Glu Ser
    1475                1480                1485

Cys Thr Arg Phe Tyr His Pro Glu Lys Glu Asp Gly Lys Leu Asn Lys
    1490                1495                1500

Leu Cys Arg Asp Glu Leu Cys Arg Cys Ala Glu Glu Asn Cys Phe Ile
1505                1510                1515                1520

Gln Lys Ser Asp Asp Lys Val Thr Leu Glu Glu Arg Leu Asp Lys Ala
            1525                1530                1535

Cys Glu Pro Gly Val Asp Tyr Val Tyr Lys Thr Arg Leu Val Lys Val
        1540                1545                1550

Gln Leu Ser Asn Asp Phe Asp Glu Tyr Ile Met Ala Ile Glu Gln Thr
    1555                1560                1565

Ile Lys Ser Gly Ser Asp Glu Val Gln Val Gly Gln Gln Arg Thr Phe
    1570                1575                1580

Ile Ser Pro Ile Lys Cys Arg Glu Ala Leu Lys Leu Glu Glu Lys Lys
1585                1590                1595                1600

His Tyr Leu Met Trp Gly Leu Ser Ser Asp Phe Trp Gly Glu Lys Pro
            1605                1610                1615

Asn Leu Ser Tyr Ile Ile Gly Lys Asp Thr Trp Val Glu His Trp Pro
        1620                1625                1630

Glu Glu Asp Glu Cys Gln Asp Glu Glu Asn Gln Lys Gln Cys Gln Asp
    1635                1640                1645

Leu Gly Ala Phe Thr Glu Ser Met Val Val Phe Gly Cys Pro Asn
    1650                1655                1660

<210> SEQ ID NO 7
<211> LENGTH: 1231
<212> TYPE: PRT
<213> ORGANISM: Homo sapiens

<400> SEQUENCE: 7

Met Arg Leu Leu Ala Lys Ile Ile Cys Leu Met Leu Trp Ala Ile Cys

-continued

```
1               5                   10                  15
Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
                35                  40                  45

Ile Tyr Lys Cys Arg Pro Gly Tyr Arg Ser Leu Gly Asn Val Ile Met
                50                  55                  60

Val Cys Arg Lys Gly Glu Trp Val Ala Leu Asn Pro Leu Arg Lys Cys
 65                 70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
                115                 120                 125

Cys Asp Thr Asp Gly Trp Thr Asn Asp Ile Pro Ile Cys Glu Val Val
                130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
                195                 200                 205

Ser Cys Lys Ser Pro Asp Val Ile Asn Gly Ser Pro Ile Ser Gln Lys
                210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
                275                 280                 285

Glu Ile Thr Tyr Gln Cys Arg Asn Gly Phe Tyr Pro Ala Thr Arg Gly
                290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
                355                 360                 365

Trp Asp His Ile His Cys Thr Gln Asp Gly Trp Ser Pro Ala Val Pro
                370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430
```

```
Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
            485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
        530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
        690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
        770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845
```

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
            885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
            930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
            995                 1000                1005

Lys Ala Gly Glu Gln Val Thr Tyr Thr Cys Ala Thr Tyr Tyr Lys Met
1010                1015                1020

Asp Gly Ala Ser Asn Val Thr Cys Ile Asn Ser Arg Trp Thr Gly Arg
1025                1030                1035                1040

Pro Thr Cys Arg Asp Thr Ser Cys Val Asn Pro Pro Thr Val Gln Asn
                1045                1050                1055

Ala Tyr Ile Val Ser Arg Gln Met Ser Lys Tyr Pro Ser Gly Glu Arg
                1060                1065                1070

Val Arg Tyr Gln Cys Arg Ser Pro Tyr Glu Met Phe Gly Asp Glu Glu
            1075                1080                1085

Val Met Cys Leu Asn Gly Asn Trp Thr Glu Pro Pro Gln Cys Lys Asp
1090                1095                1100

Ser Thr Gly Lys Cys Gly Pro Pro Pro Ile Asp Asn Gly Asp Ile
1105                1110                1115                1120

Thr Ser Phe Pro Leu Ser Val Tyr Ala Pro Ala Ser Ser Val Glu Tyr
            1125                1130                1135

Gln Cys Gln Asn Leu Tyr Gln Leu Glu Gly Asn Lys Arg Ile Thr Cys
            1140                1145                1150

Arg Asn Gly Gln Trp Ser Glu Pro Pro Lys Cys Leu His Pro Cys Val
            1155                1160                1165

Ile Ser Arg Glu Ile Met Glu Asn Tyr Asn Ile Ala Leu Arg Trp Thr
1170                1175                1180

Ala Lys Gln Lys Leu Tyr Ser Arg Thr Gly Glu Ser Val Glu Phe Val
1185                1190                1195                1200

Cys Lys Arg Gly Tyr Arg Leu Ser Ser Arg Ser His Thr Leu Arg Thr
            1205                1210                1215

Thr Cys Trp Asp Gly Lys Leu Glu Tyr Pro Thr Cys Ala Lys Arg
            1220                1225                1230

<210> SEQ ID NO 8
<211> LENGTH: 518
<212> TYPE: PRT
<213> ORGANISM: Homo sapiens

<400> SEQUENCE: 8

```
Met Asp Trp Thr Trp Arg Ile Leu Phe Leu Val Ala Ala Thr Gly
1               5                   10                  15

Ala His Ser Gln Val His Leu Val Gln Ser Gly Ala Glu Val Lys Lys
            20                  25                  30

Pro Gly Ala Ser Val Lys Val Ser Cys Thr Ala Ser Gly Tyr Pro Phe
            35                  40                  45

Thr Asn His Phe Ile Asn Trp Val Arg Gln Ala Pro Gly Gln Ser Leu
        50                  55                  60

Glu Trp Met Gly Trp Ile Asn Thr Gly Asn Gly Asn Thr Lys Tyr Ser
65                  70                  75                  80

Gln Lys Phe Gln Gly Arg Val Thr Ile Thr Arg Asp Thr Trp Thr Thr
                85                  90                  95

Thr Ala Tyr Met Asp Leu Ser Ser Leu Arg Ser Glu Asp Thr Ala Val
            100                 105                 110

Tyr Trp Cys Ala Arg Asp Ala Pro Gln Gly Val Thr Thr Thr Tyr Phe
        115                 120                 125

Asp Tyr Trp Gly Gln Gly Thr Leu Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Gly Gly Thr Ala Ala Leu Gly Cys Leu Val Lys Asp Tyr Phe Pro Glu
            165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Thr Cys
        210                 215                 220

Asn Val Asn His Lys Pro Ser Asn Thr Lys Val Asp Lys Arg Val Glu
225                 230                 235                 240

Leu Lys Thr Pro Leu Gly Asp Thr Thr His Thr Cys Pro Arg Cys Pro
            245                 250                 255

Glu Pro Lys Pro Cys Asp Thr Pro Pro Cys Pro Arg Cys Pro Glu
            260                 265                 270

Pro Lys Ser Cys Asp Thr Pro Pro Cys Pro Arg Cys Pro Glu Pro
            275                 280                 285

Lys Ser Cys Asp Thr Pro Pro Cys Pro Arg Cys Pro Ala Pro Glu
            290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
            325                 330                 335

Val Ser His Glu Asp Pro Glu Val Gln Phe Lys Trp Tyr Val Asp Gly
            340                 345                 350

Val Glu Val His Asn Ala Lys Thr Lys Pro Arg Glu Glu Gln Tyr Asn
            355                 360                 365

Ser Thr Phe Arg Val Val Ser Val Leu Thr Val Leu His Gln Asp Trp
        370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Thr Lys Gly Gln Pro Arg Glu
            405                 410                 415
```

```
Pro Gln Val Tyr Thr Leu Pro Pro Ser Arg Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Ser Gly Gln Pro Glu Asn Asn Tyr Asn Thr
    450                 455                 460

Thr Pro Pro Met Leu Asp Ser Asp Gly Ser Phe Phe Leu Tyr Ser Lys
465                 470                 475                 480

Leu Thr Val Asp Lys Ser Arg Trp Gln Gln Gly Asn Ile Phe Ser Cys
                485                 490                 495

Ser Val Met His Glu Ala Leu His Asn Arg Phe Thr Gln Lys Ser Leu
                500                 505                 510

Ser Leu Ser Pro Gly Lys
            515

<210> SEQ ID NO 9
<211> LENGTH: 482
<212> TYPE: PRT
<213> ORGANISM: Homo sapiens

<400> SEQUENCE: 9

Met Glu Phe Gly Leu Thr Trp Val Phe Val Ala Leu Leu Arg Gly
1               5                   10                  15

Val Gln Cys Gln Ala Gln Val Val Glu Ser Gly Gly Ser Val Val Gln
            20                  25                  30

Pro Gly Arg Ser Leu Arg Leu Ser Cys Ile Ala Ser Gly Phe Ser Phe
        35                  40                  45

Ser Gly Ser Ala Met His Trp Leu Arg Gln Ile Pro Gly Lys Gly Leu
    50                  55                  60

Glu Trp Val Ala Val Ile Ser Tyr Asp Gly Asn His Lys Leu Tyr Ser
65                  70                  75                  80

Asp Ser Val Lys Gly Arg Phe Thr Ile Ser Arg Asp Asn Ser Lys Ser
                85                  90                  95

Leu Leu Phe Leu His Val Asn Ser Leu Thr Ser Ala Asp Thr Ala Ile
            100                 105                 110

Tyr Tyr Cys Ala Arg Asp Phe His Ser Lys Thr Thr Ser Ile Phe Gly
        115                 120                 125

Leu Ile Pro Leu Tyr Phe Tyr Tyr Ser Ala Met Asp Thr Trp Gly Arg
    130                 135                 140

Gly Thr Thr Val Ile Val Ser Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Leu Leu Gly Gly
            260                 265                 270
```

```
Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Gly Leu His Asn His Tyr Thr Gln Lys Ser Leu Ser Leu Ser Pro
465                 470                 475                 480

Gly Lys

<210> SEQ ID NO 10
<211> LENGTH: 644
<212> TYPE: PRT
<213> ORGANISM: Homo sapiens

<400> SEQUENCE: 10

Met Ser Arg Gln Phe Ser Ser Arg Ser Gly Tyr Arg Ser Gly Gly Gly
1               5                   10                  15

Phe Ser Ser Gly Ser Ala Gly Ile Ile Asn Tyr Gln Arg Arg Thr Thr
                20                  25                  30

Ser Ser Ser Thr Arg Arg Ser Gly Gly Gly Gly Arg Phe Ser Ser
            35                  40                  45

Cys Gly Gly Gly Gly Ser Phe Gly Ala Gly Gly Phe Gly Ser
    50                  55                  60

Arg Ser Leu Val Asn Leu Gly Gly Ser Lys Ser Ile Ser Ile Ser Val
65                  70                  75                  80

Ala Arg Gly Gly Arg Gly Ser Gly Phe Gly Gly Tyr Gly Gly
                85                  90                  95

Gly Gly Phe Gly Gly Gly Phe Gly Gly Gly Phe Gly Gly
        100                 105                 110

Gly Ile Gly Gly Gly Phe Gly Phe Gly Ser Gly Gly Gly
    115                 120                 125

Phe Gly Gly Gly Phe Gly Gly Gly Tyr Gly Gly Tyr Gly
    130                 135                 140

Pro Val Cys Pro Pro Gly Gly Ile Gln Glu Val Thr Ile Asn Gln Ser
145                 150                 155                 160
```

```
Leu Leu Gln Pro Leu Asn Val Glu Ile Asp Pro Glu Ile Gln Lys Val
                165                 170                 175

Lys Ser Arg Glu Arg Glu Gln Ile Lys Ser Leu Asn Asn Gln Phe Ala
            180                 185                 190

Ser Phe Ile Asp Lys Val Arg Phe Leu Glu Gln Gln Asn Gln Val Leu
        195                 200                 205

Gln Thr Lys Trp Glu Leu Leu Gln Gln Val Asp Thr Ser Thr Arg Thr
    210                 215                 220

His Asn Leu Glu Pro Tyr Phe Glu Ser Phe Ile Asn Asn Leu Arg Arg
225                 230                 235                 240

Arg Val Asp Gln Leu Lys Ser Asp Gln Ser Arg Leu Asp Ser Glu Leu
                245                 250                 255

Lys Asn Met Gln Asp Met Val Glu Asp Tyr Arg Asn Lys Tyr Glu Asp
            260                 265                 270

Glu Ile Asn Lys Arg Thr Asn Ala Glu Asn Glu Phe Val Thr Ile Lys
        275                 280                 285

Lys Asp Val Asp Gly Ala Tyr Met Thr Lys Val Asp Leu Gln Ala Lys
    290                 295                 300

Leu Asp Asn Leu Gln Gln Glu Ile Asp Phe Leu Thr Ala Leu Tyr Gln
305                 310                 315                 320

Ala Glu Leu Ser Gln Met Gln Thr Gln Ile Ser Glu Thr Asn Val Ile
                325                 330                 335

Leu Ser Met Asp Asn Asn Arg Ser Leu Asp Leu Asp Ser Ile Ile Ala
            340                 345                 350

Glu Val Lys Ala Gln Tyr Glu Asp Ile Ala Gln Lys Ser Lys Ala Glu
        355                 360                 365

Ala Glu Ser Leu Tyr Gln Ser Lys Tyr Glu Glu Leu Gln Ile Thr Ala
    370                 375                 380

Gly Arg His Gly Asp Ser Val Arg Asn Ser Lys Ile Glu Ile Ser Glu
385                 390                 395                 400

Leu Asn Arg Val Ile Gln Arg Leu Arg Ser Glu Ile Asp Asn Val Lys
                405                 410                 415

Lys Gln Ile Ser Asn Leu Gln Gln Ser Ile Ser Asp Ala Glu Gln Arg
            420                 425                 430

Gly Glu Asn Ala Leu Lys Asp Ala Lys Asn Lys Leu Asn Asp Leu Glu
    435                 440                 445

Asp Ala Leu Gln Gln Ala Lys Glu Asp Leu Ala Arg Leu Leu Arg Asp
450                 455                 460

Tyr Gln Glu Leu Met Asn Thr Lys Leu Ala Leu Asp Leu Glu Ile Ala
465                 470                 475                 480

Thr Tyr Arg Thr Leu Leu Glu Gly Glu Glu Ser Arg Met Ser Gly Glu
                485                 490                 495

Cys Ala Pro Asn Val Ser Val Ser Val Ser Thr Ser His Thr Thr Ile
            500                 505                 510

Ser Gly Gly Gly Ser Arg Gly Gly Gly Gly Tyr Gly Ser Gly
        515                 520                 525

Gly Ser Ser Tyr Gly Ser Gly Gly Ser Tyr Gly Ser Gly Gly
    530                 535                 540

Gly Gly Gly Gly Arg Gly Ser Tyr Ser Gly Ser Ser Tyr Gly
545                 550                 555                 560

Ser Gly Gly Gly Ser Tyr Gly Ser Gly Gly Gly Gly His Gly
                565                 570                 575
```

```
Ser Tyr Gly Ser Gly Ser Ser Gly Gly Tyr Arg Gly Gly Ser Gly
            580                 585                 590

Gly Gly Gly Gly Gly Ser Gly Gly Arg Gly Ser Gly Gly Gly Ser
            595                 600                 605

Ser Gly Gly Ser Ile Gly Gly Arg Gly Ser Ser Gly Gly Val Lys
            610                 615                 620

Ser Ser Gly Gly Ser Ser Val Lys Phe Val Ser Thr Thr Tyr Ser
625                 630                 635                 640

Gly Val Thr Arg

<210> SEQ ID NO 11
<211> LENGTH: 584
<212> TYPE: PRT
<213> ORGANISM: Homo sapiens

<400> SEQUENCE: 11

Met Ser Val Arg Tyr Ser Ser Lys His Tyr Ser Ser Arg Ser
1               5                   10                  15

Gly Gly Gly Gly Gly Gly Gly Cys Gly Gly Gly Gly Val Ser
                20                  25                  30

Ser Leu Arg Ile Ser Ser Ser Lys Gly Ser Leu Gly Gly Gly Phe Ser
            35                  40                  45

Ser Gly Gly Phe Ser Gly Ser Phe Ser Arg Gly Ser Ser Gly Gly
            50                  55                  60

Gly Cys Phe Gly Gly Ser Ser Gly Gly Tyr Gly Gly Leu Gly Gly Phe
65                  70                  75                  80

Gly Gly Gly Ser Phe Arg Gly Ser Tyr Gly Ser Ser Phe Gly Gly
            85                  90                  95

Ser Tyr Gly Gly Ile Phe Gly Gly Ser Phe Gly Gly Ser Phe
            100                 105                 110

Gly Gly Gly Ser Phe Gly Gly Gly Phe Gly Gly Gly Phe Gly
            115                 120                 125

Gly Gly Phe Gly Gly Gly Phe Gly Gly Asp Gly Gly Leu Leu Ser Gly
            130                 135                 140

Asn Glu Lys Val Thr Met Gln Asn Leu Asn Asp Arg Leu Ala Ser Tyr
145                 150                 155                 160

Leu Asp Lys Val Arg Ala Leu Glu Glu Ser Asn Tyr Glu Leu Glu Gly
                165                 170                 175

Lys Ile Lys Glu Trp Tyr Glu Lys His Gly Asn Ser His Gln Gly Glu
            180                 185                 190

Pro Arg Asp Tyr Ser Lys Tyr Tyr Lys Thr Ile Asp Asp Leu Lys Asn
            195                 200                 205

Gln Ile Leu Asn Leu Thr Thr Asp Asn Ala Asn Ile Leu Leu Gln Ile
    210                 215                 220

Asp Asn Ala Arg Leu Ala Ala Asp Asp Phe Arg Leu Lys Tyr Glu Asn
225                 230                 235                 240

Glu Val Ala Leu Arg Gln Ser Val Glu Ala Asp Ile Asn Gly Leu Arg
                245                 250                 255

Arg Val Leu Asp Glu Leu Thr Leu Thr Lys Ala Asp Leu Glu Met Gln
            260                 265                 270

Ile Glu Ser Leu Thr Glu Glu Leu Ala Tyr Leu Lys Lys Asn His Glu
        275                 280                 285

Glu Glu Met Lys Asp Leu Arg Asn Val Ser Thr Gly Asp Val Asn Val
            290                 295                 300
```

```
Glu Met Asn Ala Ala Pro Gly Val Asp Leu Thr Gln Leu Leu Asn Asn
305                 310                 315                 320

Met Arg Ser Gln Tyr Glu Gln Leu Ala Glu Gln Asn Arg Lys Asp Ala
            325                 330                 335

Glu Ala Trp Phe Asn Glu Lys Ser Lys Glu Leu Thr Thr Glu Ile Asp
            340                 345                 350

Asn Asn Ile Glu Gln Ile Ser Ser Tyr Lys Ser Glu Ile Thr Glu Leu
            355                 360                 365

Arg Arg Asn Val Gln Ala Leu Glu Ile Glu Leu Gln Ser Gln Leu Ala
370                 375                 380

Leu Lys Gln Ser Leu Glu Ala Ser Leu Ala Glu Thr Glu Gly Arg Tyr
385                 390                 395                 400

Cys Val Gln Leu Ser Gln Ile Gln Ala Gln Ile Ser Ala Leu Glu Glu
            405                 410                 415

Gln Leu Gln Gln Ile Arg Ala Glu Thr Glu Cys Gln Asn Thr Glu Tyr
            420                 425                 430

Gln Gln Leu Leu Asp Ile Lys Ile Arg Leu Glu Asn Glu Ile Gln Thr
            435                 440                 445

Tyr Arg Ser Leu Leu Glu Gly Glu Gly Ser Ser Gly Gly Gly Gly Arg
450                 455                 460

Gly Gly Gly Ser Phe Gly Gly Tyr Gly Gly Ser Ser Gly Gly
465                 470                 475                 480

Gly Ser Ser Gly Gly Gly His Gly Gly His Gly Gly Ser Ser Gly
            485                 490                 495

Gly Gly Tyr Gly Gly Gly Ser Ser Gly Gly Gly Ser Gly Gly Gly
            500                 505                 510

Tyr Gly Gly Ser Ser Ser Gly Gly His Gly Gly Ser Ser Ser Gly
            515                 520                 525

Gly Tyr Gly Gly Ser Ser Gly Gly Gly Gly Tyr Gly Gly
            530                 535                 540

Gly Ser Ser Gly Gly Gly Ser Ser Gly Gly Gly Tyr Gly Gly Gly
545                 550                 555                 560

Ser Ser Ser Gly Gly His Lys Ser Ser Ser Gly Ser Val Gly Glu
            565                 570                 575

Ser Ser Ser Lys Gly Pro Arg Tyr
            580

<210> SEQ ID NO 12
<211> LENGTH: 585
<212> TYPE: PRT
<213> ORGANISM: Homo sapiens

<400> SEQUENCE: 12

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
            35                  40                  45

Cys Asp Asn Leu Trp Asp Leu Thr Asp Ala Ser Val Val Cys Arg Ala
50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
            85                  90                  95
```

```
Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
            115                 120                 125

Ser Thr His Thr Leu Asp Leu Ser Arg Glu Leu Ser Glu Ala Leu Gly
        130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
                165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205

Leu Arg Tyr Phe Tyr Ser Arg Arg Ile Asp Ile Thr Leu Ser Ser Val
    210                 215                 220

Lys Cys Phe His Lys Leu Ala Ser Ala Tyr Gly Ala Arg Gln Leu Gln
225                 230                 235                 240

Gly Tyr Cys Ala Ser Leu Phe Ala Ile Leu Leu Pro Gln Asp Pro Ser
                245                 250                 255

Phe Gln Met Pro Leu Asp Leu Tyr Ala Tyr Ala Val Ala Thr Gly Asp
            260                 265                 270

Ala Leu Leu Glu Lys Leu Cys Leu Gln Phe Leu Ala Trp Asn Phe Glu
        275                 280                 285

Ala Leu Thr Gln Ala Glu Ala Trp Pro Ser Val Pro Thr Asp Leu Leu
    290                 295                 300

Gln Leu Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
                325                 330                 335

Glu Glu Val Glu Gly Leu Val Glu Lys Ile Arg Phe Pro Met Met Leu
            340                 345                 350

Pro Glu Glu Leu Phe Glu Leu Gln Phe Asn Leu Ser Leu Tyr Trp Ser
        355                 360                 365

His Glu Ala Leu Phe Gln Lys Lys Thr Leu Gln Ala Leu Glu Phe His
    370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
                405                 410                 415

Phe Val Thr Asp Ser Ser Trp Ser Ala Arg Lys Ser Gln Leu Val Tyr
            420                 425                 430

Gln Ser Arg Arg Gly Pro Leu Val Lys Tyr Ser Ser Asp Tyr Phe Gln
        435                 440                 445

Ala Pro Ser Asp Tyr Arg Tyr Tyr Pro Tyr Gln Ser Phe Gln Thr Pro
    450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
                485                 490                 495

Ser Ser Asp Glu Leu Pro Val Leu Gly Leu Thr Lys Ser Gly Gly Ser
            500                 505                 510
```

Asp Arg Thr Ile Ala Tyr Glu Asn Lys Ala Leu Met Leu Cys Glu Gly
            515                 520                 525

Leu Phe Val Ala Asp Val Thr Asp Phe Glu Gly Trp Lys Ala Ala Ile
        530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
                565                 570                 575

Tyr Leu Thr Asn Ser Ser Gly Val Asp
            580                 585

<210> SEQ ID NO 13
<211> LENGTH: 114
<212> TYPE: PRT
<213> ORGANISM: Homo sapiens

<400> SEQUENCE: 13

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 14
<211> LENGTH: 418
<212> TYPE: PRT
<213> ORGANISM: Homo sapiens

<400> SEQUENCE: 14

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu

```
            130                 135                 140
Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
                195                 200                 205

Val Asn Tyr Ile Phe Phe Lys Gly Lys Trp Glu Arg Pro Phe Glu Val
210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 15
<211> LENGTH: 495
<212> TYPE: PRT
<213> ORGANISM: Homo sapiens

<400> SEQUENCE: 15

Met Ser Met Leu Val Val Phe Leu Leu Leu Trp Gly Val Thr Trp Gly
1               5                   10                  15

Pro Val Thr Glu Ala Ala Ile Phe Tyr Glu Thr Gln Pro Ser Leu Trp
                20                  25                  30

Ala Glu Ser Glu Ser Leu Leu Lys Pro Leu Ala Asn Val Thr Leu Thr
            35                  40                  45

Cys Gln Ala His Leu Glu Thr Pro Asp Phe Gln Leu Phe Lys Asn Gly
        50                  55                  60

Val Ala Gln Glu Pro Val His Leu Asp Ser Pro Ala Ile Lys His Gln
65                  70                  75                  80

Phe Leu Leu Thr Gly Asp Thr Gln Gly Arg Tyr Arg Cys Arg Ser Gly
```

```
                    85                  90                  95
Leu Ser Thr Gly Trp Thr Gln Leu Ser Lys Leu Leu Glu Leu Thr Gly
                100                 105                 110

Pro Lys Ser Leu Pro Ala Pro Trp Leu Ser Met Ala Pro Val Ser Trp
                115                 120                 125

Ile Thr Pro Gly Leu Lys Thr Thr Ala Val Cys Arg Gly Val Leu Arg
                130                 135                 140

Gly Val Thr Phe Leu Leu Arg Arg Glu Gly Asp His Glu Phe Leu Glu
145                 150                 155                 160

Val Pro Glu Ala Gln Glu Asp Val Glu Ala Thr Phe Pro Val His Gln
                165                 170                 175

Pro Gly Asn Tyr Ser Cys Ser Tyr Arg Thr Asp Gly Glu Gly Ala Leu
                180                 185                 190

Ser Glu Pro Ser Ala Thr Val Thr Ile Glu Glu Leu Ala Ala Pro Pro
                195                 200                 205

Pro Pro Val Leu Met His His Gly Glu Ser Ser Gln Val Leu His Pro
                210                 215                 220

Gly Asn Lys Val Thr Leu Thr Cys Val Ala Pro Leu Ser Gly Val Asp
225                 230                 235                 240

Phe Gln Leu Arg Arg Gly Glu Lys Glu Leu Leu Val Pro Arg Ser Ser
                245                 250                 255

Thr Ser Pro Asp Arg Ile Phe Phe His Leu Asn Ala Val Ala Leu Gly
                260                 265                 270

Asp Gly Gly His Tyr Thr Cys Arg Tyr Arg Leu His Asp Asn Gln Asn
                275                 280                 285

Gly Trp Ser Gly Asp Ser Ala Pro Val Glu Leu Ile Leu Ser Asp Glu
                290                 295                 300

Thr Leu Pro Ala Pro Glu Phe Ser Pro Glu Pro Glu Ser Gly Arg Ala
305                 310                 315                 320

Leu Arg Leu Arg Cys Leu Ala Pro Leu Glu Gly Ala Arg Phe Ala Leu
                325                 330                 335

Val Arg Glu Asp Arg Gly Gly Arg Arg Val His Arg Phe Gln Ser Pro
                340                 345                 350

Ala Gly Thr Glu Ala Leu Phe Glu Leu His Asn Ile Ser Val Ala Asp
                355                 360                 365

Ser Ala Asn Tyr Ser Cys Val Tyr Val Asp Leu Lys Pro Pro Phe Gly
                370                 375                 380

Gly Ser Ala Pro Ser Glu Arg Leu Glu Leu His Val Asp Gly Pro Pro
385                 390                 395                 400

Pro Arg Pro Gln Leu Arg Ala Thr Trp Ser Gly Ala Val Leu Ala Gly
                405                 410                 415

Arg Asp Ala Val Leu Arg Cys Glu Gly Pro Ile Pro Asp Val Thr Phe
                420                 425                 430

Glu Leu Leu Arg Glu Gly Glu Thr Lys Ala Val Lys Thr Val Arg Thr
                435                 440                 445

Pro Gly Ala Ala Ala Asn Leu Glu Leu Ile Phe Val Gly Pro Gln His
450                 455                 460

Ala Gly Asn Tyr Arg Cys Arg Tyr Arg Ser Trp Val Pro His Thr Phe
465                 470                 475                 480

Glu Ser Glu Leu Ser Asp Pro Val Glu Leu Leu Val Ala Glu Ser
                485                 490                 495

<210> SEQ ID NO 16
```

```
<211> LENGTH: 609
<212> TYPE: PRT
<213> ORGANISM: Homo sapiens

<400> SEQUENCE: 16

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
```

```
         385                 390                 395                 400
     Phe Lys Pro Leu Val Glu Glu Pro Gln Asn Leu Ile Lys Gln Asn Cys
                     405                 410                 415

Glu Leu Phe Glu Gln Leu Gly Glu Tyr Lys Phe Gln Asn Ala Leu Leu
                 420                 425                 430

Val Arg Tyr Thr Lys Lys Val Pro Gln Val Ser Thr Pro Thr Leu Val
                     435                 440                 445

Glu Val Ser Arg Asn Leu Gly Lys Val Gly Ser Lys Cys Cys Lys His
                 450                 455                 460

Pro Glu Ala Lys Arg Met Pro Cys Ala Glu Asp Tyr Leu Ser Val Val
     465                 470                 475                 480

Leu Asn Gln Leu Cys Val Leu His Glu Lys Thr Pro Val Ser Asp Arg
                         485                 490                 495

Val Thr Lys Cys Cys Thr Glu Ser Leu Val Asn Arg Arg Pro Cys Phe
                     500                 505                 510

Ser Ala Leu Glu Val Asp Glu Thr Tyr Val Pro Lys Glu Phe Asn Ala
                 515                 520                 525

Glu Thr Phe Thr Phe His Ala Asp Ile Cys Thr Leu Ser Glu Lys Glu
                 530                 535                 540

Arg Gln Ile Lys Lys Gln Thr Ala Leu Val Glu Leu Val Lys His Lys
     545                 550                 555                 560

Pro Lys Ala Thr Lys Glu Gln Leu Lys Ala Val Met Asp Asp Phe Ala
                     565                 570                 575

Ala Phe Val Glu Lys Cys Cys Lys Ala Asp Asp Lys Glu Thr Cys Phe
                 580                 585                 590

Ala Glu Glu Gly Lys Lys Leu Val Ala Ala Ser Gln Ala Ala Leu Gly
                 595                 600                 605

Leu

<210> SEQ ID NO 17
<211> LENGTH: 398
<212> TYPE: PRT
<213> ORGANISM: Homo sapiens

<400> SEQUENCE: 17

Met Glu Gly Ala Ala Leu Leu Arg Val Ser Val Leu Cys Ile Trp Met
     1               5                  10                  15

Ser Ala Leu Phe Leu Gly Val Gly Val Arg Ala Glu Ala Gly Ala
                     20                  25                  30

Arg Val Gln Gln Asn Val Pro Ser Gly Thr Asp Thr Gly Asp Pro Gln
                 35                  40                  45

Ser Lys Pro Leu Gly Asp Trp Ala Ala Gly Thr Met Asp Pro Glu Ser
     50                  55                  60

Ser Ile Phe Ile Glu Asp Ala Ile Lys Tyr Phe Lys Glu Lys Val Ser
     65                  70                  75                  80

Thr Gln Asn Leu Leu Leu Leu Thr Asp Asn Glu Ala Trp Asn Gly
                     85                  90                  95

Phe Val Ala Ala Ala Glu Leu Pro Arg Asn Glu Ala Asp Glu Leu Arg
                     100                 105                 110

Lys Ala Leu Asp Asn Leu Ala Arg Gln Met Ile Met Lys Asp Lys Asn
                 115                 120                 125

Trp His Asp Lys Gly Gln Gln Tyr Arg Asn Trp Phe Leu Lys Glu Phe
             130                 135                 140

Pro Arg Leu Lys Ser Glu Leu Glu Asp Asn Ile Arg Arg Leu Arg Ala
```

```
                145                 150                 155                 160
Leu Ala Asp Gly Val Gln Lys Val His Lys Gly Thr Thr Ile Ala Asn
                    165                 170                 175
Val Val Ser Gly Ser Leu Ser Ile Ser Ser Gly Ile Leu Thr Leu Val
                    180                 185                 190
Gly Met Gly Leu Ala Pro Phe Thr Glu Gly Gly Ser Leu Val Leu Leu
                    195                 200                 205
Glu Pro Gly Met Glu Leu Gly Ile Thr Ala Ala Leu Thr Gly Ile Thr
                    210                 215                 220
Ser Ser Thr Met Asp Tyr Gly Lys Lys Trp Trp Thr Gln Ala Gln Ala
225                 230                 235                 240
His Asp Leu Val Ile Lys Ser Leu Asp Lys Leu Lys Glu Val Arg Glu
                    245                 250                 255
Phe Leu Gly Glu Asn Ile Ser Asn Phe Leu Ser Leu Ala Gly Asn Thr
                    260                 265                 270
Tyr Gln Leu Thr Arg Gly Ile Gly Lys Asp Ile Arg Ala Leu Arg Arg
                    275                 280                 285
Ala Arg Ala Asn Leu Gln Ser Val Pro His Ala Ser Ala Ser Arg Pro
                    290                 295                 300
Arg Val Thr Glu Pro Ile Ser Ala Glu Ser Gly Glu Gln Val Glu Arg
305                 310                 315                 320
Val Asn Glu Pro Ser Ile Leu Glu Met Ser Arg Gly Val Lys Leu Thr
                    325                 330                 335
Asp Val Ala Pro Val Ser Phe Phe Leu Val Leu Asp Val Val Tyr Leu
                    340                 345                 350
Val Tyr Glu Ser Lys His Leu His Glu Gly Ala Lys Ser Glu Thr Ala
                    355                 360                 365
Glu Glu Leu Lys Lys Val Ala Gln Glu Leu Glu Lys Leu Asn Ile
                    370                 375                 380
Leu Asn Asn Asn Tyr Lys Ile Leu Gln Ala Asp Gln Glu Leu
385                 390                 395

<210> SEQ ID NO 18
<211> LENGTH: 1744
<212> TYPE: PRT
<213> ORGANISM: Homo sapiens

<400> SEQUENCE: 18

Met Arg Leu Leu Trp Gly Leu Ile Trp Ala Ser Ser Phe Phe Thr Leu
1               5                   10                  15
Ser Leu Gln Lys Pro Arg Leu Leu Leu Phe Ser Pro Ser Val Val His
                    20                  25                  30
Leu Gly Val Pro Leu Ser Val Gly Val Gln Leu Gln Asp Val Pro Arg
                    35                  40                  45
Gly Gln Val Val Lys Gly Ser Val Phe Leu Arg Asn Pro Ser Arg Asn
                50                  55                  60
Asn Val Pro Cys Ser Pro Lys Val Asp Phe Thr Leu Ser Ser Glu Arg
65                  70                  75                  80
Asp Phe Ala Leu Leu Ser Leu Gln Val Pro Leu Lys Asp Ala Lys Ser
                    85                  90                  95
Cys Gly Leu His Gln Leu Leu Arg Gly Pro Glu Val Gln Leu Val Ala
                    100                 105                 110
His Ser Pro Trp Leu Lys Asp Ser Leu Ser Arg Thr Thr Asn Ile Gln
                    115                 120                 125
```

-continued

```
Gly Ile Asn Leu Leu Phe Ser Ser Arg Arg Gly His Leu Phe Leu Gln
            130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
            195                 200                 205

Glu Pro Gly Thr Trp Lys Ile Ser Ala Arg Phe Ser Asp Gly Leu Glu
210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
            275                 280                 285

Glu Asp Gly Lys Lys Thr Phe Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
            355                 360                 365

Leu Asp Leu Ser Lys Thr Lys Arg His Leu Val Pro Gly Ala Pro Phe
370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
```

```
                545                 550                 555                 560
        Asp Val Gln Ala Gly Ala Cys Glu Gly Lys Leu Glu Leu Ser Val Asp
                        565                 570                 575

Gly Ala Lys Gln Tyr Arg Asn Gly Glu Ser Val Lys Leu His Leu Glu
                        580                 585                 590

Thr Asp Ser Leu Ala Leu Val Ala Leu Gly Ala Leu Asp Thr Ala Leu
                        595                 600                 605

Tyr Ala Ala Gly Ser Lys Ser His Lys Pro Leu Asn Met Gly Lys Val
                        610                 615                 620

Phe Glu Ala Met Asn Ser Tyr Asp Leu Gly Cys Gly Pro Gly Gly Gly
        625                 630                 635                 640

Asp Ser Ala Leu Gln Val Phe Gln Ala Ala Gly Leu Ala Phe Ser Asp
                        645                 650                 655

Gly Asp Gln Trp Thr Leu Ser Arg Lys Arg Leu Ser Cys Pro Lys Glu
                        660                 665                 670

Lys Thr Thr Arg Lys Lys Arg Asn Val Asn Phe Gln Lys Ala Ile Asn
                        675                 680                 685

Glu Lys Leu Gly Gln Tyr Ala Ser Pro Thr Ala Lys Arg Cys Cys Gln
                        690                 695                 700

Asp Gly Val Thr Arg Leu Pro Met Met Arg Ser Cys Glu Gln Arg Ala
        705                 710                 715                 720

Ala Arg Val Gln Gln Pro Asp Cys Arg Glu Pro Phe Leu Ser Cys Cys
                        725                 730                 735

Gln Phe Ala Glu Ser Leu Arg Lys Lys Ser Arg Asp Lys Gly Gln Ala
                        740                 745                 750

Gly Leu Gln Arg Ala Leu Glu Ile Leu Gln Glu Glu Asp Leu Ile Asp
                        755                 760                 765

Glu Asp Asp Ile Pro Val Arg Ser Phe Phe Pro Glu Asn Trp Leu Trp
        770                 775                 780

Arg Val Glu Thr Val Asp Arg Phe Gln Ile Leu Thr Leu Trp Leu Pro
        785                 790                 795                 800

Asp Ser Leu Thr Thr Trp Glu Ile His Gly Leu Ser Leu Ser Lys Thr
                        805                 810                 815

Lys Gly Leu Cys Val Ala Thr Pro Val Gln Leu Arg Val Phe Arg Glu
                        820                 825                 830

Phe His Leu His Leu Arg Leu Pro Met Ser Val Arg Arg Phe Glu Gln
                        835                 840                 845

Leu Glu Leu Arg Pro Val Leu Tyr Asn Tyr Leu Asp Lys Asn Leu Thr
                        850                 855                 860

Val Ser Val His Val Ser Pro Val Glu Gly Leu Cys Leu Ala Gly Gly
        865                 870                 875                 880

Gly Gly Leu Ala Gln Gln Val Leu Val Pro Ala Gly Ser Ala Arg Pro
                        885                 890                 895

Val Ala Phe Ser Val Val Pro Thr Ala Ala Ala Val Ser Leu Lys
                        900                 905                 910

Val Val Ala Arg Gly Ser Phe Glu Phe Pro Val Gly Asp Ala Val Ser
                        915                 920                 925

Lys Val Leu Gln Ile Glu Lys Glu Gly Ala Ile His Arg Glu Glu Leu
                        930                 935                 940

Val Tyr Glu Leu Asn Pro Leu Asp His Arg Gly Arg Thr Leu Glu Ile
        945                 950                 955                 960

Pro Gly Asn Ser Asp Pro Asn Met Ile Pro Asp Gly Asp Phe Asn Ser
                        965                 970                 975
```

```
Tyr Val Arg Val Thr Ala Ser Asp Pro Leu Asp Thr Leu Gly Ser Glu
            980                 985                 990

Gly Ala Leu Ser Pro Gly Gly Val Ala Ser Leu Leu Arg Leu Pro Arg
            995                 1000                1005

Gly Cys Gly Glu Gln Thr Met Ile Tyr Leu Ala Pro Thr Leu Ala Ala
            1010                1015                1020

Ser Arg Tyr Leu Asp Lys Thr Glu Gln Trp Ser Thr Leu Pro Pro Glu
1025                1030                1035                1040

Thr Lys Asp His Ala Val Asp Leu Ile Gln Lys Gly Tyr Met Arg Ile
            1045                1050                1055

Gln Gln Phe Arg Lys Ala Asp Gly Ser Tyr Ala Ala Trp Leu Ser Arg
            1060                1065                1070

Asp Ser Ser Thr Trp Leu Thr Ala Phe Val Leu Lys Val Leu Ser Leu
            1075                1080                1085

Ala Gln Glu Gln Val Gly Gly Ser Pro Glu Lys Leu Gln Glu Thr Ser
            1090                1095                1100

Asn Trp Leu Leu Ser Gln Gln Gln Ala Asp Gly Ser Phe Gln Asp Leu
1105                1110                1115                1120

Ser Pro Val Ile His Arg Ser Met Gln Gly Gly Leu Val Gly Asn Asp
            1125                1130                1135

Glu Thr Val Ala Leu Thr Ala Phe Val Thr Ile Ala Leu His His Gly
            1140                1145                1150

Leu Ala Val Phe Gln Asp Glu Gly Ala Glu Pro Leu Lys Gln Arg Val
            1155                1160                1165

Glu Ala Ser Ile Ser Lys Ala Asn Ser Phe Leu Gly Glu Lys Ala Ser
            1170                1175                1180

Ala Gly Leu Leu Gly Ala His Ala Ala Ile Thr Ala Tyr Ala Leu
1185                1190                1195                1200

Ser Leu Thr Lys Ala Pro Val Asp Leu Leu Gly Val Ala His Asn Asn
            1205                1210                1215

Leu Met Ala Met Ala Gln Glu Thr Gly Asp Asn Leu Tyr Trp Gly Ser
            1220                1225                1230

Val Thr Gly Ser Gln Ser Asn Ala Val Ser Pro Thr Pro Ala Pro Arg
            1235                1240                1245

Asn Pro Ser Asp Pro Met Pro Gln Ala Pro Ala Leu Trp Ile Glu Thr
1250                1255                1260

Thr Ala Tyr Ala Leu Leu His Leu Leu Leu His Glu Gly Lys Ala Glu
1265                1270                1275                1280

Met Ala Asp Gln Ala Ser Ala Trp Leu Thr Arg Gln Gly Ser Phe Gln
            1285                1290                1295

Gly Gly Phe Arg Ser Thr Gln Asp Thr Val Ile Ala Leu Asp Ala Leu
            1300                1305                1310

Ser Ala Tyr Trp Ile Ala Ser His Thr Thr Glu Glu Arg Gly Leu Asn
            1315                1320                1325

Val Thr Leu Ser Ser Thr Gly Arg Asn Gly Phe Lys Ser His Ala Leu
            1330                1335                1340

Gln Leu Asn Asn Arg Gln Ile Arg Gly Leu Glu Glu Glu Leu Gln Phe
1345                1350                1355                1360

Ser Leu Gly Ser Lys Ile Asn Val Lys Val Gly Gly Asn Ser Lys Gly
            1365                1370                1375

Thr Leu Lys Val Leu Arg Thr Tyr Asn Val Leu Asp Met Lys Asn Thr
            1380                1385                1390
```

-continued

```
Thr Cys Gln Asp Leu Gln Ile Glu Val Thr Lys Gly His Val Glu
            1395                1400                1405

Tyr Thr Met Glu Ala Asn Glu Asp Tyr Glu Asp Tyr Glu Tyr Asp Glu
    1410                1415                1420

Leu Pro Ala Lys Asp Asp Pro Asp Ala Pro Leu Gln Pro Val Thr Pro
1425                1430                1435                1440

Leu Gln Leu Phe Glu Gly Arg Arg Asn Arg Arg Arg Glu Ala Pro
            1445                1450                1455

Lys Val Val Glu Gln Glu Ser Arg Val His Tyr Thr Val Cys Ile
            1460                1465                1470

Trp Arg Asn Gly Lys Val Gly Leu Ser Gly Met Ala Ile Ala Asp Val
            1475                1480                1485

Thr Leu Leu Ser Gly Phe His Ala Leu Arg Ala Asp Leu Glu Lys Leu
            1490                1495                1500

Thr Ser Leu Ser Asp Arg Tyr Val Ser His Phe Glu Thr Glu Gly Pro
1505                1510                1515                1520

His Val Leu Leu Tyr Phe Asp Ser Val Pro Thr Ser Arg Glu Cys Val
            1525                1530                1535

Gly Phe Glu Ala Val Gln Glu Val Pro Val Gly Leu Val Gln Pro Ala
            1540                1545                1550

Ser Ala Thr Leu Tyr Asp Tyr Tyr Asn Pro Glu Arg Arg Cys Ser Val
            1555                1560                1565

Phe Tyr Gly Ala Pro Ser Lys Ser Arg Leu Leu Ala Thr Leu Cys Ser
            1570                1575                1580

Ala Glu Val Cys Gln Cys Ala Glu Gly Lys Cys Pro Arg Gln Arg Arg
1585                1590                1595                1600

Ala Leu Glu Arg Gly Leu Gln Asp Glu Asp Gly Tyr Arg Met Lys Phe
            1605                1610                1615

Ala Cys Tyr Tyr Pro Arg Val Glu Tyr Gly Phe Gln Val Lys Val Leu
            1620                1625                1630

Arg Glu Asp Ser Arg Ala Ala Phe Arg Leu Phe Glu Thr Lys Ile Thr
            1635                1640                1645

Gln Val Leu His Phe Thr Lys Asp Val Lys Ala Ala Ala Asn Gln Met
            1650                1655                1660

Arg Asn Phe Leu Val Arg Ala Ser Cys Arg Leu Arg Leu Glu Pro Gly
1665                1670                1675                1680

Lys Glu Tyr Leu Ile Met Gly Leu Asp Gly Ala Thr Tyr Asp Leu Glu
            1685                1690                1695

Gly His Pro Gln Tyr Leu Leu Asp Ser Asn Ser Trp Ile Glu Glu Met
            1700                1705                1710

Pro Ser Glu Arg Leu Cys Arg Ser Thr Arg Gln Arg Ala Ala Cys Ala
            1715                1720                1725

Gln Leu Asn Asp Phe Leu Gln Glu Tyr Gly Thr Gln Gly Cys Gln Val
            1730                1735                1740

<210> SEQ ID NO 19
<211> LENGTH: 559
<212> TYPE: PRT
<213> ORGANISM: Homo sapiens

<400> SEQUENCE: 19

Met Ser Ala Cys Arg Ser Phe Ala Val Ala Ile Cys Ile Leu Glu Ile
1               5                   10                  15

Ser Ile Leu Thr Ala Gln Tyr Thr Thr Ser Tyr Asp Pro Glu Leu Thr
            20                  25                  30
```

-continued

Glu Ser Ser Gly Ser Ala Ser His Ile Asp Cys Arg Met Ser Pro Trp
        35                  40                  45

Ser Glu Trp Ser Gln Cys Asp Pro Cys Leu Arg Gln Met Phe Arg Ser
    50                  55                  60

Arg Ser Ile Glu Val Phe Gly Gln Phe Asn Gly Lys Arg Cys Thr Asp
65                  70                  75                  80

Ala Val Gly Asp Arg Arg Gln Cys Val Pro Thr Glu Pro Cys Glu Asp
                85                  90                  95

Ala Glu Asp Asp Cys Gly Asn Asp Phe Gln Cys Ser Thr Gly Arg Cys
            100                 105                 110

Ile Lys Met Arg Leu Arg Cys Asn Gly Asp Asn Asp Cys Gly Asp Phe
                115                 120                 125

Ser Asp Glu Asp Asp Cys Glu Ser Glu Pro Arg Pro Pro Cys Arg Asp
            130                 135                 140

Arg Val Val Glu Glu Ser Glu Leu Ala Arg Thr Ala Gly Tyr Gly Ile
145                 150                 155                 160

Asn Ile Leu Gly Met Asp Pro Leu Ser Thr Pro Phe Asp Asn Glu Phe
                165                 170                 175

Tyr Asn Gly Leu Cys Asn Arg Asp Arg Asp Gly Asn Thr Leu Thr Tyr
                180                 185                 190

Tyr Arg Arg Pro Trp Asn Val Ala Ser Leu Ile Tyr Glu Thr Lys Gly
            195                 200                 205

Glu Lys Asn Phe Arg Thr Glu His Tyr Glu Glu Gln Ile Glu Ala Phe
        210                 215                 220

Lys Ser Ile Ile Gln Glu Lys Thr Ser Asn Phe Asn Ala Ala Ile Ser
225                 230                 235                 240

Leu Lys Phe Thr Pro Thr Glu Thr Asn Lys Ala Glu Gln Cys Cys Glu
                245                 250                 255

Glu Thr Ala Ser Ser Ile Ser Leu His Gly Lys Gly Ser Phe Arg Phe
            260                 265                 270

Ser Tyr Ser Lys Asn Glu Thr Tyr Gln Leu Phe Leu Ser Tyr Ser Ser
        275                 280                 285

Lys Lys Glu Lys Met Phe Leu His Val Lys Gly Glu Ile His Leu Gly
290                 295                 300

Arg Phe Val Met Arg Asn Arg Asp Val Val Leu Thr Thr Thr Phe Val
305                 310                 315                 320

Asp Asp Ile Lys Ala Leu Pro Thr Thr Tyr Glu Lys Gly Glu Tyr Phe
                325                 330                 335

Ala Phe Leu Glu Thr Tyr Gly Thr His Tyr Ser Ser Ser Gly Ser Leu
            340                 345                 350

Gly Gly Leu Tyr Glu Leu Ile Tyr Val Leu Asp Lys Ala Ser Met Lys
        355                 360                 365

Arg Lys Gly Val Glu Leu Lys Asp Ile Lys Arg Cys Leu Gly Tyr His
    370                 375                 380

Leu Asp Val Ser Leu Ala Phe Ser Glu Ile Ser Val Gly Ala Glu Phe
385                 390                 395                 400

Asn Lys Asp Asp Cys Val Lys Arg Gly Glu Gly Arg Ala Val Asn Ile
                405                 410                 415

Thr Ser Glu Asn Leu Ile Asp Asp Val Val Ser Leu Ile Arg Gly Gly
            420                 425                 430

Thr Arg Lys Tyr Ala Phe Glu Leu Lys Glu Lys Leu Leu Arg Gly Thr
        435                 440                 445

```
Val Ile Asp Val Thr Asp Phe Val Asn Trp Ala Ser Ser Ile Asn Asp
450                 455                 460

Ala Pro Val Leu Ile Ser Gln Lys Leu Ser Pro Ile Tyr Asn Leu Val
465                 470                 475                 480

Pro Val Lys Met Lys Asn Ala His Leu Lys Lys Gln Asn Leu Glu Arg
            485                 490                 495

Ala Ile Glu Asp Tyr Ile Asn Glu Phe Ser Val Arg Lys Cys His Thr
                500                 505                 510

Cys Gln Asn Gly Gly Thr Val Ile Leu Met Asp Gly Lys Cys Leu Cys
            515                 520                 525

Ala Cys Pro Phe Lys Phe Glu Gly Ile Ala Cys Glu Ile Ser Lys Gln
530                 535                 540

Lys Ile Ser Glu Gly Leu Pro Ala Leu Glu Phe Pro Asn Glu Lys
545                 550                 555

<210> SEQ ID NO 20
<211> LENGTH: 615
<212> TYPE: PRT
<213> ORGANISM: Homo sapiens

<400> SEQUENCE: 20

Met Arg Ala Leu Leu Leu Gly Phe Leu Leu Val Ser Leu Glu Ser
1               5                   10                  15  Ser

Thr Leu Ser Ile Pro Pro Trp Glu Ala Pro Lys Glu His Lys Tyr Lys
            20                  25                  30

Ala Glu Glu His Thr Val Val Leu Thr Val Thr Gly Glu Pro Cys His
                35                  40                  45

Phe Pro Phe Gln Tyr His Arg Gln Leu Tyr His Lys Cys Thr His Lys
50                  55                  60

Gly Arg Pro Gly Pro Gln Pro Trp Cys Ala Thr Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
                100                 105                 110

Met Pro Ser Gly Pro His Cys Leu Cys Pro Gln His Leu Thr Gly Asn
            115                 120                 125

His Cys Gln Lys Glu Lys Cys Phe Glu Pro Gln Leu Leu Arg Phe Phe
130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
                180                 185                 190

Glu Gly His Arg Leu Cys His Cys Pro Val Gly Tyr Thr Gly Ala Phe
                195                 200                 205

Cys Asp Val Asp Thr Lys Ala Ser Cys Tyr Asp Gly Arg Gly Leu Ser
210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
                260                 265                 270
```

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
            355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
                405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
            435                 440                 445

Leu His Glu Ala Phe Ser Pro Val Ser Tyr Gln His Asp Leu Ala Leu
        450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
            500                 505                 510

Glu Glu Tyr Ala Ser Phe Leu Gln Glu Ala Gln Val Pro Phe Leu Ser
        515                 520                 525

Leu Glu Arg Cys Ser Ala Pro Asp Val His Gly Ser Ser Ile Leu Pro
530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
            580                 585                 590

Arg Asn Lys Pro Gly Val Tyr Thr Asp Val Ala Tyr Tyr Leu Ala Trp
        595                 600                 605

Ile Arg Glu His Thr Val Ser
    610                 615

<210> SEQ ID NO 21
<211> LENGTH: 1014
<212> TYPE: PRT
<213> ORGANISM: Homo sapiens

<400> SEQUENCE: 21

Met Arg Val Thr Trp Ala Pro Pro Ser Ile Asp Leu Thr Asn Phe
1               5                   10                  15

Leu Val Arg Tyr Ser Pro Val Lys Asn Glu Glu Asp Val Ala Glu Leu

```
            20                  25                  30
Ser Ile Ser Pro Ser Asp Asn Ala Val Val Leu Thr Asn Leu Leu Pro
            35                  40                  45
Gly Thr Glu Tyr Val Val Ser Val Ser Ser Val Tyr Glu Gln His Glu
        50                  55                  60
Ser Thr Pro Leu Arg Gly Arg Gln Lys Thr Gly Leu Asp Ser Pro Thr
65                  70                  75                  80
Gly Ile Asp Phe Ser Asp Ile Thr Gly Asn Ser Phe Thr Val His Trp
                85                  90                  95
Ile Ala Pro Arg Ala Thr Ile Thr Gly Tyr Arg Ile Arg His His Pro
            100                 105                 110
Glu His Phe Ser Gly Arg Pro Arg Glu Asp Arg Val Pro His Ser Arg
            115                 120                 125
Asn Ser Ile Thr Leu Thr Asn Leu Thr Pro Gly Thr Glu Tyr Val Val
            130                 135                 140
Ser Ile Val Ala Leu Asn Gly Arg Glu Glu Ser Pro Leu Leu Ile Gly
145                 150                 155                 160
Gln Gln Ser Thr Val Ser Asp Val Pro Arg Asp Leu Glu Val Val Ala
                165                 170                 175
Ala Thr Pro Thr Ser Leu Leu Ile Ser Trp Asp Ala Pro Ala Val Thr
            180                 185                 190
Val Arg Tyr Tyr Arg Ile Thr Tyr Gly Glu Thr Gly Gly Asn Ser Pro
            195                 200                 205
Val Gln Glu Phe Thr Val Pro Gly Ser Lys Ser Thr Ala Thr Ile Ser
            210                 215                 220
Gly Leu Lys Pro Gly Val Asp Tyr Thr Ile Thr Val Tyr Ala Val Thr
225                 230                 235                 240
Gly Arg Gly Asp Ser Pro Ala Ser Ser Lys Pro Ile Ser Ile Asn Tyr
                245                 250                 255
Arg Thr Glu Ile Asp Lys Pro Ser Gln Met Gln Val Thr Asp Val Gln
            260                 265                 270
Asp Asn Ser Ile Ser Val Lys Trp Leu Pro Ser Ser Ser Pro Val Thr
            275                 280                 285
Gly Tyr Arg Val Thr Thr Thr Pro Lys Asn Gly Pro Gly Pro Thr Lys
            290                 295                 300
Thr Lys Thr Ala Gly Pro Asp Gln Thr Glu Met Thr Ile Glu Gly Leu
305                 310                 315                 320
Gln Pro Thr Val Glu Tyr Val Val Ser Val Tyr Ala Gln Asn Pro Ser
                325                 330                 335
Gly Glu Ser Gln Pro Leu Val Gln Thr Ala Val Thr Thr Ile Pro Ala
            340                 345                 350
Pro Thr Asp Leu Lys Phe Thr Gln Val Thr Pro Thr Ser Leu Ser Ala
            355                 360                 365
Gln Trp Thr Pro Pro Asn Val Gln Leu Thr Gly Tyr Arg Val Arg Val
            370                 375                 380
Thr Pro Lys Glu Lys Thr Gly Pro Met Lys Glu Ile Asn Leu Ala Pro
385                 390                 395                 400
Asp Ser Ser Ser Val Val Val Ser Gly Leu Met Val Ala Thr Lys Tyr
                405                 410                 415
Glu Val Ser Val Tyr Ala Leu Lys Asp Thr Leu Thr Ser Arg Pro Ala
            420                 425                 430
Gln Gly Val Val Thr Thr Leu Glu Asn Val Ser Pro Pro Arg Arg Ala
            435                 440                 445
```

```
Arg Val Thr Asp Ala Thr Glu Thr Thr Ile Thr Ile Ser Trp Arg Thr
    450                 455                 460
Lys Thr Glu Thr Ile Thr Gly Phe Gln Val Asp Ala Val Pro Ala Asn
465                 470                 475                 480
Gly Gln Thr Pro Ile Gln Arg Thr Ile Lys Pro Asp Val Arg Ser Tyr
                485                 490                 495
Thr Ile Thr Gly Leu Gln Pro Gly Thr Asp Tyr Lys Ile Tyr Leu Tyr
            500                 505                 510
Thr Leu Asn Asp Asn Ala Arg Ser Ser Pro Val Val Ile Asp Ala Ser
        515                 520                 525
Thr Ala Ile Asp Ala Pro Ser Asn Leu Arg Phe Leu Ala Thr Thr Pro
    530                 535                 540
Asn Ser Leu Leu Val Ser Trp Gln Pro Pro Arg Ala Arg Ile Thr Gly
545                 550                 555                 560
Tyr Ile Ile Lys Tyr Glu Lys Pro Gly Ser Pro Pro Arg Glu Val Val
                565                 570                 575
Pro Arg Pro Arg Pro Gly Val Thr Glu Ala Thr Ile Thr Gly Leu Glu
            580                 585                 590
Pro Gly Thr Glu Tyr Thr Ile Tyr Val Ile Ala Leu Lys Asn Asn Gln
        595                 600                 605
Lys Ser Glu Pro Leu Ile Gly Arg Lys Lys Thr Asp Glu Leu Pro Gln
    610                 615                 620
Leu Val Thr Leu Pro His Pro Asn Leu His Gly Pro Glu Ile Leu Asp
625                 630                 635                 640
Val Pro Ser Thr Val Gln Lys Thr Pro Phe Val Thr His Pro Gly Tyr
                645                 650                 655
Asp Thr Gly Asn Gly Ile Gln Leu Pro Gly Thr Ser Gly Gln Gln Pro
            660                 665                 670
Ser Val Gly Gln Gln Met Ile Phe Glu Glu His Gly Phe Arg Arg Thr
        675                 680                 685
Thr Pro Pro Thr Thr Ala Thr Pro Ile Arg His Arg Pro Arg Pro Tyr
    690                 695                 700
Pro Pro Asn Val Gly Glu Glu Ile Gln Ile Gly His Ile Pro Arg Glu
705                 710                 715                 720
Asp Val Asp Tyr His Leu Tyr Pro His Gly Pro Gly Leu Asn Pro Asn
                725                 730                 735
Ala Ser Thr Gly Gln Glu Ala Leu Ser Gln Thr Thr Ile Ser Trp Ala
            740                 745                 750
Pro Phe Gln Asp Thr Ser Glu Tyr Ile Ile Ser Cys His Pro Val Gly
        755                 760                 765
Thr Asp Glu Glu Pro Leu Gln Phe Arg Val Pro Gly Thr Ser Thr Ser
    770                 775                 780
Ala Thr Leu Thr Gly Leu Thr Arg Gly Ala Thr Tyr Asn Ile Ile Val
785                 790                 795                 800
Glu Ala Leu Lys Asp Gln Gln Arg His Lys Val Arg Glu Glu Val Val
                805                 810                 815
Thr Val Gly Asn Ser Val Asn Glu Gly Leu Asn Gln Pro Thr Asp Asp
            820                 825                 830
Ser Cys Phe Asp Pro Tyr Thr Val Ser His Tyr Ala Val Gly Asp Glu
        835                 840                 845
Trp Glu Arg Met Ser Glu Ser Gly Phe Lys Leu Leu Cys Gln Cys Leu
    850                 855                 860
```

```
Gly Phe Gly Ser Gly His Phe Arg Cys Asp Ser Arg Trp Cys His
865                 870                 875                 880

Asp Asn Gly Val Asn Tyr Lys Ile Gly Glu Lys Trp Asp Arg Gln Gly
            885                 890                 895

Glu Asn Gly Gln Met Met Ser Cys Thr Cys Leu Gly Asn Gly Lys Gly
            900                 905                 910

Glu Phe Lys Cys Asp Pro His Glu Ala Thr Cys Tyr Asp Asp Gly Lys
            915                 920                 925

Thr Tyr His Val Gly Glu Gln Trp Gln Lys Glu Tyr Leu Gly Ala Ile
            930                 935                 940

Cys Ser Cys Thr Cys Phe Gly Gly Gln Arg Gly Trp Arg Cys Asp Asn
945                 950                 955                 960

Cys Arg Arg Pro Gly Gly Glu Pro Ser Pro Glu Gly Thr Thr Gly Gln
            965                 970                 975

Ser Tyr Asn Gln Tyr Ser Gln Arg Tyr His Gln Arg Thr Asn Thr Asn
            980                 985                 990

Val Asn Cys Pro Ile Glu Cys Phe Met Pro Leu Asp Val Gln Ala Asp
            995                 1000                1005

Arg Glu Asp Ser Arg Glu
            1010

<210> SEQ ID NO 22
<211> LENGTH: 474
<212> TYPE: PRT
<213> ORGANISM: Homo sapiens

<400> SEQUENCE: 22

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220
```

```
Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
            245                 250                 255

Asp Ile Thr Asn Ile Leu Ser Lys Cys Cys Glu Ser Ala Ser Glu Asp
        260                 265                 270

Cys Met Ala Lys Glu Leu Pro Glu His Thr Val Lys Leu Cys Asp Asn
    275                 280                 285

Leu Ser Thr Lys Asn Ser Lys Phe Glu Asp Cys Cys Gln Glu Lys Thr
290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430

Ala Thr Pro Lys Glu Leu Ala Lys Leu Val Asn Lys Arg Ser Asp Phe
        435                 440                 445

Ala Ser Asn Cys Cys Ser Ile Asn Ser Pro Pro Leu Tyr Cys Asp Ser
450                 455                 460

Glu Ile Asp Ala Glu Leu Lys Asn Ile Leu
465                 470

<210> SEQ ID NO 23
<211> LENGTH: 353
<212> TYPE: PRT
<213> ORGANISM: Homo sapiens

<400> SEQUENCE: 23

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
```

```
                115                 120                 125
Leu His Arg Pro Ala Leu Glu Asp Leu Leu Gly Ser Glu Ala Asn
        130                 135                 140
Leu Thr Cys Thr Leu Thr Gly Leu Arg Asp Ala Ser Gly Val Thr Phe
145                 150                 155                 160
Thr Trp Thr Pro Ser Ser Gly Lys Ser Ala Val Gln Gly Pro Pro Glu
                165                 170                 175
Arg Asp Leu Cys Gly Cys Tyr Ser Val Ser Ser Val Leu Pro Gly Cys
            180                 185                 190
Ala Glu Pro Trp Asn His Gly Lys Thr Phe Thr Cys Thr Ala Ala Tyr
        195                 200                 205
Pro Glu Ser Lys Thr Pro Leu Thr Ala Thr Leu Ser Lys Ser Gly Asn
    210                 215                 220
Thr Phe Arg Pro Glu Val His Leu Leu Pro Pro Ser Glu Glu Leu
225                 230                 235                 240
Ala Leu Asn Glu Leu Val Thr Leu Thr Cys Leu Ala Arg Gly Phe Ser
                245                 250                 255
Pro Lys Asp Val Leu Val Arg Trp Leu Gln Gly Ser Gln Glu Leu Pro
            260                 265                 270
Arg Glu Lys Tyr Leu Thr Trp Ala Ser Arg Gln Glu Pro Ser Gln Gly
        275                 280                 285
Thr Thr Thr Phe Ala Val Thr Ser Ile Leu Arg Val Ala Ala Glu Asp
    290                 295                 300
Trp Lys Lys Gly Asp Thr Phe Ser Cys Met Val Gly His Glu Ala Leu
305                 310                 315                 320
Pro Leu Ala Phe Thr Gln Lys Thr Ile Asp Arg Leu Ala Gly Lys Pro
                325                 330                 335
Thr His Val Asn Val Ser Val Val Met Ala Glu Val Asp Gly Thr Cys
            340                 345                 350
Tyr

<210> SEQ ID NO 24
<211> LENGTH: 473
<212> TYPE: PRT
<213> ORGANISM: Homo sapiens

<400> SEQUENCE: 24

Gly Ser Ala Ser Ala Pro Thr Leu Phe Pro Leu Val Ser Cys Glu Asn
1               5                   10                  15
Ser Pro Ser Asp Thr Ser Ser Val Ala Val Gly Cys Leu Ala Gln Asp
                20                  25                  30
Phe Leu Pro Asp Ser Ile Thr Leu Ser Trp Lys Tyr Lys Asn Asn Ser
            35                  40                  45
Asp Ile Ser Ser Thr Arg Gly Phe Pro Ser Val Leu Arg Gly Gly Lys
        50                  55                  60
Tyr Ala Ala Thr Ser Gln Val Leu Leu Pro Ser Lys Asp Val Met Gln
65                  70                  75                  80
Gly Thr Asp Glu His Val Val Cys Lys Val Gln His Pro Asn Gly Asn
                85                  90                  95
Lys Glu Lys Asn Val Pro Leu Pro Val Ile Ala Glu Leu Pro Pro Lys
            100                 105                 110
Val Ser Val Phe Val Pro Pro Arg Asp Gly Phe Phe Gly Asn Pro Arg
        115                 120                 125
Lys Ser Lys Leu Ile Cys Gln Ala Thr Gly Phe Ser Pro Arg Gln Ile
```

```
            130                 135                 140
Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Glu Gly Glu Val Ser Ala Asp Glu Gly Phe Glu Asn Leu Trp Ala
        435                 440                 445

Thr Ala Ser Thr Phe Ile Val Leu Phe Leu Leu Ser Leu Phe Tyr Ser
450                 455                 460

Thr Thr Val Thr Leu Phe Lys Val Lys
465                 470

<210> SEQ ID NO 25
<211> LENGTH: 106
<212> TYPE: PRT
<213> ORGANISM: Homo sapiens

<400> SEQUENCE: 25

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30
```

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 26
<211> LENGTH: 213
<212> TYPE: PRT
<213> ORGANISM: Homo sapiens

<400> SEQUENCE: 26

Met Arg Pro Gly Thr Gly Gln Gly Gly Leu Glu Ala Pro Gly Glu Pro
 1                5                  10                  15

Gly Pro Asn Leu Arg Gln Arg Trp Pro Leu Leu Leu Leu Gly Leu Ala
                 20                  25                  30

Val Val Thr His Gly Leu Leu Arg Pro Thr Ala Ala Ser Gln Ser Arg
             35                  40                  45

Ala Leu Gly Pro Gly Ala Pro Gly Gly Ser Ser Arg Ser Ser Leu Arg
 50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
                 85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
            115                 120                 125

Asn Lys Ala Thr Leu Val Cys Leu Met Asn Asp Phe Tyr Pro Gly Ile
        130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
            195                 200                 205

Pro Ala Glu Cys Ser
    210

<210> SEQ ID NO 27
<211> LENGTH: 911
<212> TYPE: PRT
<213> ORGANISM: Homo sapiens

<400> SEQUENCE: 27

Met Asp Gly Ala Met Gly Pro Arg Gly Leu Leu Leu Cys Met Tyr Leu
 1                5                  10                  15

Val Ser Leu Leu Ile Leu Gln Ala Met Pro Ala Leu Gly Ser Ala Thr
                 20                  25                  30

-continued

Gly Arg Ser Lys Ser Ser Glu Lys Arg Gln Ala Val Asp Thr Ala Val
            35                  40                  45

Asp Gly Val Phe Ile Arg Ser Leu Lys Val Asn Cys Lys Val Thr Ser
 50                  55                  60

Arg Phe Ala His Tyr Val Val Thr Ser Gln Val Val Asn Thr Ala Asn
 65                  70                  75                  80

Glu Ala Arg Glu Val Ala Phe Asp Leu Glu Ile Pro Lys Thr Ala Phe
                85                  90                  95

Ile Ser Asp Phe Ala Val Thr Ala Asp Gly Asn Ala Phe Ile Gly Asp
                100                 105                 110

Ile Lys Asp Lys Val Thr Ala Trp Lys Gln Tyr Arg Lys Ala Ala Ile
            115                 120                 125

Ser Gly Glu Asn Ala Gly Leu Val Arg Ala Ser Gly Arg Thr Met Glu
        130                 135                 140

Gln Phe Thr Ile His Leu Thr Val Asn Pro Gln Ser Lys Val Thr Phe
145                 150                 155                 160

Gln Leu Thr Tyr Glu Glu Val Leu Lys Arg Asn His Met Gln Tyr Glu
                165                 170                 175

Ile Val Ile Lys Val Lys Pro Lys Gln Leu Val His His Phe Glu Ile
                180                 185                 190

Asp Val Asp Ile Phe Glu Pro Gln Gly Ile Ser Lys Leu Asp Ala Gln
            195                 200                 205

Ala Ser Phe Leu Pro Lys Glu Leu Ala Ala Gln Thr Ile Lys Lys Ser
        210                 215                 220

Phe Ser Gly Lys Lys Gly His Val Leu Phe Arg Pro Thr Val Ser Gln
225                 230                 235                 240

Gln Gln Ser Cys Pro Thr Cys Ser Thr Ser Leu Leu Asn Gly His Phe
                245                 250                 255

Lys Val Thr Tyr Asp Val Ser Arg Asp Lys Ile Cys Asp Leu Leu Val
                260                 265                 270

Ala Asn Asn His Phe Ala His Phe Phe Ala Pro Gln Asn Leu Thr Asn
            275                 280                 285

Met Asn Lys Asn Val Val Phe Val Ile Asp Ile Ser Gly Ser Met Arg
        290                 295                 300

Gly Gln Lys Val Lys Gln Thr Lys Glu Ala Leu Leu Lys Ile Leu Gly
305                 310                 315                 320

Asp Met Gln Pro Gly Asp Tyr Phe Asp Leu Val Leu Phe Gly Thr Arg
                325                 330                 335

Val Gln Ser Trp Lys Gly Ser Leu Val Gln Ala Ser Glu Ala Asn Leu
            340                 345                 350

Gln Ala Ala Gln Asp Phe Val Arg Gly Phe Ser Leu Asp Glu Ala Thr
        355                 360                 365

Asn Leu Asn Gly Gly Leu Leu Arg Gly Ile Glu Ile Leu Asn Gln Val
370                 375                 380

Gln Glu Ser Leu Pro Glu Leu Ser Asn His Ala Ser Ile Leu Ile Met
385                 390                 395                 400

Leu Thr Asp Gly Asp Pro Thr Glu Gly Val Thr Asp Arg Ser Gln Ile
                405                 410                 415

Leu Lys Asn Val Arg Asn Ala Ile Arg Gly Arg Phe Pro Leu Tyr Asn
            420                 425                 430

Leu Gly Phe Gly His Asn Val Asp Phe Asn Phe Leu Glu Val Met Ser
        435                 440                 445

Met Glu Asn Asn Gly Arg Ala Gln Arg Ile Tyr Glu Asp His Asp Ala

-continued

```
              450                 455                 460
Thr Gln Gln Leu Gln Gly Phe Tyr Ser Gln Val Ala Lys Pro Leu Leu
465                 470                 475                 480

Val Asp Val Asp Leu Gln Tyr Pro Gln Asp Ala Val Leu Ala Leu Thr
                485                 490                 495

Gln Asn His His Lys Gln Tyr Tyr Glu Gly Ser Glu Ile Val Val Ala
                    500                 505                 510

Gly Arg Ile Ala Asp Asn Lys Gln Ser Ser Phe Lys Ala Asp Val Gln
                515                 520                 525

Ala His Gly Glu Gly Gln Glu Phe Ser Ile Thr Cys Leu Val Asp Glu
                530                 535                 540

Glu Glu Met Lys Lys Leu Leu Arg Glu Arg Gly His Met Leu Glu Asn
545                 550                 555                 560

His Val Glu Arg Leu Trp Ala Tyr Leu Thr Ile Gln Glu Leu Leu Ala
                565                 570                 575

Lys Arg Met Lys Val Asp Arg Glu Arg Ala Asn Leu Ser Ser Gln
                580                 585                 590

Ala Leu Gln Met Ser Leu Asp Tyr Gly Phe Val Thr Pro Leu Thr Ser
                595                 600                 605

Met Ser Ile Arg Gly Met Ala Asp Gln Asp Gly Leu Lys Pro Thr Ile
610                 615                 620

Asp Lys Pro Ser Glu Asp Ser Pro Leu Glu Met Leu Gly Pro Arg
625                 630                 635                 640

Arg Thr Phe Val Leu Ser Ala Leu Gln Pro Ser Pro Thr His Ser Ser
                645                 650                 655

Ser Asn Thr Gln Arg Leu Pro Asp Arg Val Thr Gly Val Asp Thr Asp
                660                 665                 670

Pro His Phe Ile Ile His Val Pro Gln Lys Glu Asp Thr Leu Cys Phe
                675                 680                 685

Asn Ile Asn Glu Glu Pro Gly Val Ile Leu Ser Leu Val Gln Asp Pro
690                 695                 700

Asn Thr Gly Phe Ser Val Asn Gly Gln Leu Ile Gly Asn Lys Ala Arg
705                 710                 715                 720

Ser Pro Gly Gln His Asp Gly Thr Tyr Phe Gly Arg Leu Gly Ile Ala
                725                 730                 735

Asn Pro Ala Thr Asp Phe Gln Leu Glu Val Thr Pro Gln Asn Ile Thr
                740                 745                 750

Leu Asn Pro Gly Phe Gly Gly Pro Val Phe Ser Trp Arg Asp Gln Ala
                755                 760                 765

Val Leu Arg Gln Asp Gly Val Val Thr Ile Asn Lys Lys Arg Asn
                770                 775                 780

Leu Val Val Ser Val Asp Gly Gly Thr Phe Glu Val Leu His
785                 790                 795                 800

Arg Val Trp Lys Gly Ser Ser Val His Gln Asp Phe Leu Gly Phe Tyr
                805                 810                 815

Val Leu Asp Ser His Arg Met Ser Ala Arg Thr His Gly Leu Leu Gly
                820                 825                 830

Gln Phe Phe His Pro Ile Gly Phe Glu Val Ser Asp Ile His Pro Gly
                835                 840                 845

Ser Asp Pro Thr Lys Pro Asp Ala Thr Met Val Val Arg Asn Arg Arg
                850                 855                 860

Leu Thr Val Thr Arg Gly Leu Gln Lys Asp Tyr Ser Lys Asp Pro Trp
865                 870                 875                 880
```

```
His Gly Ala Glu Val Ser Cys Trp Phe Ile His Asn Gly Ala Gly
                885                 890                 895

Leu Ile Asp Gly Ala Tyr Thr Asp Tyr Ile Val Pro Asp Ile Phe
                900                 905                 910

<210> SEQ ID NO 28
<211> LENGTH: 946
<212> TYPE: PRT
<213> ORGANISM: Homo sapiens

<400> SEQUENCE: 28

Met Lys Arg Leu Thr Cys Phe Phe Ile Cys Phe Phe Leu Ser Glu Val
1               5                   10                  15

Ser Gly Phe Glu Ile Pro Ile Asn Gly Leu Ser Glu Phe Val Asp Tyr
                20                  25                  30

Glu Asp Leu Val Glu Leu Ala Pro Gly Lys Phe Gln Leu Val Ala Glu
            35                  40                  45

Asn Arg Arg Tyr Gln Arg Ser Leu Pro Gly Ser Glu Glu Met Met
        50                  55                  60

Glu Glu Val Asp Gln Val Thr Leu Tyr Ser Tyr Lys Val Gln Ser Thr
65                  70                  75                  80

Ile Thr Ser Arg Met Ala Thr Thr Met Ile Gln Ser Lys Val Val Asn
                85                  90                  95

Asn Ser Pro Gln Pro Gln Asn Val Val Phe Asp Val Gln Ile Pro Lys
                100                 105                 110

Gly Ala Phe Ile Ser Asn Phe Ser Met Thr Val Asp Gly Lys Thr Phe
            115                 120                 125

Arg Ser Ser Ile Lys Glu Lys Thr Val Gly Arg Ala Leu Tyr Ala Gln
130                 135                 140

Ala Arg Ala Lys Gly Lys Thr Ala Gly Leu Val Arg Ser Ser Ala Leu
145                 150                 155                 160

Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
                180                 185                 190

Ser Tyr Glu His Arg Ile Tyr Leu Gln Pro Gly Arg Leu Ala Lys His
            195                 200                 205

Leu Glu Val Asp Val Trp Val Ile Glu Pro Gln Gly Leu Arg Phe Leu
        210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Asn Cys Arg Glu Thr Ala Val Asp Gly Glu
                260                 265                 270

Leu Val Val Leu Tyr Asp Val Lys Arg Glu Glu Lys Ala Gly Glu Leu
            275                 280                 285

Glu Val Phe Asn Gly Tyr Phe Val His Phe Phe Ala Pro Asp Asn Leu
        290                 295                 300

Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
```

```
            340                 345                 350
Gln Asn Ile Arg Thr Trp Arg Asn Asp Leu Ile Ser Ala Thr Lys Thr
            355                 360                 365
Gln Val Ala Asp Ala Lys Arg Tyr Ile Glu Lys Ile Gln Pro Ser Gly
        370                 375                 380
Gly Thr Asn Ile Asn Glu Ala Leu Leu Arg Ala Ile Phe Ile Leu Asn
385                 390                 395                 400
Glu Ala Asn Asn Leu Gly Leu Leu Asp Pro Asn Ser Val Ser Leu Ile
                405                 410                 415
Ile Leu Val Ser Asp Gly Asp Pro Thr Val Gly Glu Leu Lys Leu Ser
                420                 425                 430
Lys Ile Gln Lys Asn Val Lys Glu Asn Ile Gln Asp Asn Ile Ser Leu
            435                 440                 445
Phe Ser Leu Gly Met Gly Phe Asp Val Asp Tyr Asp Phe Leu Lys Arg
        450                 455                 460
Leu Ser Asn Glu Asn His Gly Ile Ala Gln Arg Ile Tyr Gly Asn Gln
465                 470                 475                 480
Asp Thr Ser Ser Gln Leu Lys Lys Phe Tyr Asn Gln Val Ser Thr Pro
                485                 490                 495
Leu Leu Arg Asn Val Gln Phe Asn Tyr Pro His Thr Ser Val Thr Asp
                500                 505                 510
Val Thr Gln Asn Asn Phe His Asn Tyr Phe Gly Gly Ser Glu Ile Val
            515                 520                 525
Val Ala Gly Lys Phe Asp Pro Ala Lys Leu Asp Gln Ile Glu Ser Val
        530                 535                 540
Ile Thr Ala Thr Ser Ala Asn Thr Gln Leu Val Leu Glu Thr Leu Ala
545                 550                 555                 560
Gln Met Asp Asp Leu Gln Asp Phe Leu Ser Lys Asp Lys His Ala Asp
                565                 570                 575
Pro Asp Phe Thr Arg Lys Leu Trp Ala Tyr Leu Thr Ile Asn Gln Leu
                580                 585                 590
Leu Ala Glu Arg Ser Leu Ala Pro Thr Ala Ala Lys Arg Arg Ile
                595                 600                 605
Thr Arg Ser Ile Leu Gln Met Ser Leu Asp His His Ile Val Thr Pro
        610                 615                 620
Leu Thr Ser Leu Val Ile Glu Asn Glu Ala Gly Asp Glu Arg Met Leu
625                 630                 635                 640
Ala Asp Ala Pro Pro Gln Asp Pro Ser Cys Cys Ser Gly Ala Leu Tyr
                645                 650                 655
Tyr Gly Ser Lys Val Val Pro Asp Ser Thr Pro Ser Trp Ala Asn Pro
                660                 665                 670
Ser Pro Thr Pro Val Ile Ser Met Leu Ala Gln Gly Ser Gln Val Leu
            675                 680                 685
Glu Ser Thr Pro Pro His Val Met Arg Val Glu Asn Asp Pro His
        690                 695                 700
Phe Ile Ile Tyr Leu Pro Lys Ser Gln Lys Asn Ile Cys Phe Asn Ile
705                 710                 715                 720
Asp Ser Glu Pro Gly Lys Ile Leu Asn Leu Val Ser Asp Pro Glu Ser
                725                 730                 735
Gly Ile Val Val Asn Gly Gln Leu Val Gly Ala Lys Lys Pro Asn Asn
                740                 745                 750
Gly Lys Leu Ser Thr Tyr Phe Gly Lys Leu Gly Phe Tyr Phe Gln Ser
            755                 760                 765
```

```
Glu Asp Ile Lys Ile Glu Ile Ser Thr Glu Thr Ile Thr Leu Ser His
    770                 775                 780

Gly Ser Ser Thr Phe Ser Leu Ser Trp Ser Asp Thr Ala Gln Val Thr
785                 790                 795                 800

Asn Gln Arg Val Gln Ile Ser Val Lys Lys Glu Lys Val Thr Ile
                805                 810                 815

Thr Leu Asp Lys Glu Met Ser Phe Ser Val Leu Leu His Arg Val Trp
            820                 825                 830

Lys Lys His Pro Val Asn Val Asp Phe Leu Gly Ile Tyr Ile Pro Pro
        835                 840                 845

Thr Asn Lys Phe Ser Pro Lys Ala His Gly Leu Ile Gly Gln Phe Met
    850                 855                 860

Gln Glu Pro Lys Ile His Ile Phe Asn Glu Arg Pro Gly Lys Asp Pro
865                 870                 875                 880

Glu Lys Pro Glu Ala Ser Met Glu Val Lys Gly Gln Lys Leu Ile Ile
                885                 890                 895

Thr Arg Gly Leu Gln Lys Asp Tyr Arg Thr Asp Leu Val Phe Gly Thr
            900                 905                 910

Asp Val Thr Cys Trp Phe Val His Asn Ser Gly Lys Gly Phe Ile Asp
        915                 920                 925

Gly His Tyr Lys Asp Tyr Phe Val Pro Gln Leu Tyr Ser Phe Leu Lys
    930                 935                 940

Arg Pro
945

<210> SEQ ID NO 29
<211> LENGTH: 930
<212> TYPE: PRT
<213> ORGANISM: Homo sapiens

<400> SEQUENCE: 29

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Asn Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
```

-continued

```
                180                 185                 190
Phe Met Thr Asn Gln Leu Val Asp Ala Leu Thr Thr Trp Gln Asn Lys
            195                 200                 205
Thr Lys Ala His Ile Arg Phe Lys Pro Thr Leu Ser Gln Gln Gln Lys
        210                 215                 220
Ser Pro Glu Gln Gln Glu Thr Val Leu Asp Gly Asn Leu Ile Ile Arg
225                 230                 235                 240
Tyr Asp Val Asp Arg Ala Ile Ser Gly Gly Ser Ile Gln Ile Glu Asn
                245                 250                 255
Gly Tyr Phe Val His Tyr Phe Ala Pro Glu Gly Leu Thr Thr Met Pro
            260                 265                 270
Lys Asn Val Val Phe Val Ile Asp Lys Ser Gly Ser Met Ser Gly Arg
        275                 280                 285
Lys Ile Gln Gln Thr Arg Glu Ala Leu Ile Lys Ile Leu Asp Asp Leu
        290                 295                 300
Ser Pro Arg Asp Gln Phe Asn Leu Ile Val Phe Ser Thr Glu Ala Thr
305                 310                 315                 320
Gln Trp Arg Pro Ser Leu Val Pro Ala Ser Ala Glu Asn Val Asn Lys
                325                 330                 335
Ala Arg Ser Phe Ala Ala Gly Ile Gln Ala Leu Gly Gly Thr Asn Ile
                340                 345                 350
Asn Asp Ala Met Leu Met Ala Val Gln Leu Leu Asp Ser Ser Asn Gln
            355                 360                 365
Glu Glu Arg Leu Pro Glu Gly Ser Val Ser Leu Ile Ile Leu Leu Thr
        370                 375                 380
Asp Gly Asp Pro Thr Val Gly Glu Thr Asn Pro Arg Ser Ile Gln Asn
385                 390                 395                 400
Asn Val Arg Glu Ala Val Ser Gly Arg Tyr Ser Leu Phe Cys Leu Gly
                405                 410                 415
Phe Gly Phe Asp Val Ser Tyr Ala Phe Leu Glu Lys Leu Ala Leu Asp
            420                 425                 430
Asn Gly Gly Leu Ala Arg Arg Ile His Glu Asp Ser Asp Ser Ala Leu
        435                 440                 445
Gln Leu Gln Asp Phe Tyr Gln Glu Val Ala Asn Pro Leu Leu Thr Ala
        450                 455                 460
Val Thr Phe Glu Tyr Pro Ser Asn Ala Val Glu Glu Val Thr Gln Asn
465                 470                 475                 480
Asn Phe Arg Leu Leu Phe Lys Gly Ser Glu Met Val Val Ala Gly Lys
                485                 490                 495
Leu Gln Asp Arg Gly Pro Asp Val Leu Thr Ala Thr Val Ser Gly Lys
            500                 505                 510
Leu Pro Thr Gln Asn Ile Thr Phe Gln Thr Glu Ser Ser Val Ala Glu
        515                 520                 525
Gln Glu Ala Glu Phe Gln Ser Pro Lys Tyr Ile Phe His Asn Phe Met
        530                 535                 540
Glu Arg Leu Trp Ala Tyr Leu Thr Ile Gln Gln Leu Leu Glu Gln Thr
545                 550                 555                 560
Val Ser Ala Ser Asp Ala Asp Gln Gln Ala Leu Arg Asn Gln Ala Leu
                565                 570                 575
Asn Leu Ser Leu Ala Tyr Ser Phe Val Thr Pro Leu Thr Ser Met Val
            580                 585                 590
Val Thr Lys Pro Asp Asp Gln Glu Gln Ser Gln Val Ala Glu Lys Pro
        595                 600                 605
```

Met Glu Gly Glu Ser Arg Asn Arg Asn Val His Ser Gly Ser Thr Phe
        610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Thr Pro Ala Thr Ser Asn Pro
690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
        915                 920                 925

Glu Leu
930

<210> SEQ ID NO 30
<211> LENGTH: 564
<212> TYPE: PRT
<213> ORGANISM: Homo sapiens

<400> SEQUENCE: 30

Met Ala Ser Thr Ser Thr Thr Ile Arg Ser His Ser Ser Ser Arg Arg
1               5                   10                  15

Gly Phe Ser Ala Asn Ser Ala Arg Leu Pro Gly Val Ser Arg Ser Gly
            20                  25                  30

Phe Ser Ser Val Ser Val Ser Arg Ser Arg Gly Ser Gly Gly Leu Gly

```
            35                  40                  45
Gly Ala Cys Gly Gly Ala Gly Phe Gly Ser Arg Ser Leu Tyr Gly Leu
 50                  55                  60
Gly Gly Ser Lys Arg Ile Ser Ile Gly Gly Ser Cys Ala Ile Ser
 65                  70                  75                  80
Gly Gly Tyr Gly Ser Arg Ala Gly Gly Ser Tyr Gly Phe Gly Gly Ala
                 85                  90                  95
Gly Ser Gly Phe Gly Phe Gly Gly Ala Gly Ile Gly Phe Gly Leu
                100                 105                 110
Gly Gly Gly Ala Gly Leu Ala Gly Gly Phe Gly Gly Pro Gly Phe Pro
                115                 120                 125
Val Cys Pro Pro Gly Gly Ile Gln Glu Val Thr Val Asn Gln Ser Leu
    130                 135                 140
Leu Thr Pro Leu Asn Leu Gln Ile Asp Pro Thr Ile Gln Arg Val Arg
145                 150                 155                 160
Ala Glu Glu Arg Glu Gln Ile Lys Thr Leu Asn Asn Lys Phe Ala Ser
                165                 170                 175
Phe Ile Asp Lys Val Arg Phe Leu Glu Gln Gln Asn Lys Val Leu Glu
                180                 185                 190
Thr Lys Trp Thr Leu Leu Gln Glu Gln Gly Thr Lys Thr Val Arg Gln
                195                 200                 205
Asn Leu Glu Pro Leu Phe Glu Gln Tyr Ile Asn Asn Leu Arg Arg Gln
    210                 215                 220
Leu Asp Ser Ile Val Gly Glu Arg Gly Arg Leu Asp Ser Glu Leu Arg
225                 230                 235                 240
Gly Met Gln Asp Leu Val Glu Asp Phe Lys Asn Lys Tyr Glu Asp Glu
                245                 250                 255
Ile Asn Lys Arg Thr Ala Ala Glu Asn Glu Phe Val Thr Leu Lys Lys
                260                 265                 270
Asp Val Asp Ala Ala Tyr Met Asn Lys Val Glu Leu Gln Ala Lys Ala
    275                 280                 285
Asp Thr Leu Thr Asp Glu Ile Asn Phe Leu Arg Ala Leu Tyr Asp Ala
    290                 295                 300
Glu Leu Ser Gln Met Gln Thr His Ile Ser Asp Thr Ser Val Val Leu
305                 310                 315                 320
Ser Met Asp Asn Arg Asn Leu Asp Leu Asp Ser Ile Ile Ala Glu
                325                 330                 335
Val Lys Ala Gln Tyr Glu Glu Ile Ala Gln Arg Ser Arg Ala Glu Ala
                340                 345                 350
Glu Ser Trp Tyr Gln Thr Lys Tyr Glu Glu Leu Gln Val Thr Ala Gly
                355                 360                 365
Arg His Gly Asp Asp Leu Arg Asn Thr Lys Gln Glu Ile Ala Glu Ile
    370                 375                 380
Asn Arg Met Ile Gln Arg Leu Arg Ser Glu Ile Asp His Val Lys Lys
385                 390                 395                 400
Gln Cys Ala Asn Leu Gln Ala Ala Ile Ala Asp Ala Glu Gln Arg Gly
                405                 410                 415
Glu Met Ala Leu Lys Asp Ala Lys Asn Lys Leu Glu Gly Leu Glu Asp
                420                 425                 430
Ala Leu Gln Lys Ala Lys Gln Asp Leu Ala Arg Leu Leu Lys Glu Tyr
                435                 440                 445
Gln Glu Leu Met Asn Val Lys Leu Ala Leu Asp Val Glu Ile Ala Thr
    450                 455                 460
```

Tyr Arg Lys Leu Leu Glu Gly Glu Cys Arg Leu Asn Gly Glu Gly
465                 470                 475                 480

Val Gly Gln Val Asn Ile Ser Val Val Gln Ser Thr Val Ser Gly
                    485                 490                 495

Tyr Gly Gly Ala Ser Gly Val Gly Ser Gly Leu Gly Leu Gly Gly
                500                 505                 510

Ser Ser Tyr Ser Tyr Gly Ser Gly Leu Gly Val Gly Gly Phe Ser
            515                 520                 525

Ser Ser Ser Gly Arg Ala Ile Gly Gly Gly Leu Ser Ser Val Gly Gly
        530                 535                 540

Gly Ser Ser Thr Ile Lys Tyr Thr Thr Thr Ser Ser Ser Arg Lys
545                 550                 555                 560

Ser Tyr Lys His

<210> SEQ ID NO 31
<211> LENGTH: 128
<212> TYPE: PRT
<213> ORGANISM: Homo sapiens

<400> SEQUENCE: 31

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
            20                  25                  30

Leu Ala Ser Ser Thr Lys Gly Gln Thr Lys Arg Asn Leu Ala Lys Gly
                35                  40                  45

Lys Glu Glu Ser Leu Asp Ser Asp Leu Tyr Ala Glu Leu Arg Cys Met
50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
                100                 105                 110

Ile Lys Lys Ile Val Gln Lys Lys Leu Ala Gly Asp Glu Ser Ala Asp
                115                 120                 125

<210> SEQ ID NO 32
<211> LENGTH: 136
<212> TYPE: PRT
<213> ORGANISM: Homo sapiens

<400> SEQUENCE: 32

Met Pro Tyr Ser Val Ile Arg Gly Glu Val Phe Thr Leu Lys Ala Thr
1               5                   10                  15

Val Leu Asn Tyr Leu Pro Lys Cys Ile Arg Val Ser Val Gln Leu Lys
            20                  25                  30

Ala Ser Pro Ala Phe Leu Ala Ser Gln Asn Thr Lys Gly Glu Glu Ser
                35                  40                  45

Tyr Cys Ile Cys Gly Ser Glu Arg Gln Thr Leu Ser Trp Thr Val Thr
50                  55                  60

Pro Lys Thr Leu Gly Asn Val Asn Phe Ser Val Ser Ala Glu Ala Met
65                  70                  75                  80

Gln Ser Leu Glu Leu Cys Gly Asn Glu Val Val Glu Val Pro Glu Ile
                85                  90                  95

```
Lys Arg Lys Asp Thr Val Ile Lys Thr Leu Leu Val Glu Ala Glu Gly
            100                 105                 110

Ile Glu Gln Glu Lys Thr Phe Ser Ser Met Thr Cys Ala Ser Asp Glu
        115                 120                 125

Asp Ile Glu Pro Lys Arg Ala Ser
    130                 135

<210> SEQ ID NO 33
<211> LENGTH: 208
<212> TYPE: PRT
<213> ORGANISM: Homo sapiens

<400> SEQUENCE: 33

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Thr Met Arg
65                  70                  75                  80

Leu Phe Thr Gly Ile Val Phe Cys Ser Leu Val Met Gly Val Thr Ser
                85                  90                  95

Glu Ser Trp Arg Ser Phe Phe Lys Glu Ala Leu Gln Gly Val Gly Asp
            100                 105                 110

Met Gly Arg Ala Tyr Trp Asp Ile Met Ile Ser Asn His Gln Asn Ser
        115                 120                 125

Asn Arg Tyr Leu Tyr Ala Arg Gly Asn Tyr Asp Ala Ala Gln Arg Gly
    130                 135                 140

Pro Gly Gly Val Trp Ala Ala Lys Leu Ile Ser Arg Ser Arg Val Tyr
145                 150                 155                 160

Leu Gln Gly Leu Ile Asp Cys Tyr Leu Phe Gly Asn Ser Ser Thr Val
                165                 170                 175

Leu Glu Asp Ser Lys Ser Asn Glu Lys Ala Glu Glu Trp Gly Arg Ser
            180                 185                 190

Gly Lys Asp Pro Asp Arg Phe Arg Pro Asp Gly Leu Pro Lys Lys Tyr
        195                 200                 205

<210> SEQ ID NO 34
<211> LENGTH: 599
<212> TYPE: PRT
<213> ORGANISM: Homo sapiens

<400> SEQUENCE: 34

Met Lys Leu Leu Lys Leu Thr Gly Phe Ile Phe Phe Leu Phe Phe Leu
1               5                   10                  15

Thr Glu Ser Leu Thr Leu Pro Thr Gln Pro Arg Asp Ile Glu Asn Phe
            20                  25                  30

Asn Ser Thr Gln Lys Phe Ile Glu Asp Asn Ile Glu Tyr Ile Thr Ile
        35                  40                  45

Ile Ala Phe Ala Gln Tyr Val Gln Glu Ala Thr Phe Glu Glu Met Glu
    50                  55                  60

Lys Leu Val Lys Asp Met Val Glu Tyr Lys Asp Arg Cys Met Ala Asp
65                  70                  75                  80
```

```
Lys Thr Leu Pro Glu Cys Ser Lys Leu Pro Asn Asn Val Leu Gln Glu
             85                  90                  95

Lys Ile Cys Ala Met Glu Gly Leu Pro Gln Lys His Asn Phe Ser His
            100                 105                 110

Cys Cys Ser Lys Val Asp Ala Gln Arg Arg Leu Cys Phe Phe Tyr Asn
            115                 120                 125

Lys Lys Ser Asp Val Gly Phe Leu Pro Pro Phe Pro Thr Leu Asp Pro
            130                 135                 140

Glu Glu Lys Cys Gln Ala Tyr Glu Ser Asn Arg Glu Ser Leu Leu Asn
145                 150                 155                 160

His Phe Leu Tyr Glu Val Ala Arg Arg Asn Pro Phe Val Phe Ala Pro
                165                 170                 175

Thr Leu Leu Thr Val Ala Val His Phe Glu Glu Val Ala Lys Ser Cys
            180                 185                 190

Cys Glu Glu Gln Asn Lys Val Asn Cys Leu Gln Thr Arg Ala Ile Pro
            195                 200                 205

Val Thr Gln Tyr Leu Lys Ala Phe Ser Ser Tyr Gln Lys His Val Cys
            210                 215                 220

Gly Ala Leu Leu Lys Phe Gly Thr Lys Val Val His Phe Ile Tyr Ile
225                 230                 235                 240

Ala Ile Leu Ser Gln Lys Phe Pro Lys Ile Glu Phe Lys Glu Leu Ile
                245                 250                 255

Ser Leu Val Glu Asp Val Ser Ser Asn Tyr Asp Gly Cys Cys Glu Gly
            260                 265                 270

Asp Val Val Gln Cys Ile Arg Asp Thr Ser Lys Val Met Asn His Ile
            275                 280                 285

Cys Ser Lys Gln Asp Ser Ile Ser Ser Lys Ile Lys Glu Cys Cys Glu
            290                 295                 300

Lys Lys Ile Pro Glu Arg Gly Gln Cys Ile Ile Asn Ser Asn Lys Asp
305                 310                 315                 320

Asp Arg Pro Lys Asp Leu Ser Leu Arg Glu Gly Lys Phe Thr Asp Ser
                325                 330                 335

Glu Asn Val Cys Gln Glu Arg Asp Ala Asp Pro Asp Thr Phe Phe Ala
            340                 345                 350

Lys Phe Thr Phe Glu Tyr Ser Arg Arg His Pro Asp Leu Ser Ile Pro
            355                 360                 365

Glu Leu Leu Arg Ile Val Gln Ile Tyr Lys Asp Leu Leu Arg Asn Cys
            370                 375                 380

Cys Asn Thr Glu Asn Pro Pro Gly Cys Tyr Arg Tyr Ala Glu Asp Lys
385                 390                 395                 400

Phe Asn Glu Thr Thr Glu Lys Ser Leu Lys Met Val Gln Gln Glu Cys
                405                 410                 415

Lys His Phe Gln Asn Leu Gly Lys Asp Gly Leu Lys Tyr His Tyr Leu
            420                 425                 430

Ile Arg Leu Thr Lys Ile Ala Pro Gln Leu Ser Thr Glu Glu Leu Val
            435                 440                 445

Ser Leu Gly Glu Lys Met Val Thr Ala Phe Thr Thr Cys Cys Thr Leu
450                 455                 460

Ser Glu Glu Phe Ala Cys Val Asp Asn Leu Ala Asp Leu Val Phe Gly
465                 470                 475                 480

Glu Leu Cys Gly Val Asn Glu Asn Arg Thr Ile Asn Pro Ala Val Asp
                485                 490                 495

His Cys Cys Lys Thr Asn Phe Ala Phe Arg Arg Pro Cys Phe Glu Ser
```

```
                    500                 505                 510
Leu Lys Ala Asp Lys Thr Tyr Val Pro Pro Phe Ser Gln Asp Leu
                515                 520                 525

Phe Thr Phe His Ala Asp Met Cys Gln Ser Gln Asn Glu Glu Leu Gln
    530                 535                 540

Arg Lys Thr Asp Arg Phe Leu Val Asn Leu Val Lys Leu Lys His Glu
545                 550                 555                 560

Leu Thr Asp Glu Glu Leu Gln Ser Leu Phe Thr Asn Phe Ala Asn Val
                565                 570                 575

Val Asp Lys Cys Cys Lys Ala Glu Ser Pro Glu Val Cys Phe Asn Glu
                580                 585                 590

Glu Ser Pro Lys Ile Gly Asn
            595

<210> SEQ ID NO 35
<211> LENGTH: 433
<212> TYPE: PRT
<213> ORGANISM: Homo sapiens

<400> SEQUENCE: 35

Met Phe Ala Gly Cys Phe Phe Leu Leu Asn Gln Ser Arg Asn His
1               5                   10                  15

Pro Val Ser Leu Cys Asn Ser Ser Gly Arg Leu Gln Gln Ile Asn Lys
                20                  25                  30

Ala His His Pro Pro Trp Val Tyr Leu Ser Gln Gln Ser Thr Trp Val
                35                  40                  45

Gly Pro Glu Ala Ser Asn His Leu His Ala Cys Gly Leu Ser Gly
    50                  55                  60

Ala Ala Met Lys Ser Leu Val Leu Leu Leu Cys Leu Ala Gln Leu Trp
65                  70                  75                  80

Gly Cys His Ser Ala Pro His Gly Pro Gly Leu Ile Tyr Arg Gln Pro
                85                  90                  95

Asn Cys Asp Asp Pro Glu Thr Glu Glu Ala Ala Leu Val Ala Ile Asp
                100                 105                 110

Tyr Ile Asn Gln Asn Leu Pro Trp Gly Tyr Lys His Thr Leu Asn Gln
                115                 120                 125

Ile Asp Glu Val Lys Val Trp Pro Gln Gln Pro Ser Gly Glu Leu Phe
130                 135                 140

Glu Ile Glu Ile Asp Thr Leu Glu Thr Thr Cys His Val Leu Asp Pro
145                 150                 155                 160

Thr Pro Val Ala Arg Cys Ser Val Arg Gln Leu Lys Glu His Ala Val
                165                 170                 175

Glu Gly Asp Cys Asp Phe Gln Leu Leu Lys Leu Asp Gly Lys Phe Ser
                180                 185                 190

Val Val Tyr Ala Lys Cys Asp Ser Ser Pro Asp Ser Ala Glu Asp Val
                195                 200                 205

Arg Lys Val Cys Gln Asp Cys Pro Leu Leu Ala Pro Leu Asn Asp Thr
210                 215                 220

Arg Val Val His Ala Ala Lys Ala Ala Leu Ala Ala Phe Asn Ala Gln
225                 230                 235                 240

Asn Asn Gly Ser Asn Phe Gln Leu Glu Glu Ile Ser Arg Ala Gln Leu
                245                 250                 255

Val Pro Leu Pro Pro Ser Thr Tyr Val Glu Phe Thr Val Ser Gly Thr
                260                 265                 270
```

```
Asp Cys Val Ala Lys Glu Ala Thr Glu Ala Ala Lys Cys Asn Leu Leu
            275                 280                 285
Ala Glu Lys Gln Tyr Gly Phe Cys Lys Ala Thr Leu Ser Glu Lys Leu
        290                 295                 300
Gly Gly Ala Glu Val Ala Val Thr Cys Met Val Phe Gln Thr Gln Pro
305                 310                 315                 320
Val Ser Ser Gln Pro Gln Pro Glu Gly Ala Asn Glu Ala Val Pro Thr
                325                 330                 335
Pro Val Val Asp Pro Asp Ala Pro Ser Pro Pro Leu Gly Ala Pro
                340                 345                 350
Gly Leu Pro Pro Ala Gly Ser Pro Pro Asp Ser His Val Leu Leu Ala
        355                 360                 365
Ala Pro Pro Gly His Gln Leu His Arg Ala His Tyr Asp Leu Arg His
    370                 375                 380
Thr Phe Met Gly Val Val Ser Leu Gly Ser Pro Ser Gly Glu Val Ser
385                 390                 395                 400
His Pro Arg Lys Thr Arg Thr Val Gln Pro Ser Val Gly Ala Ala
                405                 410                 415
Ala Gly Pro Val Val Pro Pro Cys Pro Gly Arg Ile Arg His Phe Lys
        420                 425                 430
Val

<210> SEQ ID NO 36
<211> LENGTH: 352
<212> TYPE: PRT
<213> ORGANISM: Homo sapiens

<400> SEQUENCE: 36

Met Arg Ser Leu Gly Ala Leu Leu Leu Leu Ser Ala Cys Leu Ala
1               5                   10                  15
Val Ser Ala Gly Pro Val Pro Thr Pro Pro Asp Asn Ile Gln Val Gln
            20                  25                  30
Glu Asn Phe Asn Ile Ser Arg Ile Tyr Gly Lys Trp Tyr Asn Leu Ala
        35                  40                  45
Ile Gly Ser Thr Cys Pro Trp Leu Lys Lys Ile Met Asp Arg Met Thr
    50                  55                  60
Val Ser Thr Leu Val Leu Gly Glu Gly Ala Thr Glu Ala Glu Ile Ser
65                  70                  75                  80
Met Thr Ser Thr Arg Trp Arg Lys Gly Val Cys Glu Glu Thr Ser Gly
                85                  90                  95
Ala Tyr Glu Lys Thr Asp Thr Asp Gly Lys Phe Leu Tyr His Lys Ser
            100                 105                 110
Lys Trp Asn Ile Thr Met Glu Ser Tyr Val Val His Thr Asn Tyr Asp
        115                 120                 125
Glu Tyr Ala Ile Phe Leu Thr Lys Lys Phe Ser Arg His His Gly Pro
    130                 135                 140
Thr Ile Thr Ala Lys Leu Tyr Gly Arg Ala Pro Gln Leu Arg Glu Thr
145                 150                 155                 160
Leu Leu Gln Asp Phe Arg Val Val Ala Gln Gly Val Gly Ile Pro Glu
                165                 170                 175
Asp Ser Ile Phe Thr Met Ala Asp Arg Gly Glu Cys Val Pro Gly Glu
            180                 185                 190
Gln Glu Pro Glu Pro Ile Leu Ile Pro Arg Val Arg Arg Ala Val Leu
        195                 200                 205
```

```
Pro Gln Glu Glu Glu Gly Ser Gly Gly Gln Leu Val Thr Glu Val
    210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
                260                 265                 270

Thr Glu Lys Glu Cys Leu Gln Thr Cys Arg Thr Val Ala Ala Cys Asn
            275                 280                 285

Leu Pro Ile Val Arg Gly Pro Cys Arg Ala Phe Ile Gln Leu Trp Ala
290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Cys Arg Glu Tyr
                325                 330                 335

Cys Gly Val Pro Gly Asp Gly Asp Glu Glu Leu Leu Arg Phe Ser Asn
                340                 345                 350

<210> SEQ ID NO 37
<211> LENGTH: 223
<212> TYPE: PRT
<213> ORGANISM: Homo sapiens

<400> SEQUENCE: 37

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
                20                  25                  30

Glu Ser Val Thr Asp His Val Asn Leu Ile Thr Pro Leu Glu Lys Pro
            35                  40                  45

Leu Gln Asn Phe Thr Leu Cys Phe Arg Ala Tyr Ser Asp Leu Ser Arg
    50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
                100                 105                 110

Ile Cys Val Ser Trp Glu Ser Ser Gly Ile Ala Glu Phe Trp Ile
            115                 120                 125

Asn Gly Thr Pro Leu Val Lys Lys Gly Leu Arg Gln Gly Tyr Phe Val
    130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
                180                 185                 190

Gln Gly Thr Pro Leu Pro Ala Asn Ile Leu Asp Trp Gln Ala Leu Asn
            195                 200                 205

Tyr Glu Ile Arg Gly Tyr Val Ile Ile Lys Pro Leu Val Trp Val
    210                 215                 220

<210> SEQ ID NO 38
```

<211> LENGTH: 267
<212> TYPE: PRT
<213> ORGANISM: Homo sapiens

<400> SEQUENCE: 38

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 39
<211> LENGTH: 189
<212> TYPE: PRT
<213> ORGANISM: Homo sapiens

<400> SEQUENCE: 39

Met Val Met Leu Leu Leu Leu Ser Ala Leu Ala Gly Leu Phe Gly
1               5                   10                  15

Ala Ala Glu Gly Gln Ala Phe His Leu Gly Lys Cys Pro Asn Pro Pro
            20                  25                  30

Val Gln Glu Asn Phe Asp Val Asn Lys Tyr Leu Gly Arg Trp Tyr Glu
        35                  40                  45

Ile Glu Lys Ile Pro Thr Thr Phe Glu Asn Gly Arg Cys Ile Gln Ala
    50                  55                  60

Asn Tyr Ser Leu Met Glu Asn Gly Lys Ile Lys Val Leu Asn Gln Glu
65                  70                  75                  80

```
Leu Arg Ala Asp Gly Thr Val Asn Gln Ile Glu Gly Glu Ala Thr Pro
                85                  90                  95

Val Asn Leu Thr Glu Pro Ala Lys Leu Glu Val Lys Phe Ser Trp Phe
            100                 105                 110

Met Pro Ser Ala Pro Tyr Trp Ile Leu Ala Thr Asp Tyr Glu Asn Tyr
            115                 120                 125

Ala Leu Val Tyr Ser Cys Thr Cys Ile Ile Gln Leu Phe His Val Asp
        130                 135                 140

Phe Ala Trp Ile Leu Ala Arg Asn Pro Asn Leu Pro Pro Glu Thr Val
145                 150                 155                 160

Asp Ser Leu Lys Asn Ile Leu Thr Ser Asn Asn Ile Asp Val Lys Lys
                165                 170                 175

Met Thr Val Thr Asp Gln Val Asn Cys Pro Lys Leu Ser
            180                 185

<210> SEQ ID NO 40
<211> LENGTH: 1429
<212> TYPE: PRT
<213> ORGANISM: Homo sapiens

<400> SEQUENCE: 40

Met Val Ala Ala Ala Ala Thr Glu Ala Arg Leu Arg Arg Thr
1               5                   10                  15

Ala Ala Thr Ala Ala Leu Ala Gly Arg Ser Gly Gly Pro His Trp Asp
            20                  25                  30

Trp Asp Val Thr Arg Ala Gly Arg Pro Gly Leu Gly Ala Gly Leu Arg
        35                  40                  45

Leu Pro Arg Leu Leu Ser Pro Pro Leu Arg Pro Arg Leu Leu Leu Leu
    50                  55                  60

Leu Leu Leu Leu Ser Pro Pro Leu Leu Leu Leu Leu Pro Cys Glu
65                  70                  75                  80

Ala Glu Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
            100                 105                 110

Pro Gly Thr Gly Gln Cys Val Cys Pro Ala Gly Trp Val Gly Glu Gln
            115                 120                 125

Cys Gln His Cys Gly Gly Arg Phe Arg Leu Thr Gly Ser Ser Gly Phe
        130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
            180                 185                 190

Ser Ile Tyr Ala Pro Leu Val Ala Ala Phe Ser Gly Leu Ile Val Pro
        195                 200                 205

Glu Arg Asp Gly Asn Glu Thr Val Pro Glu Val Val Ala Thr Ser Gly
    210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Asp Thr Val Glu Cys Glu
```

-continued

```
                260                 265                 270
Cys Ser Glu Asn Trp Lys Gly Glu Ala Cys Asp Ile Pro His Cys Thr
            275                 280                 285
Asp Asn Cys Gly Phe Pro His Arg Gly Ile Cys Asn Ser Ser Asp Val
        290                 295                 300
Arg Gly Cys Ser Cys Phe Ser Asp Trp Gln Pro Gly Cys Ser Val
305                 310                 315                 320
Pro Val Pro Ala Asn Gln Ser Phe Trp Thr Arg Glu Tyr Ser Asn
                325                 330                 335
Leu Lys Leu Pro Arg Ala Ser His Lys Ala Val Asn Gly Asn Ile
            340                 345                 350
Met Trp Val Val Gly Gly Tyr Met Phe Asn His Ser Asp Tyr Asn Met
        355                 360                 365
Val Leu Ala Tyr Asp Leu Ala Ser Arg Glu Trp Leu Pro Leu Asn Arg
    370                 375                 380
Ser Val Asn Asn Val Val Val Arg Tyr Gly His Ser Leu Ala Leu Tyr
385                 390                 395                 400
Lys Asp Lys Ile Tyr Met Tyr Gly Gly Lys Ile Asp Ser Thr Gly Asn
                405                 410                 415
Val Thr Asn Glu Leu Arg Val Phe His Ile His Asn Glu Ser Trp Val
            420                 425                 430
Leu Leu Thr Pro Lys Ala Lys Glu Gln Tyr Ala Val Val Gly His Ser
        435                 440                 445
Ala His Ile Val Thr Leu Lys Asn Gly Arg Val Met Leu Val Ile
    450                 455                 460
Phe Gly His Cys Pro Leu Tyr Gly Tyr Ile Ser Asn Val Gln Glu Tyr
465                 470                 475                 480
Asp Leu Asp Lys Asn Thr Trp Ser Ile Leu His Thr Gln Gly Ala Leu
                485                 490                 495
Val Gln Gly Gly Tyr Gly His Ser Ser Val Tyr Asp His Arg Thr Arg
            500                 505                 510
Ala Leu Tyr Val His Gly Gly Tyr Lys Ala Phe Ser Ala Asn Lys Tyr
        515                 520                 525
Arg Leu Ala Asp Asp Leu Tyr Arg Tyr Asp Val Asp Thr Gln Met Trp
    530                 535                 540
Thr Ile Leu Lys Asp Ser Arg Phe Phe Arg Tyr Leu His Thr Ala Val
545                 550                 555                 560
Ile Val Ser Gly Thr Met Leu Val Phe Gly Gly Asn Thr His Asn Asp
                565                 570                 575
Thr Ser Met Ser His Gly Ala Lys Cys Phe Ser Ser Asp Phe Met Ala
            580                 585                 590
Tyr Asp Ile Ala Cys Asp Arg Trp Ser Val Leu Pro Arg Pro Asp Leu
        595                 600                 605
His His Asp Val Asn Arg Phe Gly His Ser Ala Val Leu His Asn Ser
    610                 615                 620
Thr Met Tyr Val Phe Gly Gly Phe Asn Ser Leu Leu Leu Ser Asp Ile
625                 630                 635                 640
Leu Val Phe Thr Ser Glu Gln Cys Asp Ala His Arg Ser Glu Ala Ala
                645                 650                 655
Cys Leu Ala Ala Gly Pro Gly Ile Arg Cys Val Trp Asn Thr Gly Ser
            660                 665                 670
Ser Gln Cys Ile Ser Trp Ala Leu Ala Thr Asp Glu Gln Glu Lys
        675                 680                 685
```

```
Leu Lys Ser Glu Cys Phe Ser Lys Arg Thr Leu Asp His Asp Arg Cys
690                 695                 700

Asp Gln His Thr Asp Cys Tyr Ser Cys Thr Ala Asn Thr Asn Asp Cys
705                 710                 715                 720

His Trp Cys Asn Asp His Cys Val Pro Arg Asn His Ser Cys Ser Glu
            725                 730                 735

Gly Gln Ile Ser Ile Phe Arg Tyr Glu Asn Cys Pro Lys Asp Asn Pro
            740                 745                 750

Met Tyr Tyr Cys Asn Lys Lys Thr Ser Cys Arg Ser Cys Ala Leu Asp
            755                 760                 765

Gln Asn Cys Gln Trp Glu Pro Arg Asn Gln Glu Cys Ile Ala Leu Pro
770                 775                 780

Glu Asn Ile Cys Gly Ile Gly Trp His Leu Val Gly Asn Ser Cys Leu
785                 790                 795                 800

Lys Ile Thr Thr Ala Lys Glu Asn Tyr Asp Asn Ala Lys Leu Phe Cys
            805                 810                 815

Arg Asn His Asn Ala Leu Leu Ala Ser Leu Thr Thr Gln Lys Lys Val
            820                 825                 830

Glu Phe Val Leu Lys Gln Leu Arg Ile Met Gln Ser Ser Gln Ser Met
            835                 840                 845

Ser Lys Leu Thr Leu Thr Pro Trp Val Gly Leu Arg Lys Ile Asn Val
850                 855                 860

Ser Tyr Trp Cys Trp Glu Asp Met Ser Pro Phe Thr Asn Ser Leu Leu
865                 870                 875                 880

Gln Trp Met Pro Ser Glu Pro Ser Asp Ala Gly Phe Cys Gly Ile Leu
            885                 890                 895

Ser Glu Pro Ser Thr Arg Gly Leu Lys Ala Ala Thr Cys Ile Asn Pro
            900                 905                 910

Leu Asn Gly Ser Val Cys Glu Arg Pro Ala Asn His Ser Ala Lys Gln
            915                 920                 925

Cys Arg Thr Pro Cys Ala Leu Arg Thr Ala Cys Gly Asp Cys Thr Ser
            930                 935                 940

Gly Ser Ser Glu Cys Met Trp Cys Ser Asn Met Lys Gln Cys Val Asp
945                 950                 955                 960

Ser Asn Ala Tyr Val Ala Ser Phe Pro Phe Gly Gln Cys Met Glu Trp
            965                 970                 975

Tyr Thr Met Ser Thr Cys Pro Pro Glu Asn Cys Ser Gly Tyr Cys Thr
            980                 985                 990

Cys Ser His Cys Leu Glu Gln Pro Gly Cys Gly Trp Cys Thr Asp Pro
            995                 1000                1005

Ser Asn Thr Gly Lys Gly Lys Cys Ile Glu Gly Ser Tyr Lys Gly Pro
            1010                1015                1020

Val Lys Met Pro Ser Gln Ala Pro Thr Gly Asn Phe Tyr Pro Gln Pro
1025                1030                1035                1040

Leu Leu Asn Ser Ser Met Cys Leu Glu Asp Ser Arg Tyr Asn Trp Ser
            1045                1050                1055

Phe Ile His Cys Pro Ala Cys Gln Cys Asn Gly His Ser Lys Cys Ile
            1060                1065                1070

Asn Gln Ser Ile Cys Glu Lys Cys Glu Asn Leu Thr Thr Gly Lys His
            1075                1080                1085

Cys Glu Thr Cys Ile Ser Gly Phe Tyr Gly Asp Pro Thr Asn Gly Gly
            1090                1095                1100
```

```
Lys Cys Gln Pro Cys Lys Cys Asn Gly His Ala Ser Leu Cys Asn Thr
1105                1110                1115                1120

Asn Thr Gly Lys Cys Phe Cys Thr Thr Lys Gly Val Lys Gly Asp Glu
            1125                1130                1135

Cys Gln Leu Cys Glu Val Glu Asn Arg Tyr Gln Gly Asn Pro Leu Arg
            1140                1145                1150

Gly Thr Cys Tyr Tyr Thr Leu Leu Ile Asp Tyr Gln Phe Thr Phe Ser
            1155                1160                1165

Leu Ser Gln Glu Asp Asp Arg Tyr Tyr Thr Ala Ile Asn Phe Val Ala
        1170                1175                1180

Thr Pro Asp Glu Gln Asn Arg Asp Leu Asp Met Phe Ile Asn Ala Ser
1185                1190                1195                1200

Lys Asn Phe Asn Leu Asn Ile Thr Trp Ala Ala Ser Phe Ser Ala Gly
            1205                1210                1215

Thr Gln Ala Gly Glu Glu Met Pro Val Val Ser Lys Thr Asn Ile Lys
            1220                1225                1230

Glu Tyr Lys Asp Ser Phe Ser Asn Glu Lys Phe Asp Phe Arg Asn His
            1235                1240                1245

Pro Asn Ile Thr Phe Phe Val Tyr Val Ser Asn Phe Thr Trp Pro Ile
        1250                1255                1260

Lys Ile Gln Ile Ala Phe Ser Gln His Ser Asn Phe Met Asp Leu Val
1265                1270                1275                1280

Gln Phe Phe Val Thr Phe Ser Cys Phe Leu Ser Leu Leu Leu Leu Val
            1285                1290                1295

Ala Ala Val Val Trp Lys Ile Lys Gln Ser Cys Trp Ala Ser Arg Arg
            1300                1305                1310

Arg Glu Gln Leu Leu Arg Glu Met Gln Gln Met Ala Ser Arg Pro Phe
            1315                1320                1325

Ala Ser Val Asn Val Ala Leu Glu Thr Asp Glu Glu Pro Pro Asp Leu
            1330                1335                1340

Ile Gly Gly Ser Ile Lys Thr Val Pro Lys Pro Ile Ala Leu Glu Pro
1345                1350                1355                1360

Cys Phe Gly Asn Lys Ala Ala Val Leu Ser Val Phe Val Arg Leu Pro
            1365                1370                1375

Arg Gly Leu Gly Gly Ile Pro Pro Gly Gln Ser Gly Leu Ala Val
            1380                1385                1390

Ala Ser Ala Leu Val Asp Ile Ser Gln Gln Met Pro Ile Val Tyr Lys
            1395                1400                1405

Glu Lys Ser Gly Ala Val Arg Asn Arg Lys Gln Gln Pro Pro Ala Gln
            1410                1415                1420

Pro Gly Thr Cys Ile
1425

<210> SEQ ID NO 41
<211> LENGTH: 291
<212> TYPE: PRT
<213> ORGANISM: Homo sapiens

<400> SEQUENCE: 41

Leu Leu Ser Leu Leu Leu Leu Gly Pro Ala Val Pro Gln Glu Asn
1                5                  10                  15

Gln Asp Gly Arg Tyr Ser Leu Thr Tyr Ile Tyr Thr Gly Leu Ser Lys
            20                  25                  30

His Val Glu Asp Val Pro Ala Phe Gln Ala Leu Gly Ser Leu Asn Asp
        35                  40                  45
```

Leu Gln Phe Phe Arg Tyr Asn Ser Lys Asp Arg Lys Ser Gln Pro Met
            50                  55                  60

Gly Leu Trp Arg Gln Val Glu Gly Met Glu Asp Trp Lys Gln Asp Ser
65                  70                  75                  80

Gln Leu Gln Lys Ala Arg Glu Asp Ile Phe Met Glu Thr Leu Lys Asp
                85                  90                  95

Ile Val Glu Tyr Tyr Asn Asp Ser Asn Gly Ser His Val Leu Gln Gly
            100                 105                 110

Arg Phe Gly Cys Glu Ile Glu Asn Asn Arg Ser Ser Gly Ala Phe Trp
        115                 120                 125

Lys Tyr Tyr Tyr Asp Gly Lys Asp Tyr Ile Glu Phe Asn Lys Glu Ile
    130                 135                 140

Pro Ala Trp Val Pro Phe Asp Pro Ala Ala Gln Ile Thr Lys Gln Lys
145                 150                 155                 160

Trp Glu Ala Glu Pro Val Tyr Val Gln Arg Ala Lys Ala Tyr Leu Glu
                165                 170                 175

Glu Glu Cys Pro Ala Thr Leu Arg Lys Tyr Leu Lys Tyr Ser Lys Asn
            180                 185                 190

Ile Leu Asp Arg Gln Asp Pro Pro Ser Val Val Val Thr Ser His Gln
        195                 200                 205

Ala Pro Gly Glu Lys Lys Lys Leu Lys Cys Leu Ala Tyr Asp Phe Tyr
    210                 215                 220

Pro Gly Lys Ile Asp Val His Trp Thr Arg Ala Gly Glu Val Gln Glu
225                 230                 235                 240

Pro Glu Leu Arg Gly Asp Val Leu His Asn Gly Asn Gly Thr Tyr Gln
                245                 250                 255

Ser Trp Val Val Val Ala Val Pro Pro Gln Asp Thr Ala Pro Tyr Ser
            260                 265                 270

Cys His Val Gln His Ser Ser Leu Ala Gln Pro Leu Val Val Pro Trp
        275                 280                 285

Glu Ala Ser
    290

<210> SEQ ID NO 42
<211> LENGTH: 245
<212> TYPE: PRT
<213> ORGANISM: Homo sapiens

<400> SEQUENCE: 42

Met Asp Val Gly Pro Ser Ser Leu Pro His Leu Gly Leu Lys Leu Leu
1               5                   10                  15

Leu Leu Leu Leu Leu Leu Pro Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr

```
                115                 120                 125
His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
                245

<210> SEQ ID NO 43
<211> LENGTH: 1744
<212> TYPE: PRT
<213> ORGANISM: Homo sapiens

<400> SEQUENCE: 43

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240
```

```
Phe Glu Val Lys Ile Thr Pro Gly Lys Pro Tyr Ile Leu Thr Val Pro
                245                 250                 255
Gly His Leu Asp Glu Met Gln Leu Asp Ile Gln Ala Arg Tyr Ile Tyr
                260                 265                 270
Gly Lys Pro Val Gln Gly Val Ala Tyr Val Arg Phe Gly Leu Leu Asp
                275                 280             285
Glu Asp Gly Lys Lys Thr Phe Phe Arg Gly Leu Glu Ser Gln Thr Lys
            290                 295                 300
Leu Val Asn Gly Gln Ser His Ile Ser Leu Ser Lys Ala Glu Phe Gln
305                 310                 315                 320
Asp Ala Leu Glu Lys Leu Asn Met Gly Ile Thr Asp Leu Gln Gly Leu
                325                 330                 335
Arg Leu Tyr Val Ala Ala Ile Ile Glu Tyr Pro Gly Gly Glu Met
                340                 345             350
Glu Glu Ala Glu Leu Thr Ser Trp Tyr Phe Val Ser Ser Pro Phe Ser
            355                 360                 365
Leu Asp Leu Ser Lys Thr Lys Arg His Leu Val Pro Gly Ala Pro Phe
370                 375                 380
Leu Leu Gln Ala Leu Val Arg Glu Met Ser Gly Ser Pro Ala Ser Gly
385                 390                 395                 400
Ile Pro Val Lys Val Ser Ala Thr Val Ser Pro Gly Ser Val Pro
                405                 410                 415
Glu Val Gln Asp Ile Gln Gln Asn Thr Asp Gly Ser Gly Gln Val Ser
                420                 425                 430
Ile Pro Ile Ile Ile Pro Gln Thr Ile Ser Glu Leu Gln Leu Ser Val
                435                 440                 445
Ser Ala Gly Ser Pro His Pro Ala Ile Ala Arg Leu Thr Val Ala Ala
                450                 455                 460
Pro Pro Ser Gly Gly Pro Gly Phe Leu Ser Ile Glu Arg Pro Asp Ser
465                 470                 475                 480
Arg Pro Pro Arg Val Gly Asp Thr Leu Asn Leu Asn Leu Arg Ala Val
                485                 490                 495
Gly Ser Gly Ala Thr Phe Ser His Tyr Tyr Tyr Met Ile Leu Ser Arg
                500                 505                 510
Gly Gln Ile Val Phe Met Asn Arg Glu Pro Lys Arg Thr Leu Thr Ser
            515                 520                 525
Val Ser Val Phe Val Asp His His Leu Ala Pro Ser Phe Tyr Phe Val
            530                 535                 540
Ala Phe Tyr Tyr His Gly Asp His Pro Val Ala Asn Ser Leu Arg Val
545                 550                 555                 560
Asp Val Gln Ala Gly Ala Cys Glu Gly Lys Leu Glu Leu Ser Val Asp
                565                 570                 575
Gly Ala Lys Gln Tyr Arg Asn Gly Glu Ser Val Lys Leu His Leu Glu
                580                 585                 590
Thr Asp Ser Leu Ala Leu Val Ala Leu Gly Ala Leu Asp Thr Ala Leu
            595                 600                 605
Tyr Ala Ala Gly Ser Lys Ser His Lys Pro Leu Asn Met Gly Lys Val
            610                 615                 620
Phe Glu Ala Met Asn Ser Tyr Asp Leu Gly Cys Gly Pro Gly Gly Gly
625                 630                 635                 640
Asp Ser Ala Leu Gln Val Phe Gln Ala Ala Gly Leu Ala Phe Ser Asp
                645                 650                 655
Gly Asp Gln Trp Thr Leu Ser Arg Lys Arg Leu Ser Cys Pro Lys Glu
```

```
                660             665             670
Lys Thr Thr Arg Lys Arg Asn Val Asn Phe Gln Lys Ala Ile Asn
            675             680             685
Glu Lys Leu Gly Gln Tyr Ala Ser Pro Thr Ala Lys Arg Cys Cys Gln
        690             695             700
Asp Gly Val Thr Arg Leu Pro Met Met Arg Ser Cys Glu Gln Arg Ala
705             710             715             720
Ala Arg Val Gln Gln Pro Asp Cys Arg Glu Pro Phe Leu Ser Cys Cys
                725             730             735
Gln Phe Ala Glu Ser Leu Arg Lys Lys Ser Arg Asp Lys Gly Gln Ala
            740             745             750
Gly Leu Gln Arg Ala Leu Glu Ile Leu Gln Glu Asp Leu Ile Asp
        755             760             765
Glu Asp Asp Ile Pro Val Arg Ser Phe Pro Glu Asn Trp Leu Trp
770             775             780
Arg Val Glu Thr Val Asp Arg Phe Gln Ile Leu Thr Leu Trp Leu Pro
785             790             795             800
Asp Ser Leu Thr Thr Trp Glu Ile His Gly Leu Ser Leu Ser Lys Thr
            805             810             815
Lys Gly Leu Cys Val Ala Thr Pro Val Gln Leu Arg Val Phe Arg Glu
            820             825             830
Phe His Leu His Leu Arg Leu Pro Met Ser Val Arg Arg Phe Glu Gln
        835             840             845
Leu Glu Leu Arg Pro Val Leu Tyr Asn Tyr Leu Asp Lys Asn Leu Thr
    850             855             860
Val Ser Val His Val Ser Pro Val Glu Gly Leu Cys Leu Ala Gly Gly
865             870             875             880
Gly Gly Leu Ala Gln Gln Val Leu Val Pro Ala Gly Ser Ala Arg Pro
            885             890             895
Val Ala Phe Ser Val Val Pro Thr Ala Ala Ala Val Ser Leu Lys
            900             905             910
Val Val Ala Arg Gly Ser Phe Glu Phe Pro Val Gly Asp Ala Val Ser
        915             920             925
Lys Val Leu Gln Ile Glu Lys Glu Gly Ala Ile His Arg Glu Glu Leu
        930             935             940
Val Tyr Glu Leu Asn Pro Leu Asp His Arg Gly Arg Thr Leu Glu Ile
945             950             955             960
Pro Gly Asn Ser Asp Pro Asn Met Ile Pro Asp Gly Asp Phe Asn Ser
            965             970             975
Tyr Val Arg Val Thr Ala Ser Asp Pro Leu Asp Thr Leu Gly Ser Glu
            980             985             990
Gly Ala Leu Ser Pro Gly Gly Val Ala Ser Leu Leu Arg Leu Pro Arg
        995             1000            1005
Gly Cys Gly Glu Gln Thr Met Ile Tyr Leu Ala Pro Thr Leu Ala Ala
    1010            1015            1020
Ser Arg Tyr Leu Asp Lys Thr Glu Gln Trp Ser Thr Leu Pro Pro Glu
1025            1030            1035            1040
Thr Lys Asp His Ala Val Asp Leu Ile Gln Lys Gly Tyr Met Arg Ile
            1045            1050            1055
Gln Gln Phe Arg Lys Ala Asp Gly Ser Tyr Ala Ala Trp Leu Ser Arg
        1060            1065            1070
Asp Ser Ser Thr Trp Leu Thr Ala Phe Val Leu Lys Val Leu Ser Leu
            1075            1080            1085
```

-continued

```
Ala Gln Glu Gln Val Gly Gly Ser Pro Glu Lys Leu Gln Glu Thr Ser
    1090                1095                1100

Asn Trp Leu Leu Ser Gln Gln Ala Asp Gly Ser Phe Gln Asp Pro
1105                1110                1115                1120

Cys Pro Val Leu Asp Arg Ser Met Gln Gly Gly Leu Val Gly Asn Asp
                1125                1130                1135

Glu Thr Val Ala Leu Thr Ala Phe Val Thr Ile Ala Leu His His Gly
            1140                1145                1150

Leu Ala Val Phe Gln Asp Glu Gly Ala Glu Pro Leu Lys Gln Arg Val
        1155                1160                1165

Glu Ala Ser Ile Ser Lys Ala Asn Ser Phe Leu Gly Glu Lys Ala Ser
    1170                1175                1180

Ala Gly Leu Leu Gly Ala His Ala Ala Ile Thr Ala Tyr Ala Leu
1185                1190                1195                1200

Thr Leu Thr Lys Ala Pro Val Asp Leu Leu Gly Val Ala His Asn Asn
                1205                1210                1215

Leu Met Ala Met Ala Gln Glu Thr Gly Asp Asn Leu Tyr Trp Gly Ser
            1220                1225                1230

Val Thr Gly Ser Gln Ser Asn Ala Val Ser Pro Thr Pro Ala Pro Arg
        1235                1240                1245

Asn Pro Ser Asp Pro Met Pro Gln Ala Pro Ala Leu Trp Ile Glu Thr
    1250                1255                1260

Thr Ala Tyr Ala Leu Leu His Leu Leu Leu His Glu Gly Lys Ala Glu
1265                1270                1275                1280

Met Ala Asp Gln Ala Ala Ala Trp Leu Thr Arg Gln Gly Ser Phe Gln
                1285                1290                1295

Gly Gly Phe Arg Ser Thr Gln Asp Thr Val Ile Ala Leu Asp Ala Leu
            1300                1305                1310

Ser Ala Tyr Trp Ile Ala Ser His Thr Thr Glu Glu Arg Gly Leu Asn
        1315                1320                1325

Val Thr Leu Ser Ser Thr Gly Arg Asn Gly Phe Lys Ser His Ala Leu
    1330                1335                1340

Gln Leu Asn Asn Arg Gln Ile Arg Gly Leu Glu Glu Glu Leu Gln Phe
1345                1350                1355                1360

Ser Leu Gly Ser Lys Ile Asn Val Lys Val Gly Gly Asn Ser Lys Gly
                1365                1370                1375

Thr Leu Lys Val Leu Arg Thr Tyr Asn Val Leu Asp Met Lys Asn Thr
            1380                1385                1390

Thr Cys Gln Asp Leu Gln Ile Glu Val Thr Val Lys Gly His Val Glu
        1395                1400                1405

Tyr Thr Met Glu Ala Asn Glu Asp Tyr Glu Asp Tyr Glu Tyr Asp Glu
    1410                1415                1420

Leu Pro Ala Lys Asp Asp Pro Asp Ala Pro Leu Gln Pro Val Thr Pro
1425                1430                1435                1440

Leu Gln Leu Phe Glu Gly Arg Arg Asn Arg Arg Arg Arg Glu Ala Pro
                1445                1450                1455

Lys Val Val Glu Glu Gln Glu Ser Arg Val His Tyr Thr Val Cys Ile
            1460                1465                1470

Trp Arg Asn Gly Lys Val Gly Leu Ser Gly Met Ala Ile Ala Asp Val
        1475                1480                1485

Thr Leu Leu Ser Gly Phe His Ala Leu Arg Ala Asp Leu Glu Lys Leu
    1490                1495                1500
```

```
Thr Ser Leu Ser Asp Arg Tyr Val Ser His Phe Glu Thr Glu Gly Pro
1505                1510                1515                1520

His Val Leu Leu Tyr Phe Asp Ser Val Pro Thr Ser Arg Glu Cys Val
                1525                1530                1535

Gly Phe Glu Ala Val Gln Glu Val Pro Val Gly Leu Val Gln Pro Ala
                1540                1545                1550

Ser Ala Thr Leu Tyr Asp Tyr Tyr Asn Pro Glu Arg Arg Cys Ser Val
                1555                1560                1565

Phe Tyr Gly Ala Pro Ser Lys Ser Arg Leu Leu Ala Thr Leu Cys Ser
                1570                1575                1580

Ala Glu Val Cys Gln Cys Ala Glu Gly Lys Cys Pro Arg Gln Arg Arg
1585                1590                1595                1600

Ala Leu Glu Arg Gly Leu Gln Asp Glu Asp Gly Tyr Arg Met Lys Phe
                1605                1610                1615

Ala Cys Tyr Tyr Pro Arg Val Glu Tyr Gly Phe Gln Val Lys Val Leu
                1620                1625                1630

Arg Glu Asp Ser Arg Ala Ala Phe Arg Leu Phe Glu Thr Lys Ile Thr
                1635                1640                1645

Gln Val Leu His Phe Thr Lys Asp Val Lys Ala Ala Asn Gln Met
                1650                1655                1660

Arg Asn Phe Leu Val Arg Ala Ser Cys Arg Leu Arg Leu Glu Pro Gly
1665                1670                1675                1680

Lys Glu Tyr Leu Ile Met Gly Leu Asp Gly Ala Thr Tyr Asp Leu Glu
                1685                1690                1695

Gly His Pro Gln Tyr Leu Leu Asp Ser Asn Ser Trp Ile Glu Glu Met
                1700                1705                1710

Pro Ser Glu Arg Leu Cys Arg Ser Thr Arg Gln Arg Ala Ala Cys Ala
                1715                1720                1725

Gln Leu Asn Asp Phe Leu Gln Glu Tyr Gly Thr Gln Gly Cys Gln Val
                1730                1735                1740

<210> SEQ ID NO 44
<211> LENGTH: 597
<212> TYPE: PRT
<213> ORGANISM: Homo sapiens

<400> SEQUENCE: 44

Met His Pro Pro Lys Thr Pro Ser Gly Ala Leu His Arg Lys Arg Lys
1               5                   10                  15

Met Ala Ala Trp Pro Phe Ser Arg Leu Trp Lys Val Ser Asp Pro Ile
                20                  25                  30

Leu Phe Gln Met Thr Leu Ile Ala Ala Leu Leu Pro Ala Val Leu Gly
            35                  40                  45

Asn Cys Gly Pro Pro Thr Leu Ser Phe Ala Ala Pro Met Asp Ile
        50                  55                  60

Thr Leu Thr Glu Thr Arg Phe Lys Thr Gly Thr Thr Leu Lys Tyr Thr
65                  70                  75                  80

Cys Leu Pro Gly Tyr Val Arg Ser His Ser Thr Gln Thr Leu Thr Cys
                85                  90                  95

Asn Ser Asp Gly Glu Trp Val Tyr Asn Thr Phe Cys Ile Tyr Lys Arg
            100                 105                 110

Cys Arg His Pro Gly Glu Leu Arg Asn Gly Gln Val Glu Ile Lys Thr
        115                 120                 125

Asp Leu Ser Phe Gly Ser Gln Ile Glu Phe Ser Cys Ser Glu Gly Phe
130                 135                 140
```

```
Phe Leu Ile Gly Ser Thr Thr Ser Arg Cys Glu Val Gln Asp Arg Gly
145                 150                 155                 160

Val Gly Trp Ser His Pro Leu Pro Gln Cys Glu Ile Val Lys Cys Lys
                165                 170                 175

Pro Pro Pro Asp Ile Arg Asn Gly Arg His Ser Gly Glu Glu Asn Phe
            180                 185                 190

Tyr Ala Tyr Gly Phe Ser Val Thr Tyr Ser Cys Asp Pro Arg Phe Ser
        195                 200                 205

Leu Leu Gly His Ala Ser Ile Ser Cys Thr Val Glu Asn Glu Thr Ile
    210                 215                 220

Gly Val Trp Arg Pro Ser Pro Thr Cys Glu Lys Ile Thr Cys Arg
225                 230                 235                 240

Lys Pro Asp Val Ser His Gly Glu Met Val Ser Gly Phe Gly Pro Ile
                245                 250                 255

Tyr Asn Tyr Lys Asp Thr Ile Val Phe Lys Cys Gln Lys Gly Phe Val
            260                 265                 270

Leu Arg Gly Ser Ser Val Ile His Cys Asp Ala Asp Ser Lys Trp Asn
        275                 280                 285

Pro Ser Pro Pro Ala Cys Glu Pro Asn Ser Cys Ile Asn Leu Pro Asp
    290                 295                 300

Ile Pro His Ala Ser Trp Glu Thr Tyr Pro Arg Pro Thr Lys Glu Asp
305                 310                 315                 320

Val Tyr Val Val Gly Thr Val Leu Arg Tyr Arg Cys His Pro Gly Tyr
                325                 330                 335

Lys Pro Thr Thr Asp Glu Pro Thr Thr Val Ile Cys Gln Lys Asn Leu
            340                 345                 350

Arg Trp Thr Pro Tyr Gln Gly Cys Glu Ala Leu Cys Cys Pro Glu Pro
        355                 360                 365

Lys Leu Asn Asn Gly Glu Ile Thr Gln His Arg Lys Ser Arg Pro Ala
    370                 375                 380

Asn His Cys Val Tyr Phe Tyr Gly Asp Glu Ile Ser Phe Ser Cys His
385                 390                 395                 400

Glu Thr Ser Arg Phe Ser Ala Ile Cys Gln Gly Asp Gly Thr Trp Ser
                405                 410                 415

Pro Arg Thr Pro Ser Cys Gly Asp Ile Cys Asn Phe Pro Pro Lys Ile
            420                 425                 430

Ala His Gly His Tyr Lys Gln Ser Ser Ser Tyr Ser Phe Phe Lys Glu
        435                 440                 445

Glu Ile Ile Tyr Glu Cys Asp Lys Gly Tyr Ile Leu Val Gly Gln Ala
    450                 455                 460

Lys Leu Ser Cys Ser Tyr Ser His Trp Ser Ala Pro Ala Pro Gln Cys
465                 470                 475                 480

Lys Ala Leu Cys Arg Lys Pro Glu Leu Val Asn Gly Arg Leu Ser Val
                485                 490                 495

Asp Lys Asp Gln Tyr Val Glu Pro Glu Asn Val Thr Ile Gln Cys Asp
            500                 505                 510

Ser Gly Tyr Gly Val Val Gly Pro Gln Ser Ile Thr Cys Ser Gly Asn
        515                 520                 525

Arg Thr Trp Tyr Pro Glu Val Pro Lys Cys Glu Trp Glu Thr Pro Glu
    530                 535                 540

Gly Cys Glu Gln Val Leu Thr Gly Lys Arg Leu Met Gln Cys Leu Pro
545                 550                 555                 560
```

```
Asn Pro Glu Asp Val Lys Met Ala Leu Glu Val Tyr Lys Leu Ser Leu
                565                 570                 575

Glu Ile Glu Gln Leu Glu Leu Gln Arg Asp Ser Ala Arg Gln Ser Thr
            580                 585                 590

Leu Asp Lys Glu Leu
        595

<210> SEQ ID NO 45
<211> LENGTH: 584
<212> TYPE: PRT
<213> ORGANISM: Homo sapiens

<400> SEQUENCE: 45

Met Phe Ala Val Val Phe Phe Ile Leu Ser Leu Met Thr Cys Gln Pro
1               5                   10                  15

Gly Val Thr Ala Gln Glu Lys Val Asn Gln Arg Val Arg Arg Ala Ala
            20                  25                  30

Thr Pro Ala Ala Val Thr Cys Gln Leu Ser Asn Trp Ser Glu Trp Thr
        35                  40                  45

Asp Cys Phe Pro Cys Gln Asp Lys Lys Tyr Arg His Arg Ser Leu Leu
    50                  55                  60

Gln Pro Asn Lys Phe Gly Gly Thr Ile Cys Ser Gly Asp Ile Trp Asp
65                  70                  75                  80

Gln Ala Ser Cys Ser Ser Ser Thr Thr Cys Val Arg Gln Ala Gln Cys
                85                  90                  95

Gly Gln Asp Phe Gln Cys Lys Glu Thr Gly Arg Cys Leu Lys Arg His
            100                 105                 110

Leu Val Cys Asn Gly Asp Gln Asp Cys Leu Asp Gly Ser Asp Glu Asp
        115                 120                 125

Asp Cys Glu Asp Val Arg Ala Ile Asp Glu Asp Cys Ser Gln Tyr Glu
    130                 135                 140

Pro Ile Pro Gly Ser Gln Lys Ala Ala Leu Gly Tyr Asn Ile Leu Thr
145                 150                 155                 160

Gln Glu Asp Ala Gln Ser Val Tyr Asp Ala Ser Tyr Tyr Gly Gly Gln
                165                 170                 175

Cys Glu Thr Val Tyr Asn Gly Glu Trp Arg Glu Leu Arg Tyr Asp Ser
            180                 185                 190

Thr Cys Glu Arg Leu Tyr Tyr Gly Asp Asp Glu Lys Tyr Phe Arg Lys
        195                 200                 205

Pro Tyr Asn Phe Leu Lys Tyr His Phe Glu Ala Leu Ala Asp Thr Gly
    210                 215                 220

Ile Ser Ser Glu Phe Tyr Asp Asn Ala Asn Asp Leu Leu Ser Lys Val
225                 230                 235                 240

Lys Lys Asp Lys Ser Asp Ser Phe Gly Val Thr Ile Gly Ile Gly Pro
                245                 250                 255

Ala Gly Ser Pro Leu Leu Val Gly Val Gly Val Ser His Ser Gln Asp
            260                 265                 270

Thr Ser Phe Leu Asn Glu Leu Asn Lys Tyr Asn Glu Lys Lys Phe Ile
        275                 280                 285

Phe Thr Arg Ile Phe Thr Lys Val Gln Thr Ala His Phe Lys Met Arg
    290                 295                 300

Lys Asp Asp Ile Met Leu Asp Glu Gly Met Leu Gln Ser Leu Met Glu
305                 310                 315                 320

Leu Pro Asp Gln Tyr Asn Tyr Gly Met Tyr Ala Lys Phe Ile Asn Asp
                325                 330                 335
```

-continued

Tyr Gly Thr His Tyr Ile Thr Ser Gly Ser Met Gly Gly Ile Tyr Glu
                340                 345                 350

Tyr Ile Leu Val Ile Asp Lys Ala Lys Met Glu Ser Leu Gly Ile Thr
            355                 360                 365

Ser Arg Asp Ile Thr Thr Cys Phe Gly Gly Ser Leu Gly Ile Gln Tyr
        370                 375                 380

Glu Asp Lys Ile Asn Val Gly Gly Leu Ser Gly Asp His Cys Lys
385                 390                 395                 400

Lys Phe Gly Gly Gly Lys Thr Glu Arg Ala Arg Lys Ala Met Ala Val
                405                 410                 415

Glu Asp Ile Ile Ser Arg Val Arg Gly Gly Ser Ser Gly Trp Ser Gly
            420                 425                 430

Gly Leu Ala Gln Asn Arg Ser Thr Ile Thr Tyr Arg Ser Trp Gly Arg
        435                 440                 445

Ser Leu Lys Tyr Asn Pro Val Val Ile Asp Phe Glu Met Gln Pro Ile
    450                 455                 460

His Glu Val Leu Arg His Thr Ser Leu Gly Pro Leu Glu Ala Lys Arg
465                 470                 475                 480

Gln Asn Leu Arg Arg Ala Leu Asp Gln Tyr Leu Met Glu Phe Asn Ala
                485                 490                 495

Cys Arg Cys Gly Pro Cys Phe Asn Asn Gly Val Pro Ile Leu Glu Gly
            500                 505                 510

Thr Ser Cys Arg Cys Gln Cys Arg Leu Gly Ser Leu Gly Ala Ala Cys
        515                 520                 525

Glu Gln Thr Gln Thr Glu Gly Ala Lys Ala Asp Gly Ser Trp Ser Cys
    530                 535                 540

Trp Ser Ser Trp Ser Val Cys Arg Ala Gly Ile Gln Glu Arg Arg Arg
545                 550                 555                 560

Glu Cys Asp Asn Pro Ala Pro Gln Asn Gly Gly Ala Ser Cys Pro Gly
                565                 570                 575

Arg Lys Val Gln Thr Gln Ala Cys
            580

<210> SEQ ID NO 46
<211> LENGTH: 347
<212> TYPE: PRT
<213> ORGANISM: Homo sapiens

<400> SEQUENCE: 46

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
            20                  25                  30

Cys Glu Gly Arg Val Glu Val Glu Gln Lys Gly Gln Trp Gly Thr Val
        35                  40                  45

Cys Asp Asp Gly Trp Asp Ile Lys Asp Val Ala Val Leu Cys Arg Glu
    50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu

```
                115                 120                 125
Ser Ser Phe Ser Pro Val Pro Glu Gly Val Arg Leu Ala Asp Gly Pro
        130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285

Lys Ser Leu Ser Pro Ser Phe Arg Asp Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
            340                 345

<210> SEQ ID NO 47
<211> LENGTH: 1065
<212> TYPE: PRT
<213> ORGANISM: Homo sapiens

<400> SEQUENCE: 47

Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr
                20                  25                  30

Trp Asp Tyr Ala Ser Asp His Gly Glu Lys Lys Leu Ile Ser Val Asp
            35                  40                  45

Thr Glu His Ser Asn Ile Tyr Leu Gln Asn Gly Pro Asp Arg Ile Gly
        50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110

Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140
```

```
Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
            180                 185                 190

Leu Ile Gly Pro Leu Ile Ile Cys Lys Lys Asp Ser Leu Asp Lys Glu
        195                 200                 205

Lys Glu Lys His Ile Asp Arg Glu Phe Val Val Met Phe Ser Val Val
    210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
            260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
    290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Asn Ala Phe Phe
            340                 345                 350

Gln Val Gln Glu Cys Asn Lys Ser Ser Lys Asp Asn Ile Arg Gly
        355                 360                 365

Lys His Val Arg His Tyr Tyr Ile Ala Ala Glu Ile Ile Trp Asn
    370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415

Gly Gly Ser Tyr Lys Lys Leu Val Tyr Arg Glu Tyr Thr Asp Ala Ser
            420                 425                 430

Phe Thr Asn Arg Lys Glu Arg Gly Pro Glu Glu Glu His Leu Gly Ile
        435                 440                 445

Leu Gly Pro Val Ile Trp Ala Glu Val Gly Asp Thr Ile Arg Val Thr
    450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
            500                 505                 510

Glu Thr Phe Thr Tyr Glu Trp Thr Val Pro Lys Glu Val Gly Pro Thr
        515                 520                 525

Asn Ala Asp Pro Val Cys Leu Ala Lys Met Tyr Tyr Ser Ala Val Asp
    530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
```

-continued

```
            565                 570                 575
Glu Phe Tyr Leu Phe Pro Thr Val Phe Asp Glu Asn Glu Ser Leu Leu
            580                 585                 590

Leu Glu Asp Asn Ile Arg Met Phe Thr Thr Ala Pro Asp Gln Val Asp
            595                 600                 605

Lys Glu Asp Glu Asp Phe Gln Glu Ser Asn Lys Met His Ser Met Asn
            610                 615                 620

Gly Phe Met Tyr Gly Asn Gln Pro Gly Leu Thr Met Cys Lys Gly Asp
625                 630                 635                 640

Ser Val Val Trp Tyr Leu Phe Ser Ala Gly Asn Glu Ala Asp Val His
                    645                 650                 655

Gly Ile Tyr Phe Ser Gly Asn Thr Tyr Leu Trp Arg Gly Glu Arg Arg
                    660                 665                 670

Asp Thr Ala Asn Leu Phe Pro Gln Thr Ser Leu Thr Leu His Met Trp
                    675                 680                 685

Pro Asp Thr Glu Gly Thr Phe Asn Val Glu Cys Leu Thr Thr Asp His
            690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Glu Arg Thr Tyr Tyr Ile
                    725                 730                 735

Ala Ala Val Glu Val Glu Trp Asp Tyr Ser Pro Gln Arg Glu Trp Glu
                    740                 745                 750

Lys Glu Leu His His Leu Gln Glu Gln Asn Val Ser Asn Ala Phe Leu
                    755                 760                 765

Asp Lys Gly Glu Phe Tyr Ile Gly Ser Lys Tyr Lys Lys Val Val Tyr
            770                 775                 780

Arg Gln Tyr Thr Asp Ser Thr Phe Arg Val Pro Val Glu Arg Lys Ala
785                 790                 795                 800

Glu Glu Glu His Leu Gly Ile Leu Gly Pro Gln Leu His Ala Asp Val
                    805                 810                 815

Gly Asp Lys Val Lys Ile Ile Phe Lys Asn Met Ala Thr Arg Pro Tyr
                    820                 825                 830

Ser Ile His Ala His Gly Val Gln Thr Glu Ser Ser Thr Val Thr Pro
                    835                 840                 845

Thr Leu Pro Gly Glu Thr Leu Thr Tyr Val Trp Lys Ile Pro Glu Arg
            850                 855                 860

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
                    885                 890                 895

Leu Ile Val Cys Arg Arg Pro Tyr Leu Lys Val Phe Asn Pro Arg Arg
                    900                 905                 910

Lys Leu Glu Phe Ala Leu Leu Phe Leu Val Phe Asp Glu Asn Glu Ser
            915                 920                 925

Trp Tyr Leu Asp Asp Asn Ile Lys Thr Tyr Ser Asp His Pro Glu Lys
            930                 935                 940

Val Asn Lys Asp Asp Glu Glu Phe Ile Glu Ser Asn Lys Met His Ala
945                 950                 955                 960

Ile Asn Gly Arg Met Phe Gly Asn Leu Gln Gly Leu Thr Met His Val
                    965                 970                 975

Gly Asp Glu Val Asn Trp Tyr Leu Met Gly Met Gly Asn Glu Ile Asp
            980                 985                 990
```

```
Leu His Thr Val His Phe His Gly His Ser Phe Gln Tyr Lys His Arg
        995                 1000                1005

Gly Val Tyr Ser Ser Asp Val Phe Asp Ile Phe Pro Gly Thr Tyr Gln
        1010                1015                1020

Thr Leu Glu Met Phe Pro Arg Thr Pro Gly Ile Trp Leu Leu His Cys
1025                1030                1035                1040

His Val Thr Asp His Ile His Ala Gly Met Glu Thr Thr Tyr Thr Val
                1045                1050                1055

Leu Gln Asn Glu Asp Thr Lys Ser Gly
        1060                1065

<210> SEQ ID NO 48
<211> LENGTH: 458
<212> TYPE: PRT
<213> ORGANISM: Homo sapiens

<400> SEQUENCE: 48

Met Ser Asp Leu Leu Ser Val Phe Leu His Leu Leu Leu Phe Lys
1               5                   10                  15

Leu Val Ala Pro Val Thr Phe Arg His His Arg Tyr Asp Asp Leu Val
                20                  25                  30

Arg Thr Leu Tyr Lys Val Gln Asn Glu Cys Pro Gly Ile Thr Arg Val
            35                  40                  45

Tyr Ser Ile Gly Arg Ser Val Glu Gly Arg His Leu Tyr Val Leu Glu
        50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
                85                  90                  95

Leu Gln Leu Ser Glu Phe Leu Cys Glu Glu Phe Arg Asn Arg Asn Gln
            100                 105                 110

Arg Ile Val Gln Leu Ile Gln Asp Thr Arg Ile His Ile Leu Pro Ser
        115                 120                 125

Met Asn Pro Asp Gly Tyr Glu Val Ala Ala Gln Gly Pro Asn Lys
130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Asn Glu Lys Tyr
                165                 170                 175

Gly Gly Pro Asn His His Leu Pro Leu Pro Asp Asn Trp Lys Ser Gln
            180                 185                 190

Val Glu Pro Glu Thr Arg Ala Val Ile Arg Trp Met His Ser Phe Asn
        195                 200                 205

Phe Val Leu Ser Ala Asn Leu His Gly Gly Ala Val Val Ala Asn Tyr
    210                 215                 220

Pro Tyr Asp Lys Ser Phe Glu His Arg Val Arg Gly Val Arg Arg Thr
225                 230                 235                 240

Ala Ser Thr Pro Thr Pro Asp Asp Lys Leu Phe Gln Lys Leu Ala Lys
                245                 250                 255

Val Tyr Ser Tyr Ala His Gly Trp Met Phe Gln Gly Trp Asn Cys Gly
            260                 265                 270

Asp Tyr Phe Pro Asp Gly Ile Thr Asn Gly Ala Ser Trp Tyr Ser Leu
        275                 280                 285

Ser Lys Gly Met Gln Asp Phe Asn Tyr Leu His Thr Asn Cys Phe Glu
```

```
             290                 295                 300
Ile Thr Leu Glu Leu Ser Cys Asp Lys Phe Pro Pro Glu Glu Leu
305                 310                 315                 320

Gln Arg Glu Trp Leu Gly Asn Arg Glu Ala Leu Ile Gln Phe Leu Glu
                325                 330                 335

Gln Val His Gln Gly Ile Lys Gly Met Val Leu Asp Glu Asn Tyr Asn
            340                 345                 350

Asn Leu Ala Asn Ala Val Ile Ser Val Ser Gly Ile Asn His Asp Val
        355                 360                 365

Thr Ser Gly Asp His Gly Asp Tyr Phe Arg Leu Leu Pro Gly Ile
    370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
            420                 425                 430

His Gly Val Arg Ala Lys Val Gln Pro Gln Ala Arg Lys Lys Glu Met
        435                 440                 445

Glu Met Arg Gln Leu Gln Arg Gly Pro Ala
    450                 455

<210> SEQ ID NO 49
<211> LENGTH: 545
<212> TYPE: PRT
<213> ORGANISM: Homo sapiens

<400> SEQUENCE: 49

Met Leu Pro Gly Ala Trp Leu Leu Trp Thr Ser Leu Leu Leu Leu Ala
1               5                   10                  15

Arg Pro Ala Gln Pro Cys Pro Met Gly Cys Asp Cys Phe Val Gln Glu
                20                  25                  30

Val Phe Cys Ser Asp Glu Glu Leu Ala Thr Val Pro Leu Asp Ile Pro
            35                  40                  45

Pro Tyr Thr Lys Asn Ile Ile Phe Val Glu Thr Ser Phe Thr Thr Leu
        50                  55                  60

Glu Thr Arg Ala Phe Gly Ser Asn Pro Asn Leu Thr Lys Val Val Phe
65                  70                  75                  80

Leu Asn Thr Gln Leu Cys Gln Phe Arg Pro Asp Ala Phe Gly Gly Leu
                85                  90                  95

Pro Arg Leu Glu Asp Leu Glu Val Thr Gly Ser Ser Phe Leu Asn Leu
            100                 105                 110

Ser Thr Asn Ile Phe Ser Asn Leu Thr Ser Leu Gly Lys Leu Thr Leu
        115                 120                 125

Asn Phe Asn Met Leu Glu Ala Leu Pro Glu Gly Leu Phe Gln His Leu
    130                 135                 140

Ala Ala Leu Glu Ser Leu His Leu Gln Gly Asn Gln Leu Gln Ala Leu
145                 150                 155                 160

Pro Arg Arg Leu Phe Gln Pro Leu Thr His Leu Lys Thr Leu Asn Leu
                165                 170                 175

Ala Gln Asn Leu Leu Ala Gln Leu Pro Glu Glu Leu Phe His Pro Leu
            180                 185                 190

Thr Ser Leu Gln Thr Leu Lys Leu Ser Asn Asn Ala Leu Ser Gly Leu
        195                 200                 205
```

```
Pro Gln Gly Val Phe Gly Lys Leu Gly Ser Leu Gln Glu Leu Phe Leu
    210                 215                 220

Asp Ser Asn Asn Ile Ser Glu Leu Pro Pro Gln Val Phe Ser Gln Leu
225                 230                 235                 240

Phe Cys Leu Glu Arg Leu Trp Leu Gln Arg Asn Ala Ile Thr His Leu
                245                 250                 255

Pro Leu Ser Ile Phe Ala Ser Leu Gly Asn Leu Thr Phe Leu Ser Leu
            260                 265                 270

Gln Trp Asn Met Leu Arg Val Leu Pro Ala Gly Leu Phe Ala His Thr
        275                 280                 285

Pro Cys Leu Val Gly Leu Ser Leu Thr His Asn Gln Leu Glu Thr Val
290                 295                 300

Ala Glu Gly Thr Phe Ala His Leu Ser Asn Leu Arg Ser Leu Met Leu
305                 310                 315                 320

Ser Tyr Asn Ala Ile Thr His Leu Pro Ala Gly Ile Phe Arg Asp Leu
                325                 330                 335

Glu Glu Leu Val Lys Leu Tyr Leu Gly Ser Asn Asn Leu Thr Ala Leu
            340                 345                 350

His Pro Ala Leu Phe Gln Asn Leu Ser Lys Leu Glu Leu Leu Ser Leu
        355                 360                 365

Ser Lys Asn Gln Leu Thr Thr Leu Pro Glu Gly Ile Phe Asp Thr Asn
370                 375                 380

Tyr Asn Leu Phe Asn Leu Ala Leu His Gly Asn Pro Trp Gln Cys Asp
385                 390                 395                 400

Cys His Leu Ala Tyr Leu Phe Asn Trp Leu Gln Gln Tyr Thr Asp Arg
                405                 410                 415

Leu Leu Asn Ile Gln Thr Tyr Cys Ala Gly Pro Ala Tyr Leu Lys Gly
            420                 425                 430

Gln Val Val Pro Ala Leu Asn Glu Lys Gln Leu Val Cys Pro Val Thr
        435                 440                 445

Arg Asp His Leu Gly Phe Gln Val Thr Trp Pro Asp Glu Ser Lys Ala
    450                 455                 460

Gly Gly Ser Trp Asp Leu Ala Val Gln Glu Arg Ala Ala Arg Ser Gln
465                 470                 475                 480

Cys Thr Tyr Ser Asn Pro Glu Gly Thr Val Val Leu Ala Cys Asp Gln
                485                 490                 495

Ala Gln Cys Arg Trp Leu Asn Val Gln Leu Ser Pro Gln Gln Gly Ser
            500                 505                 510

Leu Gly Leu Gln Tyr Asn Ala Ser Gln Glu Trp Asp Leu Arg Ser Ser
        515                 520                 525

Cys Gly Ser Leu Arg Leu Thr Val Ser Ile Glu Ala Arg Ala Ala Gly
    530                 535                 540

Pro
545

<210> SEQ ID NO 50
<211> LENGTH: 622
<212> TYPE: PRT
<213> ORGANISM: Homo sapiens

<400> SEQUENCE: 50

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30
```

```
Gln Ala Arg Ser Leu Leu Gln Arg Val Arg Ala Asn Thr Phe Leu
            35                  40                  45
Glu Glu Val Arg Lys Gly Asn Leu Glu Arg Glu Cys Val Glu Glu Thr
 50                  55                  60
Cys Ser Tyr Glu Glu Ala Phe Glu Ala Leu Glu Ser Ser Thr Ala Thr
 65                  70                  75                  80
Asp Val Phe Trp Ala Lys Tyr Thr Ala Cys Glu Thr Ala Arg Thr Pro
                 85                  90                  95
Arg Asp Lys Leu Ala Ala Cys Leu Glu Gly Asn Cys Ala Glu Gly Leu
            100                 105                 110
Gly Thr Asn Tyr Arg Gly His Val Asn Ile Thr Arg Ser Gly Ile Glu
            115                 120                 125
Cys Gln Leu Trp Arg Ser Arg Tyr Pro His Lys Pro Glu Ile Asn Ser
130                 135                 140
Thr Thr His Pro Gly Ala Asp Leu Gln Glu Asn Phe Cys Arg Asn Pro
145                 150                 155                 160
Asp Ser Ser Thr Thr Gly Pro Trp Cys Tyr Thr Thr Asp Pro Thr Val
                165                 170                 175
Arg Arg Gln Glu Cys Ser Ile Pro Val Cys Gly Gln Asp Gln Val Thr
            180                 185                 190
Val Ala Met Thr Pro Arg Ser Glu Gly Ser Ser Val Asn Leu Ser Pro
            195                 200                 205
Pro Leu Glu Gln Cys Val Pro Asp Arg Gly Gln Gln Tyr Gln Gly Arg
210                 215                 220
Leu Ala Val Thr Thr His Gly Leu Pro Cys Leu Ala Trp Ala Ser Ala
225                 230                 235                 240
Gln Ala Lys Ala Leu Ser Lys His Gln Asp Phe Asn Ser Ala Val Gln
                245                 250                 255
Leu Val Glu Asn Phe Cys Arg Asn Pro Asp Gly Asp Glu Glu Gly Val
            260                 265                 270
Trp Cys Tyr Val Ala Gly Lys Pro Gly Asp Phe Gly Tyr Cys Asp Leu
            275                 280                 285
Asn Tyr Cys Glu Glu Ala Val Glu Glu Glu Thr Gly Asp Gly Leu Asp
            290                 295                 300
Glu Asp Ser Asp Arg Ala Ile Glu Gly Arg Thr Ala Thr Ser Glu Tyr
305                 310                 315                 320
Gln Thr Phe Phe Asn Pro Arg Thr Phe Gly Ser Gly Glu Ala Asp Cys
                325                 330                 335
Gly Leu Arg Pro Leu Phe Glu Lys Lys Ser Leu Glu Asp Lys Thr Glu
            340                 345                 350
Arg Glu Leu Leu Glu Ser Tyr Ile Asp Gly Arg Ile Val Glu Gly Ser
            355                 360                 365
Asp Ala Glu Ile Gly Met Ser Pro Trp Gln Val Met Leu Phe Arg Lys
370                 375                 380
Ser Pro Gln Glu Leu Leu Cys Gly Ala Ser Leu Ile Ser Asp Arg Trp
385                 390                 395                 400
Val Leu Thr Ala Ala His Cys Leu Leu Tyr Pro Pro Trp Asp Lys Asn
                405                 410                 415
Phe Thr Glu Asn Asp Leu Leu Val Arg Ile Gly Lys His Ser Arg Thr
            420                 425                 430
Arg Tyr Glu Arg Asn Ile Glu Lys Ile Ser Met Leu Glu Lys Ile Tyr
            435                 440                 445
```

```
Ile His Pro Arg Tyr Asn Trp Arg Glu Asn Leu Asp Arg Asp Ile Ala
    450                 455                 460
Leu Met Lys Leu Lys Lys Pro Val Ala Phe Ser Asp Tyr Ile His Pro
465                 470                 475                 480
Val Cys Leu Pro Asp Arg Glu Thr Ala Ala Ser Leu Leu Gln Ala Gly
                485                 490                 495
Tyr Lys Gly Arg Val Thr Gly Trp Gly Asn Leu Lys Glu Thr Trp Thr
                500                 505                 510
Ala Asn Val Gly Lys Gly Gln Pro Ser Val Leu Gln Val Asn Leu
                515                 520                 525
Pro Ile Val Glu Arg Pro Val Cys Lys Asp Ser Thr Arg Ile Arg Ile
530                 535                 540
Thr Asp Asn Met Phe Cys Ala Gly Tyr Lys Pro Asp Glu Gly Lys Arg
545                 550                 555                 560
Gly Asp Ala Cys Glu Gly Asp Ser Gly Gly Pro Phe Val Met Lys Ser
                565                 570                 575
Pro Phe Asn Arg Trp Tyr Gln Met Gly Ile Val Ser Trp Gly Glu
                580                 585                 590
Gly Cys Asp Arg Asp Gly Lys Tyr Gly Phe Tyr Thr His Val Phe Arg
                595                 600                 605
Leu Lys Lys Trp Ile Gln Lys Val Ile Asp Gln Phe Gly Glu
610                 615                 620

<210> SEQ ID NO 51
<211> LENGTH: 721
<212> TYPE: PRT
<213> ORGANISM: Homo sapiens

<400> SEQUENCE: 51

Met Glu Arg Ala Ala Pro Ser Arg Arg Val Pro Leu Pro Leu Leu Leu
1               5                   10                  15
Leu Gly Gly Leu Ala Leu Leu Ala Ala Gly Val Asp Ala Asp Val Leu
                20                  25                  30
Leu Glu Ala Cys Cys Ala Asp Gly His Arg Met Ala Thr His Gln Lys
            35                  40                  45
Asp Cys Ser Leu Pro Tyr Ala Thr Glu Ser Lys Glu Cys Arg Ala Val
    50                  55                  60
Gly Leu Ala Ser Leu Cys Gln Asp Leu Asn Gly Ala Trp Ala Val Trp
65                  70                  75                  80
Lys Val Gly Arg Ala Ser Gln Ala Glu Gly Thr Ala Ser Ala Arg Ala
                85                  90                  95
Gln Arg Arg Gly Met Val Gln Glu Gln Cys Cys His Ser Gln Leu Glu
                100                 105                 110
Glu Leu His Cys Ala Thr Gly Ile Ser Leu Ala Asn Glu Gln Asp Arg
            115                 120                 125
Cys Ala Thr Pro His Gly Asp Asn Ala Ser Leu Glu Ala Thr Phe Val
    130                 135                 140
Lys Arg Cys Cys His Cys Cys Leu Leu Gly Arg Ala Ala Gln Ala Gln
145                 150                 155                 160
Gly Gln Ser Cys Glu Tyr Ser Leu Met Val Gly Tyr Gln Cys Gly Gln
                165                 170                 175
Val Phe Gln Ala Cys Cys Val Lys Ser Gln Glu Thr Gly Asp Leu Asp
                180                 185                 190
Val Gly Gly Leu Gln Glu Thr Asp Lys Ile Ile Glu Val Glu Glu Glu
            195                 200                 205
```

```
Gln Glu Asp Pro Tyr Leu Asn Asp Arg Cys Arg Gly Gly Pro Cys
    210                 215                 220
Lys Gln Gln Cys Arg Asp Thr Gly Asp Glu Val Cys Ser Cys Phe
225                 230                 235                 240
Val Gly Tyr Gln Leu Leu Ser Asp Gly Val Ser Cys Glu Asp Val Asn
                    245                 250                 255
Glu Cys Ile Thr Gly Ser His Ser Cys Arg Leu Gly Glu Ser Cys Ile
                260                 265                 270
Asn Thr Val Gly Ser Phe Arg Cys Gln Arg Asp Ser Ser Cys Gly Thr
            275                 280                 285
Gly Tyr Glu Leu Thr Glu Asp Asn Ser Cys Lys Asp Ile Asp Glu Cys
        290                 295                 300
Glu Ser Gly Ile His Asn Cys Leu Pro Asp Phe Ile Cys Gln Asn Thr
305                 310                 315                 320
Leu Gly Ser Phe Arg Cys Arg Pro Lys Leu Gln Cys Lys Ser Gly Phe
                325                 330                 335
Ile Gln Asp Ala Leu Gly Asn Cys Ile Asp Ile Asn Glu Cys Leu Ser
                340                 345                 350
Ile Ser Ala Pro Cys Pro Ile Gly His Thr Cys Ile Asn Thr Glu Gly
            355                 360                 365
Ser Tyr Thr Cys Gln Lys Asn Val Pro Asn Cys Gly Arg Gly Tyr His
        370                 375                 380
Leu Asn Glu Glu Gly Thr Arg Cys Val Asp Val Asp Glu Cys Ala Pro
385                 390                 395                 400
Pro Ala Glu Pro Cys Gly Lys Gly His Arg Cys Val Asn Ser Pro Gly
                405                 410                 415
Ser Phe Arg Cys Glu Cys Lys Thr Gly Tyr Tyr Phe Asp Gly Ile Ser
                420                 425                 430
Arg Met Cys Val Asp Val Asn Glu Cys Gln Arg Tyr Pro Gly Arg Leu
            435                 440                 445
Cys Gly His Lys Cys Glu Asn Thr Leu Gly Ser Tyr Leu Cys Ser Cys
            450                 455                 460
Ser Val Gly Phe Arg Leu Ser Val Asp Gly Arg Ser Cys Glu Asp Ile
465                 470                 475                 480
Asn Glu Cys Ser Ser Ser Pro Cys Ser Gln Glu Cys Ala Asn Val Tyr
                485                 490                 495
Gly Ser Tyr Gln Cys Tyr Cys Arg Arg Gly Tyr Gln Leu Ser Asp Val
            500                 505                 510
Asp Gly Val Thr Cys Glu Asp Ile Asp Glu Cys Ala Leu Pro Thr Gly
        515                 520                 525
Gly His Ile Cys Ser Tyr Arg Cys Ile Asn Ile Pro Gly Ser Phe Gln
        530                 535                 540
Cys Ser Cys Pro Ser Ser Gly Tyr Arg Leu Ala Pro Asn Gly Arg Asn
545                 550                 555                 560
Cys Gln Asp Ile Asp Glu Cys Val Thr Gly Ile His Asn Cys Ser Ile
                565                 570                 575
Asn Glu Thr Cys Phe Asn Ile Gln Gly Gly Phe Arg Cys Leu Ala Phe
            580                 585                 590
Glu Cys Pro Glu Asn Tyr Arg Arg Ser Ala Ala Thr Arg Cys Glu Arg
            595                 600                 605
Leu Pro Cys His Glu Asn Arg Glu Cys Ser Lys Leu Pro Leu Arg Ile
        610                 615                 620
```

-continued

```
Thr Tyr Tyr His Leu Ser Phe Pro Thr Asn Ile Gln Ala Pro Ala Val
625                 630                 635                 640

Val Phe Arg Met Gly Pro Ser Ser Ala Val Pro Gly Asp Ser Met Gln
            645                 650                 655

Leu Ala Ile Thr Gly Gly Asn Glu Glu Gly Phe Phe Thr Thr Arg Lys
            660                 665                 670

Val Ser Pro His Ser Gly Val Val Ala Leu Thr Lys Pro Val Pro Glu
        675                 680                 685

Pro Arg Asp Leu Leu Leu Thr Val Lys Met Asp Leu Ser Arg His Gly
        690                 695                 700

Thr Val Ser Ser Phe Val Ala Lys Leu Phe Ile Phe Val Ser Ala Glu
705                 710                 715                 720

Leu

<210> SEQ ID NO 52
<211> LENGTH: 2386
<212> TYPE: PRT
<213> ORGANISM: Homo sapiens

<400> SEQUENCE: 52

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270
```

-continued

His Thr Ser Val Gln Thr Ser Ser Gly Ser Gly Pro Phe Thr Asp
        275                 280                 285

Val Arg Ala Ala Val Tyr Gln Pro Gln Pro His Pro Gln Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr

```
                690              695              700
Pro Val Thr Ser Asn Thr Val Thr Gly Glu Thr Thr Pro Phe Ser Pro
705              710              715              720
Leu Val Ala Thr Ser Glu Ser Val Thr Glu Ile Thr Ala Ser Ser Phe
                725              730              735
Val Val Ser Trp Val Ser Ala Ser Asp Thr Val Ser Gly Phe Arg Val
                740              745              750
Glu Tyr Glu Leu Ser Glu Glu Gly Asp Glu Pro Gln Tyr Leu Asp Leu
                755              760              765
Pro Ser Thr Ala Thr Ser Val Asn Ile Pro Asp Leu Leu Pro Gly Arg
770              775              780
Lys Tyr Ile Val Asn Val Tyr Gln Ile Ser Glu Asp Gly Glu Gln Ser
785              790              795              800
Leu Ile Leu Ser Thr Ser Gln Thr Thr Ala Pro Asp Ala Pro Pro Asp
                805              810              815
Thr Thr Val Asp Gln Val Asp Asp Thr Ser Ile Val Val Arg Trp Ser
                820              825              830
Arg Pro Gln Ala Pro Ile Thr Gly Tyr Arg Ile Val Tyr Ser Pro Ser
                835              840              845
Val Glu Gly Ser Ser Thr Glu Leu Asn Leu Pro Glu Thr Ala Asn Ser
                850              855              860
Val Thr Leu Ser Asp Leu Gln Pro Gly Val Gln Tyr Asn Ile Thr Ile
865              870              875              880
Tyr Ala Val Glu Glu Asn Gln Glu Ser Thr Pro Val Val Ile Gln Gln
                885              890              895
Glu Thr Thr Gly Thr Pro Arg Ser Asp Thr Val Pro Ser Pro Arg Asp
                900              905              910
Leu Gln Phe Val Glu Val Thr Asp Val Lys Val Thr Ile Met Trp Thr
                915              920              925
Pro Pro Glu Ser Ala Val Thr Gly Tyr Arg Val Asp Val Ile Pro Val
                930              935              940
Asn Leu Pro Gly Glu His Gly Gln Arg Leu Pro Ile Ser Arg Asn Thr
945              950              955              960
Phe Ala Glu Val Thr Gly Leu Ser Pro Gly Val Thr Tyr Tyr Phe Lys
                965              970              975
Val Phe Ala Val Ser His Gly Arg Glu Ser Lys Pro Leu Thr Ala Gln
                980              985              990
Gln Thr Thr Lys Leu Asp Ala Pro Thr Asn Leu Gln Phe Val Asn Glu
                995              1000             1005
Thr Asp Ser Thr Val Leu Val Arg Trp Thr Pro Pro Arg Ala Gln Ile
1010             1015             1020
Thr Gly Tyr Arg Leu Thr Val Gly Leu Thr Arg Arg Gly Gln Pro Arg
1025             1030             1035             1040
Gln Tyr Asn Val Gly Pro Ser Val Ser Lys Tyr Pro Leu Arg Asn Leu
                1045             1050             1055
Gln Pro Ala Ser Glu Tyr Thr Val Ser Leu Val Ala Ile Lys Gly Asn
                1060             1065             1070
Gln Glu Ser Pro Lys Ala Thr Gly Val Phe Thr Thr Leu Gln Pro Gly
                1075             1080             1085
Ser Ser Ile Pro Pro Tyr Asn Thr Glu Val Thr Glu Thr Thr Ile Val
                1090             1095             1100
Ile Thr Trp Thr Pro Ala Pro Arg Ile Gly Phe Lys Leu Gly Val Arg
1105             1110             1115             1120
```

```
Pro Ser Gln Gly Gly Glu Ala Pro Arg Glu Val Thr Ser Asp Ser Gly
            1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
            1155                1160                1165

Lys Val Val Thr Pro Leu Ser Pro Pro Thr Asn Leu His Leu Glu Ala
            1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
            1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
            1235                1240                1245

Thr Val Lys Asp Asp Lys Glu Ser Val Pro Ile Ser Asp Thr Ile Ile
            1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
            1285                1290                1295

Asn Phe Leu Val Arg Tyr Ser Pro Val Lys Asn Glu Glu Asp Val Ala
            1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Ser Val Tyr Glu Gln
            1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
            1395                1400                1405

Ser Arg Asn Ser Ile Thr Leu Thr Asn Leu Thr Pro Gly Thr Glu Tyr
            1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
            1475                1480                1485

Ser Pro Val Gln Glu Phe Thr Val Pro Gly Ser Lys Ser Thr Ala Thr
            1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535
```

```
Asn Tyr Arg Thr Glu Ile Asp Lys Pro Ser Gln Met Gln Val Thr Asp
            1540                1545                1550

Val Gln Asp Asn Ser Ile Ser Val Lys Trp Leu Pro Ser Ser Ser Pro
        1555                1560                1565

Val Thr Gly Tyr Arg Val Thr Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Asn Ile
            1620                1625                1630

Asp Arg Pro Lys Gly Leu Ala Phe Thr Asp Val Asp Val Asp Ser Ile
        1635                1640                1645

Lys Ile Ala Trp Glu Ser Pro Gln Gly Gln Val Ser Arg Tyr Arg Val
    1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
                1685                1690                1695

Glu Tyr Thr Val Ser Val Val Ala Leu His Asp Asp Met Glu Ser Gln
            1700                1705                1710

Pro Leu Ile Gly Thr Gln Ser Thr Ala Ile Pro Ala Pro Thr Asp Leu
        1715                1720                1725

Lys Phe Thr Gln Val Thr Pro Thr Ser Leu Ser Ala Gln Trp Thr Pro
    1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
                1765                1770                1775

Val Val Val Ser Gly Leu Met Val Ala Thr Lys Tyr Glu Val Ser Val
            1780                1785                1790

Tyr Ala Leu Lys Asp Thr Leu Thr Ser Arg Pro Ala Gln Gly Val Val
        1795                1800                1805

Thr Thr Leu Glu Asn Val Ser Pro Pro Arg Arg Ala Arg Val Thr Asp
    1810                1815                1820

Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
                1845                1850                1855

Ile Gln Arg Thr Ile Lys Pro Asp Val Arg Ser Tyr Thr Ile Thr Gly
            1860                1865                1870

Leu Gln Pro Gly Thr Asp Tyr Lys Ile Tyr Leu Tyr Thr Leu Asn Asp
        1875                1880                1885

Asn Ala Arg Ser Ser Pro Val Val Ile Asp Ala Ser Thr Ala Ile Asp
    1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
                1925                1930                1935

Tyr Glu Lys Pro Gly Ser Pro Pro Arg Glu Val Val Pro Arg Pro Arg
            1940                1945                1950

Pro Gly Val Thr Glu Ala Thr Ile Thr Gly Leu Glu Pro Gly Thr Glu
```

-continued

Tyr Thr Ile Tyr Val Ile Ala Leu Lys Asn Asn Gln Lys Ser Glu Pro
           1970                1975                1980

Leu Ile Gly Arg Lys Lys Thr Asp Glu Leu Pro Gln Leu Val Thr Leu
1985                1990                1995                2000

Pro His Pro Asn Leu His Gly Pro Glu Ile Leu Asp Val Pro Ser Thr
                2005                2010                2015

Val Gln Lys Thr Pro Phe Val Thr His Pro Gly Tyr Asp Thr Gly Asn
           2020                2025                2030

Gly Ile Gln Leu Pro Gly Thr Ser Gly Gln Gln Pro Ser Val Gly Gln
           2035                2040                2045

Gln Met Ile Phe Glu Glu His Gly Phe Arg Arg Thr Thr Pro Pro Thr
           2050                2055                2060

Thr Ala Thr Pro Ile Arg His Arg Pro Arg Pro Tyr Pro Pro Asn Val
2065                2070                2075                2080

Gly Glu Glu Ile Gln Ile Gly His Ile Pro Arg Glu Asp Val Asp Tyr
                2085                2090                2095

His Leu Tyr Pro His Gly Pro Gly Leu Asn Pro Asn Ala Ser Thr Gly
                2100                2105                2110

Gln Glu Ala Leu Ser Gln Thr Thr Ile Ser Trp Ala Pro Phe Gln Asp
           2115                2120                2125

Thr Ser Glu Tyr Ile Ile Ser Cys His Pro Val Gly Thr Asp Glu Glu
           2130                2135                2140

Pro Leu Gln Phe Arg Val Pro Gly Thr Ser Thr Ser Ala Thr Leu Thr
2145                2150                2155                2160

Gly Leu Thr Arg Gly Ala Thr Tyr Asn Val Ile Val Glu Ala Leu Lys
                2165                2170                2175

Asp Gln Gln Arg His Lys Val Arg Glu Glu Val Val Thr Val Gly Asn
           2180                2185                2190

Ser Val Asn Glu Gly Leu Asn Gln Pro Thr Asp Asp Ser Cys Phe Asp
           2195                2200                2205

Pro Tyr Thr Val Ser His Tyr Ala Val Gly Asp Glu Trp Glu Arg Met
           2210                2215                2220

Ser Glu Ser Gly Phe Lys Leu Leu Cys Gln Cys Leu Gly Phe Gly Ser
2225                2230                2235                2240

Gly His Phe Arg Cys Asp Ser Ser Arg Trp Cys His Asp Asn Gly Val
                2245                2250                2255

Asn Tyr Lys Ile Gly Glu Lys Trp Asp Arg Gln Gly Glu Asn Gly Gln
           2260                2265                2270

Met Met Ser Cys Thr Cys Leu Gly Asn Gly Lys Gly Glu Phe Lys Cys
           2275                2280                2285

Asp Pro His Glu Ala Thr Cys Tyr Asp Asp Gly Lys Thr Tyr His Val
           2290                2295                2300

Gly Glu Gln Trp Gln Lys Glu Tyr Leu Gly Ala Ile Cys Ser Cys Thr
2305                2310                2315                2320

Cys Phe Gly Gly Gln Arg Gly Trp Arg Cys Asp Asn Cys Arg Arg Pro
                2325                2330                2335

Gly Gly Glu Pro Ser Pro Glu Gly Thr Thr Gly Gln Ser Tyr Asn Gln
                2340                2345                2350

Tyr Ser Gln Arg Tyr His Gln Arg Thr Asn Thr Asn Val Asn Cys Pro
           2355                2360                2365

Ile Glu Cys Phe Met Pro Leu Asp Val Gln Ala Asp Arg Glu Asp Ser
           2370                2375                2380

Arg Glu
2385

<210> SEQ ID NO 53
<211> LENGTH: 406
<212> TYPE: PRT
<213> ORGANISM: Homo sapiens

<400> SEQUENCE: 53

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
                20                  25                  30

Cys Pro Lys Pro Pro Glu Ile Ala His Gly Tyr Val Glu His Ser Val
            35                  40                  45

Arg Tyr Gln Cys Lys Asn Tyr Tyr Lys Leu Arg Thr Glu Gly Asp Gly
        50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr

```
                355                 360                 365
Trp Tyr Ala Thr Gly Ile Leu Ser Phe Asp Lys Ser Cys Ala Val Ala
        370                 375                 380
Glu Tyr Gly Val Tyr Val Lys Val Thr Ser Ile Gln Asp Trp Val Gln
385                 390                 395                 400
Lys Thr Ile Ala Glu Asn
                405

<210> SEQ ID NO 54
<211> LENGTH: 348
<212> TYPE: PRT
<213> ORGANISM: Homo sapiens

<400> SEQUENCE: 54

Met Ser Asp Leu Gly Ala Val Ile Ser Leu Leu Trp Gly Arg Gln
1               5                   10                  15
Leu Phe Ala Leu Tyr Ser Gly Asn Asp Val Thr Asp Ile Ser Asp Asp
            20                  25                  30
Arg Phe Pro Lys Pro Glu Ile Ala Asn Gly Tyr Val Glu His Leu
        35                  40                  45
Phe Arg Tyr Gln Cys Lys Asn Tyr Tyr Arg Leu Arg Thr Glu Gly Asp
50                  55                  60
Gly Val Tyr Thr Leu Asn Asp Lys Lys Gln Trp Ile Asn Lys Ala Val
65                  70                  75                  80
Gly Asp Lys Leu Pro Glu Cys Glu Ala Val Cys Gly Lys Pro Lys Asn
                85                  90                  95
Pro Ala Asn Pro Val Gln Arg Ile Leu Gly Gly His Leu Asp Ala Lys
            100                 105                 110
Gly Ser Phe Pro Trp Gln Ala Lys Met Val Ser His His Asn Leu Thr
        115                 120                 125
Thr Gly Ala Thr Leu Ile Asn Glu Gln Trp Leu Leu Thr Thr Ala Lys
130                 135                 140
Asn Leu Phe Leu Asn His Ser Glu Asn Ala Thr Ala Lys Asp Ile Ala
145                 150                 155                 160
Pro Thr Leu Thr Leu Tyr Val Gly Lys Lys Gln Leu Val Glu Ile Glu
                165                 170                 175
Lys Val Val Leu His Pro Asn Tyr His Gln Val Asp Ile Gly Leu Ile
            180                 185                 190
Lys Leu Lys Gln Lys Val Leu Val Asn Glu Arg Val Met Pro Ile Cys
        195                 200                 205
Leu Pro Ser Lys Asn Tyr Ala Glu Val Gly Arg Val Gly Tyr Val Ser
210                 215                 220
Gly Trp Gly Gln Ser Asp Asn Phe Lys Leu Thr Asp His Leu Lys Tyr
225                 230                 235                 240
Val Met Leu Pro Val Ala Asp Gln Tyr Asp Cys Ile Thr His Tyr Glu
                245                 250                 255
Gly Ser Thr Cys Pro Lys Trp Lys Ala Pro Lys Ser Pro Val Gly Val
            260                 265                 270
Gln Pro Ile Leu Asn Glu His Thr Phe Cys Val Gly Met Ser Lys Tyr
        275                 280                 285
Gln Glu Asp Thr Cys Tyr Gly Asp Ala Gly Ser Ala Phe Ala Val His
            290                 295                 300
Asp Leu Glu Glu Asp Thr Trp Tyr Ala Ala Gly Ile Leu Ser Phe Asp
305                 310                 315                 320
```

```
Lys Ser Cys Ala Val Ala Glu Tyr Gly Val Tyr Val Lys Val Thr Ser
                325                 330                 335

Ile Gln His Trp Val Gln Lys Thr Ile Ala Glu Asn
            340                 345

<210> SEQ ID NO 55
<211> LENGTH: 462
<212> TYPE: PRT
<213> ORGANISM: Homo sapiens

<400> SEQUENCE: 55

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
            20                  25                  30

Gly Asn Val Ala Glu Gly Glu Thr Lys Pro Asp Pro Asp Val Thr Glu
        35                  40                  45

Arg Cys Ser Asp Gly Trp Ser Phe Asp Ala Thr Thr Leu Asp Asp Asn
50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
        115                 120                 125

Pro Lys Leu Leu Gln Asp Glu Phe Pro Gly Ile Pro Ser Pro Leu Asp
130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
        195                 200                 205

Phe Asp Pro Val Arg Gly Glu Val Pro Pro Arg Tyr Pro Arg Asp Val
210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
        275                 280                 285

Arg Asp Gly Trp His Ser Trp Pro Ile Ala His Gln Trp Pro Gln Gly
290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
                325                 330                 335

Leu Val Ser Gly Tyr Pro Lys Arg Leu Glu Lys Glu Val Gly Thr Pro
            340                 345                 350
```

His Gly Ile Ile Leu Asp Ser Val Asp Ala Ala Phe Ile Cys Pro Gly
            355                 360                 365

Ser Ser Arg Leu His Ile Met Ala Gly Arg Arg Leu Trp Trp Leu Asp
    370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
                405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
    450                 455                 460

<210> SEQ ID NO 56
<211> LENGTH: 416
<212> TYPE: PRT
<213> ORGANISM: Homo sapiens

<400> SEQUENCE: 56

Pro Gly Lys Gly Leu Glu Trp Val Ser Arg Ile Ser Ser Ser Gly Asp
1               5                   10                  15

Thr Val Asp Tyr Ala Asp Ser Val Lys Gly Arg Phe Thr Val Ser Arg
            20                  25                  30

Asp Thr Ala Lys Asn Ser Leu Ser Leu Gln Met Ser Ser Leu Arg Val
            35                  40                  45

Glu Asp Thr Ala Val Tyr Tyr Cys Ala Arg Thr Tyr Tyr Gly Met Asp
        50                  55                  60

Val Trp Gly Gln Gly Thr Thr Val Thr Val Ser Ser Ala Ser Pro Thr
65              70                  75                  80

Ser Pro Lys Val Phe Pro Leu Ser Leu Asp Ser Thr Pro Gln Asp Gly
            85                  90                  95

Asn Val Val Val Ala Cys Leu Val Gln Gly Phe Phe Pro Gln Glu Pro
                100                 105                 110

Leu Ser Val Thr Trp Ser Glu Ser Gly Gln Asn Val Thr Ala Arg Asn
            115                 120                 125

Phe Pro Pro Ser Gln Asp Ala Ser Gly Asp Leu Tyr Thr Thr Ser Ser
        130                 135                 140

Gln Leu Thr Leu Pro Ala Thr Gln Cys Pro Asp Gly Lys Ser Val Thr
145                 150                 155                 160

Cys His Val Lys His Tyr Thr Asn Pro Ser Gln Asp Val Thr Val Pro
                165                 170                 175

Cys Pro Val Pro Pro Pro Pro Cys Cys His Pro Arg Leu Ser Leu
            180                 185                 190

His Arg Pro Ala Leu Glu Asp Leu Leu Leu Gly Ser Glu Ala Asn Leu
        195                 200                 205

Thr Cys Thr Leu Thr Gly Leu Arg Asp Ala Ser Gly Ala Thr Phe Thr
    210                 215                 220

Trp Thr Pro Ser Ser Gly Lys Ser Ala Val Gln Gly Pro Pro Glu Arg
225                 230                 235                 240

Asp Leu Cys Gly Cys Tyr Ser Val Ser Ser Val Leu Pro Gly Cys Ala
                245                 250                 255

Gln Pro Trp Asn His Gly Glu Thr Phe Thr Cys Thr Ala Ala His Pro

```
                 260                 265                 270
Glu Leu Lys Thr Pro Leu Thr Ala Asn Ile Thr Lys Ser Gly Asn Thr
            275                 280                 285

Phe Arg Pro Glu Val His Leu Leu Pro Pro Ser Glu Glu Leu Ala
        290                 295                 300

Leu Asn Glu Leu Val Thr Leu Thr Cys Leu Ala Arg Gly Phe Ser Pro
305                 310                 315                 320

Lys Asp Val Leu Val Arg Trp Leu Gln Gly Ser Gln Glu Leu Pro Arg
                325                 330                 335

Glu Lys Tyr Leu Thr Trp Ala Ser Arg Gln Glu Pro Ser Gln Gly Thr
            340                 345                 350

Thr Thr Phe Ala Val Thr Ser Ile Leu Arg Val Ala Ala Glu Asp Trp
        355                 360                 365

Lys Lys Gly Asp Thr Phe Ser Cys Met Val Gly His Glu Ala Leu Pro
        370                 375                 380

Leu Ala Phe Thr Gln Lys Thr Ile Asp Arg Leu Ala Gly Lys Pro Thr
385                 390                 395                 400

His Val Asn Val Ser Val Val Met Ala Glu Val Asp Gly Thr Cys Tyr
                405                 410                 415

<210> SEQ ID NO 57
<211> LENGTH: 327
<212> TYPE: PRT
<213> ORGANISM: Homo sapiens

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 58
<211> LENGTH: 452
<212> TYPE: PRT
<213> ORGANISM: Homo sapiens

<400> SEQUENCE: 58

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270
```

```
Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 59
<211> LENGTH: 375
<212> TYPE: PRT
<213> ORGANISM: Homo sapiens

<400> SEQUENCE: 59

Met Gln Gly Thr Asp Glu His Val Val Cys Lys Val Gln His Pro Asn
1               5                   10                  15

Gly Asn Lys Glu Lys Asn Val Pro Leu Pro Val Ile Ala Glu Leu Pro
            20                  25                  30

Pro Lys Val Ser Val Phe Val Pro Pro Arg Asp Gly Phe Phe Gly Asn
        35                  40                  45

Pro Arg Lys Ser Lys Leu Ile Cys Gln Ala Thr Gly Phe Ser Pro Arg
    50                  55                  60

Gln Ile Gln Val Ser Trp Leu Arg Glu Gly Lys Gln Val Gly Ser Gly
65                  70                  75                  80

Val Thr Thr Asp Gln Val Gln Ala Glu Ala Lys Glu Ser Gly Pro Thr
                85                  90                  95

Thr Tyr Lys Val Thr Ser Thr Leu Thr Ile Lys Glu Ser Asp Trp Leu
            100                 105                 110

Ser Gln Ser Met Phe Thr Cys Arg Val Asp His Arg Gly Leu Thr Phe
        115                 120                 125

Gln Gln Asn Ala Ser Ser Met Cys Gly Pro Asp Gln Asp Thr Ala Ile
    130                 135                 140

Arg Val Phe Ala Ile Pro Pro Ser Phe Ala Ser Ile Phe Leu Thr Lys
145                 150                 155                 160

Ser Thr Lys Leu Thr Cys Leu Val Thr Asp Leu Thr Thr Tyr Asp Ser
                165                 170                 175

Val Thr Ile Ser Trp Thr Arg Gln Asn Gly Glu Ala Val Lys Thr His
```

```
                180             185             190
Thr Asn Ile Ser Glu Ser His Pro Asn Ala Thr Phe Ser Ala Val Gly
            195                 200                 205
Glu Ala Ser Ile Cys Glu Asp Asp Trp Asn Ser Gly Glu Arg Phe Thr
            210                 215                 220
Cys Thr Val Thr His Thr Asp Leu Pro Ser Pro Leu Lys Gln Thr Ile
225                 230                 235                 240
Ser Arg Pro Lys Gly Val Ala Leu His Arg Pro Asp Val Tyr Leu Leu
            245                 250                 255
Pro Pro Ala Arg Glu Gln Leu Asn Leu Arg Glu Ser Ala Thr Ile Thr
            260                 265                 270
Cys Leu Val Thr Gly Phe Ser Pro Ala Asp Val Phe Val Gln Trp Met
            275                 280                 285
Gln Arg Gly Gln Pro Leu Ser Pro Glu Lys Tyr Val Thr Ser Ala Pro
            290                 295                 300
Met Pro Glu Pro Gln Ala Pro Gly Arg Tyr Phe Ala His Ser Ile Leu
305                 310                 315                 320
Thr Val Ser Glu Glu Glu Trp Asn Thr Gly Glu Thr Tyr Thr Cys Val
            325                 330                 335
Val Ala His Glu Ala Leu Pro Asn Arg Val Thr Glu Arg Thr Val Asp
            340                 345                 350
Lys Ser Thr Gly Lys Pro Thr Leu Tyr Asn Val Ser Leu Val Met Ser
            355                 360                 365
Asp Thr Ala Gly Thr Cys Tyr
    370             375

<210> SEQ ID NO 60
<211> LENGTH: 131
<212> TYPE: PRT
<213> ORGANISM: Homo sapiens

<400> SEQUENCE: 60

Leu Val Gln Leu Val Glu Ser Gly Gly Gly Leu Val Gln Pro Gly Arg
1               5                   10                  15
Ser Leu Arg Leu Ser Cys Thr Ala Pro Gly Phe Thr Phe Gly Asp Tyr
            20                  25                  30
Ala Met Ser Trp Val Arg Gln Ala Pro Gly Lys Gly Leu Glu Trp Val
            35                  40                  45
Gly Phe Ile Arg Ser Lys Ala Tyr Gly Gly Thr Thr Glu Tyr Ala Ala
        50                  55                  60
Ser Val Lys Gly Arg Phe Thr Ile Ser Arg Asp Asp Ser Lys Ser Ile
65                  70                  75                  80
Ala Tyr Leu Gln Met Asn Ser Leu Lys Thr Glu Asp Thr Ala Val Tyr
            85                  90                  95
Tyr Cys Thr Arg Asp Gln Asp Cys Thr Asn Gly Val Cys Tyr Thr Phe
            100                 105                 110
Gly Val Glu Asn Trp Phe Asp Pro Trp Gly Gln Gly Thr Leu Val Thr
            115                 120                 125
Val Ser Ser
    130

<210> SEQ ID NO 61
<211> LENGTH: 473
<212> TYPE: PRT
<213> ORGANISM: Homo sapiens
```

```
<400> SEQUENCE: 61

Met Glu Leu Gly Leu Cys Trp Val Leu Leu Val Ala Ile Leu Glu Gly
1               5                   10                  15

Val Gln Cys Glu Ile Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Glu Met Asn Trp Val Arg Gln Ala Pro Gly Lys Gly Leu
50                  55                  60

Glu Trp Leu Ser Tyr Ile Thr Arg Ser Gly Asn Thr Val Tyr Tyr Ala
65                  70                  75                  80

Asp Ser Leu Gln Gly Arg Phe Thr Ile Ser Arg Asp Asn Ala Arg Asn
                85                  90                  95

Ser Leu Tyr Leu Gln Met Asn Ser Leu Arg Ala Glu Asp Thr Ala Val
            100                 105                 110

Tyr Tyr Cys Ala Arg Gln Asn Glu His Thr Ser Pro Trp Tyr Pro Ser
        115                 120                 125

Phe Phe Asp Tyr Trp Gly Gln Gly Ile Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Leu Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415
```

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 62
<211> LENGTH: 157
<212> TYPE: PRT
<213> ORGANISM: Homo sapiens

<400> SEQUENCE: 62

Met Lys Asn His Leu Leu Phe Trp Gly Val Leu Ala Val Phe Ile Lys
1               5                   10                  15

Ala Val His Val Lys Gly Ser Arg Asp Ser Ser Ala Ser Ala Ser Arg
                20                  25                  30

Val Ala Gly Ile Thr Ala Gln Glu Asp Glu Arg Ile Val Leu Val Asp
            35                  40                  45

Asn Lys Cys Lys Cys Ala Arg Ile Thr Ser Arg Ile Ile Arg Ser Ser
    50                  55                  60

Glu Asp Pro Asn Glu Asp Ile Val Glu Arg Asn Ile Arg Ile Ile Val
65                  70                  75                  80

Pro Leu Asn Asn Arg Glu Asn Ile Ser Asp Pro Thr Ser Pro Leu Arg
                85                  90                  95

Thr Arg Phe Val Tyr His Leu Ser Asp Leu Cys Lys Lys Cys Asp Pro
            100                 105                 110

Thr Glu Val Glu Leu Asp Asn Gln Ile Val Thr Ala Thr Gln Ser Asn
        115                 120                 125

Ile Cys Asp Glu Asp Ser Ala Thr Glu Thr Cys Tyr Thr Tyr Asp Arg
    130                 135                 140

Asn Lys Cys Tyr Thr Ala Val Val Pro Leu Val Tyr Gly
145                 150                 155

<210> SEQ ID NO 63
<211> LENGTH: 117
<212> TYPE: PRT
<213> ORGANISM: Homo sapiens

<400> SEQUENCE: 63

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
                20                  25                  30

Leu Ser Ala Ser Val Gly Asp Arg Val Thr Ile Thr Cys Arg Ala Ser
            35                  40                  45

Gln Gly Ile Ser Ser Tyr Leu Ala Trp Tyr Gln Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Gln Gln
            100                 105                 110

```
Leu Asn Ser Tyr Pro
        115

<210> SEQ ID NO 64
<211> LENGTH: 106
<212> TYPE: PRT
<213> ORGANISM: Homo sapiens

<400> SEQUENCE: 64

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 65
<211> LENGTH: 233
<212> TYPE: PRT
<213> ORGANISM: Homo sapiens

<400> SEQUENCE: 65

Met Ala Trp Thr Pro Leu Trp Leu Thr Leu Leu Thr Leu Cys Ile Gly
1               5                   10                  15

Ser Val Val Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Ala Lys Asp Asn Arg Pro Ser Gly Val Pro Asp Arg Phe
65                  70                  75                  80

Ser Gly Ser Gly Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Ser Ser
            100                 105                 110

Gly Ser His Leu Val Phe Gly Thr Gly Thr Lys Val Thr Val Leu Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205
```

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 66
<211> LENGTH: 98
<212> TYPE: PRT
<213> ORGANISM: Homo sapiens

<400> SEQUENCE: 66

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Leu Leu Ser Tyr Ser Gly
                85                  90                  95

Ala Arg

<210> SEQ ID NO 67
<211> LENGTH: 890
<212> TYPE: PRT
<213> ORGANISM: Homo sapiens

<400> SEQUENCE: 67

Met Ala Phe Ala Trp Trp Pro Cys Leu Ile Leu Ala Leu Leu Ser Ser
1               5                   10                  15

Leu Ala Ala Ser Gly Phe Pro Arg Ser Pro Phe Arg Leu Leu Gly Lys
            20                  25                  30

Arg Ser Leu Pro Glu Gly Val Ala Asn Gly Ile Glu Val Tyr Ser Thr
        35                  40                  45

Lys Ile Asn Ser Lys Val Thr Ser Arg Phe Ala His Asn Val Val Thr
    50                  55                  60

Met Arg Ala Val Asn Arg Ala Asp Thr Ala Lys Glu Val Ser Phe Asp
65                  70                  75                  80

Val Glu Leu Pro Lys Thr Ala Phe Ile Thr Asn Phe Thr Leu Thr Ile
                85                  90                  95

Asp Gly Val Thr Tyr Pro Gly Asn Val Lys Glu Lys Glu Val Ala Lys
                100                 105                 110

Lys Gln Tyr Glu Lys Ala Val Ser Gln Gly Lys Thr Ala Gly Leu Val
            115                 120                 125

Lys Ala Ser Gly Arg Lys Leu Glu Lys Phe Thr Val Ser Val Asn Val
        130                 135                 140

Ala Ala Gly Ser Lys Val Thr Phe Glu Leu Thr Tyr Glu Glu Leu Leu
145                 150                 155                 160

Lys Arg His Lys Gly Lys Tyr Glu Met Tyr Leu Lys Val Gln Pro Lys
                165                 170                 175

Gln Leu Val Lys His Phe Glu Ile Glu Val Asp Ile Phe Glu Pro Gln
                180                 185                 190

-continued

```
Gly Ile Ser Met Leu Asp Ala Glu Ala Ser Phe Ile Thr Asn Asp Leu
            195                 200                 205
Leu Gly Ser Ala Leu Thr Lys Ser Phe Ser Gly Lys Lys Gly His Val
210                 215                 220
Ser Phe Lys Pro Ser Leu Asp Gln Gln Arg Ser Cys Pro Thr Cys Thr
225                 230                 235                 240
Asp Ser Leu Leu Asn Gly Asp Phe Thr Ile Thr Tyr Asp Val Asn Arg
            245                 250                 255
Glu Ser Pro Gly Asn Val Gln Ile Val Asn Gly Tyr Phe Val His Phe
            260                 265                 270
Phe Ala Pro Gln Gly Leu Pro Val Val Pro Lys Asn Val Ala Phe Val
            275                 280                 285
Ile Asp Ile Ser Gly Ser Met Ala Gly Arg Lys Leu Glu Gln Thr Lys
290                 295                 300
Glu Ala Leu Leu Arg Ile Leu Glu Asp Met Gln Glu Asp Tyr Leu
305                 310                 315                 320
Asn Phe Ile Leu Phe Ser Gly Asp Val Ser Thr Trp Lys Glu His Leu
            325                 330                 335
Val Gln Ala Thr Pro Glu Asn Leu Gln Glu Ala Arg Thr Phe Val Lys
            340                 345                 350
Ser Met Glu Asp Lys Gly Met Thr Asn Ile Asn Asp Gly Leu Leu Arg
355                 360                 365
Gly Ile Ser Met Leu Asn Lys Ala Arg Glu Glu His Arg Ile Pro Glu
            370                 375                 380
Arg Ser Thr Ser Ile Val Ile Met Leu Thr Asp Gly Asp Ala Asn Val
385                 390                 395                 400
Gly Glu Ser Arg Pro Glu Lys Ile Gln Glu Asn Val Arg Asn Ala Ile
                405                 410                 415
Gly Gly Lys Phe Pro Leu Tyr Asn Leu Gly Phe Gly Asn Asn Leu Asn
            420                 425                 430
Tyr Asn Phe Leu Glu Asn Met Ala Leu Glu Asn His Gly Phe Ala Arg
            435                 440                 445
Arg Ile Tyr Glu Asp Ser Asp Ala Asp Leu Gln Leu Gln Gly Phe Tyr
450                 455                 460
Glu Glu Val Ala Asn Pro Leu Leu Thr Gly Val Glu Met Glu Tyr Pro
465                 470                 475                 480
Glu Asn Ala Ile Leu Asp Leu Thr Gln Asn Thr Tyr Gln His Phe Tyr
                485                 490                 495
Asp Gly Ser Glu Ile Val Val Ala Gly Arg Leu Val Asp Glu Asp Met
                500                 505                 510
Asn Ser Phe Lys Ala Asp Val Lys Gly His Gly Ala Thr Asn Asp Leu
            515                 520                 525
Thr Phe Thr Glu Glu Val Asp Met Lys Glu Met Glu Lys Ala Leu Gln
530                 535                 540
Glu Arg Asp Tyr Ile Phe Gly Asn Tyr Ile Glu Arg Leu Trp Ala Tyr
545                 550                 555                 560
Leu Thr Ile Glu Gln Leu Leu Glu Lys Arg Lys Asn Ala His Gly Glu
                565                 570                 575
Glu Lys Glu Asn Leu Thr Ala Arg Ala Leu Asp Leu Ser Leu Lys Tyr
            580                 585                 590
His Phe Val Thr Pro Leu Thr Ser Met Val Val Thr Lys Pro Glu Asp
            595                 600                 605
Asn Glu Asp Glu Arg Ala Ile Ala Asp Lys Pro Gly Glu Asp Ala Glu
```

```
                610             615             620
Ala Thr Pro Val Ser Pro Ala Met Ser Tyr Leu Thr Ser Tyr Gln Pro
625                 630                 635                 640

Pro Gln Asn Pro Tyr Tyr Val Asp Gly Asp Pro His Phe Ile Ile
                645                 650                 655

Gln Ile Pro Glu Lys Asp Ala Leu Cys Phe Asn Ile Asp Glu Ala
            660                 665                 670

Pro Gly Thr Val Leu Arg Leu Ile Gln Asp Ala Val Thr Gly Leu Thr
            675                 680                 685

Val Asn Gly Gln Ile Thr Gly Asp Lys Arg Gly Ser Pro Asp Ser Lys
    690                 695                 700

Thr Arg Lys Thr Tyr Phe Gly Lys Leu Gly Ile Ala Asn Ala Gln Met
705                 710                 715                 720

Asp Phe Gln Val Glu Val Thr Thr Glu Lys Ile Thr Leu Trp Asn Arg
                725                 730                 735

Ala Val Pro Ser Thr Phe Ser Trp Leu Asp Thr Val Thr Val Thr Gln
                740                 745                 750

Asp Gly Leu Ser Met Met Ile Asn Arg Lys Asn Met Val Val Ser Phe
            755                 760                 765

Gly Asp Gly Val Thr Phe Val Val Leu His Gln Val Trp Lys Lys
770                 775                 780

His Pro Val His Arg Asp Phe Leu Gly Phe Tyr Val Val Asp Ser His
785                 790                 795                 800

Arg Met Ser Ala Gln Thr His Gly Leu Leu Gly Gln Phe Phe Gln Pro
                805                 810                 815

Phe Asp Phe Lys Val Ser Asp Ile Arg Pro Gly Ser Asp Pro Thr Lys
                820                 825                 830

Pro Asp Ala Thr Leu Val Val Lys Asn His Gln Leu Ile Val Thr Arg
            835                 840                 845

Gly Ser Gln Lys Asp Tyr Arg Lys Asp Ala Ser Ile Gly Thr Lys Val
            850                 855                 860

Val Cys Trp Phe Val His Asn Asn Gly Glu Gly Leu Ile Asp Gly Val
865                 870                 875                 880

His Thr Asp Tyr Ile Val Pro Asn Leu Phe
                885                 890

<210> SEQ ID NO 68
<211> LENGTH: 638
<212> TYPE: PRT
<213> ORGANISM: Homo sapiens

<400> SEQUENCE: 68

Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
                20                  25                  30

Gly Gly Asp Val Ala Ser Met Tyr Thr Pro Asn Ala Gln Tyr Cys Gln
            35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95
```

```
Ser Gly His Ser Leu Lys Gln Cys Gly His Gln Ile Ser Ala Cys His
            100                 105                 110
Arg Asp Ile Tyr Lys Gly Val Asp Met Arg Gly Val Asn Phe Asn Val
        115                 120                 125
Ser Lys Val Ser Ser Val Glu Glu Cys Gln Lys Arg Cys Thr Asn Asn
    130                 135                 140
Ile Arg Cys Gln Phe Phe Ser Tyr Ala Thr Gln Thr Phe His Lys Ala
145                 150                 155                 160
Glu Tyr Arg Asn Asn Cys Leu Leu Lys Tyr Ser Pro Gly Gly Thr Pro
                165                 170                 175
Thr Ala Ile Lys Val Leu Ser Asn Val Glu Ser Gly Phe Ser Leu Lys
            180                 185                 190
Pro Cys Ala Leu Ser Glu Ile Gly Cys His Met Asn Ile Phe Gln His
        195                 200                 205
Leu Ala Phe Ser Asp Val Asp Val Ala Arg Val Leu Thr Pro Asp Ala
    210                 215                 220
Phe Val Cys Arg Thr Ile Cys Thr Tyr His Pro Asn Cys Leu Phe Phe
225                 230                 235                 240
Thr Phe Tyr Thr Asn Val Trp Lys Ile Glu Ser Gln Arg Asn Val Cys
                245                 250                 255
Leu Leu Lys Thr Ser Glu Ser Gly Thr Pro Ser Ser Ser Thr Pro Gln
            260                 265                 270
Glu Asn Thr Ile Ser Gly Tyr Ser Leu Leu Thr Cys Lys Arg Thr Leu
        275                 280                 285
Pro Glu Pro Cys His Ser Lys Ile Tyr Pro Gly Val Asp Phe Gly Gly
    290                 295                 300
Glu Glu Leu Asn Val Thr Phe Val Lys Gly Val Asn Val Cys Gln Glu
305                 310                 315                 320
Thr Cys Thr Lys Met Ile Arg Cys Gln Phe Phe Thr Tyr Ser Leu Leu
                325                 330                 335
Pro Glu Asp Cys Lys Glu Glu Lys Cys Lys Cys Phe Leu Arg Leu Ser
            340                 345                 350
Met Asp Gly Ser Pro Thr Arg Ile Ala Tyr Gly Thr Gln Gly Ser Ser
        355                 360                 365
Gly Tyr Ser Leu Arg Leu Cys Asn Thr Gly Asp Asn Ser Val Cys Thr
    370                 375                 380
Thr Lys Thr Ser Thr Arg Ile Val Gly Gly Thr Asn Ser Ser Trp Gly
385                 390                 395                 400
Glu Trp Pro Trp Gln Val Ser Leu Gln Val Lys Leu Thr Ala Gln Arg
                405                 410                 415
His Leu Cys Gly Gly Ser Leu Ile Gly His Gln Trp Val Leu Thr Ala
            420                 425                 430
Ala His Cys Phe Asp Gly Leu Pro Leu Gln Asp Val Trp Arg Ile Tyr
        435                 440                 445
Ser Gly Ile Leu Asn Leu Ser Asp Ile Thr Lys Asp Thr Pro Phe Ser
    450                 455                 460
Gln Ile Lys Glu Ile Ile Ile His Gln Asn Tyr Lys Val Ser Glu Gly
465                 470                 475                 480
Asn His Asp Ile Ala Leu Ile Lys Leu Gln Ala Pro Leu Asn Tyr Thr
                485                 490                 495
Glu Phe Gln Lys Pro Ile Cys Leu Pro Ser Lys Gly Asp Thr Ser Thr
            500                 505                 510
Ile Tyr Thr Asn Cys Trp Val Thr Gly Trp Gly Phe Ser Lys Glu Lys
```

```
                515                 520                 525
Gly Glu Ile Gln Asn Ile Leu Gln Lys Val Asn Ile Pro Leu Val Thr
            530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Lys Asp Ala Cys Lys Gly
                565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
                595                 600                 605

Gly Val Tyr Thr Lys Val Ala Glu Tyr Met Asp Trp Ile Leu Glu Lys
            610                 615                 620

Thr Gln Ser Ser Asp Gly Lys Ala Gln Met Gln Ser Pro Ala
625                 630                 635

<210> SEQ ID NO 69
<211> LENGTH: 639
<212> TYPE: PRT
<213> ORGANISM: Homo sapiens

<400> SEQUENCE: 69

Met Ser Cys Gln Ile Ser Cys Lys Ser Arg Gly Arg Gly Gly Gly Gly
1               5                   10                  15

Gly Gly Phe Arg Gly Phe Ser Ser Gly Ser Ala Val Val Ser Gly Gly
                20                  25                  30

Ser Arg Arg Ser Thr Ser Ser Phe Ser Cys Leu Ser Arg His Gly Gly
            35                  40                  45

Gly Gly Gly Gly Phe Gly Gly Gly Phe Gly Ser Arg Ser Leu Val
Gly Leu Gly Gly Thr Lys Ser Ile Ser Ile Ser Val Ala Gly Gly Gly
65                  70                  75                  80

Gly Gly Phe Gly Ala Ala Gly Gly Phe Gly Gly Arg Gly Gly Gly Phe
                85                  90                  95

Gly Gly Gly Ser Ser Phe Gly Gly Ser Gly Phe Ser Gly Gly Gly
            100                 105                 110

Phe Gly Gly Gly Phe Gly Gly Gly Arg Phe Gly Gly Phe Gly Gly
                115                 120                 125

Pro Gly Gly Val Gly Gly Leu Gly Gly Pro Gly Gly Phe Gly Pro Gly
            130                 135                 140

Gly Tyr Pro Gly Gly Ile His Glu Val Ser Val Asn Gln Ser Leu Leu
145                 150                 155                 160

Gln Pro Leu Asn Val Lys Val Asp Pro Glu Ile Gln Asn Val Lys Ala
                165                 170                 175

Gln Glu Arg Glu Gln Ile Lys Thr Leu Asn Asn Lys Phe Ala Ser Phe
            180                 185                 190

Ile Asp Lys Val Arg Phe Leu Glu Gln Gln Asn Gln Val Leu Gln Thr
                195                 200                 205

Lys Trp Glu Leu Leu Gln Gln Met Asn Val Gly Thr Arg Pro Ile Asn
            210                 215                 220

Leu Glu Pro Ile Phe Gln Gly Tyr Ile Asp Ser Leu Lys Arg Tyr Leu
225                 230                 235                 240

Asp Gly Leu Thr Ala Glu Arg Thr Ser Gln Asn Ser Glu Leu Asn Asn
                245                 250                 255
```

```
Met Gln Asp Leu Val Glu Asp Tyr Lys Lys Tyr Glu Asp Ile
            260                 265                 270

Asn Lys Arg Thr Ala Ala Glu Asn Asp Phe Val Thr Leu Lys Lys Asp
            275                 280                 285

Val Asp Asn Ala Tyr Met Ile Lys Val Glu Leu Gln Ser Lys Val Asp
290                 295                 300

Leu Leu Asn Gln Glu Ile Glu Phe Leu Lys Val Leu Tyr Asp Ala Glu
305                 310                 315                 320

Ile Ser Gln Ile His Gln Ser Val Thr Asp Thr Asn Val Ile Leu Ser
                325                 330                 335

Met Asp Asn Ser Arg Asn Leu Asp Leu Asp Ser Ile Ile Ala Glu Val
            340                 345                 350

Lys Ala Gln Tyr Glu Glu Ile Ala Gln Arg Ser Lys Glu Glu Ala Glu
            355                 360                 365

Ala Leu Tyr His Ser Lys Tyr Glu Glu Leu Gln Val Thr Val Gly Arg
            370                 375                 380

His Gly Asp Ser Leu Lys Glu Ile Lys Ile Glu Ile Ser Glu Leu Asn
385                 390                 395                 400

Arg Val Ile Gln Arg Leu Gln Gly Glu Ile Ala His Val Lys Lys Gln
                405                 410                 415

Cys Lys Asn Val Gln Asp Ala Ile Ala Asp Ala Glu Gln Arg Gly Glu
            420                 425                 430

His Ala Leu Lys Asp Ala Arg Asn Lys Leu Asn Asp Leu Glu Glu Ala
            435                 440                 445

Leu Gln Gln Ala Lys Glu Asp Leu Ala Arg Leu Leu Arg Asp Tyr Gln
450                 455                 460

Glu Leu Met Asn Val Lys Leu Ala Leu Asp Val Glu Ile Ala Thr Tyr
465                 470                 475                 480

Arg Lys Leu Leu Glu Gly Glu Cys Arg Met Ser Gly Asp Leu Ser
                485                 490                 495

Ser Asn Val Thr Val Ser Val Thr Ser Ser Thr Ile Ser Ser Asn Val
            500                 505                 510

Ala Ser Lys Ala Ala Phe Gly Gly Ser Gly Gly Arg Gly Ser Ser Ser
            515                 520                 525

Gly Gly Gly Tyr Ser Ser Gly Ser Ser Tyr Gly Ser Gly Gly Arg
            530                 535                 540

Gln Ser Gly Ser Arg Gly Gly Ser Gly Gly Gly Ser Ile Ser Gly
545                 550                 555                 560

Gly Gly Tyr Gly Ser Gly Gly Ser Gly Gly Arg Tyr Gly Ser Gly
                565                 570                 575

Gly Gly Ser Lys Gly Gly Ser Ile Ser Gly Gly Tyr Gly Ser Gly
            580                 585                 590

Gly Gly Lys His Ser Ser Gly Gly Gly Ser Arg Gly Gly Ser Ser Ser
            595                 600                 605

Gly Gly Gly Tyr Gly Ser Gly Gly Gly Ser Ser Ser Val Lys Gly
            610                 615                 620

Ser Ser Gly Glu Ala Phe Gly Ser Ser Val Thr Phe Ser Phe Arg
625                 630                 635

<210> SEQ ID NO 70
<211> LENGTH: 4548
<212> TYPE: PRT
<213> ORGANISM: Homo sapiens

<400> SEQUENCE: 70
```

```
Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
            20                  25                  30

Gly Gln Ser Tyr Arg Gly Thr Tyr Ser Thr Thr Val Thr Gly Arg Thr
        35                  40                  45

Cys Gln Ala Trp Ser Ser Met Thr Pro His Gln His Asn Arg Thr Thr
50                  55                      60

Glu Asn Tyr Pro Asn Ala Gly Leu Ile Met Asn Tyr Cys Arg Asn Pro
65              70                  75                      80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
                100                 105                 110

Val Ala Pro Pro Thr Val Thr Pro Val Pro Ser Leu Glu Ala Pro Ser
            115                 120                 125

Glu Gln Ala Pro Thr Glu Gln Arg Pro Gly Val Gln Glu Cys Tyr His
    130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
                165                 170                 175

Thr Pro Glu Tyr Tyr Pro Asn Ala Gly Leu Ile Met Asn Tyr Cys Arg
            180                 185                 190

Asn Pro Asp Ala Val Ala Ala Pro Tyr Cys Tyr Thr Arg Asp Pro Gly
        195                 200                 205

Val Arg Trp Glu Tyr Cys Asn Leu Thr Gln Cys Ser Asp Ala Glu Gly
210                 215                 220

Thr Ala Val Ala Pro Pro Thr Val Thr Pro Val Pro Ser Leu Glu Ala
225                 230                 235                 240

Pro Ser Glu Gln Ala Pro Thr Glu Gln Arg Pro Gly Val Gln Glu Cys
            245                 250                 255

Tyr His Gly Asn Gly Gln Ser Tyr Arg Gly Thr Tyr Ser Thr Thr Val
                260                 265                 270

Thr Gly Arg Thr Cys Gln Ala Trp Ser Ser Met Thr Pro His Ser His
            275                 280                 285

Ser Arg Thr Pro Glu Tyr Tyr Pro Asn Ala Gly Leu Ile Met Asn Tyr
    290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
            325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
            355                 360                 365

Glu Cys Tyr His Gly Asn Gly Gln Ser Tyr Arg Gly Thr Tyr Ser Thr
    370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
                405                 410                 415
```

```
Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
        435                 440                 445

Asp Ala Glu Gly Thr Ala Val Ala Pro Pro Thr Val Thr Pro Val Pro
    450                 455                 460

Ser Leu Glu Ala Pro Ser Glu Gln Ala Pro Thr Glu Gln Arg Pro Gly
465                 470                 475                 480

Val Gln Glu Cys Tyr His Gly Asn Gly Gln Ser Tyr Arg Gly Thr Tyr
                485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
        515                 520                 525

Ile Met Asn Tyr Cys Arg Asn Pro Asp Ala Val Ala Ala Pro Tyr Cys
    530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
                565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
        595                 600                 605

Thr Tyr Ser Thr Thr Val Thr Gly Arg Thr Cys Gln Ala Trp Ser Ser
    610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                645                 650                 655

Tyr Cys Tyr Thr Arg Asp Pro Gly Val Arg Trp Glu Tyr Cys Asn Leu
            660                 665                 670

Thr Gln Cys Ser Asp Ala Glu Gly Thr Ala Val Ala Pro Pro Thr Val
        675                 680                 685

Thr Pro Val Pro Ser Leu Glu Ala Pro Ser Glu Gln Ala Pro Thr Glu
    690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
        755                 760                 765

Ala Pro Tyr Cys Tyr Thr Arg Asp Pro Gly Val Arg Trp Glu Tyr Cys
    770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
```

```
                835                 840                 845
Ala Trp Ser Ser Met Thr Pro His Ser His Ser Arg Thr Pro Glu Tyr
850                 855                 860
Tyr Pro Asn Ala Gly Leu Ile Met Asn Tyr Cys Arg Asn Pro Asp Ala
865                 870                 875                 880
Val Ala Ala Pro Tyr Cys Tyr Thr Arg Asp Pro Gly Val Arg Trp Glu
                885                 890                 895
Tyr Cys Asn Leu Thr Gln Cys Ser Asp Ala Glu Gly Thr Ala Val Ala
                900                 905                 910
Pro Pro Thr Val Thr Pro Val Pro Ser Leu Glu Ala Pro Ser Glu Gln
                915                 920                 925
Ala Pro Thr Glu Gln Arg Pro Gly Val Gln Glu Cys Tyr His Gly Asn
930                 935                 940
Gly Gln Ser Tyr Arg Gly Thr Tyr Ser Thr Thr Val Thr Gly Arg Thr
945                 950                 955                 960
Cys Gln Ala Trp Ser Ser Met Thr Pro His Ser His Ser Arg Thr Pro
                965                 970                 975
Glu Tyr Tyr Pro Asn Ala Gly Leu Ile Met Asn Tyr Cys Arg Asn Pro
                980                 985                 990
Asp Ala Val Ala Ala Pro Tyr Cys Tyr Thr Arg Asp Pro Gly Val Arg
                995                1000                1005
Trp Glu Tyr Cys Asn Leu Thr Gln Cys Ser Asp Ala Glu Gly Thr Ala
               1010                1015                1020
Val Ala Pro Pro Thr Val Thr Pro Val Pro Ser Leu Glu Ala Pro Ser
1025                1030                1035                1040
Glu Gln Ala Pro Thr Glu Gln Arg Pro Gly Val Gln Glu Cys Tyr His
               1045                1050                1055
Gly Asn Gly Gln Ser Tyr Arg Gly Thr Tyr Ser Thr Thr Val Thr Gly
               1060                1065                1070
Arg Thr Cys Gln Ala Trp Ser Ser Met Thr Pro His Ser His Ser Arg
               1075                1080                1085
Thr Pro Glu Tyr Tyr Pro Asn Ala Gly Leu Ile Met Asn Tyr Cys Arg
               1090                1095                1100
Asn Pro Asp Ala Val Ala Ala Pro Tyr Cys Tyr Thr Arg Asp Pro Gly
1105                1110                1115                1120
Val Arg Trp Glu Tyr Cys Asn Leu Thr Gln Cys Ser Asp Ala Glu Gly
               1125                1130                1135
Thr Ala Val Ala Pro Pro Thr Val Thr Pro Val Pro Ser Leu Glu Ala
               1140                1145                1150
Pro Ser Glu Gln Ala Pro Thr Glu Gln Arg Pro Gly Val Gln Glu Cys
               1155                1160                1165
Tyr His Gly Asn Gly Gln Ser Tyr Arg Gly Thr Tyr Ser Thr Thr Val
               1170                1175                1180
Thr Gly Arg Thr Cys Gln Ala Trp Ser Ser Met Thr Pro His Ser His
1185                1190                1195                1200
Ser Arg Thr Pro Glu Tyr Tyr Pro Asn Ala Gly Leu Ile Met Asn Tyr
               1205                1210                1215
Cys Arg Asn Pro Asp Ala Val Ala Ala Pro Tyr Cys Tyr Thr Arg Asp
               1220                1225                1230
Pro Gly Val Arg Trp Glu Tyr Cys Asn Leu Thr Gln Cys Ser Asp Ala
               1235                1240                1245
Glu Gly Thr Ala Val Ala Pro Pro Thr Val Thr Pro Val Pro Ser Leu
               1250                1255                1260
```

```
Glu Ala Pro Ser Glu Gln Ala Pro Thr Glu Gln Arg Pro Gly Val Gln
1265                1270                1275                1280

Glu Cys Tyr His Gly Asn Gly Gln Ser Tyr Arg Gly Thr Tyr Ser Thr
                1285                1290                1295

Thr Val Thr Gly Arg Thr Cys Gln Ala Trp Ser Ser Met Thr Pro His
            1300                1305                1310

Ser His Ser Arg Thr Pro Glu Tyr Tyr Pro Asn Ala Gly Leu Ile Met
        1315                1320                1325

Asn Tyr Cys Arg Asn Pro Asp Ala Val Ala Ala Pro Tyr Cys Tyr Thr
    1330                1335                1340

Arg Asp Pro Gly Val Arg Trp Glu Tyr Cys Asn Leu Thr Gln Cys Ser
1345                1350                1355                1360

Asp Ala Glu Gly Thr Ala Val Ala Pro Pro Thr Val Thr Pro Val Pro
                1365                1370                1375

Ser Leu Glu Ala Pro Ser Glu Gln Ala Pro Thr Glu Gln Arg Pro Gly
            1380                1385                1390

Val Gln Glu Cys Tyr His Gly Asn Gly Gln Ser Tyr Arg Gly Thr Tyr
        1395                1400                1405

Ser Thr Thr Val Thr Gly Arg Thr Cys Gln Ala Trp Ser Ser Met Thr
    1410                1415                1420

Pro His Ser His Ser Arg Thr Pro Glu Tyr Tyr Pro Asn Ala Gly Leu
1425                1430                1435                1440

Ile Met Asn Tyr Cys Arg Asn Pro Asp Ala Val Ala Ala Pro Tyr Cys
                1445                1450                1455

Tyr Thr Arg Asp Pro Gly Val Arg Trp Glu Tyr Cys Asn Leu Thr Gln
            1460                1465                1470

Cys Ser Asp Ala Glu Gly Thr Ala Val Ala Pro Pro Thr Val Thr Pro
        1475                1480                1485

Val Pro Ser Leu Glu Ala Pro Ser Glu Gln Ala Pro Thr Glu Gln Arg
    1490                1495                1500

Pro Gly Val Gln Glu Cys Tyr His Gly Asn Gly Gln Ser Tyr Arg Gly
1505                1510                1515                1520

Thr Tyr Ser Thr Thr Val Thr Gly Arg Thr Cys Gln Ala Trp Ser Ser
                1525                1530                1535

Met Thr Pro His Ser His Ser Arg Thr Pro Glu Tyr Tyr Pro Asn Ala
            1540                1545                1550

Gly Leu Ile Met Asn Tyr Cys Arg Asn Pro Asp Ala Val Ala Ala Pro
        1555                1560                1565

Tyr Cys Tyr Thr Arg Asp Pro Gly Val Arg Trp Glu Tyr Cys Asn Leu
    1570                1575                1580

Thr Gln Cys Ser Asp Ala Glu Gly Thr Ala Val Ala Pro Pro Thr Val
1585                1590                1595                1600

Thr Pro Val Pro Ser Leu Glu Ala Pro Ser Glu Gln Ala Pro Thr Glu
                1605                1610                1615

Gln Arg Pro Gly Val Gln Glu Cys Tyr His Gly Asn Gly Gln Ser Tyr
            1620                1625                1630

Arg Gly Thr Tyr Ser Thr Thr Val Thr Gly Arg Thr Cys Gln Ala Trp
        1635                1640                1645

Ser Ser Met Thr Pro His Ser His Ser Arg Thr Pro Glu Tyr Tyr Pro
    1650                1655                1660

Asn Ala Gly Leu Ile Met Asn Tyr Cys Arg Asn Pro Asp Ala Val Ala
1665                1670                1675                1680
```

-continued

```
Ala Pro Tyr Cys Tyr Thr Arg Asp Pro Gly Val Arg Trp Glu Tyr Cys
            1685                1690                1695

Asn Leu Thr Gln Cys Ser Asp Ala Glu Gly Thr Ala Val Ala Pro Pro
            1700                1705                1710

Thr Val Thr Pro Val Pro Ser Leu Glu Ala Pro Ser Glu Gln Ala Pro
            1715                1720                1725

Thr Glu Gln Arg Pro Gly Val Gln Glu Cys Tyr His Gly Asn Gly Gln
            1730                1735                1740

Ser Tyr Arg Gly Thr Tyr Ser Thr Thr Val Thr Gly Arg Thr Cys Gln
1745                1750                1755                1760

Ala Trp Ser Ser Met Thr Pro His Ser His Ser Arg Thr Pro Glu Tyr
            1765                1770                1775

Tyr Pro Asn Ala Gly Leu Ile Met Asn Tyr Cys Arg Asn Pro Asp Ala
            1780                1785                1790

Val Ala Ala Pro Tyr Cys Tyr Thr Arg Asp Pro Gly Val Arg Trp Glu
            1795                1800                1805

Tyr Cys Asn Leu Thr Gln Cys Ser Asp Ala Glu Gly Thr Ala Val Ala
            1810                1815                1820

Pro Pro Thr Val Thr Pro Val Pro Ser Leu Glu Ala Pro Ser Glu Gln
1825                1830                1835                1840

Ala Pro Thr Glu Gln Arg Pro Gly Val Gln Glu Cys Tyr His Gly Asn
            1845                1850                1855

Gly Gln Ser Tyr Arg Gly Thr Tyr Ser Thr Thr Val Thr Gly Arg Thr
            1860                1865                1870

Cys Gln Ala Trp Ser Ser Met Thr Pro His Ser His Ser Arg Thr Pro
            1875                1880                1885

Glu Tyr Tyr Pro Asn Ala Gly Leu Ile Met Asn Tyr Cys Arg Asn Pro
            1890                1895                1900

Asp Ala Val Ala Ala Pro Tyr Cys Tyr Thr Arg Asp Pro Gly Val Arg
1905                1910                1915                1920

Trp Glu Tyr Cys Asn Leu Thr Gln Cys Ser Asp Ala Glu Gly Thr Ala
            1925                1930                1935

Val Ala Pro Pro Thr Val Thr Pro Val Pro Ser Leu Glu Ala Pro Ser
            1940                1945                1950

Glu Gln Ala Pro Thr Glu Gln Arg Pro Gly Val Gln Glu Cys Tyr His
            1955                1960                1965

Gly Asn Gly Gln Ser Tyr Arg Gly Thr Tyr Ser Thr Thr Val Thr Gly
            1970                1975                1980

Arg Thr Cys Gln Ala Trp Ser Ser Met Thr Pro His Ser His Ser Arg
1985                1990                1995                2000

Thr Pro Glu Tyr Tyr Pro Asn Ala Gly Leu Ile Met Asn Tyr Cys Arg
            2005                2010                2015

Asn Pro Asp Ala Val Ala Ala Pro Tyr Cys Tyr Thr Arg Asp Pro Gly
            2020                2025                2030

Val Arg Trp Glu Tyr Cys Asn Leu Thr Gln Cys Ser Asp Ala Glu Gly
            2035                2040                2045

Thr Ala Val Ala Pro Pro Thr Val Thr Pro Val Pro Ser Leu Glu Ala
            2050                2055                2060

Pro Ser Glu Gln Ala Pro Thr Glu Gln Arg Pro Gly Val Gln Glu Cys
2065                2070                2075                2080

Tyr His Gly Asn Gly Gln Ser Tyr Arg Gly Thr Tyr Ser Thr Thr Val
            2085                2090                2095

Thr Gly Arg Thr Cys Gln Ala Trp Ser Ser Met Thr Pro His Ser His
```

```
                     2100              2105              2110

Ser Arg Thr Pro Glu Tyr Tyr Pro Asn Ala Gly Leu Ile Met Asn Tyr
        2115                2120                2125

Cys Arg Asn Pro Asp Ala Val Ala Ala Pro Tyr Cys Tyr Thr Arg Asp
        2130                2135                2140

Pro Gly Val Arg Trp Glu Tyr Cys Asn Leu Thr Gln Cys Ser Asp Ala
2145                2150                2155                2160

Glu Gly Thr Ala Val Ala Pro Pro Thr Val Thr Pro Val Pro Ser Leu
                2165                2170                2175

Glu Ala Pro Ser Glu Gln Ala Pro Thr Glu Gln Arg Pro Gly Val Gln
            2180                2185                2190

Glu Cys Tyr His Gly Asn Gly Gln Ser Tyr Arg Gly Thr Tyr Ser Thr
        2195                2200                2205

Thr Val Thr Gly Arg Thr Cys Gln Ala Trp Ser Ser Met Thr Pro His
        2210                2215                2220

Ser His Ser Arg Thr Pro Glu Tyr Tyr Pro Asn Ala Gly Leu Ile Met
2225                2230                2235                2240

Asn Tyr Cys Arg Asn Pro Asp Ala Val Ala Ala Pro Tyr Cys Tyr Thr
                2245                2250                2255

Arg Asp Pro Gly Val Arg Trp Glu Tyr Cys Asn Leu Thr Gln Cys Ser
            2260                2265                2270

Asp Ala Glu Gly Thr Ala Val Ala Pro Pro Thr Val Thr Pro Val Pro
        2275                2280                2285

Ser Leu Glu Ala Pro Ser Glu Gln Ala Pro Thr Glu Gln Arg Pro Gly
        2290                2295                2300

Val Gln Glu Cys Tyr His Gly Asn Gly Gln Ser Tyr Arg Gly Thr Tyr
2305                2310                2315                2320

Ser Thr Thr Val Thr Gly Arg Thr Cys Gln Ala Trp Ser Ser Met Thr
                2325                2330                2335

Pro His Ser His Ser Arg Thr Pro Glu Tyr Tyr Pro Asn Ala Gly Leu
            2340                2345                2350

Ile Met Asn Tyr Cys Arg Asn Pro Asp Ala Val Ala Ala Pro Tyr Cys
        2355                2360                2365

Tyr Thr Arg Asp Pro Gly Val Arg Trp Glu Tyr Cys Asn Leu Thr Gln
        2370                2375                2380

Cys Ser Asp Ala Glu Gly Thr Ala Val Ala Pro Pro Thr Val Thr Pro
2385                2390                2395                2400

Val Pro Ser Leu Glu Ala Pro Ser Glu Gln Ala Pro Thr Glu Gln Arg
                2405                2410                2415

Pro Gly Val Gln Glu Cys Tyr His Gly Asn Gly Gln Ser Tyr Arg Gly
            2420                2425                2430

Thr Tyr Ser Thr Thr Val Thr Gly Arg Thr Cys Gln Ala Trp Ser Ser
        2435                2440                2445

Met Thr Pro His Ser His Ser Arg Thr Pro Glu Tyr Tyr Pro Asn Ala
        2450                2455                2460

Gly Leu Ile Met Asn Tyr Cys Arg Asn Pro Asp Ala Val Ala Ala Pro
2465                2470                2475                2480

Tyr Cys Tyr Thr Arg Asp Pro Gly Val Arg Trp Glu Tyr Cys Asn Leu
                2485                2490                2495

Thr Gln Cys Ser Asp Ala Glu Gly Thr Ala Val Ala Pro Pro Thr Val
            2500                2505                2510

Thr Pro Val Pro Ser Leu Glu Ala Pro Ser Glu Gln Ala Pro Thr Glu
        2515                2520                2525
```

```
Gln Arg Pro Gly Val Gln Glu Cys Tyr His Gly Asn Gly Gln Ser Tyr
    2530                2535                2540

Arg Gly Thr Tyr Ser Thr Thr Val Thr Gly Arg Thr Cys Gln Ala Trp
2545                2550                2555                2560

Ser Ser Met Thr Pro His Ser His Ser Arg Thr Pro Glu Tyr Tyr Pro
            2565                2570                2575

Asn Ala Gly Leu Ile Met Asn Tyr Cys Arg Asn Pro Asp Ala Val Ala
        2580                2585                2590

Ala Pro Tyr Cys Tyr Thr Arg Asp Pro Gly Val Arg Trp Glu Tyr Cys
    2595                2600                2605

Asn Leu Thr Gln Cys Ser Asp Ala Glu Gly Thr Ala Val Ala Pro Pro
    2610                2615                2620

Thr Val Thr Pro Val Pro Ser Leu Glu Ala Pro Ser Glu Gln Ala Pro
2625                2630                2635                2640

Thr Glu Gln Arg Pro Gly Val Gln Glu Cys Tyr His Gly Asn Gly Gln
            2645                2650                2655

Ser Tyr Arg Gly Thr Tyr Ser Thr Thr Val Thr Gly Arg Thr Cys Gln
            2660                2665                2670

Ala Trp Ser Ser Met Thr Pro His Ser His Ser Arg Thr Pro Glu Tyr
        2675                2680                2685

Tyr Pro Asn Ala Gly Leu Ile Met Asn Tyr Cys Arg Asn Pro Asp Ala
    2690                2695                2700

Val Ala Ala Pro Tyr Cys Tyr Thr Arg Asp Pro Gly Val Arg Trp Glu
2705                2710                2715                2720

Tyr Cys Asn Leu Thr Gln Cys Ser Asp Ala Glu Gly Thr Ala Val Ala
            2725                2730                2735

Pro Pro Thr Val Thr Pro Val Pro Ser Leu Glu Ala Pro Ser Glu Gln
            2740                2745                2750

Ala Pro Thr Glu Gln Arg Pro Gly Val Gln Glu Cys Tyr His Gly Asn
        2755                2760                2765

Gly Gln Ser Tyr Arg Gly Thr Tyr Ser Thr Thr Val Thr Gly Arg Thr
    2770                2775                2780

Cys Gln Ala Trp Ser Ser Met Thr Pro His Ser His Ser Arg Thr Pro
2785                2790                2795                2800

Glu Tyr Tyr Pro Asn Ala Gly Leu Ile Met Asn Tyr Cys Arg Asn Pro
            2805                2810                2815

Asp Ala Val Ala Ala Pro Tyr Cys Tyr Thr Arg Asp Pro Gly Val Arg
            2820                2825                2830

Trp Glu Tyr Cys Asn Leu Thr Gln Cys Ser Asp Ala Glu Gly Thr Ala
        2835                2840                2845

Val Ala Pro Pro Thr Val Thr Pro Val Pro Ser Leu Glu Ala Pro Ser
    2850                2855                2860

Glu Gln Ala Pro Thr Glu Gln Arg Pro Gly Val Gln Glu Cys Tyr His
2865                2870                2875                2880

Gly Asn Gly Gln Ser Tyr Arg Gly Thr Tyr Ser Thr Thr Val Thr Gly
            2885                2890                2895

Arg Thr Cys Gln Ala Trp Ser Ser Met Thr Pro His Ser His Ser Arg
            2900                2905                2910

Thr Pro Glu Tyr Tyr Pro Asn Ala Gly Leu Ile Met Asn Tyr Cys Arg
        2915                2920                2925

Asn Pro Asp Ala Val Ala Ala Pro Tyr Cys Tyr Thr Arg Asp Pro Gly
    2930                2935                2940
```

```
Val Arg Trp Glu Tyr Cys Asn Leu Thr Gln Cys Ser Asp Ala Glu Gly
2945                2950                2955                2960

Thr Ala Val Ala Pro Pro Thr Val Thr Pro Val Pro Ser Leu Glu Ala
            2965                2970                2975

Pro Ser Glu Gln Ala Pro Thr Glu Gln Arg Pro Gly Val Gln Glu Cys
        2980                2985                2990

Tyr His Gly Asn Gly Gln Ser Tyr Arg Gly Thr Tyr Ser Thr Thr Val
    2995                3000                3005

Thr Gly Arg Thr Cys Gln Ala Trp Ser Ser Met Thr Pro His Ser His
3010                3015                3020

Ser Arg Thr Pro Glu Tyr Tyr Pro Asn Ala Gly Leu Ile Met Asn Tyr
3025            3030                3035                3040

Cys Arg Asn Pro Asp Ala Val Ala Ala Pro Tyr Cys Tyr Thr Arg Asp
            3045                3050                3055

Pro Gly Val Arg Trp Glu Tyr Cys Asn Leu Thr Gln Cys Ser Asp Ala
        3060                3065                3070

Glu Gly Thr Ala Val Ala Pro Pro Thr Val Thr Pro Val Pro Ser Leu
    3075                3080                3085

Glu Ala Pro Ser Glu Gln Ala Pro Thr Glu Gln Arg Pro Gly Val Gln
3090                3095                3100

Glu Cys Tyr His Gly Asn Gly Gln Ser Tyr Arg Gly Thr Tyr Ser Thr
3105            3110                3115                3120

Thr Val Thr Gly Arg Thr Cys Gln Ala Trp Ser Ser Met Thr Pro His
            3125                3130                3135

Ser His Ser Arg Thr Pro Glu Tyr Tyr Pro Asn Ala Gly Leu Ile Met
        3140                3145                3150

Asn Tyr Cys Arg Asn Pro Asp Ala Val Ala Ala Pro Tyr Cys Tyr Thr
    3155                3160                3165

Arg Asp Pro Gly Val Arg Trp Glu Tyr Cys Asn Leu Thr Gln Cys Ser
3170                3175                3180

Asp Ala Glu Gly Thr Ala Val Ala Pro Pro Thr Val Thr Pro Val Pro
3185                3190                3195                3200

Ser Leu Glu Ala Pro Ser Glu Gln Ala Pro Thr Glu Gln Arg Pro Gly
            3205                3210                3215

Val Gln Glu Cys Tyr His Gly Asn Gly Gln Ser Tyr Arg Gly Thr Tyr
        3220                3225                3230

Ser Thr Thr Val Thr Gly Arg Thr Cys Gln Ala Trp Ser Ser Met Thr
    3235                3240                3245

Pro His Ser His Ser Arg Thr Pro Glu Tyr Tyr Pro Asn Ala Gly Leu
3250                3255                3260

Ile Met Asn Tyr Cys Arg Asn Pro Asp Ala Val Ala Ala Pro Tyr Cys
3265                3270                3275                3280

Tyr Thr Arg Asp Pro Gly Val Arg Trp Glu Tyr Cys Asn Leu Thr Gln
            3285                3290                3295

Cys Ser Asp Ala Glu Gly Thr Ala Val Ala Pro Pro Thr Val Thr Pro
        3300                3305                3310

Val Pro Ser Leu Glu Ala Pro Ser Glu Gln Ala Pro Thr Glu Gln Arg
    3315                3320                3325

Pro Gly Val Gln Glu Cys Tyr His Gly Asn Gly Gln Ser Tyr Arg Gly
3330                3335                3340

Thr Tyr Ser Thr Thr Val Thr Gly Arg Thr Cys Gln Ala Trp Ser Ser
3345                3350                3355                3360

Met Thr Pro His Ser His Ser Arg Thr Pro Glu Tyr Tyr Pro Asn Ala
```

```
                      3365           3370           3375

Gly Leu Ile Met Asn Tyr Cys Arg Asn Pro Asp Pro Val Ala Ala Pro
                3380           3385           3390

Tyr Cys Tyr Thr Arg Asp Pro Ser Val Arg Trp Glu Tyr Cys Asn Leu
                3395           3400           3405

Thr Gln Cys Ser Asp Ala Glu Gly Thr Ala Val Ala Pro Pro Thr Ile
                3410           3415           3420

Thr Pro Ile Pro Ser Leu Glu Ala Pro Ser Glu Gln Ala Pro Thr Glu
3425           3430           3435           3440

Gln Arg Pro Gly Val Gln Glu Cys Tyr His Gly Asn Gly Gln Ser Tyr
                3445           3450           3455

Gln Gly Thr Tyr Phe Ile Thr Val Thr Gly Arg Thr Cys Gln Ala Trp
                3460           3465           3470

Ser Ser Met Thr Pro His Ser His Ser Arg Thr Pro Ala Tyr Tyr Pro
                3475           3480           3485

Asn Ala Gly Leu Ile Lys Asn Tyr Cys Arg Asn Pro Asp Pro Val Ala
                3490           3495           3500

Ala Pro Trp Cys Tyr Thr Thr Asp Pro Ser Val Arg Trp Glu Tyr Cys
3505           3510           3515           3520

Asn Leu Thr Arg Cys Ser Asp Ala Glu Trp Thr Ala Phe Val Pro Pro
                3525           3530           3535

Asn Val Ile Leu Ala Pro Ser Leu Glu Ala Phe Phe Glu Gln Ala Leu
                3540           3545           3550

Thr Glu Glu Thr Pro Gly Val Gln Asp Cys Tyr Tyr His Tyr Gly Gln
                3555           3560           3565

Ser Tyr Arg Gly Thr Tyr Ser Thr Thr Val Thr Gly Arg Thr Cys Gln
                3570           3575           3580

Ala Trp Ser Ser Met Thr Pro His Gln His Ser Arg Thr Pro Glu Asn
3585           3590           3595           3600

Tyr Pro Asn Ala Gly Leu Thr Arg Asn Tyr Cys Arg Asn Pro Asp Ala
                3605           3610           3615

Glu Ile Arg Pro Trp Cys Tyr Thr Met Asp Pro Ser Val Arg Trp Glu
                3620           3625           3630

Tyr Cys Asn Leu Thr Gln Cys Leu Val Thr Glu Ser Ser Val Leu Ala
                3635           3640           3645

Thr Leu Thr Val Val Pro Asp Pro Ser Thr Glu Ala Ser Ser Glu Glu
                3650           3655           3660

Ala Pro Thr Glu Gln Ser Pro Gly Val Gln Asp Cys Tyr His Gly Asp
3665           3670           3675           3680

Gly Gln Ser Tyr Arg Gly Ser Phe Ser Thr Thr Val Thr Gly Arg Thr
                3685           3690           3695

Cys Gln Ser Trp Ser Ser Met Thr Pro His Trp His Gln Arg Thr Thr
                3700           3705           3710

Glu Tyr Tyr Pro Asn Gly Gly Leu Thr Arg Asn Tyr Cys Arg Asn Pro
                3715           3720           3725

Asp Ala Glu Ile Ser Pro Trp Cys Tyr Thr Met Asp Pro Asn Val Arg
                3730           3735           3740

Trp Glu Tyr Cys Asn Leu Thr Gln Cys Pro Val Thr Glu Ser Ser Val
3745           3750           3755           3760

Leu Ala Thr Ser Thr Ala Val Ser Glu Gln Ala Pro Thr Glu Gln Ser
                3765           3770           3775

Pro Thr Val Gln Asp Cys Tyr His Gly Asp Gly Gln Ser Tyr Arg Gly
                3780           3785           3790
```

```
Ser Phe Ser Thr Thr Val Thr Gly Arg Thr Cys Gln Ser Trp Ser Ser
        3795                3800                3805

Met Thr Pro His Trp His Gln Arg Thr Glu Tyr Tyr Pro Asn Gly
    3810                3815                3820

Gly Leu Thr Arg Asn Tyr Cys Arg Asn Pro Asp Ala Glu Ile Arg Pro
3825                3830                3835                3840

Trp Cys Tyr Thr Met Asp Pro Ser Val Arg Trp Glu Tyr Cys Asn Leu
            3845                3850                3855

Thr Gln Cys Pro Val Met Glu Ser Thr Leu Leu Thr Pro Thr Val
            3860                3865                3870

Val Pro Val Pro Ser Thr Glu Leu Pro Ser Glu Ala Pro Thr Glu
    3875                3880                3885

Asn Ser Thr Gly Val Gln Asp Cys Tyr Arg Gly Asp Gly Gln Ser Tyr
    3890                3895                3900

Arg Gly Thr Leu Ser Thr Thr Ile Thr Gly Arg Thr Cys Gln Ser Trp
3905                3910                3915                3920

Ser Ser Met Thr Pro His Trp His Arg Arg Ile Pro Leu Tyr Tyr Pro
            3925                3930                3935

Asn Ala Gly Leu Thr Arg Asn Tyr Cys Arg Asn Pro Asp Ala Glu Ile
        3940                3945                3950

Arg Pro Trp Cys Tyr Thr Met Asp Pro Ser Val Arg Trp Glu Tyr Cys
        3955                3960                3965

Asn Leu Thr Arg Cys Pro Val Thr Glu Ser Ser Val Leu Thr Thr Pro
    3970                3975                3980

Thr Val Ala Pro Val Pro Ser Thr Glu Ala Pro Ser Glu Gln Ala Pro
3985                3990                3995                4000

Pro Glu Lys Ser Pro Val Val Gln Asp Cys Tyr His Gly Asp Gly Arg
            4005                4010                4015

Ser Tyr Arg Gly Ile Ser Ser Thr Thr Val Thr Gly Arg Thr Cys Gln
            4020                4025                4030

Ser Trp Ser Ser Met Ile Pro His Trp His Gln Arg Thr Pro Glu Asn
            4035                4040                4045

Tyr Pro Asn Ala Gly Leu Thr Glu Asn Tyr Cys Arg Asn Pro Asp Ser
    4050                4055                4060

Gly Lys Gln Pro Trp Cys Tyr Thr Thr Asp Pro Cys Val Arg Trp Glu
4065                4070                4075                4080

Tyr Cys Asn Leu Thr Gln Cys Ser Glu Thr Glu Ser Gly Val Leu Glu
            4085                4090                4095

Thr Pro Thr Val Val Pro Val Pro Ser Met Glu Ala His Ser Glu Ala
            4100                4105                4110

Ala Pro Thr Glu Gln Thr Pro Val Val Arg Gln Cys Tyr His Gly Asn
            4115                4120                4125

Gly Gln Ser Tyr Arg Gly Thr Phe Ser Thr Thr Val Thr Gly Arg Thr
    4130                4135                4140

Cys Gln Ser Trp Ser Ser Met Thr Pro His Arg His Gln Arg Thr Pro
4145                4150                4155                4160

Glu Asn Tyr Pro Asn Asp Gly Leu Thr Met Asn Tyr Cys Arg Asn Pro
            4165                4170                4175

Asp Ala Asp Thr Gly Pro Trp Cys Phe Thr Met Asp Pro Ser Ile Arg
        4180                4185                4190

Trp Glu Tyr Cys Asn Leu Thr Arg Cys Ser Asp Thr Glu Gly Thr Val
    4195                4200                4205
```

```
Val Ala Pro Pro Thr Val Ile Gln Val Pro Ser Leu Gly Pro Pro Ser
    4210                4215                4220

Glu Gln Asp Cys Met Phe Gly Asn Gly Lys Gly Tyr Arg Gly Lys Lys
4225                4230                4235                4240

Ala Thr Thr Val Thr Gly Thr Pro Cys Gln Glu Trp Ala Ala Gln Glu
            4245                4250                4255

Pro His Arg His Ser Thr Phe Ile Pro Gly Thr Asn Lys Trp Ala Gly
            4260                4265                4270

Leu Glu Lys Asn Tyr Cys Arg Asn Pro Asp Gly Asp Ile Asn Gly Pro
        4275                4280                4285

Trp Cys Tyr Thr Met Asn Pro Arg Lys Leu Phe Asp Tyr Cys Asp Ile
    4290                4295                4300

Pro Leu Cys Ala Ser Ser Phe Asp Cys Gly Lys Pro Gln Val Glu
4305                4310                4315                4320

Pro Lys Lys Cys Pro Gly Ser Ile Val Gly Gly Cys Val Ala His Pro
                4325                4330                4335

His Ser Trp Pro Trp Gln Val Ser Leu Arg Thr Arg Phe Gly Lys His
            4340                4345                4350

Phe Cys Gly Gly Thr Leu Ile Ser Pro Glu Trp Val Leu Thr Ala Ala
        4355                4360                4365

His Cys Leu Lys Lys Ser Ser Arg Pro Ser Ser Tyr Lys Val Ile Leu
    4370                4375                4380

Gly Ala His Gln Glu Val Asn Leu Glu Ser His Val Gln Glu Ile Glu
4385                4390                4395                4400

Val Ser Arg Leu Phe Leu Glu Pro Thr Gln Ala Asp Ile Ala Leu Leu
                4405                4410                4415

Lys Leu Ser Arg Pro Ala Val Ile Thr Asp Lys Val Met Pro Ala Cys
            4420                4425                4430

Leu Pro Ser Pro Asp Tyr Met Val Thr Ala Arg Thr Glu Cys Tyr Ile
        4435                4440                4445

Thr Gly Trp Gly Glu Thr Gln Gly Thr Phe Gly Thr Gly Leu Leu Lys
    4450                4455                4460

Glu Ala Gln Leu Leu Val Ile Glu Asn Glu Val Cys Asn His Tyr Lys
4465                4470                4475                4480

Tyr Ile Cys Ala Glu His Leu Ala Arg Gly Thr Asp Ser Cys Gln Gly
                4485                4490                4495

Asp Ser Gly Gly Pro Leu Val Cys Phe Glu Lys Asp Lys Tyr Ile Leu
            4500                4505                4510

Gln Gly Val Thr Ser Trp Gly Leu Gly Cys Ala Arg Pro Asn Lys Pro
        4515                4520                4525

Gly Val Tyr Ala Arg Val Ser Arg Phe Val Thr Trp Ile Glu Gly Met
    4530                4535                4540

Met Arg Asn Asn
4545

<210> SEQ ID NO 71
<211> LENGTH: 133
<212> TYPE: PRT
<213> ORGANISM: Homo sapiens

<400> SEQUENCE: 71

Leu Glu Ser Gly Gly Gly Val Val Gln Pro Gly Lys Ser Leu Arg Leu
1               5                   10                  15

Ser Cys Ala Ala Ser Gly Phe Thr Phe Arg Asn Tyr Gly Met His Trp
            20                  25                  30
```

Val Arg Gln Ala Pro Gly Lys Gly Leu Glu Trp Val Ala Gly Ile Ser
            35                  40                  45

Ser Asp Gly Arg Lys Lys Tyr Val Asp Ser Val Lys Gly Arg Phe
 50                  55                  60

Phe Ile Ser Arg Asp Asn Ser Lys Asn Thr Leu Tyr Leu Gln Leu Asn
 65                  70                  75                  80

Ser Leu Arg Ala Glu Asp Thr Ala Val Tyr Tyr Cys Ala Lys Asp Glu
                85                  90                  95

Phe Ser Ser Thr Arg Lys Asn Phe Leu Thr Gly Gln Ser Lys Thr Phe
                100                 105                 110

Ala Ala Tyr Tyr Gly Met Asp Val Trp Gly Gln Gly Thr Thr Val Thr
            115                 120                 125

Val Ser Ser Ala Ser
        130

<210> SEQ ID NO 72
<211> LENGTH: 201
<212> TYPE: PRT
<213> ORGANISM: Homo sapiens

<400> SEQUENCE: 72

Met Ala Leu Ser Trp Val Leu Thr Val Leu Ser Leu Leu Pro Leu Leu
 1               5                  10                  15

Glu Ala Gln Ile Pro Leu Cys Ala Asn Leu Val Pro Val Pro Ile Thr
                20                  25                  30

Asn Ala Thr Leu Asp Gln Ile Thr Gly Lys Trp Phe Tyr Ile Ala Ser
            35                  40                  45

Ala Phe Arg Asn Glu Glu Tyr Asn Lys Ser Val Gln Glu Ile Gln Ala
 50                  55                  60

Thr Phe Phe Tyr Phe Thr Pro Asn Lys Thr Glu Asp Thr Ile Phe Leu
 65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
                100                 105                 110

Gln Glu His Phe Ala His Leu Leu Ile Leu Arg Asp Thr Lys Thr Tyr
            115                 120                 125

Met Leu Ala Phe Asp Val Asn Asp Glu Lys Asn Trp Gly Leu Ser Val
 130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
                180                 185                 190

Glu Arg Lys Gln Glu Gly Glu Ser
            195                 200

<210> SEQ ID NO 73
<211> LENGTH: 201
<212> TYPE: PRT
<213> ORGANISM: Homo sapiens

<400> SEQUENCE: 73

Met Ala Leu Ser Trp Val Leu Thr Val Leu Ser Leu Leu Pro Leu Leu
 1               5                  10                  15

```
Glu Ala Gln Ile Pro Leu Cys Ala Asn Leu Val Pro Val Pro Ile Thr
             20                  25                  30

Asn Ala Thr Leu Asp Arg Ile Thr Gly Lys Trp Phe Tyr Ile Ala Ser
         35                  40                  45

Ala Phe Arg Asn Glu Glu Tyr Asn Lys Ser Val Gln Glu Ile Gln Ala
     50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asn Gln Cys Phe Tyr Asn Ser Ser Tyr
                 85                  90                  95

Leu Asn Val Gln Arg Glu Asn Gly Thr Val Ser Arg Tyr Glu Gly Gly
            100                 105                 110

Arg Glu His Val Ala His Leu Leu Phe Leu Arg Asp Thr Lys Thr Leu
        115                 120                 125

Met Phe Gly Ser Tyr Leu Asp Asp Glu Lys Asn Trp Gly Leu Ser Phe
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Cys Ile Pro Arg Ser Asp Val Met Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200

<210> SEQ ID NO 74
<211> LENGTH: 101
<212> TYPE: PRT
<213> ORGANISM: Homo sapiens

<400> SEQUENCE: 74

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 75
<211> LENGTH: 1482
<212> TYPE: PRT
<213> ORGANISM: Homo sapiens

<400> SEQUENCE: 75

Met Arg Lys Asp Arg Leu Leu His Leu Cys Leu Val Leu Leu Leu Ile
1               5                   10                  15

Leu Leu Ser Ala Ser Asp Ser Asn Ser Thr Glu Pro Gln Tyr Met Val
            20                  25                  30
```

```
Leu Val Pro Ser Leu Leu His Thr Glu Ala Pro Lys Lys Gly Cys Val
        35                  40                  45

Leu Leu Ser His Leu Asn Glu Thr Val Thr Val Ser Ala Ser Leu Glu
 50                  55                  60

Ser Gly Arg Glu Asn Arg Ser Leu Phe Thr Asp Leu Val Ala Glu Lys
 65                  70                  75                  80

Asp Leu Phe His Cys Val Ser Phe Thr Leu Pro Arg Ile Ser Ala Ser
                 85                  90                  95

Ser Glu Val Ala Phe Leu Ser Ile Gln Ile Lys Gly Pro Thr Gln Asp
                100                 105                 110

Phe Arg Lys Arg Asn Thr Val Leu Val Leu Asn Thr Gln Ser Leu Val
        115                 120                 125

Phe Val Gln Thr Asp Lys Pro Met Tyr Lys Pro Gly Gln Thr Val Arg
        130                 135                 140

Phe Arg Val Val Ser Val Asp Glu Asn Phe Arg Pro Arg Asn Glu Leu
145                 150                 155                 160

Ile Pro Leu Ile Tyr Leu Glu Asn Pro Arg Arg Asn Arg Ile Ala Gln
                165                 170                 175

Trp Gln Ser Leu Lys Leu Glu Ala Gly Ile Asn Gln Leu Ser Phe Pro
        180                 185                 190

Leu Ser Ser Glu Pro Ile Gln Gly Ser Tyr Arg Val Val Val Gln Thr
        195                 200                 205

Glu Ser Gly Gly Arg Ile Gln His Pro Phe Thr Val Glu Glu Phe Val
        210                 215                 220

Leu Pro Lys Phe Glu Val Lys Val Gln Val Pro Lys Ile Ile Ser Ile
225                 230                 235                 240

Met Asp Glu Lys Val Asn Ile Thr Val Cys Gly Glu Tyr Thr Tyr Gly
                245                 250                 255

Lys Pro Val Pro Gly Leu Ala Thr Val Ser Leu Cys Arg Lys Leu Ser
                260                 265                 270

Arg Val Leu Asn Cys Asp Lys Gln Glu Val Cys Glu Glu Phe Ser Gln
        275                 280                 285

Gln Leu Asn Ser Asn Gly Cys Ile Thr Gln Gln Val His Thr Lys Met
        290                 295                 300

Leu Gln Ile Thr Asn Thr Gly Phe Glu Met Lys Leu Arg Val Glu Ala
305                 310                 315                 320

Arg Ile Arg Glu Glu Gly Thr Asp Leu Glu Val Thr Ala Asn Arg Ile
                325                 330                 335

Ser Glu Ile Thr Asn Ile Val Ser Lys Leu Lys Phe Val Lys Val Asp
                340                 345                 350

Ser His Phe Arg Gln Gly Ile Pro Phe Phe Ala Gln Val Leu Leu Val
        355                 360                 365

Asp Gly Lys Gly Val Pro Ile Pro Asn Lys Leu Phe Phe Ile Ser Val
        370                 375                 380

Asn Asp Ala Asn Tyr Tyr Ser Asn Ala Thr Thr Asn Glu Gln Gly Leu
385                 390                 395                 400

Ala Gln Phe Ser Ile Asn Thr Thr Ser Ile Ser Val Asn Lys Leu Phe
                405                 410                 415

Val Arg Val Phe Thr Val His Pro Asn Leu Cys Phe His Tyr Ser Trp
                420                 425                 430

Val Ala Glu Asp His Gln Gly Ala Gln His Thr Ala Asn Arg Val Phe
        435                 440                 445
```

-continued

Ser Leu Ser Gly Ser Tyr Ile His Leu Glu Pro Val Ala Gly Thr Leu
450                 455                 460

Pro Cys Gly His Thr Glu Thr Ile Thr Ala His Tyr Thr Leu Asn Arg
465                 470                 475                 480

Gln Ala Met Gly Glu Leu Ser Glu Leu Ser Phe His Tyr Leu Ile Met
            485                 490                 495

Ala Lys Gly Val Ile Val Arg Ser Gly Thr His Thr Leu Pro Val Glu
                500                 505                 510

Ser Gly Asp Met Lys Gly Ser Phe Ala Leu Ser Phe Pro Val Glu Ser
            515                 520                 525

Asp Val Ala Pro Ile Ala Arg Met Phe Ile Phe Ala Ile Leu Pro Asp
530                 535                 540

Gly Glu Val Val Gly Asp Ser Glu Lys Phe Glu Ile Glu Asn Cys Leu
545                 550                 555                 560

Ala Asn Lys Val Asp Leu Ser Phe Ser Pro Ala Gln Ser Pro Pro Ala
                565                 570                 575

Ser His Ala His Leu Gln Val Ala Ala Pro Gln Ser Leu Cys Ala
            580                 585                 590

Leu Arg Ala Val Asp Gln Ser Val Leu Leu Met Lys Pro Glu Ala Glu
            595                 600                 605

Leu Ser Val Ser Ser Val Tyr Asn Leu Leu Thr Val Lys Asp Leu Thr
            610                 615                 620

Asn Phe Pro Asp Asn Val Asp Gln Gln Glu Glu Gln Gly His Cys
625                 630                 635                 640

Pro Arg Pro Phe Phe Ile His Asn Gly Ala Ile Tyr Val Pro Leu Ser
            645                 650                 655

Ser Asn Glu Ala Asp Ile Tyr Ser Phe Leu Lys Gly Met Gly Leu Lys
            660                 665                 670

Val Phe Thr Asn Ser Lys Ile Arg Lys Pro Lys Ser Cys Ser Val Ile
            675                 680                 685

Pro Ser Val Ser Ala Gly Ala Val Gly Gln Gly Tyr Tyr Gly Ala Gly
690                 695                 700

Leu Gly Val Val Glu Arg Pro Tyr Val Pro Gln Leu Gly Thr Tyr Asn
705                 710                 715                 720

Val Ile Pro Leu Asn Asn Glu Gln Ser Ser Gly Pro Val Pro Glu Thr
                725                 730                 735

Val Arg Ser Tyr Phe Pro Glu Thr Trp Ile Trp Glu Leu Val Ala Val
            740                 745                 750

Asn Ser Ser Gly Val Ala Glu Val Gly Val Thr Val Pro Asp Thr Ile
            755                 760                 765

Thr Glu Trp Lys Ala Gly Ala Phe Cys Leu Ser Glu Asp Ala Gly Leu
770                 775                 780

Gly Ile Ser Ser Thr Ala Ser Leu Arg Ala Phe Gln Pro Phe Phe Val
785                 790                 795                 800

Glu Leu Thr Met Pro Tyr Ser Val Ile Arg Gly Glu Val Phe Thr Leu
            805                 810                 815

Lys Ala Thr Val Leu Asn Tyr Leu Pro Lys Cys Ile Arg Val Ser Val
            820                 825                 830

Gln Leu Lys Ala Ser Pro Ala Phe Leu Ala Ser Gln Asn Thr Lys Gly
            835                 840                 845

Glu Glu Ser Tyr Cys Ile Cys Gly Asn Glu Arg Gln Thr Leu Ser Trp
850                 855                 860

Thr Val Thr Pro Lys Thr Leu Gly Asn Val Asn Phe Ser Val Ser Ala

-continued

```
865                 870                 875                 880
Glu Ala Met Gln Ser Leu Glu Leu Cys Gly Asn Glu Val Val Glu Val
                    885                 890                 895
Pro Glu Ile Lys Arg Lys Asp Thr Val Ile Lys Thr Leu Leu Val Glu
                    900                 905                 910
Ala Glu Gly Ile Glu Gln Glu Lys Thr Phe Ser Ser Met Thr Cys Ala
                    915                 920                 925
Ser Gly Ala Asn Val Ser Glu Gln Leu Ser Leu Lys Leu Pro Ser Asn
                    930                 935                 940
Val Val Lys Glu Ser Ala Arg Ala Ser Phe Ser Val Leu Gly Asp Ile
945                 950                 955                 960
Leu Gly Ser Ala Met Gln Asn Ile Gln Asn Leu Leu Gln Met Pro Tyr
                    965                 970                 975
Gly Cys Gly Glu Gln Asn Met Val Leu Phe Ala Pro Asn Ile Tyr Val
                    980                 985                 990
Leu Asn Tyr Leu Asn Glu Thr Gln Gln Leu Thr Gln Glu Ile Lys Ala
                    995                 1000                1005
Lys Ala Val Gly Tyr Leu Ile Thr Gly Tyr Gln Arg Gln Leu Asn Tyr
    1010                1015                1020
Lys His Gln Asp Gly Ser Tyr Ser Thr Phe Gly Glu Arg Tyr Gly Arg
1025                1030                1035                1040
Asn Gln Gly Asn Thr Trp Leu Thr Ala Phe Val Leu Lys Thr Phe Ala
                    1045                1050                1055
Gln Ala Arg Ser Tyr Ile Phe Ile Asp Glu Ala His Ile Thr Gln Ser
                    1060                1065                1070
Leu Thr Trp Leu Ser Gln Met Gln Lys Asp Asn Gly Cys Phe Arg Ser
        1075                1080                1085
Ser Gly Ser Leu Leu Asn Asn Ala Ile Lys Gly Gly Val Glu Asp Glu
                    1090                1095                1100
Ala Thr Leu Ser Ala Tyr Val Thr Ile Ala Leu Leu Glu Ile Pro Leu
1105                1110                1115                1120
Pro Val Thr Asn Pro Ile Val Arg Asn Ala Leu Phe Cys Leu Glu Ser
                    1125                1130                1135
Ala Trp Asn Val Ala Lys Glu Gly Thr His Gly Ser His Val Tyr Thr
                    1140                1145                1150
Lys Ala Leu Leu Ala Tyr Ala Phe Ser Leu Leu Gly Lys Gln Asn Gln
        1155                1160                1165
Asn Arg Glu Ile Leu Asn Ser Leu Asp Lys Glu Ala Val Lys Glu Asp
    1170                1175                1180
Asn Leu Val His Trp Glu Arg Pro Gln Arg Pro Lys Ala Pro Val Gly
1185                1190                1195                1200
His Leu Tyr Gln Thr Gln Ala Pro Ser Ala Glu Val Glu Met Thr Ser
                    1205                1210                1215
Tyr Val Leu Leu Ala Tyr Leu Thr Ala Gln Pro Ala Pro Thr Ser Gly
                    1220                1225                1230
Asp Leu Thr Ser Ala Thr Asn Ile Val Lys Trp Ile Met Lys Gln Gln
        1235                1240                1245
Asn Ala Gln Gly Gly Phe Ser Ser Thr Gln Asp Thr Val Val Ala Leu
    1250                1255                1260
His Ala Leu Ser Arg Tyr Gly Ala Ala Thr Phe Thr Arg Thr Glu Lys
1265                1270                1275                1280
Thr Ala Gln Val Thr Val Gln Asp Ser Gln Thr Phe Ser Thr Asn Phe
                    1285                1290                1295
```

```
Gln Val Asp Asn Asn Leu Leu Leu Gln Gln Ile Ser Leu Pro
            1300                1305                1310

Glu Leu Pro Gly Glu Tyr Val Ile Thr Val Thr Gly Glu Arg Cys Val
        1315                1320                1325

Tyr Leu Gln Thr Ser Met Lys Tyr Asn Ile Leu Pro Glu Lys Glu Asp
        1330                1335                1340

Ser Pro Phe Ala Leu Lys Val Gln Thr Val Pro Gln Thr Cys Asp Gly
1345                1350                1355                1360

His Lys Ala His Thr Ser Phe Gln Ile Ser Leu Thr Ile Ser Tyr Thr
            1365                1370                1375

Gly Asn Arg Pro Ala Ser Asn Met Val Ile Val Asp Val Lys Met Val
            1380                1385                1390

Ser Gly Phe Ile Pro Leu Lys Pro Thr Val Lys Met Leu Glu Arg Ser
            1395                1400                1405

Ser Ser Val Ser Arg Thr Glu Val Ser Asn Asn His Val Leu Ile Tyr
        1410                1415                1420

Val Glu Gln Val Thr Asn Gln Thr Leu Ser Phe Ser Phe Met Val Leu
1425                1430                1435                1440

Gln Asp Ile Pro Val Gly Asp Leu Lys Pro Ala Ile Val Lys Val Tyr
            1445                1450                1455

Asp Tyr Tyr Glu Thr Asp Glu Ser Val Val Ala Glu Tyr Ile Ala Pro
            1460                1465                1470

Cys Ser Thr Asp Thr Glu His Gly Asn Val
            1475                1480

<210> SEQ ID NO 76
<211> LENGTH: 134
<212> TYPE: PRT
<213> ORGANISM: Homo sapiens

<400> SEQUENCE: 76

Met Glu Thr Pro Ala Gln Leu Leu Phe Leu Leu Leu Val Trp Leu Pro
1               5                   10                  15

Asp Met Ser Glu Glu Ile Ile Leu Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Thr Asn Leu Ala Trp Tyr Gln Gln Lys Pro Gly Gln Ala Pro
    50                  55                  60

Arg Leu Leu Ile Tyr Gly Ala Ser Ile Arg Ala Thr Gly Ile Ser Ala
65                  70                  75                  80

Arg Phe Ser Gly Ser Gly Ser Gly Thr Glu Phe Thr Leu Asn Ile Thr
                85                  90                  95

Ser Leu Gln Ser Gly Asp Leu Ala Leu Tyr Phe Cys Gln Gln Tyr Gly
            100                 105                 110

Asp Trp Pro Pro Tyr Thr Phe Gly Gln Gly Thr Lys Leu Glu Ile Lys
        115                 120                 125

Arg Thr Val Ala Ala Pro
        130

<210> SEQ ID NO 77
<211> LENGTH: 93
<212> TYPE: PRT
<213> ORGANISM: Homo sapiens

<400> SEQUENCE: 77
```

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 78
<211> LENGTH: 238
<212> TYPE: PRT
<213> ORGANISM: Homo sapiens

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Phe Ser Phe Asp Tyr Trp Gly Gln Gly Thr Leu Val
            100                 105                 110

Thr Val Ser Ser Gly Asp Gly Ser Gly Gly Ser Gly Gly Ala Ser
            115                 120                 125

Thr Gly Glu Ile Val Leu Thr Gln Ser Pro Gly Thr Leu Ser Leu Ser
130                 135                 140

Pro Gly Glu Arg Ala Thr Leu Ser Cys Arg Ala Ser Gln Ser Val Ser
145                 150                 155                 160

Ser Ser Tyr Leu Ala Trp Tyr Gln Gln Lys Pro Gly Gln Ala Pro Arg
                165                 170                 175

Leu Leu Ile Tyr Gly Ala Ser Ser Arg Ala Thr Gly Ile Pro Asp Arg
            180                 185                 190

Phe Ser Gly Ser Gly Ser Gly Thr Asp Phe Leu Thr Ile Ser Arg
            195                 200                 205

Leu Glu Pro Glu Asp Phe Ala Val Tyr Tyr Cys Gln Gln Gly Gly Trp
        210                 215                 220

Leu Pro Tyr Thr Phe Gly Gln Gly Thr Lys Val Glu Ile Lys
225                 230                 235

<210> SEQ ID NO 79
<211> LENGTH: 464
<212> TYPE: PRT
<213> ORGANISM: Homo sapiens

<400> SEQUENCE: 79

```
Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65              70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415
```

```
Ser Thr Ala Val Val Ile Ala Gly Arg Ser Leu Asn Pro Asn Arg Val
                420                 425                 430

Thr Phe Lys Ala Asn Arg Pro Phe Leu Val Phe Ile Arg Glu Val Pro
            435                 440                 445

Leu Asn Thr Ile Ile Phe Met Gly Arg Val Ala Asn Pro Cys Val Lys
        450                 455                 460

<210> SEQ ID NO 80
<211> LENGTH: 491
<212> TYPE: PRT
<213> ORGANISM: Homo sapiens

<400> SEQUENCE: 80

Met Ala Leu Leu Trp Gly Leu Val Leu Ser Trp Ser Cys Leu Gln
1               5                   10                  15

Gly Pro Cys Ser Val Phe Ser Pro Val Ser Ala Met Glu Pro Leu Gly
                20                  25                  30

Arg Gln Leu Thr Ser Gly Pro Asn Gln Glu Gln Val Ser Pro Leu Thr
            35                  40                  45

Leu Leu Lys Leu Gly Asn Gln Glu Pro Gly Gly Gln Thr Ala Leu Lys
50                  55                  60

Ser Pro Pro Gly Val Cys Ser Arg Asp Pro Thr Pro Glu Gln Thr His
65                  70                  75                  80

Arg Leu Ala Arg Ala Met Met Ala Phe Thr Ala Asp Leu Phe Ser Leu
                85                  90                  95

Val Ala Gln Thr Ser Thr Cys Pro Asn Leu Ile Leu Ser Pro Leu Ser
                100                 105                 110

Val Ala Leu Ala Leu Ser His Leu Ala Leu Gly Ala Gln Asn His Thr
            115                 120                 125

Leu Gln Arg Leu Gln Gln Val Leu His Ala Gly Ser Gly Pro Cys Leu
130                 135                 140

Pro His Leu Leu Ser Arg Leu Cys Gln Asp Leu Gly Pro Gly Ala Phe
145                 150                 155                 160

Arg Leu Ala Ala Arg Met Tyr Leu Gln Lys Gly Phe Pro Ile Lys Glu
                165                 170                 175

Asp Phe Leu Glu Gln Ser Glu Gln Leu Phe Gly Ala Lys Pro Val Ser
            180                 185                 190

Leu Thr Gly Lys Gln Glu Asp Asp Leu Ala Asn Ile Asn Gln Trp Val
        195                 200                 205

Lys Glu Ala Thr Glu Gly Lys Ile Gln Glu Phe Leu Ser Gly Leu Pro
210                 215                 220

Glu Asp Thr Val Leu Leu Leu Leu Asn Ala Ile His Phe Gln Gly Phe
225                 230                 235                 240

Trp Arg Asn Lys Phe Asp Pro Ser Leu Thr Gln Arg Asp Ser Phe His
                245                 250                 255

Leu Asp Glu Gln Phe Thr Val Pro Val Glu Met Met Gln Ala Arg Thr
            260                 265                 270

Tyr Pro Leu Arg Trp Phe Leu Leu Glu Gln Pro Glu Ile Gln Val Ala
        275                 280                 285

His Phe Pro Phe Lys Asn Asn Met Ser Phe Val Val Leu Val Pro Thr
290                 295                 300

His Phe Glu Trp Asn Val Ser Gln Val Leu Ala Asn Leu Ser Trp Asp
305                 310                 315                 320

Thr Leu His Pro Pro Leu Val Trp Glu Arg Pro Thr Lys Val Arg Leu
                325                 330                 335
```

```
Pro Lys Leu Tyr Leu Lys His Gln Met Asp Leu Val Ala Thr Leu Ser
             340                 345                 350

Gln Leu Gly Leu Gln Glu Leu Phe Gln Ala Pro Asp Leu Arg Gly Ile
             355                 360                 365

Ser Glu Gln Ser Leu Val Val Ser Gly Val Gln His Gln Ser Thr Leu
        370                 375                 380

Glu Leu Ser Glu Val Gly Val Glu Ala Ala Ala Thr Ser Ile Ala
385                 390                 395                 400

Met Ser Arg Met Ser Leu Ser Ser Phe Ser Val Asn Arg Pro Phe Leu
             405                 410                 415

Phe Phe Ile Phe Glu Asp Thr Thr Gly Leu Pro Leu Phe Val Gly Ser
             420                 425                 430

Val Arg Asn Pro Asn Pro Ser Ala Pro Arg Glu Leu Lys Glu Gln Gln
        435                 440                 445

Asp Ser Pro Gly Asn Lys Asp Phe Leu Gln Ser Leu Lys Gly Phe Pro
        450                 455                 460

Arg Gly Asp Lys Leu Phe Gly Pro Asp Leu Lys Leu Val Pro Pro Met
465                 470                 475                 480

Glu Glu Asp Tyr Pro Gln Phe Gly Ser Pro Lys
             485                 490

<210> SEQ ID NO 81
<211> LENGTH: 505
<212> TYPE: PRT
<213> ORGANISM: Homo sapiens

<400> SEQUENCE: 81

Met Ala Ser Arg Leu Thr Leu Thr Leu Leu Leu Leu Leu Leu Ala
1               5                   10                  15

Gly Phe Leu Glu Pro Gln Asp Arg Ala Ser Ser Asn Pro Asn Ala Thr
             20                  25                  30

Ser Ser Ser Ser Gln Asp Pro Glu Ser Leu Gln Asp Arg Gly Glu Gly
        35                  40                  45

Lys Val Ala Thr Thr Val Ile Ser Lys Met Leu Phe Val Glu Pro Ile
50                  55                  60

Leu Glu Val Ser Ser Leu Pro Thr Thr Asn Ser Thr Thr Asn Ser Ala
65                  70                  75                  80

Thr Lys Ile Thr Ala Asn Thr Thr Asp Glu Pro Thr Thr Gln Pro Thr
                85                  90                  95

Thr Glu Pro Thr Thr Gln Pro Thr Ile Gln Pro Thr Gln Pro Thr Thr
            100                 105                 110

Gln Leu Pro Thr Asp Ser Pro Thr Gln Pro Thr Thr Gly Ser Phe Cys
        115                 120                 125

Pro Gly Pro Val Thr Leu Cys Ser Asp Leu Glu Ser His Ser Thr Glu
        130                 135                 140

Ala Val Leu Gly Asp Ala Leu Val Asp Phe Ser Leu Lys Leu Tyr His
145                 150                 155                 160

Ala Phe Ser Ala Met Lys Lys Val Glu Thr Asn Met Ala Phe Ser Pro
                165                 170                 175

Phe Ser Ile Ala Ser Leu Leu Thr Gln Val Leu Leu Gly Ala Gly Glu
            180                 185                 190

Asn Thr Lys Thr Asn Leu Glu Ser Ile Leu Ser Tyr Pro Lys Asp Phe
        195                 200                 205

Thr Cys Val His Gln Ala Leu Lys Gly Phe Thr Thr Lys Gly Val Thr
```

```
            210                 215                 220
Ser Val Ser Gln Ile Phe His Ser Pro Asp Leu Ala Ile Arg Asp Thr
225                 230                 235                 240

Phe Val Asn Ala Ser Arg Thr Leu Tyr Ser Ser Pro Arg Val Leu
                245                 250                 255

Ser Asn Asn Ser Asp Ala Asn Leu Glu Leu Ile Asn Thr Trp Val Ala
            260                 265                 270

Lys Asn Thr Asn Asn Lys Ile Ser Arg Leu Leu Asp Ser Leu Pro Ser
                275                 280                 285

Asp Thr Arg Leu Val Leu Leu Asn Ala Ile Tyr Leu Ser Ala Lys Trp
            290                 295                 300

Lys Thr Thr Phe Asp Pro Lys Lys Thr Arg Met Glu Pro Phe His Phe
305                 310                 315                 320

Lys Asn Ser Val Ile Lys Val Pro Met Met Asn Ser Lys Lys Tyr Pro
                325                 330                 335

Val Ala His Phe Ile Asp Gln Thr Leu Lys Ala Lys Val Gly Gln Leu
            340                 345                 350

Gln Leu Ser His Asn Leu Ser Leu Val Ile Leu Val Pro Gln Asn Leu
                355                 360                 365

Lys His Arg Leu Glu Asp Met Glu Gln Ala Leu Ser Pro Ser Val Phe
            370                 375                 380

Lys Ala Ile Met Glu Lys Leu Glu Met Ser Lys Phe Gln Pro Thr Leu
385                 390                 395                 400

Leu Thr Leu Pro Arg Ile Lys Val Thr Thr Ser Gln Asp Met Leu Ser
                405                 410                 415

Ile Met Glu Lys Leu Glu Phe Phe Asp Phe Ser Tyr Asp Leu Asn Leu
            420                 425                 430

Cys Gly Leu Thr Glu Asp Pro Asp Leu Gln Val Ser Ala Met Gln His
                435                 440                 445

Gln Thr Val Leu Glu Leu Thr Glu Thr Gly Val Glu Ala Ala Ala Ala
            450                 455                 460

Ser Ala Ile Ser Val Ala Arg Thr Leu Leu Val Phe Glu Val Gln Gln
465                 470                 475                 480

Pro Phe Leu Phe Val Leu Trp Asp Gln Gln His Lys Phe Pro Val Phe
                485                 490                 495

Met Gly Arg Val Tyr Asp Pro Arg Ala
                500                 505

<210> SEQ ID NO 82
<211> LENGTH: 698
<212> TYPE: PRT
<213> ORGANISM: Homo sapiens

<400> SEQUENCE: 82

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
                20                  25                  30

His Glu Ala Thr Lys Cys Gln Ser Phe Arg Asp His Met Lys Ser Val
            35                  40                  45

Ile Pro Ser Asp Gly Pro Ser Val Ala Cys Val Lys Lys Ala Ser Tyr
        50                  55                  60

Leu Asp Cys Ile Arg Ala Ile Ala Ala Asn Glu Ala Asp Ala Val Thr
65                  70                  75                  80
```

```
Leu Asp Ala Gly Leu Val Tyr Asp Ala Tyr Leu Ala Pro Asn Asn Leu
             85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
            115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
            165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
            195                 200                 205

Gly Ala Phe Lys Cys Leu Lys Asp Gly Ala Gly Asp Val Ala Phe Val
            210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
            245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
            275                 280                 285

Ala Gln Glu His Phe Gly Lys Asp Lys Ser Lys Glu Phe Gln Leu Phe
            290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
            325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
            355                 360                 365

His Glu Arg Leu Lys Cys Asp Glu Trp Ser Val Asn Ser Val Gly Lys
            370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
            405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Ile
            435                 440                 445

Ala Val Val Lys Lys Ser Ala Ser Asp Leu Thr Trp Asp Asn Leu Lys
            450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
            485                 490                 495

Glu Phe Phe Ser Glu Gly Cys Ala Pro Gly Ser Lys Lys Asp Ser Ser
```

```
                500             505             510
Leu Cys Lys Leu Cys Met Gly Ser Gly Leu Asn Leu Cys Glu Pro Asn
            515                 520                 525

Asn Lys Glu Gly Tyr Tyr Gly Tyr Thr Gly Ala Phe Arg Cys Leu Val
            530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
            565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
            595                 600                 605

Arg Lys Asp Lys Glu Ala Cys Val His Lys Ile Leu Arg Gln Gln Gln
            610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
            645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
690                 695

<210> SEQ ID NO 83
<211> LENGTH: 1170
<212> TYPE: PRT
<213> ORGANISM: Homo sapiens

<400> SEQUENCE: 83

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
            85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
            165                 170                 175
```

```
Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
    370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
    530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
```

```
                 595                 600                 605
Glu Asn Thr Asp Pro Gly Tyr Asn Cys Leu Pro Cys Pro Arg Phe
610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
                660                 665                 670

Met Tyr Arg Cys Glu Cys Lys Pro Gly Tyr Ala Gly Asn Gly Ile Ile
                675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
                740                 745                 750

Asn Cys Pro Phe His Tyr Asn Pro Ala Gln Tyr Asp Tyr Asp Arg Asp
                755                 760                 765

Asp Val Gly Asp Arg Cys Asp Asn Cys Pro Tyr Asn His Asn Pro Asp
                770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
                820                 825                 830

Cys Asp Asn Cys Pro Leu Glu His Asn Pro Asp Gln Leu Asp Ser Asp
                835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
                900                 905                 910

Val Pro Asn Pro Asp Gln Lys Asp Ser Asp Gly Asp Gly Arg Gly Asp
                915                 920                 925

Ala Cys Lys Asp Asp Phe Asp His Asp Ser Val Pro Asp Ile Asp Asp
930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
                980                 985                 990

Asp Pro Gly Leu Ala Val Gly Tyr Asp Glu Phe Asn Ala Val Asp Phe
                995                 1000                1005

Ser Gly Thr Phe Phe Ile Asn Thr Glu Arg Asp Asp Asp Tyr Ala Gly
                1010                1015                1020
```

```
Phe Val Phe Gly Tyr Gln Ser Ser Arg Phe Tyr Val Val Met Trp
1025                1030                1035                1040

Lys Gln Val Thr Gln Ser Tyr Trp Asp Thr Asn Pro Thr Arg Ala Gln
            1045                1050                1055

Gly Tyr Ser Gly Leu Ser Val Lys Val Val Asn Ser Thr Thr Gly Pro
        1060                1065                1070

Gly Glu His Leu Arg Asn Ala Leu Trp His Thr Gly Asn Thr Pro Gly
    1075                1080                1085

Gln Val Arg Thr Leu Trp His Asp Pro Arg His Ile Gly Trp Lys Asp
1090                1095                1100

Phe Thr Ala Tyr Arg Trp Arg Leu Ser His Arg Pro Lys Thr Gly Phe
1105                1110                1115                1120

Ile Arg Val Val Met Tyr Glu Gly Lys Lys Ile Met Ala Asp Ser Gly
                1125                1130                1135

Pro Ile Tyr Asp Lys Thr Tyr Ala Gly Gly Arg Leu Gly Leu Phe Val
            1140                1145                1150

Phe Ser Gln Glu Met Val Phe Phe Ser Asp Leu Lys Tyr Glu Cys Arg
        1155                1160                1165

Asp Pro
    1170

<210> SEQ ID NO 84
<211> LENGTH: 147
<212> TYPE: PRT
<213> ORGANISM: Homo sapiens

<400> SEQUENCE: 84

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
                20                  25                  30

Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
        50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 85
<211> LENGTH: 478
<212> TYPE: PRT
<213> ORGANISM: Homo sapiens

<400> SEQUENCE: 85

Met Ala Pro Leu Arg Pro Leu Leu Ile Leu Ala Leu Leu Ala Trp Val
1               5                   10                  15
```

```
Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
            115                 120                 125

Ala Ser Lys Pro Glu Gly Ile Asp Ser Arg Pro Glu Thr Leu His Pro
130                 135                 140

Gly Arg Pro Gln Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
        355                 360                 365

Gln Arg Phe Arg His Arg Asn Arg Lys Gly Tyr Arg Ser Gln Arg Gly
    370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430
```

Ile Gln Ser Val Phe Phe Ser Gly Asp Lys Tyr Tyr Arg Val Asn
            435                 440                 445

Leu Arg Thr Arg Val Asp Thr Val Asp Pro Pro Tyr Pro Arg Ser
450                 455                 460

Ile Ala Gln Tyr Trp Leu Gly Cys Pro Ala Pro Gly His Leu
465                 470                 475

<210> SEQ ID NO 86
<211> LENGTH: 2813
<212> TYPE: PRT
<213> ORGANISM: Homo sapiens

<400> SEQUENCE: 86

Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

-continued

```
Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
            450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750
```

-continued

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
        770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Gln Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn Ser
    1010                1015                1020

Trp Lys Val Ser Ser Gln Cys Ala Asp Thr Arg Lys Val Pro Leu Asp
1025                1030                1035                1040

Ser Ser Pro Ala Thr Cys His Asn Asn Ile Met Lys Gln Thr Met Val
                1045                1050                1055

Asp Ser Ser Cys Arg Ile Leu Thr Ser Asp Val Phe Gln Asp Cys Asn
            1060                1065                1070

Lys Leu Val Asp Pro Glu Pro Tyr Leu Asp Val Cys Ile Tyr Asp Thr
        1075                1080                1085

Cys Ser Cys Glu Ser Ile Gly Asp Cys Ala Cys Phe Cys Asp Thr Ile
    1090                1095                1100

Ala Ala Tyr Ala His Val Cys Ala Gln His Gly Lys Val Val Thr Trp
1105                1110                1115                1120

Arg Thr Ala Thr Leu Cys Pro Gln Ser Cys Glu Glu Arg Asn Leu Arg
                1125                1130                1135

Glu Asn Gly Tyr Glu Cys Glu Trp Arg Tyr Asn Ser Cys Ala Pro Ala
            1140                1145                1150

Cys Gln Val Thr Cys Gln His Pro Glu Pro Leu Ala Cys Pro Val Gln
        1155                1160                1165

Cys Val Glu Gly Cys His Ala His Cys Pro Pro Gly Lys Ile Leu Asp

-continued

```
            1170            1175            1180
Glu Leu Leu Gln Thr Cys Val Asp Pro Glu Asp Cys Pro Val Cys Glu
1185            1190            1195            1200

Val Ala Gly Arg Arg Phe Ala Ser Gly Lys Lys Val Thr Leu Asn Pro
            1205            1210            1215

Ser Asp Pro Glu His Cys Gln Ile Cys His Cys Asp Val Val Asn Leu
            1220            1225            1230

Thr Cys Glu Ala Cys Gln Glu Pro Gly Gly Leu Val Val Pro Pro Thr
            1235            1240            1245

Asp Ala Pro Val Ser Pro Thr Thr Leu Tyr Val Glu Asp Ile Ser Glu
            1250            1255            1260

Pro Pro Leu His Asp Phe Tyr Cys Ser Arg Leu Leu Asp Leu Val Phe
1265            1270            1275            1280

Leu Leu Asp Gly Ser Ser Arg Leu Ser Glu Ala Glu Phe Glu Val Leu
            1285            1290            1295

Lys Ala Phe Val Val Asp Met Met Glu Arg Leu Arg Ile Ser Gln Lys
            1300            1305            1310

Trp Val Arg Val Ala Val Val Glu Tyr His Asp Gly Ser His Ala Tyr
            1315            1320            1325

Ile Gly Leu Lys Asp Arg Lys Arg Pro Ser Glu Leu Arg Arg Ile Ala
            1330            1335            1340

Ser Gln Val Lys Tyr Ala Gly Ser Gln Val Ala Ser Thr Ser Glu Val
1345            1350            1355            1360

Leu Lys Tyr Thr Leu Phe Gln Ile Phe Ser Lys Ile Asp Arg Pro Glu
            1365            1370            1375

Ala Ser Arg Ile Thr Leu Leu Leu Met Ala Ser Gln Glu Pro Gln Arg
            1380            1385            1390

Met Ser Arg Asn Phe Val Arg Tyr Val Gln Gly Leu Lys Lys Lys Lys
            1395            1400            1405

Val Ile Val Ile Pro Val Gly Ile Gly Pro His Ala Asn Leu Lys Gln
            1410            1415            1420

Ile Arg Leu Ile Glu Lys Gln Ala Pro Glu Asn Lys Ala Phe Val Leu
1425            1430            1435            1440

Ser Ser Val Asp Glu Leu Glu Gln Gln Arg Asp Glu Ile Val Ser Tyr
            1445            1450            1455

Leu Cys Asp Leu Ala Pro Glu Ala Pro Pro Thr Leu Pro Pro Asp
            1460            1465            1470

Met Ala Gln Val Thr Val Gly Pro Gly Leu Leu Gly Val Ser Thr Leu
            1475            1480            1485

Gly Pro Lys Arg Asn Ser Met Val Leu Asp Val Ala Phe Val Leu Glu
            1490            1495            1500

Gly Ser Asp Lys Ile Gly Glu Ala Asp Phe Asn Arg Ser Lys Glu Phe
1505            1510            1515            1520

Met Glu Glu Val Ile Gln Arg Met Asp Val Gly Gln Asp Ser Ile His
            1525            1530            1535

Val Thr Val Leu Gln Tyr Ser Tyr Met Val Thr Val Glu Tyr Pro Phe
            1540            1545            1550

Ser Glu Ala Gln Ser Lys Gly Asp Ile Leu Gln Arg Val Arg Glu Ile
            1555            1560            1565

Arg Tyr Gln Gly Gly Asn Arg Thr Asn Thr Gly Leu Ala Leu Arg Tyr
            1570            1575            1580

Leu Ser Asp His Ser Phe Leu Val Ser Gln Gly Asp Arg Glu Gln Ala
1585            1590            1595            1600
```

```
Pro Asn Leu Val Tyr Met Val Thr Gly Asn Pro Ala Ser Asp Glu Ile
            1605                1610                1615

Lys Arg Leu Pro Gly Asp Ile Gln Val Val Pro Ile Gly Val Gly Pro
            1620                1625                1630

Asn Ala Asn Val Gln Glu Leu Glu Arg Ile Gly Trp Pro Asn Ala Pro
            1635                1640                1645

Ile Leu Ile Gln Asp Phe Glu Thr Leu Pro Arg Glu Ala Pro Asp Leu
            1650                1655                1660

Val Leu Gln Arg Cys Cys Ser Gly Glu Gly Leu Gln Ile Pro Thr Leu
1665                1670                1675                1680

Ser Pro Ala Pro Asp Cys Ser Gln Pro Leu Asp Val Ile Leu Leu Leu
            1685                1690                1695

Asp Gly Ser Ser Ser Phe Pro Ala Ser Tyr Phe Asp Glu Met Lys Ser
            1700                1705                1710

Phe Ala Lys Ala Phe Ile Ser Lys Ala Asn Ile Gly Pro Arg Leu Thr
            1715                1720                1725

Gln Val Ser Val Leu Gln Tyr Gly Ser Ile Thr Thr Ile Asp Val Pro
            1730                1735                1740

Trp Asn Val Val Pro Glu Lys Ala His Leu Leu Ser Leu Val Asp Val
1745                1750                1755                1760

Met Gln Arg Glu Gly Gly Pro Ser Gln Ile Gly Asp Ala Leu Gly Phe
            1765                1770                1775

Ala Val Arg Tyr Leu Thr Ser Glu Met His Gly Ala Arg Pro Gly Ala
            1780                1785                1790

Ser Lys Ala Val Val Ile Leu Val Thr Asp Val Ser Val Asp Ser Val
            1795                1800                1805

Asp Ala Ala Ala Asp Ala Ala Arg Ser Asn Arg Val Thr Val Phe Pro
            1810                1815                1820

Ile Gly Ile Gly Asp Arg Tyr Asp Ala Ala Gln Leu Arg Ile Leu Ala
1825                1830                1835                1840

Gly Pro Ala Gly Asp Ser Asn Val Val Lys Leu Gln Arg Ile Glu Asp
            1845                1850                1855

Leu Pro Thr Met Val Thr Leu Gly Asn Ser Phe Leu His Lys Leu Cys
            1860                1865                1870

Ser Gly Phe Val Arg Ile Cys Met Asp Glu Asp Gly Asn Glu Lys Arg
            1875                1880                1885

Pro Gly Asp Val Trp Thr Leu Pro Asp Gln Cys His Thr Val Thr Cys
            1890                1895                1900

Gln Pro Asp Gly Gln Thr Leu Leu Lys Ser His Arg Val Asn Cys Asp
1905                1910                1915                1920

Arg Gly Leu Arg Pro Ser Cys Pro Asn Ser Gln Ser Pro Val Lys Val
            1925                1930                1935

Glu Glu Thr Cys Gly Cys Arg Trp Thr Cys Pro Cys Val Cys Thr Gly
            1940                1945                1950

Ser Ser Thr Arg His Ile Val Thr Phe Asp Gly Gln Asn Phe Lys Leu
            1955                1960                1965

Thr Gly Ser Cys Ser Tyr Val Leu Phe Gln Asn Lys Glu Gln Asp Leu
            1970                1975                1980

Glu Val Ile Leu His Asn Gly Ala Cys Ser Pro Gly Ala Arg Gln Gly
1985                1990                1995                2000

Cys Met Lys Ser Ile Glu Val Lys His Ser Ala Leu Ser Val Glu Leu
            2005                2010                2015
```

His Ser Asp Met Glu Val Thr Val Asn Gly Arg Leu Val Ser Val Pro
                2020                2025                2030

Tyr Val Gly Gly Asn Met Glu Val Asn Val Tyr Gly Ala Ile Met His
        2035                2040                2045

Glu Val Arg Phe Asn His Leu Gly His Ile Phe Thr Phe Thr Pro Gln
    2050                2055                2060

Asn Asn Glu Phe Gln Leu Gln Leu Ser Pro Lys Thr Phe Ala Ser Lys
2065                2070                2075                2080

Thr Tyr Gly Leu Cys Gly Ile Cys Asp Glu Asn Gly Ala Asn Asp Phe
            2085                2090                2095

Met Leu Arg Asp Gly Thr Val Thr Thr Asp Trp Lys Thr Leu Val Gln
        2100                2105                2110

Glu Trp Thr Val Gln Arg Pro Gly Gln Thr Cys Gln Pro Ile Leu Glu
            2115                2120                2125

Glu Gln Cys Leu Val Pro Asp Ser Ser His Cys Gln Val Leu Leu Leu
    2130                2135                2140

Pro Leu Phe Ala Glu Cys His Lys Val Leu Ala Pro Ala Thr Phe Tyr
2145                2150                2155                2160

Ala Ile Cys Gln Gln Asp Ser Cys His Gln Glu Gln Val Cys Glu Val
            2165                2170                2175

Ile Ala Ser Tyr Ala His Leu Cys Arg Thr Asn Gly Val Cys Val Asp
        2180                2185                2190

Trp Arg Thr Pro Asp Phe Cys Ala Met Ser Cys Pro Pro Ser Leu Val
            2195                2200                2205

Tyr Asn His Cys Glu His Gly Cys Pro Arg His Cys Asp Gly Asn Val
        2210                2215                2220

Ser Ser Cys Gly Asp His Pro Ser Glu Gly Cys Phe Cys Pro Pro Asp
2225                2230                2235                2240

Lys Val Met Leu Glu Gly Ser Cys Val Pro Glu Ala Cys Thr Gln
            2245                2250                2255

Cys Ile Gly Glu Asp Gly Val Gln His Gln Phe Leu Glu Ala Trp Val
    2260                2265                2270

Pro Asp His Gln Pro Cys Gln Ile Cys Thr Cys Leu Ser Gly Arg Lys
    2275                2280                2285

Val Asn Cys Thr Thr Gln Pro Cys Pro Thr Ala Lys Ala Pro Thr Cys
    2290                2295                2300

Gly Leu Cys Glu Val Ala Arg Leu Arg Gln Asn Ala Asp Gln Cys Cys
2305                2310                2315                2320

Pro Glu Tyr Glu Cys Val Cys Asp Pro Val Ser Cys Asp Leu Pro Pro
            2325                2330                2335

Val Pro His Cys Glu Arg Gly Leu Gln Pro Thr Leu Thr Asn Pro Gly
            2340                2345                2350

Glu Cys Arg Pro Asn Phe Thr Cys Ala Cys Arg Lys Glu Glu Cys Lys
        2355                2360                2365

Arg Val Ser Pro Pro Ser Cys Pro Pro His Arg Leu Pro Thr Leu Arg
    2370                2375                2380

Lys Thr Gln Cys Cys Asp Glu Tyr Glu Cys Ala Cys Asn Cys Val Asn
2385                2390                2395                2400

Ser Thr Val Ser Cys Pro Leu Gly Tyr Leu Ala Ser Thr Ala Thr Asn
            2405                2410                2415

Asp Cys Gly Cys Thr Thr Thr Thr Cys Leu Pro Asp Lys Val Cys Val
        2420                2425                2430

His Arg Ser Thr Ile Tyr Pro Val Gly Gln Phe Trp Glu Glu Gly Cys 2435                2440                2445

Asp Val Cys Thr Cys Thr Asp Met Glu Asp Ala Val Met Gly Leu Arg
    2450                2455                2460

Val Ala Gln Cys Ser Gln Lys Pro Cys Glu Asp Ser Cys Arg Ser Gly
2465                2470                2475                2480

Phe Thr Tyr Val Leu His Glu Gly Glu Cys Gly Arg Cys Leu Pro
            2485                2490                2495

Ser Ala Cys Glu Val Val Thr Gly Ser Pro Arg Gly Asp Ser Gln Ser
        2500                2505                2510

Ser Trp Lys Ser Val Gly Ser Gln Trp Ala Ser Pro Glu Asn Pro Cys
            2515                2520                2525

Leu Ile Asn Glu Cys Val Arg Val Lys Glu Glu Val Phe Ile Gln Gln
        2530                2535                2540

Arg Asn Val Ser Cys Pro Gln Leu Glu Val Pro Val Cys Pro Ser Gly
2545                2550                2555                2560

Phe Gln Leu Ser Cys Lys Thr Ser Ala Cys Cys Pro Ser Cys Arg Cys
            2565                2570                2575

Glu Arg Met Glu Ala Cys Met Leu Asn Gly Thr Val Ile Gly Pro Gly
        2580                2585                2590

Lys Thr Val Met Ile Asp Val Cys Thr Thr Cys Arg Cys Met Val Gln
        2595                2600                2605

Val Gly Val Ile Ser Gly Phe Lys Leu Glu Cys Arg Lys Thr Thr Cys
        2610                2615                2620

Asn Pro Cys Pro Leu Gly Tyr Lys Glu Glu Asn Asn Thr Gly Glu Cys
2625                2630                2635                2640

Cys Gly Arg Cys Leu Pro Thr Ala Cys Thr Ile Gln Leu Arg Gly Gly
            2645                2650                2655

Gln Ile Met Thr Leu Lys Arg Asp Glu Thr Leu Gln Asp Gly Cys Asp
        2660                2665                2670

Thr His Phe Cys Lys Val Asn Glu Arg Gly Glu Tyr Phe Trp Glu Lys
        2675                2680                2685

Arg Val Thr Gly Cys Pro Pro Phe Asp Glu His Lys Cys Leu Ala Glu
        2690                2695                2700

Gly Gly Lys Ile Met Lys Ile Pro Gly Thr Cys Cys Asp Thr Cys Glu
2705                2710                2715                2720

Glu Pro Glu Cys Asn Asp Ile Thr Ala Arg Leu Gln Tyr Val Lys Val
            2725                2730                2735

Gly Ser Cys Lys Ser Glu Val Glu Val Asp Ile His Tyr Cys Gln Gly
        2740                2745                2750

Lys Cys Ala Ser Lys Ala Met Tyr Ser Ile Asp Ile Asn Asp Val Gln
        2755                2760                2765

Asp Gln Cys Ser Cys Cys Ser Pro Thr Arg Thr Glu Pro Met Gln Val
        2770                2775                2780

Ala Leu His Cys Thr Asn Gly Ser Val Val Tyr His Glu Val Leu Asn
2785                2790                2795                2800

Ala Met Glu Cys Lys Cys Ser Pro Arg Lys Cys Ser Lys
            2805                2810

<210> SEQ ID NO 87
<211> LENGTH: 234
<212> TYPE: PRT
<213> ORGANISM: Homo sapiens

<400> SEQUENCE: 87

```
Met Ala Trp Thr Val Leu Leu Gly Leu Ser His Cys Thr Asp
1               5                   10                  15

Ser Val Ala Ser Tyr Val Leu Thr Gln Pro Pro Ser Val Ser Val Ala
                20                  25                  30

Pro Gly Lys Thr Ala Arg Ile Thr Cys Gly Ala Asp Asn Ile Gly Ala
            35                  40                  45

Lys Ser Val His Trp Tyr Gln Gln Lys Thr Asp Gln Ala Pro Val Leu
50                  55                  60

Val Val His Asp Asp Asn Asp Arg Pro Ser Gly Ile Pro Glu Arg Phe
65                  70                  75                  80

Ser Gly Ser Asn Ser Gly Asn Thr Ala Thr Leu Ser Ile Ser Arg Val
                85                  90                  95

Glu Pro Gly Asp Glu Ala Asp Tyr Phe Cys Gln Val Trp Asp Asn Ser
            100                 105                 110

Gly Gly Gln Leu Trp Met Phe Gly Gly Gly Thr Lys Leu Thr Val Leu
        115                 120                 125

Arg Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Lys Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 88
<211> LENGTH: 177
<212> TYPE: PRT
<213> ORGANISM: Homo sapiens

<400> SEQUENCE: 88

Met Gly Cys Cys Gly Cys Ser Arg Gly Cys Gly Ser Gly Cys Gly Gly
1               5                   10                  15

Cys Gly Ser Ser Cys Gly Gly Cys Gly Ser Gly Cys Gly Gly Cys Gly
                20                  25                  30

Ser Gly Arg Gly Gly Cys Gly Ser Gly Cys Gly Gly Cys Ser Ser Ser
            35                  40                  45

Cys Gly Gly Cys Gly Ser Arg Cys Tyr Val Pro Val Cys Cys Cys Lys
        50                  55                  60

Pro Val Cys Ser Trp Val Pro Ala Cys Ser Cys Thr Ser Cys Gly Ser
65                  70                  75                  80

Cys Gly Gly Ser Lys Gly Gly Cys Gly Ser Cys Gly Gly Ser Lys Gly
                85                  90                  95

Gly Cys Gly Ser Cys Gly Gly Ser Lys Gly Gly Cys Gly Ser Cys Gly
            100                 105                 110

Cys Ser Gln Ser Ser Cys Cys Lys Pro Cys Cys Ser Ser Gly Cys
        115                 120                 125

Gly Ser Ser Cys Cys Gln Ser Cys Cys Lys Pro Cys Cys Cys Gln
    130                 135                 140
```

```
Ser Ser Cys Cys Val Pro Val Cys Cys Gln Ser Ser Cys Cys Lys Pro
145                 150                 155                 160

Cys Cys Cys Gln Ser Asn Cys Cys Val Pro Val Cys Cys Gln Cys Lys
                165                 170                 175

Ile

<210> SEQ ID NO 89
<211> LENGTH: 222
<212> TYPE: PRT
<213> ORGANISM: Homo sapiens

<400> SEQUENCE: 89

Met Lys Leu Pro Leu Leu Ala Leu Leu Phe Gly Ala Val Ser Ala
1               5                   10                  15

Leu His Leu Arg Ser Glu Thr Ser Thr Phe Glu Thr Pro Leu Gly Ala
                20                  25                  30

Lys Thr Leu Pro Glu Asp Glu Glu Thr Pro Glu Gln Glu Met Glu Glu
                35                  40                  45

Thr Pro Cys Arg Glu Leu Glu Glu Glu Glu Trp Gly Ser Gly Ser
    50                  55                  60

Glu Asp Ala Ser Lys Lys Asp Gly Ala Val Glu Ser Ile Ser Val Pro
65                  70                  75                  80

Asp Met Val Asp Lys Asn Leu Thr Cys Pro Glu Glu Glu Asp Thr Val
                85                  90                  95

Lys Val Val Gly Ile Pro Gly Cys Gln Thr Cys Arg Tyr Leu Leu Val
                100                 105                 110

Arg Ser Leu Gln Thr Phe Ser Gln Ala Trp Phe Thr Cys Arg Arg Cys
                115                 120                 125

Tyr Arg Gly Asn Leu Val Ser Ile His Asn Phe Asn Ile Asn Tyr Arg
                130                 135                 140

Ile Gln Cys Ser Val Ser Ala Leu Asn Gln Gly Gln Val Trp Ile Gly
145                 150                 155                 160

Gly Arg Ile Thr Gly Ser Gly Arg Cys Arg Arg Phe Gln Trp Val Asp
                165                 170                 175

Gly Ser Arg Trp Asn Phe Ala Tyr Trp Ala Ala His Gln Pro Trp Ser
                180                 185                 190

Arg Gly Gly His Cys Val Ala Leu Cys Thr Arg Gly Gly His Trp Arg
                195                 200                 205

Arg Ala His Cys Leu Arg Arg Leu Pro Phe Ile Cys Ser Tyr
                210                 215                 220

<210> SEQ ID NO 90
<211> LENGTH: 188
<212> TYPE: PRT
<213> ORGANISM: Homo sapiens

<400> SEQUENCE: 90

Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
                20                  25                  30

Gly Val Asp Gly Lys Glu Phe Pro Glu Val His Leu Gly Gln Trp Tyr
                35                  40                  45

Phe Ile Ala Gly Ala Ala Pro Thr Lys Glu Glu Leu Ala Thr Phe Asp
                50                  55                  60
```

```
Pro Val Asp Asn Ile Val Phe Asn Met Ala Ala Gly Ser Ala Pro Met
 65                  70                  75                  80

Gln Leu His Leu Arg Ala Thr Ile Arg Met Lys Asp Gly Leu Cys Val
                 85                  90                  95

Pro Arg Lys Trp Ile Tyr His Leu Thr Glu Gly Ser Thr Asp Leu Arg
            100                 105                 110

Thr Glu Gly Arg Pro Asp Met Lys Thr Glu Leu Phe Ser Ser Ser Cys
        115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
            180                 185

<210> SEQ ID NO 91
<211> LENGTH: 1676
<212> TYPE: PRT
<213> ORGANISM: Homo sapiens

<400> SEQUENCE: 91

Met Gly Leu Leu Gly Ile Leu Cys Phe Leu Ile Phe Leu Gly Lys Thr
  1               5                  10                  15

Trp Gly Gln Glu Gln Thr Tyr Val Ile Ser Ala Pro Lys Ile Phe Arg
                 20                  25                  30

Val Gly Ala Ser Glu Asn Ile Val Ile Gln Val Tyr Gly Tyr Thr Glu
             35                  40                  45

Ala Phe Asp Ala Thr Ile Ser Ile Lys Ser Tyr Pro Asp Lys Lys Phe
         50                  55                  60

Ser Tyr Ser Ser Gly His Val His Leu Ser Ser Glu Asn Lys Phe Gln
 65                  70                  75                  80

Asn Ser Ala Ile Leu Thr Ile Gln Pro Lys Gln Leu Pro Gly Gly Gln
                 85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255
```

```
Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
            275                 280                 285

Asn Thr Met Leu Ile Asn Gly Ile Ala Gln Val Thr Phe Asp Ser Glu
290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
            355                 360                 365

Tyr Pro Ile Lys Val Gln Val Lys Asp Ser Leu Asp Gln Leu Val Gly
        370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
            435                 440                 445

Arg Glu Gly Tyr Arg Ala Ile Ala Tyr Ser Ser Leu Ser Gln Ser Tyr
    450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
            515                 520                 525

Pro Val Thr Gln Asn Met Val Pro Ser Ser Arg Leu Leu Val Tyr Tyr
        530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
            595                 600                 605

Val Tyr Gly Val Gln Arg Gly Ala Lys Lys Pro Leu Glu Arg Val Phe
        610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670
```

-continued

```
Leu Arg Pro Arg Arg Thr Leu Gln Lys Lys Ile Glu Glu Ile Ala Ala
            675                 680                 685

Lys Tyr Lys His Ser Val Val Lys Lys Cys Cys Tyr Asp Gly Ala Cys
        690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
    770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
        915                 920                 925

Val Val Pro Glu Gly Val Lys Arg Glu Ser Tyr Ser Gly Val Thr Leu
    930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His Tyr
    1010                1015                1020

Leu Glu Thr Gly Asn His Trp Asn Ile Phe His Ser Asp Pro Leu Ile
1025                1030                1035                1040

Glu Lys Gln Lys Leu Lys Lys Lys Leu Lys Glu Gly Met Leu Ser Ile
                1045                1050                1055

Met Ser Tyr Arg Asn Ala Asp Tyr Ser Tyr Ser Val Trp Lys Gly Gly
            1060                1065                1070

Ser Ala Ser Thr Trp Leu Thr Ala Phe Ala Leu Arg Val Leu Gly Gln
        1075                1080                1085

Val Asn Lys Tyr Val Glu Gln Asn Gln Asn Ser Ile Cys Asn Ser Leu
```

-continued

```
            1090               1095             1100
Leu Trp Leu Val Glu Asn Tyr Gln Leu Asp Asn Gly Ser Phe Lys Glu
1105                1110              1115              1120

Asn Ser Gln Tyr Gln Pro Ile Lys Leu Gln Gly Thr Leu Pro Val Glu
                1125              1130              1135

Ala Arg Glu Asn Ser Leu Tyr Leu Thr Ala Phe Thr Val Ile Gly Ile
            1140              1145              1150

Arg Lys Ala Phe Asp Ile Cys Pro Leu Val Lys Ile Asp Thr Ala Leu
        1155              1160              1165

Ile Lys Ala Asp Asn Phe Leu Leu Glu Asn Thr Leu Pro Ala Gln Ser
1170              1175              1180

Thr Phe Thr Leu Ala Ile Ser Ala Tyr Ala Leu Ser Leu Gly Asp Lys
1185              1190              1195              1200

Thr His Pro Gln Phe Arg Ser Ile Val Ser Ala Leu Lys Arg Glu Ala
            1205              1210              1215

Leu Val Lys Gly Asn Pro Pro Ile Tyr Arg Phe Trp Lys Asp Asn Leu
                1220              1225              1230

Gln His Lys Asp Ser Ser Val Pro Asn Thr Gly Thr Ala Arg Met Val
            1235              1240              1245

Glu Thr Thr Ala Tyr Ala Leu Leu Thr Ser Leu Asn Leu Lys Asp Ile
        1250              1255              1260

Asn Tyr Val Asn Pro Val Ile Lys Trp Leu Ser Glu Glu Gln Arg Tyr
1265              1270              1275              1280

Gly Gly Gly Phe Tyr Ser Thr Gln Asp Thr Ile Asn Ala Ile Glu Gly
            1285              1290              1295

Leu Thr Glu Tyr Ser Leu Leu Val Lys Gln Leu Arg Leu Ser Met Asp
        1300              1305              1310

Ile Asp Val Ser Tyr Lys His Lys Gly Ala Leu His Asn Tyr Lys Met
        1315              1320              1325

Thr Asp Lys Asn Phe Leu Gly Arg Pro Val Glu Val Leu Leu Asn Asp
        1330              1335              1340

Asp Leu Ile Val Ser Thr Gly Phe Gly Ser Gly Leu Ala Thr Val His
1345              1350              1355              1360

Val Thr Thr Val Val His Lys Thr Ser Thr Ser Glu Glu Val Cys Ser
            1365              1370              1375

Phe Tyr Leu Lys Ile Asp Thr Gln Asp Ile Glu Ala Ser His Tyr Arg
            1380              1385              1390

Gly Tyr Gly Asn Ser Asp Tyr Lys Arg Ile Val Ala Cys Ala Ser Tyr
            1395              1400              1405

Lys Pro Ser Arg Glu Glu Ser Ser Gly Ser Ser His Ala Val Met
1410              1415              1420

Asp Ile Ser Leu Pro Thr Gly Ile Ser Ala Asn Glu Glu Asp Leu Lys
1425              1430              1435              1440

Ala Leu Val Glu Gly Val Asp Gln Leu Phe Thr Asp Tyr Gln Ile Lys
                1445              1450              1455

Asp Gly His Val Ile Leu Gln Leu Asn Ser Ile Pro Ser Ser Asp Phe
            1460              1465              1470

Leu Cys Val Arg Phe Arg Ile Phe Glu Leu Phe Glu Val Gly Phe Leu
        1475              1480              1485

Ser Pro Ala Thr Phe Thr Val Tyr Glu Tyr His Arg Pro Asp Lys Gln
            1490              1495              1500

Cys Thr Met Phe Tyr Ser Thr Ser Asn Ile Lys Ile Gln Lys Val Cys
1505              1510              1515              1520
```

Glu Gly Ala Ala Cys Lys Cys Val Glu Ala Asp Cys Gly Gln Met Gln
              1525                1530                1535

Glu Glu Leu Asp Leu Thr Ile Ser Ala Glu Thr Arg Lys Gln Thr Ala
              1540                1545                1550

Cys Lys Pro Glu Ile Ala Tyr Ala Tyr Lys Val Ser Ile Thr Ser Ile
              1555                1560                1565

Thr Val Glu Asn Val Phe Val Lys Tyr Lys Ala Thr Leu Leu Asp Ile
    1570                1575                1580

Tyr Lys Thr Gly Glu Ala Val Ala Glu Lys Asp Ser Glu Ile Thr Phe
1585                1590                1595                1600

Ile Lys Lys Val Thr Cys Thr Asn Ala Glu Leu Val Lys Gly Arg Gln
              1605                1610                1615

Tyr Leu Ile Met Gly Lys Glu Ala Leu Gln Ile Lys Tyr Asn Phe Ser
              1620                1625                1630

Phe Arg Tyr Ile Tyr Pro Leu Asp Ser Leu Thr Trp Ile Glu Tyr Trp
              1635                1640                1645

Pro Arg Asp Thr Thr Cys Ser Ser Cys Gln Ala Phe Leu Ala Asn Leu
              1650                1655                1660

Asp Glu Phe Ala Glu Asp Ile Phe Leu Asn Gly Cys
1665                1670                1675

<210> SEQ ID NO 92
<211> LENGTH: 110
<212> TYPE: PRT
<213> ORGANISM: Homo sapiens

<400> SEQUENCE: 92

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Lys Asn
            20                  25                  30

Tyr Val Ser Trp Tyr Gln Gln Leu Pro Gly Ala Ala Pro Lys Leu Leu
            35                  40                  45

Ile Tyr Glu Ser Asp Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Ala Tyr Tyr Cys Gly Thr Trp Asp His Ser Leu
                85                  90                  95

Asn Ala Gly Val Phe Gly Gly Gly Thr Thr Leu Thr Val Leu
            100                 105                 110

<210> SEQ ID NO 93
<211> LENGTH: 764
<212> TYPE: PRT
<213> ORGANISM: Homo sapiens

<400> SEQUENCE: 93

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Trp
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
50                  55                  60

```
Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
            115                 120                 125

Phe His Cys Tyr Asp Gly Tyr Thr Leu Arg Gly Ser Ala Asn Arg Thr
            130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
            195                 200                 205

Gly Ser Trp Ser Gly Thr Glu Pro Ser Cys Gln Asp Ser Phe Met Tyr
            210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
            290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
            355                 360                 365

Pro Asp Asp Val Pro Pro Glu Gly Trp Asn Arg Thr Arg His Val Ile
            370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
            450                 455                 460

Phe Tyr Gln Met Ile Asp Glu Ser Gln Ser Leu Ser Leu Cys Gly Met
465                 470                 475                 480
```

```
Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
    690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
    755                 760

<210> SEQ ID NO 94
<211> LENGTH: 544
<212> TYPE: PRT
<213> ORGANISM: Homo sapiens

<400> SEQUENCE: 94

Met Ser Ser Pro Gly Pro Ser Gln Pro Pro Ala Glu Asp Pro Pro Trp
1               5                   10                  15

Pro Ala Arg Leu Leu Arg Ala Pro Leu Gly Leu Leu Arg Leu Asp Pro
                20                  25                  30

Ser Gly Gly Ala Leu Leu Leu Cys Gly Leu Val Ala Leu Leu Gly Trp
            35                  40                  45

Ser Trp Leu Arg Arg Arg Ala Arg Gly Ile Pro Pro Gly Pro Thr
        50                  55                  60

Pro Trp Pro Leu Val Gly Asn Phe Gly His Val Leu Leu Pro Phe
65                  70                  75              80

Leu Arg Arg Arg Ser Trp Leu Ser Ser Arg Thr Arg Ala Ala Gly Ile
                85                  90                  95
```

```
Asp Pro Ser Val Ile Gly Pro Gln Val Leu Leu Ala His Leu Ala Arg
            100                 105                 110

Val Tyr Gly Ser Ile Phe Ser Phe Ile Gly His Tyr Leu Val Val
            115                 120                 125

Val Leu Ser Asp Phe His Ser Val Arg Glu Ala Leu Val Gln Gln Ala
130                 135                 140

Glu Val Phe Ser Asp Arg Pro Arg Val Pro Leu Ile Ser Ile Val Thr
145                 150                 155                 160

Lys Glu Lys Gly Val Val Phe Ala His Tyr Gly Pro Val Trp Arg Gln
                165                 170                 175

Gln Arg Lys Phe Ser His Ser Thr Leu Arg His Phe Gly Leu Gly Lys
            180                 185                 190

Leu Ser Leu Glu Pro Lys Ile Ile Glu Glu Phe Lys Tyr Val Lys Ala
        195                 200                 205

Glu Met Gln Lys His Gly Glu Asp Pro Phe Cys Pro Phe Ser Ile Ile
    210                 215                 220

Ser Asn Ala Val Ser Asn Ile Ile Cys Ser Leu Cys Phe Gly Gln Arg
225                 230                 235                 240

Phe Asp Tyr Thr Asn Ser Glu Phe Lys Lys Met Leu Gly Phe Met Ser
                245                 250                 255

Arg Gly Leu Glu Ile Cys Leu Asn Ser Gln Val Leu Leu Val Asn Ile
            260                 265                 270

Cys Pro Trp Leu Tyr Tyr Leu Pro Phe Gly Pro Phe Lys Glu Leu Arg
        275                 280                 285

Gln Ile Glu Lys Asp Ile Thr Ser Phe Leu Lys Lys Ile Ile Lys Asp
    290                 295                 300

His Gln Glu Ser Leu Asp Arg Glu Asn Pro Gln Asp Phe Ile Asp Met
305                 310                 315                 320

Tyr Leu Leu His Met Glu Glu Arg Lys Asn Asn Ser Asn Ser Ser
                325                 330                 335

Phe Asp Glu Glu Tyr Leu Phe Tyr Ile Ile Gly Asp Leu Phe Ile Ala
            340                 345                 350

Gly Thr Asp Thr Thr Thr Asn Ser Leu Leu Trp Cys Leu Leu Tyr Met
        355                 360                 365

Ser Leu Asn Pro Asp Val Gln Glu Lys Val His Glu Glu Ile Glu Arg
370                 375                 380

Val Ile Gly Ala Asn Arg Ala Pro Ser Leu Thr Asp Lys Ala Gln Met
385                 390                 395                 400

Pro Tyr Thr Glu Ala Thr Ile Met Glu Val Gln Arg Leu Thr Val Val
                405                 410                 415

Val Pro Leu Ala Ile Pro His Met Thr Ser Glu Asn Thr Val Leu Gln
            420                 425                 430

Gly Tyr Thr Ile Pro Lys Gly Thr Leu Ile Leu Pro Asn Leu Trp Ser
        435                 440                 445

Val His Arg Asp Pro Ala Ile Trp Glu Lys Pro Glu Asp Phe Tyr Pro
    450                 455                 460

Asn Arg Phe Leu Asp Asp Gln Gly Gln Leu Ile Lys Lys Glu Thr Phe
465                 470                 475                 480

Ile Pro Phe Gly Ile Gly Lys Arg Val Cys Met Gly Glu Gln Leu Ala
                485                 490                 495

Lys Met Glu Leu Phe Leu Met Phe Val Ser Leu Met Gln Ser Phe Ala
            500                 505                 510
```

```
Phe Ala Leu Pro Glu Asp Ser Lys Lys Pro Leu Leu Thr Gly Arg Phe
            515                 520                 525

Gly Leu Thr Leu Ala Pro His Pro Phe Asn Ile Thr Ile Ser Arg Arg
530                 535                 540
```

<210> SEQ ID NO 95
<211> LENGTH: 782
<212> TYPE: PRT
<213> ORGANISM: Homo sapiens

<400> SEQUENCE: 95

```
Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
    130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Val Gln Arg Leu Phe Gln Val
            180                 185                 190

Lys Gly Arg Arg Val Val Arg Ala Thr Glu Val Pro Val Ser Trp Glu
        195                 200                 205

Ser Phe Asn Asn Gly Asp Cys Phe Ile Leu Asp Leu Gly Asn Asn Ile
    210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
    290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350
```

Glu Arg Lys Ala Ala Leu Lys Thr Ala Ser Asp Phe Ile Thr Lys
     355                 360                 365
Met Asp Tyr Pro Lys Gln Thr Gln Val Ser Val Leu Pro Glu Gly Gly
     370                 375                 380
Glu Thr Pro Leu Phe Lys Gln Phe Phe Lys Asn Trp Arg Asp Pro Asp
385                 390                 395                 400
Gln Thr Asp Gly Leu Gly Leu Ser Tyr Leu Ser Ser His Ile Ala Asn
                405                 410                 415
Val Glu Arg Val Pro Phe Asp Ala Ala Thr Leu His Thr Ser Thr Ala
                420                 425                 430
Met Ala Ala Gln His Gly Met Asp Asp Asp Gly Thr Gly Gln Lys Gln
                435                 440                 445
Ile Trp Arg Ile Glu Gly Ser Asn Lys Val Pro Val Asp Pro Ala Thr
                450                 455                 460
Tyr Gly Gln Phe Tyr Gly Gly Asp Ser Tyr Ile Ile Leu Tyr Asn Tyr
465                 470                 475                 480
Arg His Gly Gly Arg Gln Gly Gln Ile Ile Tyr Asn Trp Gln Gly Ala
                485                 490                 495
Gln Ser Thr Gln Asp Glu Val Ala Ala Ser Ala Ile Leu Thr Ala Gln
                500                 505                 510
Leu Asp Glu Glu Leu Gly Gly Thr Pro Val Gln Ser Arg Val Val Gln
                515                 520                 525
Gly Lys Glu Pro Ala His Leu Met Ser Leu Phe Gly Gly Lys Pro Met
                530                 535                 540
Ile Ile Tyr Lys Gly Gly Thr Ser Arg Glu Gly Gly Gln Thr Ala Pro
545                 550                 555                 560
Ala Ser Thr Arg Leu Phe Gln Val Arg Ala Asn Ser Ala Gly Ala Thr
                565                 570                 575
Arg Ala Val Glu Val Leu Pro Lys Ala Gly Ala Leu Asn Ser Asn Asp
                580                 585                 590
Ala Phe Val Leu Lys Thr Pro Ser Ala Ala Tyr Leu Trp Val Gly Thr
                595                 600                 605
Gly Ala Ser Glu Ala Glu Lys Thr Gly Ala Gln Glu Leu Leu Arg Val
                610                 615                 620
Leu Arg Ala Gln Pro Val Gln Val Ala Glu Gly Ser Glu Pro Asp Gly
625                 630                 635                 640
Phe Trp Glu Ala Leu Gly Gly Lys Ala Ala Tyr Arg Thr Ser Pro Arg
                645                 650                 655
Leu Lys Asp Lys Lys Met Asp Ala His Pro Pro Arg Leu Phe Ala Cys
                660                 665                 670
Ser Asn Lys Ile Gly Arg Phe Val Ile Glu Glu Val Pro Gly Glu Leu
                675                 680                 685
Met Gln Glu Asp Leu Ala Thr Asp Asp Val Met Leu Leu Asp Thr Trp
                690                 695                 700
Asp Gln Val Phe Val Trp Val Gly Lys Asp Ser Gln Glu Glu Glu Lys
705                 710                 715                 720
Thr Glu Ala Leu Thr Ser Ala Lys Arg Tyr Ile Glu Thr Asp Pro Ala
                725                 730                 735
Asn Arg Asp Arg Arg Thr Pro Ile Thr Val Val Lys Gln Gly Phe Glu
                740                 745                 750
Pro Pro Ser Phe Val Gly Trp Phe Leu Gly Trp Asp Asp Asp Tyr Trp
                755                 760                 765

-continued

Ser Val Asp Pro Leu Asp Arg Ala Met Ala Glu Leu Ala Ala
    770             775             780

<210> SEQ ID NO 96
<211> LENGTH: 108
<212> TYPE: PRT
<213> ORGANISM: Homo sapiens

<400> SEQUENCE: 96

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Cys Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Phe
65                  70                  75                  80

Glu Asp Phe Ala Val Tyr Tyr Cys Gln His Tyr Asn Asn Trp Pro Phe
                85                  90                  95

Thr Phe Gly Pro Gly Thr Lys Val Asp Ile Lys Arg
            100                 105

<210> SEQ ID NO 97
<211> LENGTH: 235
<212> TYPE: PRT
<213> ORGANISM: Homo sapiens

<400> SEQUENCE: 97

Met Thr Cys Ser Pro Leu Leu Leu Thr Leu Leu Ile His Cys Thr Gly
1               5                   10                  15

Ser Trp Ala Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Val Ser Trp Tyr Gln Gln Leu Pro Gly Thr Ala Pro
50                  55                  60

Lys Leu Leu Ile Tyr Asp Asn Asn Lys Arg Pro Ser Gly Ile Pro Asp
65                  70                  75                  80

Arg Phe Ser Gly Ser Lys Ser Gly Thr Ser Ala Thr Leu Gly Ile Thr
                85                  90                  95

Gly Leu Gln Thr Gly Asp Glu Ala Asp Tyr Tyr Cys Gly Thr Trp Asp
            100                 105                 110

Ser Ser Leu Ser Ala Gly Val Phe Gly Gly Gly Thr Lys Leu Thr Val
        115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
210                215                220

Val Glu Lys Thr Val Ala Pro Thr Glu Cys Ser
225                230                235

<210> SEQ ID NO 98
<211> LENGTH: 234
<212> TYPE: PRT
<213> ORGANISM: Homo sapiens

<400> SEQUENCE: 98

Met Ala Trp Thr Phe Leu Leu Gly Leu Leu Ser His Cys Thr Asp
1               5                   10                  15

Ser Val Ala Ser Tyr Val Leu Thr Gln Pro Pro Ser Val Leu Val Ala
                20                  25                  30

Pro Gly Lys Thr Ala Arg Ile Thr Cys Gly Gly Asp Asn Val Gly Ser
            35                  40                  45

Lys Ala Val His Trp Tyr Gln Gln Lys Pro Gly Gln Ala Pro Val Leu
50                  55                  60

Val Ile Tyr Tyr Asp Thr Asp Arg Pro Ser Gly Ile Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Ile Trp Asp Thr Gly
            100                 105                 110

Pro Asp His Phe Tyr Val Phe Gly Thr Gly Thr Lys Val Thr Val Leu
        115                 120                 125

Gly Gln Pro Lys Ala Asn Pro Thr Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Gly Ser Pro
                165                 170                 175

Val Lys Ala Gly Val Glu Thr Thr Lys Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
210                 215                 220

Glu Lys Thr Val Ala Pro Thr Glu Cys Ser
225                 230

<210> SEQ ID NO 99
<211> LENGTH: 644
<212> TYPE: PRT
<213> ORGANISM: Homo sapiens

<400> SEQUENCE: 99

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
                20                  25                  30

Leu Phe Lys Ala Val Asp Ala Ala Leu Lys Lys Tyr Asn Ser Gln Asn
            35                  40                  45

Gln Ser Asn Asn Gln Phe Val Leu Tyr Arg Ile Thr Glu Ala Thr Lys
50                  55                  60

-continued

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
        195                 200                 205

Glu Asn Phe Leu Phe Leu Thr Pro Asp Cys Lys Ser Leu Trp Asn Gly
210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
        275                 280                 285

Leu Asn Ala Glu Asn Asn Ala Thr Phe Tyr Phe Lys Ile Asp Asn Val
    290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
370                 375                 380

Phe Ser Pro Phe Arg Ser Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
        435                 440                 445

Arg Asp Gln Gly His Gly His Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys

His Lys His Gly His Gly His Gly Lys His Lys Asn Lys Gly Lys Lys
            485                 490                 495
                500                 505                 510

Asn Gly Lys His Asn Gly Trp Lys Thr Glu His Leu Ala Ser Ser Ser
                515                 520                 525

Glu Asp Ser Thr Thr Pro Ser Ala Gln Thr Gln Glu Lys Thr Glu Gly
                530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
                580                 585                 590

Ile Asp Pro Asn Gly Leu Ser Phe Asn Pro Ile Ser Asp Phe Pro Asp
                595                 600                 605

Thr Thr Ser Pro Lys Cys Pro Gly Arg Pro Trp Lys Ser Val Ser Glu
                610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 100
<211> LENGTH: 623
<212> TYPE: PRT
<213> ORGANISM: Homo sapiens

<400> SEQUENCE: 100

Met Ser Cys Arg Gln Phe Ser Ser Ser Tyr Leu Ser Arg Ser Gly Gly
1               5                   10                  15

Gly Gly Gly Gly Gly Leu Gly Ser Gly Gly Ser Ile Arg Ser Ser Tyr
                20                  25                  30

Ser Arg Phe Ser Ser Ser Gly Gly Gly Gly Gly Arg Phe Ser
                35                  40                  45

Ser Ser Ser Gly Tyr Gly Gly Gly Ser Ser Arg Val Cys Gly Arg Gly
                50                  55                  60

Gly Gly Gly Ser Phe Gly Tyr Ser Tyr Gly Gly Gly Ser Gly Gly Gly
65              70                  75                  80

Phe Ser Ala Ser Ser Leu Gly Gly Gly Phe Gly Gly Gly Ser Arg Gly
                85                  90                  95

Phe Gly Gly Ala Ser Gly Gly Gly Tyr Ser Ser Ser Gly Gly Phe Gly
                100                 105                 110

Gly Gly Phe Gly Gly Gly Ser Gly Gly Gly Phe Gly Gly Gly Tyr Gly
                115                 120                 125

Ser Gly Phe Gly Gly Phe Gly Gly Phe Gly Gly Gly Ala Gly Gly Gly
                130                 135                 140

Asp Gly Gly Ile Leu Thr Ala Asn Glu Lys Ser Thr Met Gln Glu Leu
145                 150                 155                 160

Asn Ser Arg Leu Ala Ser Tyr Leu Asp Lys Val Gln Ala Leu Glu Glu
                165                 170                 175

Ala Asn Asn Asp Leu Glu Asn Lys Ile Gln Asp Trp Tyr Asp Lys Lys
                180                 185                 190

Gly Pro Ala Ala Ile Gln Lys Asn Tyr Ser Pro Tyr Tyr Asn Thr Ile
                195                 200                 205

Asp Asp Leu Lys Asp Gln Ile Val Asp Leu Thr Val Gly Asn Asn Lys

-continued

Thr Leu Leu Asp Ile Asp Asn Thr Arg Met Thr Leu Asp Asp Phe Arg
225                 230                 235                 240

Ile Lys Phe Glu Met Glu Gln Asn Leu Arg Gln Gly Val Asp Ala Asp
                245                 250                 255

Ile Asn Gly Leu Arg Gln Val Leu Asp Asn Leu Thr Met Glu Lys Ser
            260                 265                 270

Asp Leu Glu Met Gln Tyr Glu Thr Leu Gln Glu Glu Leu Met Ala Leu
        275                 280                 285

Lys Lys Asn His Lys Glu Glu Met Ser Gln Leu Thr Gly Gln Asn Ser
    290                 295                 300

Gly Asp Val Asn Val Glu Ile Asn Val Ala Pro Gly Lys Asp Leu Thr
305                 310                 315                 320

Lys Thr Leu Asn Asp Met Arg Gln Glu Tyr Glu Gln Leu Ile Ala Lys
                325                 330                 335

Asn Arg Lys Asp Ile Glu Asn Gln Tyr Glu Thr Gln Ile Thr Gln Ile
            340                 345                 350

Glu His Glu Val Ser Ser Gly Gln Glu Val Gln Ser Ser Ala Lys
        355                 360                 365

Glu Val Thr Gln Leu Arg His Gly Val Gln Glu Leu Glu Ile Glu Leu
    370                 375                 380

Gln Ser Gln Leu Ser Lys Lys Ala Ala Leu Glu Lys Ser Leu Glu Asp
385                 390                 395                 400

Thr Lys Asn Arg Tyr Cys Gly Gln Leu Gln Met Ile Gln Glu Gln Ile
                405                 410                 415

Ser Asn Leu Glu Ala Gln Ile Thr Asp Val Arg Gln Glu Ile Glu Cys
            420                 425                 430

Gln Asn Gln Glu Tyr Ser Leu Leu Leu Ser Ile Lys Met Arg Leu Glu
        435                 440                 445

Lys Glu Ile Glu Thr Tyr His Asn Leu Leu Glu Gly Gly Gln Glu Asp
    450                 455                 460

Phe Glu Ser Ser Gly Ala Gly Lys Ile Gly Leu Gly Arg Gly Gly
465                 470                 475                 480

Ser Gly Gly Ser Tyr Gly Arg Gly Ser Arg Gly Gly Ser Gly Gly Ser
                485                 490                 495

Tyr Gly Gly Gly Ser Gly Gly Tyr Gly Gly Ser Gly Ser
            500                 505                 510

Arg Gly Gly Ser Gly Gly Ser Tyr Gly Gly Ser Gly Ser Gly Gly
        515                 520                 525

Gly Ser Gly Gly Gly Tyr Gly Gly Ser Gly Gly His Ser Gly
    530                 535                 540

Gly Ser Gly Gly Gly His Ser Gly Gly Ser Gly Asn Tyr Gly Gly
545                 550                 555                 560

Gly Ser Gly Ser Gly Gly Gly Ser Gly Gly Tyr Gly Gly Gly Ser
                565                 570                 575

Gly Ser Arg Gly Gly Ser Gly Ser His Gly Gly Ser Gly Phe
            580                 585                 590

Gly Gly Glu Ser Gly Gly Ser Tyr Gly Gly Glu Glu Ala Ser Gly
        595                 600                 605

Ser Gly Gly Gly Tyr Gly Gly Gly Ser Gly Lys Ser Ser His Ser
    610                 615                 620

TREATMENT OF SPONTANEOUS PRETERM BIRTH

CROSS-REFERENCE TO RELATED APPLICATIONS

This application is a U.S. National Stage of PCT/US2013/077868, filed Dec. 26, 2013, which is a continuation-in-part of U.S. application Ser. No. 13/797,933 filed Mar. 12, 2013, and claims the benefit of U.S. Provisional Application No. 61/747,150 filed Dec. 28, 2012, which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 674982000830SeqList.txt, date recorded: Jun. 25, 2015, size: 525 KB).

FIELD

The present disclosure relates to biomarkers of preterm birth, biomarkers of term birth, and methods of use thereof. In particular, the present disclosure provides methods of determining whether a pregnant woman is at an increased risk for premature delivery. The present disclosure further provides methods for decreasing a pregnant woman's risk for premature delivery.

BACKGROUND

In humans, preterm birth (PTB) is defined as delivery of a pregnancy before 37 weeks of gestation (Honest et al., Health Technology Assessment, 13:1-3, 2009). PTB is associated with significant morbidity and mortality. Premature babies born before 37 weeks, if they survive, have a high incidence of visual and hearing defects, lung disease, developmental delays, and cerebral palsy (Ables and Chauhan, J Family Practice, 54:245-252, 2005).

Preterm deliveries are categorized as elective (about 25% of all premature births) or spontaneous (about 75% of all premature births). Elective preterm deliveries occur as a result of maternal or fetal complications such as hypertension and diabetes (Honest et al., supra, 2009). Spontaneous preterm deliveries occur as a result of preterm labor or preterm premature rupture of membranes (Ables and Chauhan, supra, 2005).

Relatively little progress has been made in determining whether a pregnant woman is at risk for PTB. The lack of tools for identifying risk early in pregnancy coupled with an inability to pinpoint underlying etiology prevents clinicians from proactively detecting and managing the at-risk pregnancy hampering their efforts to improve pregnancy outcomes. In fact, the rate of preterm birth has steadily increased and reflects approximately 15 million of the 187 million births worldwide. In the United States, the preterm birth rate approaches 12.7% resulting in over 500,000 premature infants born each year. Moreover, during the first year of life, between 10 and 20% of premature infants die (March of Dimes, Born Too Soon, 2012; and Society for Maternal Fetal Medicine, High Risk Pregnancy Care, Research, and Education for Over 35 Years, 2010).

A pregnancy ending prematurely is multifactorial in its etiology and remains difficult to predict. For a pregnancy to progress uneventfully, an exquisite balance between numerous physiological systems must be maintained—including the dynamic immunological status of host and fetus at the placental interface. Subtle changes in this balance may be reflected in the identification of a unique set of blood-derived biomarkers found only in pregnancies that end prematurely. The utility and accuracy of novel biomarkers to predict spontaneous preterm birth remains elusive (Conde-Agudelo et al., BJOG, 118:1042-1054, 2011). Further compounding the problem is the complexity of harvesting such markers from biological fluids, the lack of stability of such markers and classic signal to noise issues incumbent to all biomarker studies.

Since the inability to accurately diagnose preterm labor or to determine a pregnant woman's risk of PTB has potentially catastrophic consequences, there is a need in the art for diagnostic and prognostic methods with improved specificity and sensitivity. This need is particularly great considering that timely administration of therapeutic agents may prevent preterm labor or otherwise prolong pregnancy.

BRIEF SUMMARY

The present disclosure relates to biomarkers of preterm birth, biomarkers of term birth, and methods of use thereof. In particular, the present disclosure provides methods of determining whether a pregnant woman is at an increased risk for premature delivery. The present disclosure further provides methods for decreasing a pregnant woman's risk for premature delivery.

In particular, the present disclosure provides methods for assessing the risk of preterm birth for a pregnant subject, the method comprising: (a) detecting a level of one or more proteins in a sample from the pregnant subject, wherein the one or more proteins are selected from the group consisting of A1BG, AFM, AHSG, ALB, AMBP, APCS, APOA1, APOD, APOH, APOL1, APOM, ATRN, AZGP1, C1QC, C1R, C1S, C3, C4A, C4B, C4BPA, C5, C8A, CD5L, CFB, CFH, CP, CPN1, CPN2, CYP2U1, F12, GSN, HP, HPR, HPX, IGHA1, IGHA2, IGHG1, IGHG4, IGHM, IGHM1, IGHM2, IGHV4-31, IGHVa, IGHVb, IGJ, IGKC, IGKV, IGKV1-9, IGKV3-20, IGKV3D-15, IGLC2, IGLL1, IGLV3-19, IGLV7-43, IGLVa, IGLVb, IGLVc, IGLVd, ITIH1, ITIH2, ITIH3, KNG1, KRT1, KRT10, KRT2, KRT6A, KRT9, KRTAP5-2, LGALS3BP, LPA, PF4, PPBP, PRG2, PZP, PZPs, SAA2-SAA4, SERPINF2, SERPING1, TF, VTN, and VWF; and (b) determining that the pregnant subject is at an increased risk of preterm birth when the level of one or more proteins of the preterm birth group consisting of A1BG, AFM, AHSG, ALB, AMBP, APOD, APOL1, APOM, ATRN, AZGP1, C8A, CD5L, CFB, CPN2, F12, GSN, HPR, IGHM1, IGHM2, IGJ, IGLVb, ITIH1, ITIH2, ITIH3, KNG1, KRT1, KRT10, KRT2, KRT6A, LGALS3BP, PRG2, SAA2-SAA4, SERPINF2, SERPING1, TF, VTN, and VWF is above a threshold level, and/or when the level of one or more of proteins of the term birth group consisting of APCS, APOA1, APOH, C1QC, C1R, C1S, C3, C4A, C4B, C4BPA, C5, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, and PZPs is below a threshold level; or determining that the pregnant subject is at not at an increased risk of preterm birth when the level of one or more proteins of the preterm birth group consisting of A1BG, AFM, AHSG, ALB, AMBP, APOD, APOL1, APOM, ATRN, AZGP1, C8A, CD5L, CFB, CPN2, F12, GSN, HPR, IGHM1, IGHM2, IGJ, IGLVb, ITIH1, ITIH2, ITIH3, KNG1, KRT1, KRT10, KRT2, KRT6A, LGALS3BP, PRG2, SAA2-SAA4, SERPINF2, SERPING1, TF, VTN, and VWF is below a threshold level, and/or when the level of one or more of proteins of the term birth group consisting of APCS, APOA1, APOH, C1QC, C1R, C1S, C3, C4A, C4B, C4BPA, C5, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, and PZPs is above a threshold level. In some preferred embodiments, the protein is detected by detecting a fragment of the protein (e.g., from four amino acids to full-length minus one amino acid).

The present disclosure provides methods for assessing the risk of preterm birth for a pregnant subject, comprising: (a) preparing a microparticle-enriched fraction from a sample from the pregnant subject; (b) detecting a level of one or more proteins in the fraction, wherein the one or more proteins are selected from the group consisting of A1BG, AFM, AHSG, ALB, AMBP, APCS, APOA1, APOD, APOH, APOL1, APOM, ATRN, AZGP1, C1QC, C1R, C1S, C3, C4A, C4B, C4BPA, C5, C8A, CD5L, CFB, CFH, CP, CPN1, CPN2, CYP2U1, F12, GSN, HP, HPR, HPX, IGHA1, IGHA2, IGHG1, IGHG4, IGHM, IGHM1, IGHM2, IGHV4-31, IGHVa, IGHVb, IGJ, IGKC, IGKV, IGKV1-9, IGKV3-20, IGKV3D-15, IGLC2, IGLL1, IGLV3-19, IGLV7-43, IGLVa, IGLVb, IGLVc, IGLVd, ITIH1, ITIH2, ITIH3, KNG1, KRT1, KRT10, KRT2, KRT6A, KRT9, KRTAP5-2, LGALS3BP, LPA, PF4, PPBP, PRG2, PZP, PZPs, SAA2-SAA4, SERPINF2, SERPING1, TF, VTN, and VWF; and (c) determining that the pregnant subject is at an increased risk of preterm birth when the level of one or more proteins of the preterm birth group consisting of A1BG, AFM, AHSG, ALB, AMBP, APOD, APOL1, APOM, ATRN, AZGP1, C8A, CD5L, CFB, CPN2, F12, GSN, HPR, IGHM1, IGHM2, IGJ, IGLVb, ITIH1, ITIH2, ITIH3, KNG1, KRT1, KRT10, KRT2, KRT6A, LGALS3BP, PRG2, SAA2-SAA4, SERPINF2, SERPING1, TF, VTN, and VWF is above a threshold level, and/or when the level of one or more of proteins of the term birth group consisting of APCS, APOA1, APOH, C1QC, C1R, C1S, C3, C4A, C4B, C4BPA, C5, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, and PZPs is below a threshold level; or determining that the pregnant subject is at not at an increased risk of preterm birth when the level of one or more proteins of the preterm birth group consisting of A1BG, AFM, AHSG, ALB, AMBP, APOD, APOL1, APOM, ATRN, AZGP1, C8A, CD5L, CFB, CPN2, F12, GSN, HPR, IGHM1, IGHM2, IGJ, IGLVb, ITIH1, ITIH2, ITIH3, KNG1, KRT1, KRT10, KRT2, KRT6A, LGALS3BP, PRG2, SAA2-SAA4, SERPINF2, SERPING1, TF, VTN, and VWF is below a threshold level, and/or when the level of one or more of proteins of the term birth group consisting of APCS, APOA1, APOH, C1QC, C1R, C1S, C3, C4A, C4B, C4BPA, C5, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, and PZPs is above a threshold level. In some preferred embodiments, the protein is detected by detecting a fragment of the protein (e.g., from four amino acids to full-length minus one amino acid).

Additionally, the present disclosure provides methods of decreasing the risk of preterm birth for a pregnant subject, comprising: (a) preparing a microparticle-enriched fraction from a sample from the pregnant subject; (b) detecting a level of one or more proteins in the fraction, wherein the one or more proteins are selected from the group consisting of A1BG, AFM, AHSG, ALB, AMBP, APCS, APOA1, APOD, APOH, APOL1, APOM, ATRN, AZGP1, C1QC, C1R, C1S, C3, C4A, C4B, C4BPA, C5, C8A, CD5L, CFB, CFH, CP, CPN1, CPN2, CYP2U1, F12, GSN, HP, HPR, HPX, IGHA1, IGHA2, IGHG1, IGHG4, IGHM, IGHM1, IGHM2, IGHV4-31, IGHVa, IGHVb, IGJ, IGKC, IGKV, IGKV1-9, IGKV3-20, IGKV3D-15, IGLC2, IGLL1, IGLV3-19, IGLV7-43, IGLVa, IGLVb, IGLVc, IGLVd, ITIH1, ITIH2, ITIH3, KNG1, KRT1, KRT10, KRT2, KRT6A, KRT9, KRTAP5-2, LGALS3BP, LPA, PF4, PPBP, PRG2, PZP, PZPs, SAA2-SAA4, SERPINF2, SERPING1, TF, VTN, and VWF; (c) determining that the pregnant subject is at an increased risk of preterm birth when the level of one or more proteins of the preterm birth group consisting of A1BG, AFM, AHSG, ALB, AMBP, APOD, APOL1, APOM, ATRN, AZGP1, C8A, CD5L, CFB, CPN2, F12, GSN, HPR, IGHM1, IGHM2, IGJ, IGLVb, ITIH1, ITIH2, ITIH3, KNG1, KRT1, KRT10, KRT2, KRT6A, LGALS3BP, PRG2, SAA2-SAA4, SERPINF2, SERPING1, TF, VTN, and VWF is above a threshold level, and/or when the level of one or more of proteins of the term birth group consisting of APCS, APOA1, APOH, C1QC, C1R, C1S, C3, C4A, C4B, C4BPA, C5, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, and PZPs is below a threshold level; and (d) administering a therapeutic agent to the subject in an amount effective to decrease the risk of preterm birth. In some preferred embodiments, the protein is detected by detecting a fragment of the protein (e.g., from four amino acids to full-length minus one amino acid).

In some embodiments, the methods of the preceding paragraphs further comprise: (b2) detecting a level of one or more further proteins in the fraction from the pregnant subject, wherein the one or more further proteins are selected from the group consisting of A2M, APOB, C9, F2, FBLN1, FN1, FN1s, GC, ITIH4, KLKB1, ORM1, ORM2, S100A8, S100A9, SERPINA1, SERPINC1, THBS1, and TTR; and (c2) determining that the pregnant subject is at an increased risk of preterm birth when the level of one or more further proteins of the further preterm birth group consisting of A2M, C9, FBLN1, FN1, FN1s, GC, ITIH4, KLKB1, ORM1, ORM2, S100A8, S100A9, SERPINA1, SERPINC1, and TTR, is above a threshold level, and/or when the level of one or more of further proteins of the further term birth group consisting of APOB, C9, and THBS1 is below a threshold level in the sample. In some embodiments, the detecting step comprises detecting the level of one or more proteins of the preterm group subset consisting of alpha-1B-glycoprotein (A1BG), serum albumin (ALB), apolipoprotein D (APOD), apolipoprotein L1 (APOL1), zinc-alpha-2-glycoprotein (AZGP1), hemopexin (HPX), Ig heavy chain mu 1 (IGHM1), IgM heavy chain mu 2 (IGHM2), and serotransferrin (TF), and/or detecting the level of one or more proteins of the term group subset consisting of complement component 1r (C1r), complement component 3 (C3), complement component 4B (C4B), complement factor H (CFH), Ig heavy chain alpha 2 (IGHA2), and Ig kappa variable1-9 (IGKV1-9). In some embodiments, the detecting step comprises detecting the level of all twelve of alpha-1B-glycoprotein (A1BG), alpha-2-macroglobulin (A2M), serum albumin (ALB), apolipoprotein D (APOD), apolipoprotein L1 (APOL1), zinc-alpha-2-glycoprotein (AZGP1), hemopexin (HPX), Ig heavy chain mu 1 (IGHM1), IgM heavy chain mu 2 (IGHM2), alpha-1-antitrypsin (SERPINA1), antithrombin-III (SERPINC1), and serotransferrin (TF). In some embodiments, the detecting step comprises detecting the level of all six of complement component 1r (C1r), complement component 3 (C3), complement component 4B (C4B), complement factor H (CFH), Ig heavy chain alpha 2 (IGHA2), and Ig kappa variable1-9 (IGKV1-9). In some embodiments, the methods comprise a further step after (c) of providing a risk score by enumerating the preterm birth markers above the threshold that were detected and the term birth markers below the threshold that were detected. In some preferred embodiments, the protein is detected by detecting a fragment of the protein (e.g., from four amino acids to full-length minus one amino acid). In some embodiments, the detecting step comprises detecting the level of at least 2, 3, 4, or 5 of the proteins in the fraction, or detecting the level of at least 2, 3, 4, 5, 6, 7, 8, 9, 10, 11, 12, 13, 14, 15, 16, 17, 18, 19 or 20 of the proteins in the fraction. In some embodiments, the detecting step comprises detecting the level of at least 5, at least 10, at least 15, at least 20, at least 25, at least 30, at least 35, at least 40, at least 45, at least 50, at least 55, at least 60, at least 65, at least 70, at least 75, or at least 80 out of the (99) proteins in the fraction. In some embodiments, the pregnant subject is a primigravida woman. In other embodiments, the pregnant subject is a multigravida woman. In some embodiments, the sample is taken from the pregnant subject during the second trimester. In some preferred embodiments, the sample is taken from the pregnant subject within 15 to 17 weeks of gestation. In some embodiments, the sample is blood, saliva, sweat, nasal secretions, tears, urine, amniotic fluid, or cervicovaginal fluid. In some embodiments, the sample is a blood sample, which in preferred embodiment is serum or plasma. In some embodiments, the preparing step does not comprise the use of EXOQUICK® exosome precipitation solution, or the like. In some embodiments, the preparing step comprises size-exclusion chromatography with an agarose (e.g., SEPHAROSE® beaded agarose) solid phase and an aqueous liquid phase. In some embodiments, the aqueous phase is water, while in other embodiments, the aqueous phase is a buffer. In some embodiments the detecting step comprises measuring binding of an antibody specific to each of the one or more proteins. In some embodiments, the detecting step comprises a technique selected from the group consisting of enzyme-linked immunosorbent assay (ELISA), western blot and antibody microarray. In some preferred embodiments, the detecting step comprises liquid chromatography/mass spectrometry (LC/MS). In some embodiments, the therapeutic agent is selected from the group consisting of a hormone, a steroid, intravenous immunoglobulin, and a tumor-necrosis factor-alpha antagonist. In some preferred embodiments the therapeutic agent is progesterone. In some preferred embodiments, the therapeutic agent comprises a cervical cerclage.

DETAILED DESCRIPTION

Figure 1:
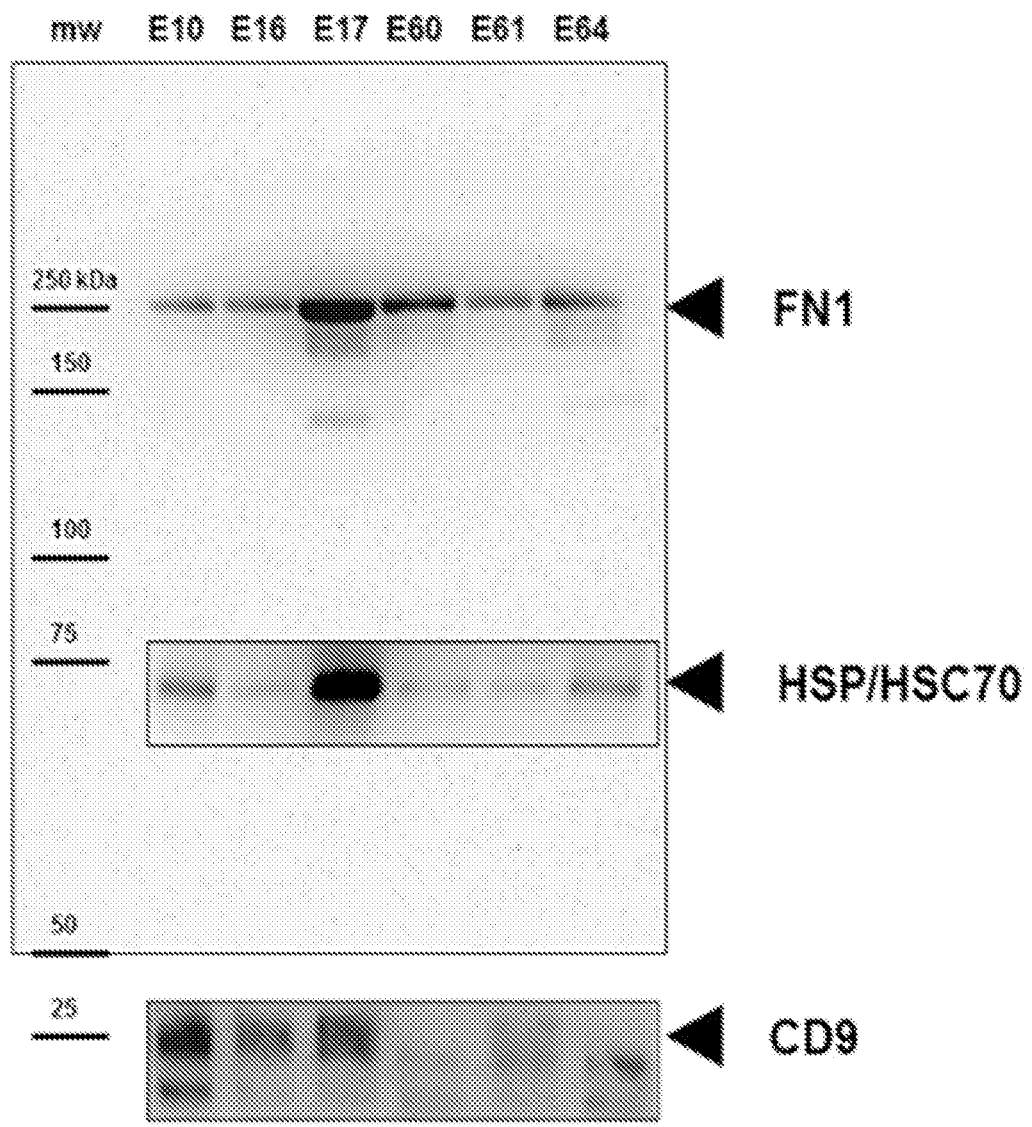
FIG. 1 provides a Western blot analysis of SEC peak 1 material derived from the serum of pregnant women. Six individual patient samples were analyzed. Antigens detected include: FN1, fibronectin; HSP, heat shock protein 70; and CD9, a tetraspanin cell surface protein commonly associated with extracellular vesicles.

Current methods indicate that placental-derived microparticles freely circulate in high titer in maternal blood and reflect the status of the syncytiotrophoblast maternal-fetal interface. Subtle homeostatic changes are reflected in a unique set of dysregulated, microparticle-associated proteins when pregnancy complications occur. As described in more detail in the example section, frozen maternal serum samples (n=48) obtained between 15-17 weeks gestation were analyzed from asymptomatic women subsequently having live births (e.g., excluded women having multiple births, still births, systemic disease, or delivering fetuses with known anomalies). Microparticles were isolated from blood samples using gel filtration, with samples blinded to outcome. Proteins were extracted and analyzed using an open proteomic LC-MS differential analysis between term (>37 wks) and preterm cohorts (<34 wks). Among 213 proteins identified, a unique pattern was observed in serum microparticles isolated from asymptomatic patients that subsequently delivered preterm. Using an ANOVA assessment and rigorous reproducibility, accuracy, and confidence criteria, 18 proteins were characterized from 99 statistically significant proteins identified across two study phases differentiating the cohorts, with functional analysis implicating inflammatory and cell injury pathways. Thus, the present disclosure provides a library of statistically-valued, microparticle-associated biomarkers that are useful for the early identification of women at risk for preterm birth.

Definitions

In order to facilitate an understanding of the disclosure, selected terms used in the application will be discussed below.

The term "microparticle" refers to an extracellular microvesicle or lipid raft protein aggregate having a hydrodynamic diameter of from about 50 to about 5000 nm. As such the term microparticle encompasses exosomes (about 50 to about 100 nm), microvesicles (about 100 to about 300 nm), ectosomes (about 50 to about 1000 nm), apoptotic bodies (about 50 to about 5000 nm) and lipid protein aggregates of the same dimensions.

The term "microparticle-associated protein" refers to a protein or fragment thereof (e.g., polypeptide) that is detectable in a microparticle-enriched sample from a mammalian (e.g., human) subject. As such the term "microparticle-associated protein" is not restricted to proteins or fragments thereof that are physically associated with microparticles at the time of detection.

The term "about" as used herein in reference to a value refers to 90 to 110% of that value. For instance a diameter of about 1000 nm is a diameter within the range of 900 nm to 1100 nm.

The phrase "increased risk of preterm birth" as used herein indicates that a pregnant subject has a greater likelihood of having a spontaneous preterm birth (before 38 weeks gestation) when one or more preterm birth markers are detected and/or when one or more term birth markers are not detected. Numerically an increased risk is associated with a hazard ratio of over 1.0, preferably over 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 for preterm birth.

Protein Biomarkers

The present disclosure relates to tools for assessing and decreasing risk of preterm birth. The methods of the present disclosure include a step of detecting the expression level of a microparticle-associated protein in a biological sample from a pregnant test subject, where the protein is selected from Table I.

TABLE I

Micróparticle-Associated Proteins Differentially Expressed in Preterm Birth

| Protein Name | Symbol | IPI | UniProtKB |
|---|---|---|---|
| Alpha-2-Macroglobulin | A2M | IPI01010737.1 | P01023 |
| Apolipoprotein B | APOB | IPI00022229.2 | P04114 |
| Apolipoprotein H | APOH | IPI00298828.3 | P02749 |
| Complement C1r | C1R | IPI00956148.2 | Q53HU9 |
| Complement C1s | C1S | IPI00017696.1 | P09871 |
| Complement C3 | C3 | IPI00783987.2 | P01024 |
| Complement Factor H | CFH | IPI00029739.5 | P08603 |
| Immunoglobulin Heavy Chain Mu | IGHM | IPI00418153.1 | Q6N030 |
| Immunoglobulin Heavy Chain Gamma 1 | IGPHG1 | IPI00384938.1 | Q7Z351 |
| Keratin 1 | KRT1 | IPI00220327.4 | P04264 |
| Keratin 10 | KRT10 | IPI00009865.4 | P13645 |
| Lectin galactoside-binding soluble 3-BP | LGALS3BP | IPI00023673.1 | Q08380 |
| S100 Calcium-Binding Protein A9 | S100A9 | IPI00027462.1 | P06702 |
| Alpha-1-Antitrypsin | SERPINA1 | IPI00553177.1 | P01009 |
| Alpha-1B-Glycoprotein | A1BG | IPI00022895.8 | P04217 |
| Albumin | ALB | IPI00745872.2 | P02768 |
| Apolipoprotein L1 | APOL1 | IPI00186903.4 | O14791 |
| Complement C4B (Chido Blood Group) | C4B | IPI00418163.3 | Q6U2E9 |
| Complement C9 | C9 | IPI00022395.1 | P02748 |
| Coagulation Factor XII | F12 | IPI00019581.2 | P00748 |
| Fibronectin 1 short | FN1s | IPI00922213.2 | B4DTK1 |
| Group-specific component (vitamin D-BP) | GC | IPI00968027.1 | P02774 |
| Immunoglobulin Heavy Chain Alpha 1 | IGHA1 | IPI00449920.1 | P01876 |
| Immunoglobulin Heavy Chain Mu 2 | IGHM2 | IPI00896380.1 | P01871 -1 |
| Immunoglobulin Kappa Constant | IGKC | IPI00979250.1 | P01834 |
| Immunoglobulin Lambda-Like 1 | IGLL1 | IPI00013438.1 | P15814 |
| Inter-alpha-trypsin inhibitor H1 | ITIH1 | IPI00292530.1 | P19827 |
| Inter-alpha-trypsin inhibitor H2 | ITIH2 | IPI00305461.4 | P19823 |
| Inter-alpha trypsin inhibitor H4 | ITIH4 | IPI00944960.1 | B2RMS9 |
| Keratin 6A | KRT6A | IPI00300725.7 | P02538 |
| Pro-platelet basic protein | PPBP | IPI00022445.1 | P02775 |
| Pregnancy zone protein short | PZPLs | IPI00922117.1 | B7Z7M2 |
| Serum amyloid A SAA2-SAA4 | SAA2-SAA4 | IPI00975939.1 | * |
| Afamin | AFM | IPI00019943.1 | P43652 |
| Alpha-2-HS-glycoprotein | AHSG | IPI00022431.2 | B7Z8Q2 |
| Alpha-1-microglobulin/bikunin precursor | AMBP | IPI00022426.1 | P02760 |
| Amyloid P component, serum | APCS | IPI00022391.1 | P02743 |
| Apolipoprotein A1 | APOA1 | IPI00021841.1 | P02647 |
| Apolipoprotein D | APOD | IPI00924574.1 | C9JF17 |
| Attractin | ATRN | IPI00027235.1 | O75882 |
| Zinc-alpha-2-glycoprotein | AZGP1 | IPI00166729.4 | P25311 |
| Complement C1q C | C1QC | IPI00022394.2 | P02747 |
| Complement C4A (Rodgers Blood Group) | C4A | IPI00843913.3 | B0V2C8 |
| Complement C4 binding protein alpha chain | C4BPA | IPI00021727.1 | P04003 |
| Complement C8 alpha chain | C8A | IPI00011252.1 | P07357 |
| CD5 antigen-like | CD5L | IPI00025204.1 | O43866 |
| Ceruloplasmin | CP | IPI00017601.1 | P00450 |
| Carboxypeptidase N, polypeptide 1 | CPN1 | IPI00010295.1 | P15169 |
| Carboxypeptidase N, polypeptide 2 | CPN2 | IPI00479116.2 | P22792 |
| Coagulation factor II (prothrombin) | F2 | IPI00019568.1 | P00734 |
| Fibulin 1 | FBLN1 | IPI00889740.1 | B1AHL2 |
| Fibronectin 1 | FN1 | IPI00022418.2 | P02751 |
| Haptoglobin | HP | IPI00641737.2 | P00738 |
| Haptoglobin-related protein | HPR | IPI00607707.2 | P00739 |
| Hemopexin | HPX | IPI00022488.1 | P02790 |
| Immunoglobulin Heavy Chain Alpha 2 | IGHA2 | IPI00940245.1 | Q9NPP6 |
| Immunoglobulin Heavy Chain Gamma 4 | IGHG4 | IPI00930442.1 | P01861 |
| Immunoglobulin Heavy Chain Mu 1 | IGHM1 | IPI00479708.6 | P01871 -1 |
| Immunoglobulin Heavy Chain Variable | IGHV | IPI00854743.1 | Q0ZCH6 |
| Immunoglobulin Heavy Chain Variable 4-31 | IGHV4-31 | IPI00930124.1 | Q6MZV7 |
| Immunoglobulin J Chain | IGJ | IPI00964840.2 | D6RHJ6 |
| Immunoglobulin Kappa Variable 1-9 | IGKV1-9 | IPI00829751.3 | A2JA19 |
| Immunoglobulin Lambda Constant 2 | IGLC2 | IPI00154742.6 | P0CG05 |
| Immunoglobulin Lambda Variable 3-19 | IGLV3-19 | IPI00829640.1 | Q6GMW4 |
| Immunoglobulin Lambda Variable 7-43 | IGLV7-43 | IPI00553092.2 | Q5NV83 |
| Inter-alpha-trypsin inhibitor H3 | ITIH3 | PI:IPI00028413.8 | Q06033 |
| Kallikrein B1 | KLKB1 | IPI00654888.4 | P03952 |
| Keratin 2 | KRT2 | IPI00021304.1 | P35908 |
| Lipoprotein A | LPA | IPI00029168.1 | P08519 |
| Immunoglobulin Heavy Chain Variable b | IGHVb | IPI00828191.3 | A2NKM7 |
| Alpha-1-acid glycoprotein 1 | ORM1 | IPI00022429.3 | P02763 |
| Alpha-1-acid glycoprotein 2 | ORM2 | IPI00020091.1 | P19652 |
| Platelet Factor 4 | PF4 | IPI00022446.1 | P02776 |
| Pregnancy Zone Protein | PZP | IPI00025426.3 | P20742 |
| Immunoglobulin Kappa Variable | IGKV | IPI00816794.1 | A0N7J6 |
| S100 Calcium Binding Protein A8 | S100A8 | IPI00007047.1 | P05109 |

TABLE I-continued

Microparticle-Associated Proteins Differentially Expressed in Preterm Birth

| Protein Name | Symbol | IPI | UniProtKB |
|---|---|---|---|
| Immunoglobulin Kappa Variable 3-20 | IGKV3-20 | IPI00916434.1 | A2KBC3 |
| Antithrombin-III | SERPINC1 | IPI00032179.3 | P01008 |
| Alpha-2-antiplasmin | SERPINF2 | IPI00879231.1 | P08697 |
| Plasma protease C1 inhibitor | SERPING1 | IPI00877698.2 | B4E1F0 |
| Transferrin | TF | IPI00022463.2 | P02787 |
| Thrombospondin-1 | THBS1 | IPI00296099.6 | P07996 |
| Transthyretin | TTR | IPI00940791.2 | P02766 |
| Vitronectin | VTN | IPI00298971.1 | P04004 |
| von Willebrand factor | VWF | IPI00023014.3 | P04275 |
| Immunoglobulin Lambda Variable a | IGLVa | IPI00973531.1 | Q7Z2U7 |
| Keratin-associated protein 5-2 | KRTAP5-2 | IPI00555784.1 | Q701N4 |
| Proteoglycan 2 | PRG2 | IPI00847535.1 | P13727 |
| Apolipoprotein M | APOM | IPI00030739.1 | O95445 |
| Complement C5 | C5 | IPI00032291.2 | P01031 |
| Immunoglobulin Lambda Variable b | IGLVb | IPI00890733.1 | B1N7B9 |
| Complement Factor B | CFB | IPI00019591.2 | Q53F89 |
| Cytochrome P450 2U1 | CYP2U1 | IPI00783946.1 | Q7Z449 |
| Gelsolin | GSN | IPI00026314.1 | P06396 |
| Immunoglobulin Kappa Variable 3D-15 | IGKV3D-15 | IPI01026045.1 | Q9UL83 |
| Immunoglobulin Lambda Variable c | IGLVc | IPI00827875.1 | A2NUT2 |
| Immunoglobulin Lambda Variable d | IGLVd | IPI00719373.3 | Q6NS95 |
| Kininogen-1 | KNG1 | IPI00215894.1 | P01042 |
| Keratin 9 | KRT9 | IPI00019359.4 | P35527 |

1. Alpha-2-Macroglobulin (A2M)

A2M is a secreted protein. The mature protein extends from residues 24-1474, after cleavage of the signal peptide extending from 1-23. A2M is a proteinase inhibitor. It possesses a domain termed the "bait region," which contains specific cleavage sites for all four classes of proteinases. When a proteinase cleaves the bait region, a conformational change is induced in A2M thereby trapping the proteinase. The amino acid sequence of full length A2M is set forth as SEQ ID NO:1 (P01023).

2. Apolipoprotein B-100 (APOB)

APOB is a secreted protein and a major protein constituent of chylomicrons, LDL, and VLDL. The mature protein extends from residues 28-4563, after cleavage of the signal peptide extending from 1-27. APOB contains a vitellogenin protein domain. The amino acid sequence of full length APOB is set forth as SEQ ID NO:2 (P04114).

3. Apolipoprotein H (APOH)

APOH, also known as beta-2-glycoprotein, is a secreted protein. The mature protein extends from residues 20-345, after cleavage of the signal peptide extending from 1-19. APOH contains four CCP/SCR domains. The amino acid sequence of full length APOH is set forth as SEQ ID NO:3 (P02749).

4. Complement Component 1, R Subcomponent (C1R)

C1R is a secreted protein belonging to the peptidase S1 family. The mature protein extends from residues 18-705, after cleavage of the signal peptide extending from 1-17. C1R is further cleaved into two peptides: complement C1r subcomponent light chain (residues 18-462) and heavy chain (residues 464-705). The amino acid sequence of full length C1R is set forth as SEQ ID NO:4 (Q53HU9).

5. Complement Component 1, S Subcomponent (C1S)

C1S is a secreted protein. The mature protein extends from residues 16-688, after cleavage of the signal peptide extending from 1-15. C1S is a serine protease that shows sequence similarity to the peptidase S1 family of proteins. The amino acid sequence of full length C1S is set forth as SEQ ID NO:5 (P09871).

6. Complement Component 3 (C3)

C3 is secreted protein. The mature protein extends from 23-1663, after cleavage of the signal peptide extending from 1-22. The mature protein may be further processed into ten fragments. C3 contains both NTR and anaphylatoxin-like domains. The amino acid sequence of full length C3 is set forth as SEQ ID NO:6 (P01024).

7. Complement Factor H (CFH)

CFH is a secreted protein. The mature protein extends from residues 19-1231, after cleavage of the signal peptide extending from 1-18. CFH contains CCP/SCR domains and functions as a cofactor in the inactivation of C3 and C5 convertase in the alternate complement pathway. The amino acid sequence of full length CFH is set forth as SEQ ID NO:7 (P08603).

8. Immunoglobulin Heavy Chain Mu (IGHM)

IGHM is an immunoglobulin heavy chain sequence. The amino acid sequence (518 residues) of IGHM is set forth as SEQ ID NO:8 (Q6N030).

9. Immunoglobulin Heavy Chain Gamma 1 (IGHG1)

IGHG1 is an immunoglobulin heavy chain sequence. The amino acid sequence (482 residues) of IGHG1 is set forth as SEQ ID NO:9 (Q7Z351).

10. Keratin 1 (KRT1)

KRT1 shows sequence similarity to members of the intermediate filament family of proteins. The amino acid sequence (644 residues) of KRT1 is set forth as SEQ ID NO:10 (P04264).

11. Keratin 10 (KRT10)

KRT10 shows sequence similarity to members of the intermediate filament family of proteins. The amino acid sequence (584 residues) of KRT10 is set forth as SEQ ID NO:11 (P13645).

12. Lectin, Galactoside-Binding, Soluble, 3-Binding Protein (LGALS3BP)

LGALS3BP is secreted protein found ubiquitously in body fluids. The mature protein extends from residues 19-585, after cleavage of the signal peptide extending from 1-18. LGALS3BP contains one of each, BACK, BTB, and SRCR protein domains. The amino acid sequence of full length LGALS3BP is set forth as SEQ ID NO:12 (Q08380).

13. S100 Calcium-Binding Protein A9 (S100A9)

S100A9, also known as calgranulin B, extends from residues 1-114. The amino acid sequence of S100A9 is set forth as SEQ ID NO:13 (P06702).

14. Alpha-1-Antitrypsin (SERPINA1)

SERPINA1 is a secreted protein. The mature protein extends from residues 25-418, after cleavage of the signal peptide extending from 1-24. SERPINA1 is an inhibitor of serine proteases, and belongs to the serpin family of proteins. The amino acid sequence of full length SERPINA1 is set forth as SEQ ID NO:14 (P01009).

15. Alpha-1-B-Glycoprotein (A1BG)

A1BG is a secreted protein. The mature protein extends from residues 22-495, after cleavage of the signal peptide extending from 1-21. A1BG shows sequence similarity to the variable regions of some immunoglobulin supergene family members. The amino acid sequence of full length A1BG is set forth as SEQ ID NO:15 (P04217).

16. Albumin (ALB)

ALB is a secreted protein. The mature protein extends from residues 25-609, after cleavage of the signal peptide extending from 1-18 and the propeptide sequence. The amino acid sequence of full length ALB is set forth as SEQ ID NO:16 (P02768).

17. Apolipoprotein L1 (APOL1)

APOL1 is a secreted protein, mainly associated with large high-density lipoprotein particles. The mature protein extends from residues 28-398, after cleavage of the signal peptide extending from 1-27. The amino acid sequence of full length APOL1 is set forth as SEQ ID NO:17 (O14791).

18. Complement Component 4B (C4B)

C4B is a secreted protein, also known as basic C4 and Chido blood group. The amino acid sequence (1744 residues) of full length C4B is set forth as SEQ ID NO:18 (Q6U2E9).

19. Complement Component 9 (C9)

C9 is a secreted protein. The mature protein extends from residues 22-559, after cleavage of the signal peptide extending from 1-21. The mature protein may be further processed into two fragments, C9a, C9b. C9 shows sequence similarity to the complement C6/C7/C8/C9 family of proteins. The amino acid sequence of full length C9 is set forth as SEQ ID NO:19 (P02748).

20. Coagulation Factor XII (F12)

F12 is a secreted protein. The mature protein extends from residues 20-615, after cleavage of the signal peptide extending from 1-19. This mature protein may further be cleaved into four peptides, beta-factor XIIa part 1 and part 2; and coagulation factor XIIa light and heavy chains. F12 shows sequence similarity to the peptidase S1 family of proteins. The amino acid sequence of full length F12 is set forth as SEQ ID NO:20 (P00748).

21. Fibronectin 1 Short (FN1s)

FN1s is a short isoform of FN1. The amino acid sequence of FN1s is set forth as SEQ ID NO:21 (B4DTK1).

22. Vitamin D-Binding Protein (GC)

GC is a secreted protein. The mature protein extends from residues 17-474, after cleavage of the signal peptide extending from 1-16. GC shows sequence similarity to the ALB/AFP/VDB family of proteins. The amino acid sequence of full length GC is set forth as SEQ ID NO:22 (P02774).

23. Immunoglobulin Heavy Chain Alpha 1 (IGHA1)

IGHA1 is an immunoglobulin heavy chain sequence. The amino acid sequence (353 residues) of IGHA1 is set forth as SEQ ID NO:23 (P01876).

24. Immunoglobulin Heavy Chain Mu 2 (IGHM2)

IGHM is an immunoglobulin heavy chain protein having two isoforms, secreted (isoform 1) and single-pass type I membrane (isoform 2). The amino acid sequence of isoform 2, which corresponds to the amino acid sequence (473 residues) of IGHM2 is set forth as SEQ ID NO:24 (P01871-2).

25. Immunoglobulin Kappa Constant (IGKC)

IGKC is an immunoglobulin light chain sequence. The amino acid sequence (106 residues) of IGKC is set forth as SEQ ID NO:25 (P01834).

26. Immunoglobulin Lambda-Like 1 (IGLL1)

IGLL1 is secreted protein. The mature protein extends from residues 38-213, after cleavage of the signal peptide from 1-17. The amino acid sequence of full length IGLL1 is set forth as SEQ ID NO:26 (P15814).

27. Inter-Alpha-Trypsin Inhibitor H1 (ITIH1)

ITIH1 is a secreted protein. The mature protein extends from residues 35-672, after cleavage of the signal peptide extending from 1-27, and the propeptides extending from 28-34, and 673-911. The amino acid sequence of full length ITIH1 is set forth as SEQ ID NO:27 (P19827).

28. Inter-Alpha-Trypsin Inhibitor H2 (ITIH2)

ITIH2 is a secreted protein. The mature protein extends from residues 55-702, after cleavage of the signal peptide extending from 1-18, and the propeptides extending from 19-54, and 703-946. The amino acid sequence of full length ITIH2 is set forth as SEQ ID NO:28 (P19823).

29. Inter-Alpha-Trypsin Inhibitor H4 (ITIH4)

ITIH4 is a secreted protein. The mature protein extends from residues 29-930, after cleavage of the signal peptide extending from 1-28. This mature protein may further be cleaved into two smaller chains by removal of the propeptide extending from 662-668. The amino acid sequence of full length ITIH4 is set forth as SEQ ID NO:29 (B2RMS9).

30. Keratin 6A (KRT6A)

KRT6A is a cytoskeleton protein. The mature protein extends from residues 2-564, after cleavage of the initiator methionine at position 1. KRT6A shows sequence similarity to the intermediate filament family of proteins. The amino acid sequence of KRT6A is set forth as SEQ ID NO:30 (P02538).

31. Pro-Platelet Basic Protein (PPBP)

PPBP is a secreted protein. The mature protein extends from residues 35-128, after cleavage of the signal peptide extending from 1-34. PPBP shows sequence similarity to the intercrine alpha family of proteins. The amino acid sequence of full length PPBP is set forth as SEQ ID NO:31 (P02775).

32. Pregnancy Zone Protein s (PZPs)

PZPs is a short form of PZP. The amino acid sequence of PZPs is set forth as SEQ ID NO:32 (B7Z7M2).

33. Serum Amyloid A2 Precursor (SAA2-SAA4)

SAA2-SAA4 is a secreted serum amyloid protein precursor. The protein extends from residues 19-208, after cleavage of the signal peptide extending from 1-18. The amino acid sequence of full length SAA2-SAA4 is set forth as SEQ ID NO:33 (GenBank Accession No. NP_001186673).

34. AFAMIN (AFM)

AFM is a secreted protein. The mature protein extends from residues 22-599, after cleavage of the signal peptide from 1-21. AFM shows sequence similarity to the ALB/AFP/VDB family of proteins. The amino acid sequence of full length AFM is set forth as SEQ ID NO:34 (P43652).

35. Alpha-2-HS-Glycoprotein (AHSG)

AHSG is a protein predicted to residue in the extracellular space. AHSG shows sequence similarity to the CY superfamily of proteins. The amino acid sequence (433 residues) of AHSG is set forth as SEQ ID NO:35 (B7Z8Q2).

36. Alpha-1-Microglobulin/Bikunin Precursor (AMBP)

AMBP is a secreted protein. The mature protein extends from residues 20-344, after cleavage of signal peptide from 1-19. The mature protein may be further processed into three peptides, alpha-1-microglobulin, inter-alpha-trypsin inhibitor light chain, and trypstatin. AMBP shows sequence similarity to the calycin superfamily, lipocalin family of proteins. The amino acid sequence of full length AMBP is set forth as SEQ ID NO:36 (P02760).

37. Amyloid P Component, Serum (APCs)

APCS is a secreted protein. The mature protein extends from residues 20-223, after cleavage of the signal peptide extending from 1-19. APCS belongs to the pentaxin family of proteins involved in immune response. It can interact with DNA and histones, and may also scavenge nuclear material from damaged circulating cells, as well as function as a calcium dependent lectin. The amino acid sequence of full length APCS is set forth as SEQ ID NO:37 (P02743).

38. Apolipoprotein A1 (APOA1)

APOA1 is a secreted protein. The mature protein extends from residues 25-267, after cleavage of signal peptide from 1-18 and a propeptide. APOA1 shows sequence similarity to the apolipoprotein A1/A4/E family of proteins. The amino acid sequence of full length APOA1 is set forth as SEQ ID NO:38 (P02647).

39. Apolipoprotein D (APOD)

APOD is a secreted protein. The mature protein extends from residues 21-189, after cleavage of the signal peptide extending from 1-20. APOD shows sequence similarity to other members of the alpha-2 microglobulin protein superfamily. The amino acid sequence of APOD is set forth as SEQ ID NO:39 (C9JF17).

40. Attractin (ATRN)

ATRN is a membrane protein (isoform 1); however, isoforms 2 and 3, produced by alternative splicing, are secreted. The mature protein (isoform 1) extends from residues 84-1429, after cleavage of the signal peptide from 1-28, and the propeptide from 29-83. The amino acid sequence of full length ATRN is set forth as SEQ ID NO:40 (O75882).

41. Zinc-Alpha-2-Glycoprotein 1 (AZGP1)

AZGP1 is a secreted protein. The mature protein extends from residues 21-298, after cleavage of the signal peptide extending from 1-20. AZGP1 belongs to the MHC class I family of proteins, and contains an Ig-like C1-type (immunoglobulin-like) domain. The amino acid sequence of full length AZGP1 is set forth as SEQ ID NO:41 (P25311).

42. Complement Component 1, Q Subcomponent, C Chain (C1QC)

C1QC is a secreted protein. The mature protein extends from residues 29-245, after cleavage of the signal peptide extending from 1-28. C1QC contains C1q and collagen-like protein domains. The amino acid sequence of full length C1QC is set forth as SEQ ID NO:42 (P02747).

43. Complement Component 4A (C4A)

C4A is a secreted protein, also known as acidic C4 and Rodgers blood group. The amino acid sequence (1744 residues) of full length C4A is set forth as SEQ ID NO:43 (B0V2C8).

44. Complement Component 4 Binding Protein Alpha (C4BPA)

C4BPA is a secreted protein. The mature protein extends from residues 49-597, after cleavage of the signal peptide extending from 1-48. C4BPA contains CCP/SCR domains and controls the classical pathway of complement activation. It also interacts with anticoagulant protein S and serum amyloid P component. The amino acid sequence of full length C4BPA is set forth as SEQ ID NO:44 (P04003).

45. Complement Component 8 Alpha Chain (C8A)

C8A is a secreted protein that is part of the membrane attack complex (MAC). The mature protein extends from residues 31-584, after cleavage of the signal peptide extending from 1-20, and the propeptide from 21-30. C8A shows sequence similarity to the complement C6/C7/C8/C9 family of proteins. The amino acid sequence of full length C8A is set forth as SEQ ID NO:45 (P07357).

46. CD5 Antigen-Like (CD5L)

CD5L is a secreted protein. The mature protein extends from residues 20-347, after cleavage of the signal peptide from 1-19. CD5L contains three SRCR protein domains. The amino acid sequence of full length CD5L is set forth as SEQ ID NO:46 (O43866).

47. Ceruloplasmin (CP)

CP, also known as ferroxidase, is a secreted protein. The mature protein extends from residues 20-1065, after cleavage of the signal peptide extending from 1-19. CP shows sequence similarity to the multicopper oxidase family of proteins. The amino acid sequence of full length CP is set forth as SEQ ID NO:47 (P00450).

48. Carboxypeptidase N, Polypeptide 1 (CPN1)

CPN1, also known as anaphylatoxin inactivator, is a secreted protein. The mature protein extends from residues 21-458, after cleavage of the signal peptide extending from 1-20. CPN1 shows sequence similarity to the peptidase M14 family of proteins. The amino acid sequence of full length CPN is set forth as SEQ ID NO:48 (P15169).

49. Carboxypeptidase N, Polypeptide 2 (CPN2)

CPN2 is a secreted protein. The mature protein extends from residues 22-545, after cleavage of the signal peptide extending from 1-21. CPN2 contains LLR, LLRCT, and LLRNT protein domains. The amino acid sequence of full length CPN2 is set forth as SEQ ID NO:49 (P22792).

50. Coagulation Factor II (F2)

F2, also known as prothrombin, is a secreted protein. The mature protein extends from residues 44-622, after cleavage of the signal peptide extending from 1-24, and the propeptide from 25-43. The mature protein may be further processed into four peptides, activation peptide fragment 1 and 2; and thrombin light and heavy chain. F2 shows sequence similarity to the peptidase S1 family of proteins. The amino acid sequence of full length F2 is set forth as SEQ ID NO:50 (P00734).

51. Fibulin 1 (FBLN1)

FBLN1 is an extracellular matrix protein than contains an EGF-like domain. The mature protein extends from residues 30-703, after cleavage of the signal peptide from 1-29. The amino acid sequence of full length FBLN1 is set forth as SEQ ID NO:51 (B1AHL2).

52. Fibronectin (FN1)

FN1 is a secreted protein. The mature protein extends from residues 32-2386, after cleavage of the signal peptide extending from 1-31. The mature protein may be cleaved into four peptides, anastellin, ugl-Y1, ugl-Y2, and ugl-Y3. FN1 contains fibronectin type-I, type-II, and type-III protein domains. There are over a dozen isoforms produced by alternative splicing. The amino acid sequence of FN1 is set forth as SEQ ID NO:52 (P02751).

53. Haptoglobin (HP)

HP is a secreted protein. The mature protein extends from residues 19-406, after cleavage of the signal peptide from 1-18. The mature protein may be further cleaved into two peptides, haptoglobin alpha and haptoglobin beta. HP shows sequence similarity to the peptidase S1 family of proteins. The amino acid sequence of full length HP is set forth as SEQ ID NO:53 (P00738).

54. Haptoglobin-Related Protein (HPR)

HPR is a secreted protein. The mature protein extends from residues 20-348, after cleavage of the signal peptide from 1-19. HPR shows sequence similarity to the peptidase S1 family of proteins. The amino acid sequence of full length HPR is set forth as SEQ ID NO:54 (P00739).

55. Hemopexin (HPX)

HPX is a secreted protein. The mature protein extends from residues 24-462, after cleavage of the signal peptide extending from 1-23. HPX belongs to a family of proteins involved in transporting heme to the liver for iron recovery. The amino acid sequence of full length HPX is set forth as SEQ ID NO:55 (P02790).

56. Immunoglobulin Heavy Chain Alpha 2 (IGHA2)

IGHA2 is an immunoglobulin heavy chain sequence. The amino acid sequence (416 residues) of IGHA2 is set forth as SEQ ID NO: 56 (Q9NPP6).

57. Immunoglobulin Heavy Chain Gamma 4 (IGHG4)

IGHG4 is an immunoglobulin heavy chain sequence. The amino acid sequence (327 residues) of IGHG4 is set forth as SEQ ID NO:57 (P01861).

58. Immunoglobulin Heavy Chain Mu 1 (IGHM1)

IGHM is an immunoglobulin heavy chain protein having two isoforms, secreted (isoform 1) and single-pass type I membrane (isoform 2). The amino acid sequence (452 residues) of isoform 1 is set forth as SEQ ID NO:58 (P01871-1).

The amino acid sequence (375 residues) of IGHM1 is set forth as SEQ ID NO:59.

59. Immunoglobulin Heavy Chain Variable Region A (IGHVa)

IGHVa is an immunoglobulin heavy chain variable region sequence that extends from residues 1-131. The amino acid sequence of IGHVa is set forth as SEQ ID NO:60 (Q0ZCH6).

60. Immunoglobulin Heavy Chain Variable Region 4-31 (IGHV4-31)

IGHV4-31 is an immunoglobulin heavy chain sequence. The amino acid sequence (473 residues) of IGHV4-31 is set forth as SEQ ID NO:61 (Q6MZV7).

61. Immunoglobulin J Chain (IGJ)

IGJ is a linker protein that links immunoglobulin monomers (IgM to pentamers, IgA to dimers) and binds these immunoglobulins polymers to the secretory component. The mature protein extends from residues 23-157, after cleavage of the signal peptide extending from 1-22. The amino acid sequence of full length IGJ is set forth as SEQ ID NO:62 (D6RHJ6).

62. Immunoglobulin Kappa Variable 1-9 (IGKV1-9)

IGKV1-9 is an immunoglobulin light chain sequence. The amino acid sequence (117 residues) of IGLV is set forth as SEQ ID NO:63.

63. Immunoglobulin Lambda Constant 2 (IGLC2)

IGLC2 is an immunoglobulin light chain sequence. The amino acid sequence of IGLC2 (106 residues) is set forth as SEQ ID NO:64 (P0CG05).

64. Immunoglobulin Lambda Chain Variable 3-19 (IGLV3-19)

IGLV3-19 is an immunoglobulin light chain sequence. The amino acid sequence (233 residues) of IGLV3-19 is set forth as SEQ ID NO:65 (Q6GMW4).

65. Immunoglobulin Lambda Chain Variable 7-46 (IGLV7-46)

IGLV7-46 is an immunoglobulin light chain sequence. The amino acid sequence (98 residues) of IGLV7-46 is set forth as SEQ ID NO:66 (Q5NV83).

66. Inter-Alpha-Trypsin Inhibitor Heavy Chain H3 (ITIH3)

ITIH3 is a secreted protein. The mature protein extends from residues 35-651, after cleavage of the signal peptide extending from 1-20, and the propeptides from 21-34, and 652-890. The amino acid sequence of full length ITIH3 is set forth as SEQ ID NO:67 (Q06033).

67. Kallikrein B1 (KLKB1)

KLKB1 is a secreted protein. The mature protein extends from residues 20-638, after cleavage of the signal peptide extending from 1-19. The mature protein may further be cleaved into two peptides, plasma kallikrein heavy chain and light chain. KLKB1 shows sequence similarity to the peptidase S1 family of proteins. The amino acid sequence of full length KLKB1 is set forth as SEQ ID NO:68 (P03952).

68. Keratin (KRT2)

KRT2 is a cytoskeletal protein. KRT2 shows sequence similarity to the intermediate filament family of proteins. The amino acid sequence (639 residues) of KRT2 is set forth as SEQ ID NO:69 (P35908).

69. Lipoprotein A (LPA)

LPA is the main constituent of lipoprotein(a). The mature protein extends from residues 20-4548, after cleavage of the signal peptide extending from 1-19. LPA shows sequence similarity to the peptidase S1 family, plasminogen subfamily of proteins. The amino acid sequence of full length LPA is set forth as SEQ ID NO:70 (P08519).

70. Immunoglobulin Heavy Chain Variable b (IGHVb)

IGHVb (fragment of the NANUC-2 antibody) is an immunoglobulin heavy chain sequence. The amino acid sequence (133 residues) of IGHVb is set forth as SEQ ID NO:71 (A2NKM7).

71. Orosomucoid-1 (ORM1)

ORM1, also known as alpha-1-acid glycoprotein 1, is a secreted protein. The mature protein extends from residues 19-201, after cleavage of the signal peptide extending from 1-18. ORM1 shows sequence similarity to the calycin superfamily, lipocalin family of proteins. The amino acid sequence of full length ORM1 is set forth as SEQ ID NO:72 (P02763).

72. Orosomucoid-2 Alpha-1-Acid Glycoprotein 2 (ORM2)

ORM2, also known as alpha-1-acid glycoprotein 2, is a secreted protein. The mature protein extends from residues 19-201, after cleavage of the signal peptide extending from 1-18. ORM2 shows sequence similarity to the calycin superfamily, lipocalin family of proteins. The amino acid sequence of full length ORM2 is set forth as SEQ ID NO:73 (P19652).

73. Platelet Factor 4 (PF4)

PF4 is a secreted protein that is released during platelet aggregation, and neutralizes the anticoagulant effect of heparin. Mature PF4 protein extends from residues 32-101, after cleavage of the signal peptide extending from 1-31. A shorter form of PF4 extends from 48-101, and is a more potent inhibitor than the longer form. The amino acid sequence of full length PF4 is set forth as SEQ ID NO:74 (P02776).

74. Pregnancy Zone Protein (PZP)

PZP is a secreted protein. The mature protein extends from residues 26-1482, after cleavage of the signal peptide extending from 1-25. PZP shows sequence similarity to the protease inhibitor I39 family of proteins. The amino acid sequence of full length PZP is set forth as SEQ ID NO:75 (P20742).

75. Immunoglobulin Kappa Chain Variable (IGKV)

IGKV (fragment of the REV25-2 antibody) is an immunoglobulin light chain sequence. The amino acid sequence (134 residues) of IGKV is set forth as SEQ ID NO:76 (A0N7J6).

76. S100 Calcium Binding Protein A8 (S100A8)

S100A8, also known as calgranulin A, extends from residues 1-93. The amino acid sequence of S100A8 is set forth as SEQ ID NO:77 (P05109).

77. Immunoglobulin Kappa Variable 3-20 (IGKV3-20)

IGKV3-20 (scFV) is an immunoglobulin light chain sequence. The amino acid sequence (238 residues) of IGKV3-20 is set forth as SEQ ID NO:78 (A2KBC3).

78. Antithrombin-III (SERPINC1)

SERPINC1 is a secreted protein. The mature protein extends from residues 33-464, after cleavage of the signal peptide extending from 1-32. SERPINC1 is an inhibitor of serine proteases, and belongs to the serpin family of proteins. It is involved in regulating the blood coagulation cascade. The amino acid sequence of full length SERPINC1 is set forth as SEQ ID NO:79 (P01008).

79. Alpha-2-Antiplasmin (SERPINF2)

SERPINF2 is a secreted protein. The mature protein extends from residues 40-491, after cleavage of the signal peptide extending from 1-27 and propeptide from 28-39. The amino acid sequence of full length SERPINF2 is set forth as SEQ ID NO:80 (P08697).

80. Plasma Protease C1 Inhibitor (SERPING1)

SERPING1 is a protease inhibitor extending from residues 1-505. The amino acid sequence of SERPING1 is set forth as SEQ ID NO:81 (B4E1F0).

81. Transferrin (TF)

TF is a secreted protein. The mature protein extends from residues 20-698, after cleavage of the signal peptide extending from 1-19. The amino acid sequence of full length TF is set forth as SEQ ID NO:82 (P02787).

82. Thrombospondin-1 (THBS1)

THBS1 is a glycoprotein that mediates cell-to-cell and cell-to-matrix interactions. The mature protein extends from residues 19-1170, after cleavage of the signal peptide extending from 1-18. The amino acid sequence of full length THBS1 is set forth as SEQ ID NO:83 (P07996).

83. Transthyretin (TTR)

TTR is a thyroid hormone-binding protein. The mature protein extends from residues 21-147, after cleavage of the signal peptide extending from 1-20. The amino acid sequence of full length TTR is set forth as SEQ ID NO:84 (P02766).

84. Vitronectin (VTN)

VTN is a secreted protein. The mature protein extends from 20-478, after cleavage of the signal peptide extending from 1-19. The mature protein may further be cleaved into three peptides, vitronectin V65 subunit, vitronectin V10 subunit, and somatomedin-B. The amino acid sequence of full length VTN is set forth as SEQ ID NO:85 (P04004).

85. Von Willebrand Factor (VWF)

VWF is a secreted protein. The mature protein extends from 23-2813, after cleavage of the signal peptide extending from 1-22. This mature protein may further be cleaved into two peptides von Willebrand antigen 2, and von Willenbrand factor. The amino acid sequence of full length VWF is set forth as SEQ ID NO:86 (P04275).

86. Immunoglobulin Lambda Chain Variable a (IGLVa)

IGLVa is an immunoglobulin light chain sequence extending from residues 1-234. The amino acid sequence of IGLVa is set forth as SEQ ID NO:87 (Q7Z2U7).

87. Keratin-Associated Protein 5-2 (KRTAP5-2)

KRTAP5-2 interacts with hair keratins, and extends from residues 1-177. The amino acid sequence of KRTAP5-2 is set forth as SEQ ID NO:88 (Q701N4).

88. Proteoglycan 2 (PRG2)

PRG2 is protein that comes in a proform that is secreted, and a processed form that is found in the matrix of the eosinophil's large specific granule. The mature protein extends from residues 106-222, after cleavage of the signal peptide extending from 1-16, and a propeptide from 17-105. PRG2 contains a C-type lectin domain. The amino acid sequence of full length PRG2 is set forth as SEQ ID NO:89 (P13727).

89. Apolipoprotein M (APOM)

APOM is a secreted protein extending from residues 1-188. APOM binds sphingosine-1-phosphate, myristic acid, palmitic acid and stearic acid, retinol, all-trans-retinoic acid and 9-cis-retinoic acid. APOM shows sequence similarity to the calycin superfamily, lipocalin family of proteins. The amino acid sequence of full length APOM is set forth as SEQ ID NO:90 (O95445).

90. Complement Component 5 (C5)

C5 is a secreted protein. A signal peptide extends from 1-18, and a propeptide extends from 674-677. C5 may further be cleaved into four peptides: C5 beta chain, C5 alpha chain, C5a anaphylatoxin, and C5 alpha' chain. The amino acid sequence (1676 residues) of full length C5 is set forth as SEQ ID NO:91 (P01031).

91. Immunoglobulin Lambda Chain Variable b

IGLVb (fragment of a cryocrystalglobulin 2 or CC2 antibody) is an immunoglobulin light chain sequence. The amino acid sequence (110 residues) of IGLVb is set forth as SEQ ID NO:92 (B1N7B9).

92. Complement Factor κ (CFB)

CFB shows sequence similarity to the peptidase S1 family of proteins. The amino acid sequence (764 residues) of CFB is set forth as SEQ ID NO:93 (Q53F89).

93. Cytochrome P450 2U1 (CYP2U1)

CYP2U1 is a multi-pass membrane protein extending from residues 1-544. CYP2U1 catalyzes the hydroxylation of arachidonic acid, docosahexaenoic acid and other long chain fatty acids. The amino acid sequence of full length CYP2U1 is set forth as SEQ ID NO:94 (Q7Z449).

94. Gelsolin (GSN)

GSN, also known as actin-depolymerizing factor, is a calcium-regulated, actin-modulating protein that binds to the plus ends of actin monomers or filaments, preventing monomer exchange. GSN exists in two isoforms: isoform 1 is secreted, and isoform 2 is cytoplasmic. The mature isoform 1 protein extends from residues 28-782, after cleavage of the signal peptide extending from 1-27. The mature isoform 2 protein extends from residues 52-782. GSN shows sequence similarity to the villin family of proteins. The amino acid sequence of full length GSN is set forth as SEQ ID NO:95 (P06396).

95. Immunoglobulin Kappa Variable 3D-15 (IGKV3D-15)

IGKV3D-15 is an immunoglobulin light chain sequence. The amino acid sequence (108 residues) of IGKV3D-15 is set forth as SEQ ID NO:96 (Q9UL83).

96. Immunoglobulin Lambda Chain Variable C (IGLVc)

IGLVc is an immunoglobulin light chain sequence. The amino acid sequence (235 residues) of IGLVc is set forth as SEQ ID NO:97 (A2NUT2).

97. Immunoglobulin Lambda Chain Variable d (IGLVd)

IGLVd is an immunoglobulin light chain sequence. The amino acid sequence (234 residues) of IGLVd is set forth as SEQ ID NO:98 (Q6NS95).

98. Kininogen-1 (KNG1)

KNG1 is a secreted protein. The mature protein extends from residues 19-434, after cleavage of the signal peptide extending from 1-18. The mature protein may further be cleaved into six peptides, T-kinin, bradykinin, lysyl-bradykinin, low molecular weight growth-promoting factor, and kininogen-1 heavy and light chains. The amino acid sequence of full length KNG1 is set forth as SEQ ID NO:99 (P01042).

99. Keratin 9 (KRT9)

KRT9 shows sequence similarity to the intermediate filament family of proteins. The amino acid sequence (623 residues) of KRT9 is set forth as SEQ ID NO:100 (P35527).

Microparticle-associated proteins of the present disclosure are not limited to the exemplary amino acid sequences shown above or listed in the sequence database entries of Table I. Rather the protein biomarkers of the present disclosure also include variants of the proteins listed in Table I. "Protein" as used herein refers to a polypeptide or fragment thereof.

"Variants" include proteins having one to several substitution(s), deletion(s), and/or addition(s) of an amino acid in comparison to a reference sequence. Conservative substitution tables providing functionally similar amino acids are well-known in the art. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

"Fragments" include polypeptides that are shorter in length than the full length or mature protein of interest. If the length of a protein is x amino acids, a fragment is x-1 amino acids of that protein. The fragment may be shorter than this (e.g., x-2, x-3, x-4, . . . ), and is preferably 100 amino acids or less (e.g., 90, 80, 70, 60, 50, 40, 30, 20 or 10 amino acids or less). The fragment may be as short as 4 amino acids, but is preferably longer (e.g., 5, 6, 7, 8, 9, 10, 12, 15, 20, 25, 30, 35, 40, 50, 60, 70, 80, 90, or 100 amino acids).

The terms "identical" or percent "identity," in the context of two or more polypeptide sequences, refer to two or more sequences or subsequences that are the same. Two sequences are "substantially identical" if two sequences have a specified percentage of amino acid residues that are the same (e.g., 75%, 80%, 85%, 90%, 95%, 96%, 97%, 98% or 99% identity over a specified region, or, when not specified, over the entire sequence), when compared and aligned for maximum correspondence over a comparison window, or designated region as measured using known sequence comparison algorithms or by manual alignment and visual inspection. Preferably, the identity exists over a region that is at least about 10 amino acids in length, or more preferably over a region that is 20, 50, 100, 200, or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, the sequences do not necessarily have to be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

Two examples of algorithms that are suitable for determining percent sequence identity and sequence similarity are the BLAST and BLAST 2.0 algorithms (Altschul et al., Nuc. Acids Res. 25:3389-3402, 1977; and Altschul et al., J. Mol. Biol. 215:403-410, 1990). Software for performing BLAST analyses is publicly available through the National Center for Biotechnology Information. This algorithm involves first identifying high-scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for amino acid sequences, a scoring matrix. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word length of 3, and expectation (E) of 10, and the BLOSUM62 scoring matrix (Henikoff and Henikoff, Proc. Natl. Acad. Sci. USA 89:109-15, 1989) alignments (B) of 50, expectation (E) of 10, M=5, N=−4, and a comparison of both strands.

The BLAST algorithm also performs a statistical analysis of the similarity between two sequences (Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The present disclosure provides tools for detecting the expression level of a microparticle-associated protein. "Detecting the expression level" includes detecting the presence (e.g., level above a threshold or detectable level) or detecting the absence (e.g., level below a threshold or undetectable level) of a microparticle-associated protein in a sample from a pregnant subject.

During development of the present disclosure numerous microparticle-associated proteins were determined to be elevated in samples from subjects having preterm births (as compared to samples from subjects have term births), and are therefore termed "preterm birth biomarkers." The preterm birth biomarkers identified as described in Example 1 include the following: A1BG, A2M, AFM, AHSG, ALB, AMBP, APOD, APOL1, APOM, ATRN, AZGP1, C8A, C9, CD5L, CFB, CPN2, F12, FBLN1, FN1, FN1s, GC, GSN, HPR, HPX, IGHM1, IGHM2, IGJ, IGLVb, ITIH1, ITIH2, ITIH3, ITIH4, KLKB1, KNG1, KRT1, KRT10, KRT2, KRT6A, LGALS3BP, ORM1, ORM2, PRG2, S100A8, S100A9, SAA2-SAA4, SERPINA1, SERPINC1, SERPINF2, SERPING1, TF, TTR, VTN, and VWF. In some embodiments, the methods of the present invention comprise detecting one or more preterm birth biomarkers selected from the group consisting of: A1BG, AFM, AHSG, ALB, AMBP, APOD, APOL1, APOM, ATRN, AZGP1, C8A, CD5L, CFB, CPN2, F12, GSN, HPR, HPX, IGHM1, IGHM2, IGJ, IGLVb, ITIH1, ITIH2, ITIH3, KNG1, KRT1, KRT10, KRT2, KRT6A, LGALS3BP, PRG2, SAA2-SAA4, SERPINF2, SERPING1, TF, VTN, and VWF. In some embodiments, the methods further comprise detecting one or more preterm birth biomarkers selected from the group consisting of A2M, C9, FBLN1, FN1, FN1s, GC, ITIH4, KLKB1, ORM1, ORM2, S100A8, S100A9, SERPINA1, SERPINC1, and TTR. In some preferred embodiments, the methods comprise detecting from four to twelve (e.g., 4, 5, 6, 7, 8, 9, 10, 11 or 12) of the preterm birth biomarkers selected from the group consisting of A1BG, A2M, ALB, APOD, APOL1, AZGP1, HPX, IGHM1, IGHM2, SERPINA1, SERPINC1 and TF.

Additionally during development of the present disclosure numerous microparticle-associated proteins were determined to be reduced in samples from subjects having preterm births (as compared to samples from subjects have term births), and are therefore termed "term birth biomarkers." The term birth biomarkers identified as described in Example 1 include the following: APCS, APOA1, APOB, APOH, C1QC, C1R, C1S, C3, C4A, C4B, C4BPA, C5, C9, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, PZPs, and THBS1. In some embodiments, the methods of the present invention comprise detecting one or more term birth biomarkers selected from the group consisting of: APCS, APOA1, APOH, C1QC, C1R, C1S, C3, C4A, C4B, C4BPA, C5, CFH, CP, CPN1, CYP2U1, F2, HP, HPX, IGHA1, IGHA2, IGHG1, IGHG4, IGHM, IGHV4-31, IGHVa, IGHVb, IGKC, IGKV, IGKV1-9, IGKV3-20, IGKV3D-15, IGLC2, IGLL1, IGLV3-19, IGLV7-43, IGLVa, IGLVc, IGLVd, KRT9, KRTAP5-2, LPA, PF4, PPBP, PZP, and PZPs. In some embodiments, the methods further comprise detecting one or more term birth biomarkers selected from the group consisting of APOB, C9 and THBS1. In some preferred embodiments, the methods comprise detecting from one to six (e.g., 1, 2, 3, 4, 5 or 6) of the term birth biomarkers selected from the group consisting of C1R, C3, C4B, CFH, IGHA2, and IGKV1-9.

Pregnant Subjects

In some embodiments of the present disclosure, the subject is a pregnant woman. In some embodiments, the pregnant woman is in the first trimester (e.g., weeks 1-12 of gestation), second trimester (e.g., weeks 13-28 of gestation) or third trimester of pregnancy (e.g., weeks 29-37 of gestation). In some embodiments, the pregnant woman is in early pregnancy (e.g., from 8, 9, 10, 11, 12, 13, 14, 15, 16, 17, 18, 19 or 20, but earlier than 21 weeks of gestation; from 20, 19, 18, 17, 16, 15, 14, 13, 12, 11, 10 or 9, but later than 8 weeks of gestation). In some embodiments, the pregnant woman is in mid-pregnancy (e.g., from 21, 22, 23, 24, 25, 26, 27, 28, 29 or 30, but earlier than 31 weeks of gestation; from 30, 29, 28, 27, 26, 25, 24, 23, 22 or 21, but later than 20 weeks of gestation). In some embodiments, the pregnant woman is in late pregnancy (e.g., from 31, 32, 33, 34, 35, 36 or 37, but earlier than 38 weeks of gestation; from 37, 36, 35, 34, 33, 32 or 31, but later than 30 weeks of gestation). The stage of pregnancy can be calculated from the first day of the last normal menstrual period of the pregnant subject.

In some embodiments, the pregnant human subject is primagravida. In other embodiments, the pregnant subject multigravida. In some embodiments, the pregnant subject may have had at least one prior spontaneous preterm birth (e.g., birth prior to week 38 of gestation). In some embodiments, the pregnant human subject is asymnptomatic. In some embodiments, the subject may have a risk factor of PTB such as a history of pre-gestational hypertension, diabetes mellitus, kidney disease, known thrombophilias and/or other significant preexisting medical condition (e.g., short cervical length).

Samples

A sample for use in the methods of the present disclosure is a biological sample obtained from a pregnant subject prior to 38 weeks of gestation. In preferred embodiments, the sample is collected during a stage of pregnancy described in the preceding section. In some embodiments, the sample is a blood, saliva, tears, sweat, nasal secretions, urine, amniotic fluid or cervicovaginal fluid sample. In some embodiments, the sample is a blood sample, which in preferred embodiments is serum or plasma. In some embodiments, the sample has been stored frozen (e.g., −20° C. or −80° C.).

Methods for Assessing Risk of Preterm Birth

Figure 2:
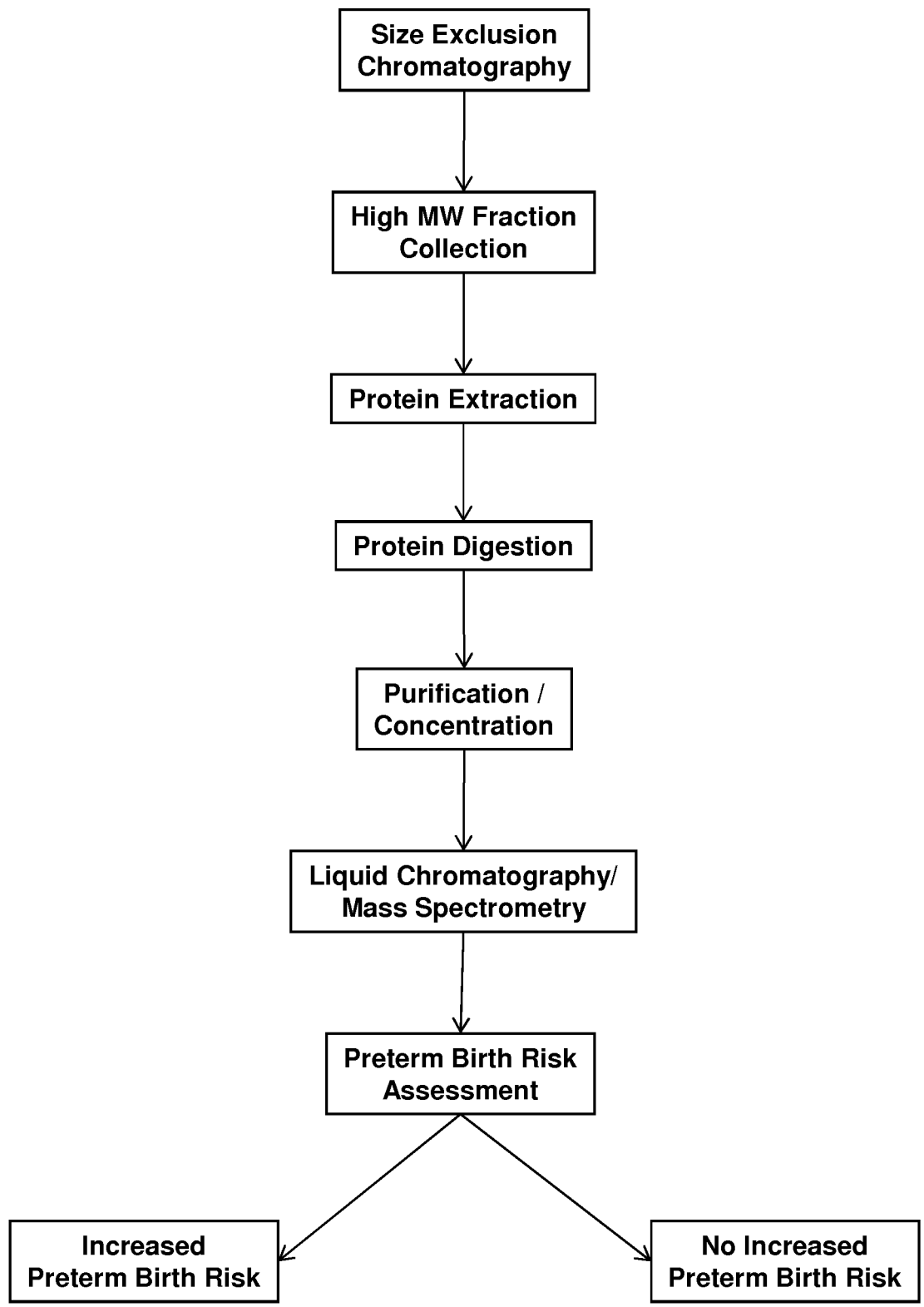
FIG. 2 provides a flow chart of an exemplary method for assessing risk of preterm birth.

In some embodiments, detecting the expression level (e.g., including detecting the presence) of one or both of preterm birth biomarkers and term birth biomarkers is done using a liquid chromatography/mass spectrometry (LC/MS)-based proteomic analysis such as that depicted in the flow chart of FIG. 2. In an exemplary embodiment the method involves subjecting a sample to size exclusion chromatography and collecting the high molecular weight fraction to obtain a microparticle-enriched sample. The microparticle-enriched sample is then extracted before digestion with a proteolytic enzyme such as trypsin to obtain a digested sample comprising a plurality of peptides. The digested sample is then subjected to a peptide purification/concentration step before liquid chromatography and mass spectrometry to obtain a proteomic profile of the sample. In some embodiments, the purification/concentration step comprises reverse phase chromatography (e.g., ZIPTIP pipette tip with 0.2 μL C18 resin, from Millipore Corporation, Billerica, Mass.). The proteomic profile is analyzed to determine the presence of one or both of preterm birth biomarkers and term birth biomarkers. In some embodiments, preparation of the proteomic profile is done using one or both of the Rosetta ELUCIDATOR data management and analysis system (Ceiba, Boston, Mass.) and the Mascot search engine (Matrix Systems, Boston Mass.), which uses mass spectrometry data to identify proteins from primary sequence databases (Pappin et al., Curr Biol, 3:327-332, 1993; Perkins et al., Electrophoresis, 20:35551-2567, 1999; and Koenig et al., J. Proteome Res, 7:3708-3717, 2008).

In some embodiments, detecting the expression level (e.g., including detecting the presence) of one or both of preterm birth biomarkers and term birth biomarkers is done using an antibody-based method. Suitable antibody-based methods include but are not limited to enzyme linked immunosorbent assay (ELISA), Western blot, and antibody microarray.

In some embodiments, the methods include calculating a risk score of preterm birth before gestational week 34 based upon the detection of the expression level of 1 to 18 microparticle-associated proteins of the smallplex consisting of all twelve of alpha-1B-glycoprotein (A1BG), alpha-2-macroglobulin (A2M), serum albumin (ALB), apolipoprotein D (APOD), apolipoprotein L1 (APOL1), zinc-alpha-2-glycoprotein (AZGP1), hemopexin (HPX), Ig heavy chain mu 1 (IGHM1), IgM heavy chain mu 2 (IGHM2), alpha-1-antitrypsin (SERPINA1), antithrombin-III (SERPINC1), and serotransferrin (TF); and all six of complement component 1r (C1r), complement component 3 (C3), complement component 4B (C4B), complement factor H (CFH), Ig heavy chain alpha 2 (IGHA2), and Ig kappa variable1-9 (IGKV1-9). The risk score is calculated based on a quintile scale shown in Table II.

TABLE II

Quintile Scale for Risk Score Calculation for Smallplex

| Preterm Birth Biomarkers above threshold and Term Birth Biomarkers below threshold (# out of 18 total) | Score |
|---|---|
| 0 | 0 (low risk) |
| 1-2 | 1 |
| 3-5 | 2 |
| 6-8 | 3 |
| 9-10 | 4 |
| 11-18 | 5 (high risk) |

Methods for Reducing Risk of Preterm Birth

Cervical cerclage and progesterone supplementation have been shown to be effective in preventing preterm birth (Committee on Practice Bulletins, Obstetrics & Gynecology, 120:964-973, 2012).

Currently progesterone supplementation for the prevention of recurrent spontaneous preterm birth is offered to: women with a singleton pregnancy and a prior spontaneous preterm birth; and women with no history of spontaneous preterm birth who have an incidentally detected very short cervix (<15 mm). The present disclosure provides tools to identify additional pregnant subjects that may benefit from progesterone supplementation. These subjects include the following: pregnant women who are primigravidas without a history of risk and without an incidentally detected very short cervix; and pregnant women who are multigravidas but who did not previously have a spontaneous preterm birth.

Pregnant subjects determined to be at increased risk for preterm birth are recommended to receive or are administered progesterone until 36 weeks of gestation (e.g., upon identification or between 16 weeks, 0 days and 20 weeks, 6 days gestation until 36 weeks gestation). In some embodiments, progesterone supplementation comprises 250 mg weekly intramuscular injections. In an exemplary embodiment, the weekly progesterone supplementation comprises administration of MAKENA® hydroxyprogesterone caproate injection (Ther-Rx Corporation, St. Louis, Mo.). In other embodiments, progesterone supplementation comprises vaginal progesterone in doses between 50 and 300 mg daily, between 75 and 200 mg daily or between 90 and 110 mg daily.

In another embodiment, in women with a singleton pregnancy determined to be at increased risk for preterm birth and who have had a documented prior spontaneous preterm birth at less than 34 weeks of gestation and short cervical length (less than 25 mm) before 24 weeks of gestation, are recommended to receive or are given a cervical cerclage (also known as tracheloplasty or cervical stitch). In some embodiments, the cervical cerclage is a McDonald cerclage, while in other embodiments it is a Shirodkar cerclage or an abdominal cerclage.

Kits

In another embodiment, a kit of reagents capable of one or both of preterm birth biomarkers and term birth biomarkers in a sample is provided. Reagents capable of detecting protein biomarkers include but are not limited to antibodies. Antibodies capable of detecting protein biomarkers are also typically directly or indirectly linked to a molecule such as a fluorophore or an enzyme, which can catalyze a detectable reaction to indicate the binding of the reagents to their respective targets.

In some embodiments, the kits further comprise sample processing materials comprising a high molecular gel filtration composition (e.g., agarose such as SEPHAROSE® beaded agarose) in a low volume (e.g., 1 ml) vertical column for rapid preparation of a microparticle-enriched sample from plasma. For instance, the microparticle-enriched sample can be prepared at the point of care before freezing and shipping to an analytical laboratory for further processing.

In some embodiments, the kits further comprise instructions for assessing risk of preterm birth. As used herein, the term "instructions" refers to directions for using the reagents contained in the kit for detecting the presence (including determining the expression level) of a protein(s) of interest in a sample from a subject. The proteins of interest may comprise one or both of preterm birth biomarkers and term birth biomarkers. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination.

EXAMPLES

Abbreviations: BSA (bovine serum albumin); LC (liquid chromatography); MS (mass spectrometry); P1 (first pregnancy); P2 (second pregnancy); PTB (preterm birth); PT/T (preterm/term ratio); QC (quality control); TIC (total ion current)

Example 1

Serum Microparticle-Associated Biomarkers Predictive of Risk of Preterm Birth

This example details the proteomic differentiation of maternal serum microparticles obtained from term and preterm patients early in the second trimester. The methods described herein exploit the fact that placental-derived microparticles freely circulate in high titer in maternal blood and reflect the status of the maternal-fetal interface.

Materials and Methods

Patient Population.

This study represents a case-controlled analysis of proteomic biomarkers collected from frozen serum samples obtained from early stage pregnant women, from July to November 2009 and released in December 2011, as part of a government initiative under informed consent by Biomnis, France. Non-fasting serum samples were collected for genetic screening and stored in a bio-repository from which a cohort of 168 serum samples were secured and evaluated for study inclusion. Inclusion criteria included normal healthy asymptomatic pregnant women with the absence of a history of pre-gestational hypertension, diabetes mellitus, kidney disease, known thrombophilias or any other significant preexisting chronic medical disease. Medical annotation confirmed gravida conditions (first or second pregnancy), no multiple gestations, live birth, absence of congenital abnormalities and non-in vitro fertilization and non-intracytoplasmic sperm injection pregnancy. Medical annotation from the repository included maternal age, weight, height, and reported tobacco use. Sample data included confirmation of blood draw at weeks 15-17 gestation, infant's birth date and calculation of gestational duration. Outcome status included baby's sex and weight, gestational age (full term birth defined as ≥37 weeks gestation), preterm birth (preterm defined as non-iatrogenic spontaneous preterm birth between 23 weeks 0/7 days and 34 weeks 0/7 days gestation).

Sample Handling.

All samples were frozen −20° C. if transit was scheduled for 4 hours or greater from the time of the initial blood draw or refrigerated if transit to the central lab was scheduled to occur less than 4 hours after serum blood draw. After being blinded by identifying the sample number, all serum samples were stored at −80° C. (Biomnis, Lyon France). Samples were transported from the repository to the analytical labs (Kannapolis, N.C.) frozen on dry ice in ~1-2 mL aliquots for the purpose of isolating serum microvesicles and characterizing the proteomic content of serum fractions. Once thawed on the bench at room temperature (~22° C.), microparticles were isolated from 1 mL serum samples by gel filtration methods (Gercel-Taylor et al., Anal Biochem, 428:44-53, 2012). All serum samples were processed and LC/MS analysis was conducted in a double-blinded manner until the end of the study.

Microparticle Isolation

Microparticles were isolated from healthy AB serum for quality control and calibration purposes (Sigma Aldrich, St. Louis, Mo.), and in a blinded manner from term and preterm patient serum samples (n=48). Serum fractions and microparticles were isolated using a 2% such as SEPHAROSE® beaded agarose size-exclusion chromatography column (Bio-Rad Econo column 2.5 cm ID×10 cm with 100 mL of 40% v/v such as SEPHAROSE® beaded agarose slurry in ddH2O). Samples were processed using a GE AKTA Purifier 10 system (GE Healthcare, Piscataway, N.J.) with a Frac 950 fraction collector at room temperature using a flow rate of 2 mL/min and a 30 second collection periodicity to obtain 1 mL elution samples.

Serum fractions yielded two partially resolved peaks (peaks 1 and 2) with retention volumes of ~10 mL and ~35 mL when monitored by A280. Peak 1 elution samples (<15 minutes) consisted of high molecular weight fractions of analytical interest that could not permeate the size exclusion column (extracellular vesicles and protein aggregates). The first 7×1 mL fractions associated with peak 1 absorbance at A280 were collected, pooled, separated into 7×1-mL aliquots for subsequent processing and stored at −80° C. Each pooled fraction was analyzed for total protein and exosomal content quantified and a split aliquot was processed by LC/MS after an ultrafiltration procedure.

The majority of the remaining elution volume and conductivity was associated with the latter peak (~40 mL) as might be expected for ions, charged amino acids/peptides and other low molecular weight species (Gercel-Taylor et al., Anal Biochem, 428:44-53, 2012). This parameter was used to demark the beginning of the contaminating second peak, which is devoid of microparticles.

Microparticle Concentration and Analysis.

A 1 mL aliquot was thawed at room temperature, and subjected to centrifugation at 4,000×g for approximately 10 min at room temperature using a 1M Da cut off VIVASPIN® ultrafiltration spin column (Sartorius, Stedim North America Inc. NY) to achieve a 3-fold reduction in sample volume. The spin column was inverted and centrifuged for 5 min at 4,000×g to collect the retentate harboring the desired microparticles. Total protein concentration in the exosomal preparation was determined using a Thermo Scientific BCA Protein Assay after concentration.

Microvesicular particles (microparticles) were quantified using the Nanoparticle Tracking Analysis (Dragovic et al., Nanomedicine, 7:780-788, 2011) method (NanoSight, LM 10 system, software: NanoSight NTA version 2.2 NanoSight Ltd. Wiltshire, UK). This stochastic single particle detection method is based on light scattering from individual particles using the Stokes-Einstein relationship to measure the average (time-averaged, field of view) number of particles and their predicted hydrodynamic diameter.

The instrument was calibrated and validated with standard beads from 50-400 nm in diameter (NanoSight, Wiltshire, UK). One hundred nm beads were run each day to calibrate the system. These notionally 100 nm diameter beads (n>30) yielded experimental diameters of ~97 (±2) nm in aqueous, low viscosity (~1 cP) solutions at room temperature. All calibrations and patient-derived microvesicles were analyzed in triplicate. Samples were blinded as to cohort of origin and were processed contemporaneously.

Protein Extraction and Purification.

Proteins were solubilized from the concentrated peak 1 fractions for LC/MS analysis using a modified TRIzol® method (Invitrogen Inc. Carlsbad, Calif.). Extraction samples were prepared in duplicate and split prior to protein precipitation to form a total of four protein pellets per sample. Initial sample extraction aliquots consisted of 240 μl of cold 50 mM ammonium bicarbonate (stored at 4° C.) and 60 μl of concentrated microparticle sample. A 1.0 mL aliquot of TRIzol® Reagent was added and the sample tube was vortexed and incubated at room temperature for 5 minutes. A total of 200 µl of chloroform was added and the sample tube was inverted several times and incubated at room temperature for three minutes. The sample was centrifuged at 12,000×g for 15 minutes at 4° C. on a Microfuge 22R centrifuge. The top aqueous phase was removed and 300 µl of pure ethanol was added to the sample and centrifuged at 2,000×g at for five minutes at 4° C. The Phenol-ethanol solution was split into two aliquots and 750 µl of isopropyl alcohol was added. The samples were centrifuged at 12,000×g for 10 minutes at 4° C. to pellet the proteins. Each protein pellet was washed in triplicate with 0.3M guanidine HCL followed by a wash with pure ethanol. Protein pellets were suspended in a solution of 50 µl of ammonium bicarbonate (50 mM) and 150 µl of 0.1% RapiGest surfactant (Waters Corporation, Milford, Mass.).

The four pellets from sample extraction were combined to provide sufficient material for digestion. A volume of each sample corresponding to 35 µg of protein (based on the protein quantitation results) was used. The sample volumes were made equal by adding 50 mM ammonium bicarbonate (AmBic) to a volume of 110 µL. Disulfide bonds were reduced by adding 200 mM dithiothreitol to each sample and heating the tubes to 80° C. for 15 minutes. Preparations were alkylated with 400 mM iodoacetamide (IA) by placing the tubes in the dark for 30 minutes at room temperature. Preparations were digested by adding 1.4 µg trypsin (Promega Corporation, Madison, Wis.) to each tube and incubating overnight at 37° C. An internal standard, alcohol dehydrogenase digest from yeast (Waters Corporation, Milford, Mass.), was added to a final concentration of 50 fmol/µg protein. The samples were then concentrated and purified prior to LC/MS analysis using a Millipore ZipTip with 0.2 µL C18 resin (Millipore Corporation, Billerica, Mass.) eluted with 60 µl of a 20% formic acid/80% acetonitrile solution. Samples were dried on a centrifugal vacuum evaporator and reconstituted in 50 µl 0.1% formic acid in water.

LC/MS Quality Control and Chromatography.

Multiple standards were prepared to evaluate method and system performance throughout the study including the use of bovine serum albumin (BSA), which was subjected to reduction/alkylation and digestion in parallel with sample digestion. In addition, a standard *E. coli* digest (Waters) and BSA digest (Michrom) were used to verify instrument performance before and after sample analysis. A 300 fmol injection of the BSA digest was identified by MASCOT with >200 peptide fragments covering greater that 70% of the protein. In addition, a 1 µg injection of an *E. coli* digest resulted in the detection of >250 proteins.

A pooled microparticle QC standard was prepared by mixing 5 µL of each of the 24 microparticle samples and used during analysis of the study sample set. Prior to sample analysis, a minimum of two injections and LC/MS/MS analyses of the pooled microparticle QC standard was performed. Data consistency and system performance were ensured by utilizing an acceptable % RSD of less than 20%. The % RSD of the sample total ion chromatogram was 5.2% and the number of proteins identified had a % RSD of 3.3%

Analytical Methods.

Analytical sample were analyzed on a Thermo Scientific LTQ Orbitrap XL mass spectrometry system (LTQ Orbitrap XL) coupled to a Waters nanoACQUITY UPLC system (nanoACQUITY UPLC) using standard sample parameters.

Study samples injections were sequenced in a blinded manner and bracketed by a pair of pooled microparticle QC standard injections after every eight sample injections. Data from all study samples were acquired using Data Dependent™ scans (Nth order double play) on the LTQ Orbitrap XL. Database searches were performed in Elucidator (Rosetta Biosoftware) using MASCOT (Matrix Sciences, London, UK).

Data Analysis.

The pooled microparticle QC and the study samples were evaluated to confirm data quality. Mass spectrometry total ion current (TIC) outputs were assessed for signal quality and changes in signal intensity. Results were also monitored for signal trends, such as a consistent increase or decrease in TIC maximum values, and MASCOT search results were used to monitor the quality of the MS data. No significant outliers were identified during this preliminary evaluation.

Raw MS data files for the pooled microparticle QCs and study samples, collected on the Thermo Orbitrap XL system, were processed in Elucidator. MS data were grouped in Elucidator based on sample groups, identified as group A (term), group B (preterm) and QC. Sample groups were used to assist in data alignment, feature identification, and for QC assessment and group comparisons. Data were processed from retention time 20-180 min.

A label-free differential expression LC/MS/MS method was used to qualitatively compare protein expression levels between two sample groups. The samples were analyzed and the results were processed using the Rosetta Elucidator software package (version 3.3.0.1.SP3_CRE52.21, Rosetta Biosoftware). Data processing in Elucidator was performed in multiple steps that included mass correction and mass signal alignment of detected signals, retention time alignment of detected signals, and feature selection, with features representing mass signals detected within the study set. Mass signals were annotated using the Peptide Tellers function in the Elucidator with the corresponding peptide and protein information based on the database search results using a 1% false discovery rate cut off. Data processing of the Thermo Orbitrap data resulted in detection of ~200 proteins. QC review of the aligned data indicated the mass signals were correctly aligned in the Elucidator software. For retention time alignment, mathematical adjustments were performed to time align the same detected signals across all samples. QC assessment of this retention time shift indicated that all adjustments had a maximum shift of <1.5 min.

The % CVs across the pooled QC samples and the study samples, grouped into groups A and B, were evaluated to confirm data quality. Data demonstrate that the % CVs for all of the isotope groups monitored across the samples were smaller for the replicate pooled QC injections compared to the A and B sample groups.

Thermo Orbitrap data files were searched using the MASCOT search engine against the IPI (Human, v3.87) database released Sep. 27, 2011 appended with yeast ADH (EMBL-European Bioinformatics Institute, Hinxton, Cambridge, UK). The aligned mass features were annotated with these database search results using the results from the system Peptide Tellers and a predicted error rate of 1%.

MS data were summarized to the feature level, normalized to the mean of the features, and an ANOVA test was performed to compare the expression results between sample groups A and B. Candidate differentially expressed features were determined based on a p<0.05, 0.01 and 0.005. Differentially expressed features were summarized by protein based on the results of the database search.

Data from the studies (n=48 patients representing ~500,000 peptide fragments), medical annotation and raw intensity and peptide scores were compiled into an automated database for subsequent interrogation. The mean intensity scores were transformed as described by the vendor (Rosetta Inpharmatics Seattle, Wash.) and blindly analyzed by an independent third party (MF, BIoIT Solutions, Silver Springs, Md.).

Significant differences at the peptide and protein levels were characterized in both the primigravida (P1) and second pregnancy (P2) populations. Biological relevance was defined when statistical significance was observed in both P1 and P2 cohorts (p<0.05). In addition, definition of biomarker relevance required that the differential significance defined by the Elucidator system be reconfirmed by blinded third party, that directional ratios in preterm and term cohorts be observed in both P1 and P2 groups, and that the significance was observed in two or more peptide fragments with an average PT/T ratio >1.0. For all determinations the protein teller criteria was set at >0.9 and false positive protein identification <1%.

Results

The demographics of the asymptomatic term and preterm populations (n=48) presenting between weeks 15 and 17 of gestation are summarized in Table 1-1. No significant differences were noted amongst these groups.

TABLE 1-1

Patient Demographics

| Parameter | Term Birth | Preterm Birth | p Value |
|---|---|---|---|
| Sample size | 24 | 24 | |
| Primigravida (P1) | 12 | 12 | NS |
| 2nd pregnancy (P2) | 12 | 12 | NS |
| Maternal age (yrs) | 28.9 +/− 1.75 | 27.75 +/− 3.8 | NS |
| Maternal body mass index | 23.9 +/− 3.57 | 28.4 +/− 4.0 | NS |
| Prior preterm delivery | 0 | 0 | NS |
| Multiparity | 0 | 0 | NS |
| Tobacco use | 1 | 4 | NS |
| Gestational age at delivery (wks) | >37 | <34 | |
| Birth weight | 3305 +/− 228 | 2415 +/− 330 | <0.01 |

The extracellular vesicles isolated from serum samples eluted by gel filtration methods were characteristic of circulating serum vesicles reported by others (Gercel-Taylor et al., Anal Biochem, 428:44-53, 2012), and expressed canonical proteins indicative of suck particles (FIG. 1)

Serum microparticles isolated from the two groups were not significantly different across any of the phenotypic parameters evaluated at weeks 15-17 gestation including particle density (4.4-6.1$\times\times10^{11}$ per ml patient serum), mean particle size (67-109 nm), and protein yield (488-560 µg/ml sera). The serum vesicles that were isolated from the high molecular (peak 1) fractions, however, differed markedly in protein signature between the preterm and term cohorts.

A total of ~500,000 peptide fragments were identified in the open proteomic assessment of the 48 patient samples and QC specimens. Study 1 (primigravida P1) identified mass features of 216 proteins with significant differential signal patterns between preterm and term cohorts, which correlated to 85 proteins with putative differentially expressed mass signals based on a cutoff of p<0.05. Study 2 (second pregnancies P2) identified mass features of 176 proteins with differential signal patterns between preterm and term cohorts using an ANOVA, which correlated to 54 proteins with differentially expressed mass signals based on a cutoff of p<0.05. Within the proteins observed in the second pregnancies cohort (P2), 32 were observed to be present and statistically significant in the primagravida cohort (P1).

An independent statistical interrogation of the label free Elucidator data were reanalyzed by an independent third party blinded to outcome. These data revealed a total of 99 proteins that were statistically different in expression. From these 99, a total of 18 proteins were selected for validation in future prospective trials. Twelve of the 18 prioritized biomarkers are highly associated with preterm outcome (Table 1-2), while six of the 18 are associated with term outcome (Table 1-3).

TABLE 1-2

Microparticle Preterm Birth Biomarkers

| Symbol | Protein Name | p Value |
|---|---|---|
| A1BG | Alpha-1B-glycoprotein | 0.01 |
| A2M | Alpha-2-macroglobulin | 0.005 |
| ALB | Albumin | 0.01 |
| APOD | Apolipoprotein D | 0.05 |
| APOL1 | Apolipoprotein L1 | 0.01 |
| AZGP1 | Zinc-alpha-2-glycoprotein | 0.05 |
| HPX | Hemopexin | 0.05 |
| IGHM1 | IgM Heavy Chain 1 (secreted) | 0.05 |
| IGHM2 | IgM Heavy Chain 2 (membrane-bound) | 0.01 |
| SERPINA1 | Alpha-1-anti-trypsin | 0.005 |
| SERPINC1 | Anti-thrombin | 0.05 |
| TF | Transferrin | 0.05 |

TABLE 1-3

Microparticle Term Birth Biomarkers

| Symbol | Protein Name | p Value |
|---|---|---|
| C1R | Complement C1r | 0.005 |
| C3 | Complement C3 | 0.005 |
| C4B | Complement C4B | 0.01 |
| CFH | Complement Factor H | 0.005 |
| IGHA2 | IgA Heavy Chain | 0.05 |
| IGKV1-9 | Ig Kappa Variable 1-9 | 0.05 |

The multiplex analysis allowed for a differential characterization of proteins and patients into hierarchical relationships of cohort relevance. Table 1-4 summarizes the accuracy and false positive rates derived from the data. The multiplexed characterization of accuracy based upon cluster analysis revealed a high level of precision in accurately defining patients at risk as early as week 15 for unexpected preterm delivery prior to week 34. The associated probability for the described events has a sensitivity range from 85.4-97.9% (41-47 accurate detection in 48 cases) depending upon the probability of error level set for the window of discrimination. The false positive rates ranged from 3-7 out of 48 samples evaluated, again depending upon the probability of error level chosen.

TABLE 1-4

Predictive Value of Term and Spontaneous Preterm Birth Markers (N = 48)

| Probability | Accurate Out of Expected | | Accurate Out of Actual | |
|---|---|---|---|---|
| Factors | Term | SPTB | Term | SPTB |
| 0.05 | 20/24 | 21/24 | 20/23 | 21/25 |
| 0.01 | 22/24 | 22/24 | 22/24 | 22/24 |
| 0.005 | 23/24 | 23/24 | 24/25 | 23/23 |

Tables 1-5 and 1-6 summarize the functional analysis of the markers identified in both the term and SPTB cohorts. Using Ingenuity Systems Pathway Analysis Software (IPA, Redwood, Calif., USA), a detailed comparison of the molecular pathway analysis of the microvesicle proteins expressed in each group revealed that the biomarkers in the SPTB population were associated with five major pathways and different markedly from the pattern in the term population when evaluated at weeks 15-17 of gestation. The focus molecules detected in the SPTB microparticles largely reflect immune, inflammatory and injury pathways. In contrast, the focus molecules in the term microparticles detected early in the second trimester were associated with cell-to-cell signaling.

TABLE 1-5

Ingenuity Pathway Analysis in SPTB Microparticles

| ID | Molecules in Network | Score | Focus Molecule | Top Functions |
|---|---|---|---|---|
| 1 | A1BG, AHSG, AMBP, APOD, C9, C4B (includes others), Complement component 1, Cytokeratin, elastase, F12, FBLN1, GC, HDL, HPR, HPX, Iti, ITIH1, ITIH2, ITIH3, ITIH4, Kallikrein, KLKB1, KRT1, KRT2, KRT10, KRT6A, NFkB (complex), SERPINC1, SERPINF2, SERPING1, Tcf 1/3/4, trypsin, TTR, VTN | 67 | 26 | Antigen Presentation, Humoral Immune Response, Inflammatory Response |
| 2 | A2M, AFM, ALB, Ap1, collagen, Collagen type IV, Collagen(s), Creb, ERK1/2, Fibrinogen, FN1, GPIIB-IIIA, Growth hormone, Iga, Ige, IgG1, IgG, IGHM*, IGJ, IGLL1/IGLL5, IL1, Immunoglobulin, Insulin, Integrin alpha V beta 3, Laminin, LDH, LDL, LGALS3BP, LRP, ORM1/ORM2, S100A8, SERPINA1, TF, TGF beta, vWF | 29 | 13 | Organismal Injury and Abnormalities, Respiratory Disease, Tissue Morphology |
| 3 | Akt, Alpha catenin, AZGP1, CCL15, CD3, CD27, CHCHD2, chemokine, CPN2, HTRA1, IGLL1/IGLL5, IL17R, Integrin, Interferon alpha, Jnk, Mapk, MMP11, Mmp, Neurotropin, P38 MAPK, PAX3, PDESA, PI3K (complex), PIK3C2B, Pkc(s), PRSS1/PRSS3, Ptk, S100, S100A8, S100A9, S100B, SLC3A2, TFEC, TNFRSF4, Vegf | 9 | 5 | Cell-to-Cell Signaling and Interaction, Inflammatory Response, Cardiovascular Disease |
| 4 | APP, C2, C5, C6, C7, C8, C9, C4B (includes others), C5-C6-C7-C8-C9, C8A, C8B, C8G, CD59 (includes EG: 25407), Cd59a, CD5L, CFB, chondroitin sulfate B, CHRNA7, chymotrypsin, Complement compound 1, CPB2, CPN1, GPR77, HABP2, hemoglobin, IL1B, membrane attack, methylamine, PPP1R15A, PRDX2, S100B, Serine Protease, SMPD2, SYVN1, TNFAIP2 | 8 | 5 | Antigen Presentation, Humoral Immune Response, Inflammatory Response |
| 5 | ADCYAP1 (includes EG: 11516), ASIP, ATRN, COPSS | 2 | 1 | Cell-to-Cell Signaling and Interaction, Cellular Assembly and Organization, Cellular Growth and Proliferation |

TABLE 1-6

Ingenuity Pathway Analysis in Term Microparticles

| ID | Molecules in Network | Score | Focus Molecule | Top Functions |
|---|---|---|---|---|
| 1 | APCS, APOA1, APOB, APOH, C3, C1q, C1QC, C1R, C1S, C4B (includes others), C4BP, C4BPA, CFH, Collagen(s), Complement component 1, CP, Fibrin, Fibrinogen, HDL, IgG1, IgG, IgG2a, IGHG4, IGHM, IGKC, Igm, IL1, Immunoglobulin, LDL, LDL-cholesterol, LPA, NFkB (complex), PF4, Pro-inflammatory Cytokine, SYK/ZAP | 44 | 17 | Cell-To-Cell Signaling and Interaction, Tissue Development, Antigen Presentation |
| 2 | Akt, BAG4, C3, Cd55/Daf2, chemokine, CR1L, CXCL16, CXCR7, ERK, ERK1/2, F2, GALNT2, GEM, HABP2, IGHM, IL12 (family), immune, jnk, Mac1, MGAT3, MS4A1, P38 MAPK, PDGF BB, PI3K (complex), Pkc(s), PLA2G6, plasminogen activator, PPBP, PZP, Rac, SERPINF2, SLAMF1, TGFBI (includes EG: 21803), THBS1, Vegf | 12 | 6 | Inflammatory Response, Cellular Movement, Hematological System Development and Function |
| 3 | CD40, CDK2API, ELANE, FCAR, IGHA1, IGHA2, IL6, IL8, ITGAM (includes EG: 16409), ITGB2, MBL2, Mucin, NFKBIA, PI3K (complex), RELA, TCF3, TGF beta, TLR4, TNF | 4 | 2 | Cell-To-Cell Signaling and Interaction, Antigen Presentation, |

TABLE 1-6-continued

Ingenuity Pathway Analysis in Term Microparticles

| ID | Molecules in Network | Score | Focus Molecule | Top Functions |
|---|---|---|---|---|
| | | | | Inflammatory Response |

The use of extracellular vesicles circulating in high titer in blood as windows to understand disease processes has recently gained considerable attention in the field of molecular biology (Olver and Vidal, Subcell Biochem, 43:99-131, 2007; Simpson et al., Proteomics, 8:4083-99, 2008; Thery, F1000 Biol Rep, 3:15, 2011; and Pant et al., Biochem Pharmacol, 83:1484-94, 2012). The present study demonstrates the clinical utility of using circulating extracellular vesicles as enrichment factors to identify protein biomarkers indicative of risk for preterm birth. A key advantage in utilizing a microparticle-enriched fraction is that it contains protease-resistant microvesicles of endocytic origin (e.g., exosomes), which are thought to capture relevant biomarkers of disease processes (Simpson et al., supra 2008). In addition to containing nucleic acid and protein markers reflective of the tissue of origin, these shed particles have been reported to play an immunomodulatory role in normal pregnancy (Taylor et al., J Immunol, 176:1534-1542, 2006; Sabapatha et al., Am J Reprod Immunol, 56:345-55, 2006; and Atay et al., Am J Reprod Immunol, 65:65-77, 2011).

The present disclosure is an in-depth, open proteomic evaluation of microvesicular biomarkers harvested from maternal serum confirming the use of multiplexed proteins as early warning signals of preterm birth. It is of interest to note that the methods used in this example do not employ expensive protein extraction and affinity purification schemes such as affinity columns for the removal of the high abundant proteins (Tang et al., J Proteome Res, 10:4005-4017, 2011). Thus these methods allow for the rapid and cost effective isolation microparticles from a biological sample from a patient. In addition to the intrinsic benefit of studying microparticle proteomics, the fractionation process allows for detection of the sub proteome proteins outside the typical high abundant species. It is of interest to note that six (e.g., A1BG, APOD, APOL1, AZGP1, HPX and SERPINC1) of the prioritized twelve biomarkers associated with preterm birth are outside of the classical 20 species associated with high abundance proteins that define 97% of the proteome. That is in an exemplary embodiment, highly abundant plasma proteins such as albumin, IgG, IgA, IgM, IgD, transferrin, fibrinogen, alpha2-macroglobulin, alpha1-antitrypsin, haptoglobin, alpha1-acid glycoprotein, ceruloplasmin, APOA1, APOA2, APOB, C1q, C3, C4, plasminogen and prealbumin are not depleted from the blood sample.

The protein biomarkers characterized as discrete entities in this study have been previously described in circulating exosomes (www.exocarta.com) but have never been defined as unique or multiplexed markers associated with preterm birth. Several protein biomarkers identified in the present study have been previously defined as potential serum biomarkers in preterm birth. Previous interest in using α1 antitrypsin (Stella et al., Am J Obstet Gynecol, 201:387, 2009), anti-thrombin (Esplin et al., Am J Obstet Gynecol, 204:391, 2011) and alpha-2-macroglobulin in recurrent pregnancy loss (Saunders et al., Am J Reprod Immunol, 68:438-49, 2012) as circulating biomarker has been reported. The present study represents the first demonstration of differential expression of these and other proteins as markers for preterm risk as early as weeks 15 to 17 of gestation in an asymptomatic population.

The present disclosure confirms the utility of a rapid isolation from sera (30 minutes versus classical 30 hour extractions) of circulating microparticles. Unique protein biomarkers were evaluation using standard LC/MS procedures amenable to a routine CLIA facility. The intended use of such an assay is to be utilized as a non-invasive test to identify pregnant women at risk for premature birth as early as 15 weeks gestation. This would represent a first in human test utilizing a standard blood sample taken between weeks 15 and 17 of gestation. The 1 ml maternal serum sample is sent to a central lab for LC/MS processing and risk results provided in 2-4 days with a targeted risk profile for the later onset of preterm birth. Importantly, this would permit the health care provider and the pregnant subject to take steps to reduce her risk of preterm birth.

We claim:

1. A method of treating a pregnant subject at risk of spontaneous preterm birth, the method comprising:
   (a) detecting the protein levels of at least Inter-alpha trypsin inhibitor H4 (ITIH4), Transferrin (TF), and Plasma protease C1 inhibitor (SERPING1) in microparticles isolated from the blood of a pregnant subject, wherein the pregnant subject (i) is asymptomatic, (ii) is either multigravida who did not previously have a spontaneous preterm birth or is primigravida, and (iii) is at 8 to 20 weeks of gestation;
   (b) selecting for treatment the pregnant subject at risk of spontaneous preterm birth, when the levels of at least ITIH4, TF, and SERPING1 are above a threshold level in the microparticles isolated from the blood of the pregnant subject; and
   (c) administering cervical cerclage or a progesterone treatment to the pregnant subject at risk of spontaneous preterm birth in an amount effective to decrease the risk of spontaneous preterm birth.

2. The method of claim 1, wherein the detecting step comprises detecting the level of at least 4 proteins in the fraction.

3. The method of claim 1, wherein the protein levels are detected in the microparticles isolated from the blood of a pregnant subject who is in the second trimester.

4. The method of claim 1, wherein the protein levels are detected in the microparticles isolated from the blood of a pregnant subject who is at 10, 11, or 12 weeks of gestation.

5. The method of claim 1, wherein the microparticles are isolated using size-exclusion chromatography with an agarose solid phase and non-buffered aqueous liquid phase.

6. The method of claim 5, wherein the non-buffered aqueous liquid phase is water.

7. The method of claim 1, wherein the detecting step comprises measuring binding of an antibody specific to each of the proteins.

8. The method of claim 1, wherein the detecting step comprises liquid chromatography/mass spectrometry (LC/MS).

9. The method of claim 1, wherein the pregnant subject is primigravida.

10. The method of claim 1, wherein the pregnant subject is multigravida.

11. The method of claim 1, wherein the protein levels are detected in the microparticles isolated from the blood of the pregnant subject who is in the first trimester.

12. The method of claim 1, wherein the microparticles are isolated from plasma.

13. A method of treating a pregnant subject at risk of spontaneous preterm birth, the method comprising:
   (a) detecting the protein levels of at least Inter-alpha trypsin inhibitor H4 (ITIH4), Transferrin (TF), and Plasma protease C1 inhibitor (SERPING1) in microparticles isolated from the blood of a pregnant subject, wherein the pregnant subject (i) is asymptomatic, (ii) is either multigravida who did not previously have a spontaneous preterm birth or is primigravida, and (iii) is at 8 to 20 weeks of gestation;
   (b) calculating a risk score of spontaneous preterm birth based on the levels of the proteins determined in step (a);
   (c) identifying a pregnant subject at risk of spontaneous preterm birth based on the risk score; and
   (d) treating the pregnant subject at risk of spontaneous preterm birth comprising administering cervical cerclage or a progesterone treatment to the pregnant subject in an amount effective to decrease the risk of spontaneous preterm birth.

14. The method of claim 13, wherein the protein levels are detected in the microparticles isolated from the blood of a pregnant subject who is at 10, 11, or 12 weeks of gestation.

15. The method of claim 13, wherein the microparticles are isolated using size-exclusion chromatography with an agarose solid phase and a non-buffered aqueous liquid phase.

16. The method of claim 13, wherein the detecting step comprises liquid chromatography/mass spectrometry (LC/MS).

17. The method of claim 13, wherein the pregnant subject is primigravida.

18. The method of claim 13, wherein the pregnant subject is multigravida.

19. The method of claim 13, wherein the protein levels are detected in the microparticles isolated from the blood of a pregnant subject who is in the first trimester.

20. The method of claim 13, wherein the protein levels are detected in the microparticles isolated from the blood of a pregnant subject who is in the second trimester.

21. The method of claim 13, wherein the microparticles are isolated from plasma.

22. A treatment method comprising administering an effective amount of cervical cerclage or a progesterone treatment to a pregnant subject characterized as having a set of differentially expressed proteins in microparticles isolated from the blood of the pregnant subject, indicative of an increased risk of spontaneous preterm birth, wherein the set of proteins comprises at least Inter-alpha trypsin inhibitor H4 (ITIH4), Transferrin (TF), and Plasma protease C1 inhibitor (SERPING1), wherein the set of proteins is expressed at above a threshold level, wherein the expression of the set of proteins is assessed in microparticles isolated from the blood of a pregnant subject, and wherein the pregnant subject (i) is asymptomatic, (ii) is either a multigravida who did not previously have a spontaneous preterm birth or is a primigravida, and (iii) is at 8 to 20 weeks of gestation.

23. The method of claim 22, wherein the protein levels are detected in the microparticles isolated from the blood of a pregnant subject who is at 10, 11, or 12 weeks of gestation.

24. The method of claim 22, wherein the pregnant subject is primigravida.

25. The method of claim 22, wherein the pregnant subject is multigravida.

26. The method of claim 22, wherein the protein levels are detected in the microparticles isolated from the blood of a pregnant subject who is in the first trimester.

27. The method of claim 22, wherein the protein levels are detected in the microparticles isolated from the blood of a pregnant subject who is in the second trimester.

28. The method of claim 22, wherein the characterization of differentially expressed proteins comprises liquid chromatography/mass spectrometry (LC/MS).

29. The method of claim 22, wherein the microparticles are isolated from plasma.

* * * * *